US011603555B2

(12) United States Patent
Lai et al.

(10) Patent No.: US 11,603,555 B2
(45) Date of Patent: *Mar. 14, 2023

(54) INTEGRATED PURIFICATION AND MEASUREMENT OF DNA METHYLATION AND CO-MEASUREMENT OF MUTATIONS AND/OR MRNA EXPRESSION LEVELS IN AN AUTOMATED REACTION CARTRIDGE

(71) Applicant: Cepheid, Sunnyvale, CA (US)

(72) Inventors: Edwin W. Lai, Santa Clara, CA (US); Andrew Kohlway, Santa Clara, CA (US); Reuel Vanatta, Palo Alto, CA (US); Russell Higuchi, Alameda, CA (US); Alexander Gall, Woodinville, WA (US); Kriszten Kocmond, Los Altos, CA (US)

(73) Assignee: CEPHEID, Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/182,394

(22) Filed: Jun. 14, 2016

(65) Prior Publication Data

US 2017/0137871 A1    May 18, 2017

Related U.S. Application Data

(60) Provisional application No. 62/175,916, filed on Jun. 15, 2015.

(51) Int. Cl.
| | |
|---|---|
| *C12Q 1/6806* | (2018.01) |
| *C12Q 1/6827* | (2018.01) |
| *C12Q 1/6886* | (2018.01) |
| *C12N 15/10* | (2006.01) |
| *B01L 7/00* | (2006.01) |

(52) U.S. Cl.
CPC ............ *C12Q 1/6827* (2013.01); *B01L 7/52* (2013.01); *C12N 15/1006* (2013.01); *C12N 15/1017* (2013.01); *C12Q 1/6806* (2013.01); *C12Q 1/6886* (2013.01); *B01L 2300/087* (2013.01); *B01L 2300/0864* (2013.01); *C12Q 2600/154* (2013.01)

(58) Field of Classification Search
None
See application file for complete search history.

(56) References Cited

U.S. PATENT DOCUMENTS

| | | |
|---|---|---|
| 5,958,349 A | 9/1999 | Petersen et al. |
| 6,403,037 B1 | 6/2002 | Chang et al. |
| 6,440,725 B1 | 8/2002 | Pourahmadi et al. |
| 6,783,736 B1 | 8/2004 | Taylor et al. |
| 6,818,185 B1 | 11/2004 | Petersen et al. |
| 8,062,849 B2 | 11/2011 | Sukumar et al. |
| 10,450,609 B2 | 10/2019 | Sukumar et al. |
| 10,533,210 B2 | 1/2020 | Nauwelaers et al. |
| 11,260,387 B2* | 3/2022 | Lai ................... C12Q 1/686 |
| 2003/0082600 A1 | 5/2003 | Olek et al. |
| 2003/0096289 A1* | 5/2003 | Suzuki ............. C12Q 1/6837 506/9 |
| 2006/0068399 A1 | 3/2006 | Mcmillan et al. |
| 2006/0134643 A1* | 6/2006 | Berlin ............. C12Q 2527/125 435/6.12 |
| 2006/0286577 A1* | 12/2006 | Jia ................... C12Q 1/6806 435/6.12 |

(Continued)

FOREIGN PATENT DOCUMENTS

| | | |
|---|---|---|
| CN | 101285096 A | 10/2008 |
| CN | 101984069 A | 3/2011 |

(Continued)

OTHER PUBLICATIONS

Sommer and Tautz, "Minimal homology requirements for PCR primers," Nucleic Acids Research, vol. 17, No. 16, p. 6749. (Year: 1989).*
PCT International Search Report and Written Opinion dated Dec. 6, 2016 issued in PCT/US2016/037422.
PCT International Preliminary Report on Patentability dated Dec. 19, 2017 issued in PCT/US2016/037422.
Analytikjena (2014) "innuCONVERT Bisulfite All-in-One Kit", *Analytic Jena AG, AJ Innuscreen Gmbh*, 4 pages; Retrieved from the Internet: URL: http://journals.plos.org/plosone/article?id=10.1371/journal.pone.0093933 [Retrieved on Nov. 11, 2015].
Bailey et al. (2010) "Single-Tube Analysis of DNA Methylation with Silica Superparamagnetic Beads" *Clinical Chemistry*, 56(6): 1022-1025.
Bianco et al. (1999) "Methylation-sensitive, single-strand conformation analysis (MS-SSCA): A rapid method to screen for and analyze methylation" *Hum. Mutat.* 14(4): 289-293.

(Continued)

*Primary Examiner* — Bradley L. Sisson
(74) *Attorney, Agent, or Firm* — Emily M. Haliday; Weaver Austin Villeneuve & Sampson LLP

(57) ABSTRACT

In various embodiments methods of determining methylation of DNA are provided. In one illustrative, but non-limiting embodiment the method comprises i) contacting a biological sample comprising a nucleic acid to a first matrix material comprising a first column or filter where said matrix material binds and/or filters nucleic acids in said sample and thereby purifies the DNA; ii) eluting the bound DNA from the first matrix material and denaturing the DNA to produce eluted denatured DNA; iii) heating the eluted DNA in the presence of bisulfite ions to produce a deaminated nucleic acid; iv) contacting said deaminated nucleic acid to a second matrix material comprising a second column to bind said deaminated nucleic acid to said second matrix material; v) desulfonating the bound deaminated nucleic acid and/or simultaneously eluting and desulfonating the nucleic acid by contacting the deaminated nucleic acid with an alkaline solution to produce a bisulfite converted nucleic acid; vi) eluting said bisulfite converted nucleic acid from said second matrix material; and vii) performing methylation specific PCR and/or nucleic acid sequencing, and/or high resolution melting analysis (HRM) on said bisulfite-converted nucleic acid to determine the methylation of said nucleic acid, wherein at least steps iv) through vi) are performed in a single reaction cartridge.

14 Claims, 45 Drawing Sheets

Specification includes a Sequence Listing.

(56) References Cited

U.S. PATENT DOCUMENTS

| | | | |
|---|---|---|---|
| 2007/0098600 A1* | 5/2007 | Kayyem | G01N 33/54386 422/400 |
| 2008/0014576 A1* | 1/2008 | Jovanovich | B01F 11/0071 435/5 |
| 2009/0036665 A1* | 2/2009 | Domingo | B01L 3/502 536/25.41 |
| 2009/0253181 A1 | 10/2009 | Vangbo et al. | |
| 2010/0041024 A1* | 2/2010 | Fuhrmann | C12Q 1/6827 435/6.12 |
| 2010/0330580 A1* | 12/2010 | Gimenez | C12Q 1/686 435/6.11 |
| 2012/0088249 A1 | 4/2012 | Jovanovich et al. | |
| 2012/0244532 A1* | 9/2012 | Craighead | B01L 3/502761 435/6.11 |
| 2012/0252015 A1* | 10/2012 | Hindson | C12Q 1/6883 435/6.11 |
| 2013/0203606 A1* | 8/2013 | Pollack | C12N 15/1006 506/2 |
| 2014/0098252 A1* | 4/2014 | Chang | G01N 35/00732 348/207.99 |
| 2014/0272967 A1 | 9/2014 | Gundling et al. | |
| 2014/0272997 A1 | 9/2014 | Ivie et al. | |
| 2014/0274735 A1* | 9/2014 | Granados | C12Q 1/6858 506/2 |
| 2015/0099670 A1* | 4/2015 | Li | C12Q 1/6855 506/26 |
| 2015/0119268 A1 | 4/2015 | Bishop | |
| 2015/0136604 A1* | 5/2015 | Nielsen | B01L 7/52 204/453 |
| 2015/0154352 A1* | 6/2015 | Johnson | G01N 33/5005 435/6.11 |
| 2015/0204813 A1 | 7/2015 | Toumazou et al. | |
| 2016/0223442 A1 | 8/2016 | Guldberg et al. | |
| 2018/0214864 A1 | 8/2018 | Lai et al. | |
| 2022/0226809 A1 | 7/2022 | Lai et al. | |

FOREIGN PATENT DOCUMENTS

| | | |
|---|---|---|
| CN | 104321442 A | 1/2015 |
| CN | 105378108 A | 3/2016 |
| CN | 107922941 A | 4/2018 |
| EP | 1 394 173 A1 | 3/2004 |
| EP | 2 218 793 A1 | 8/2010 |
| JP | 2009-519023 A | 5/2009 |
| JP | 2009-236933 A | 10/2009 |
| KR | 20150014469 A | 2/2015 |
| KR | 20150038944 A | 4/2015 |
| RU | 2332462 C2 | 8/2008 |
| WO | WO 98/56952 A1 | 12/1998 |
| WO | WO 99/33559 A1 | 7/1999 |
| WO | WO 00/73412 A2 | 12/2000 |
| WO | WO 2004/096825 A1 | 11/2004 |
| WO | WO 2006/136990 A2 | 12/2006 |
| WO | WO 2007/004103 A1 | 1/2007 |
| WO | WO 2007/068437 A1 | 6/2007 |
| WO | WO 2009/024019 A1 | 2/2009 |
| WO | WO 2014/052551 A1 | 4/2014 |
| WO | WO 2016/205233 A2 | 12/2016 |
| WO | WO 2018/111935 A1 | 6/2018 |

OTHER PUBLICATIONS

Butkus, Ben (2015) "Hopkins Lab, Cepheid Developing Methylated DNA Panel for Breast Cancer Dx, Monitoring GenomeWeb" *Genomeweb* Retrieved from the Internet: URL:https://www.genomeweb.com/molecular-diagnostics/hopkins-lab-cepheid-developing-methylated-dna-panel-breast-cancer-dx#.Wq97n2fderg [retrieved on Mar. 19, 2018] 3 pages.

Clark et al. (1994) "Hign Sensitivity mapping of methylated cytosines" *Nucleic Acid Research*, 22(15): 2990-2997.

Colella et al. (2003) "Sensitive and quantitative universal Pyrosequencing methylation analysis of CpG sites." *BioTechniques* 35(1): 146-150.

Eads et al. (1999) "CpG Island Hypermethylation in Human Colorectal Tumors Is Not Associated with DNA Methyltransferase Overexpression" *Cancer Res.*, 59: 2302-2306.

Eads et al. (2000) "MethyLight: a high-throughput assay to measure DNA methylation" *Nucleic Acids Research*, 28(8): e32 (9 pages).

Ehrich et al. (2005) "Quantitative high-throughput analysis of DNA methylation patterns by base-specific cleavage and mass spectrometry." *Proc. Natl. Acad. Sci. USA*, 102 (44): 15785-15790.

Esteller et al. (1999) "Detection of Aberrant Promoter Hypermethylation of Tumor Suppressor Genes in Serum DNA from Non-Small Cell Lung Cancer Patients" *Cancer Research*, 59: 67-70.

Fink et al. (1998) "Real-time quantitative RT-PCR after laser-assisted cell picking." *Nat. Med.*, 4(11): 1329-1333.

Frommer et al. (1992) "A genomic sequencing protocol that yields a positive display of 5-methylcytosine residues in individual DNA strands." *Proc. Natl. Acad. Sci. USA*, 89 (5): 1827-1831.

Herman et al. (1996) "Methylation-specific PCR: a novel PCR assay for methylation status of CpG islands." *Proc. Natl. Acad. Sci. USA*, 93: 9821-9826.

Holmes et al. (2014) "Performance Evaluation of Kits for Bisulfite-Conversion of DNA from Tissues, Cell Lines, FFPE Tissues, Aspirates, Lavages, Effusions, Plasma, Serum, and Urine" *PLOS One*, 9(4): e93933 (14 pages).

Lee et al. (1993) "Allelic discrimination by nick-translation PCR with fluorogenic probes." *Nucleic Acids Res.*, 21(16): 3761-3766.

Livak et al. (1995) "Oligonucleotides With Fluorescent Dyes at Opposite Ends Provide a Quenched Probe System Useful for Detecting PCR Product and Nucleic Acid Hybridization" *Genome Res. PCR Meth. Appl.*, 4: 357-362.

Meissner et al. (2005) "Reduced representation bisulfite sequencing for comparative high-resolution DNA methylation analysis" *Nucleic Acid Research*, 33(18): 5868-5877.

Qian and Brent (1997) "Methylation Hot Spots in the 5' Flanking Region Denote Silencing of the $O^6$-Methylguanine-DNA Methyltransferase Gene" *Cancer Research*, 57: 3672-3677.

Rand et al. (2002) "Conversion-specific detection of DNA methylation using real-time polymerase chain reaction (ConLight-MSP) to avoid false positives" *Methods* 27(2): 114-120.

Shin et al. (2013) "Droplet Bisulfite Conversion Platform for Epigenetic Cancer Biomarker Detection" *Transducers & Eurosensors XXVII: The 17th International Conference on Solid-State Sensors, Actuators and Microsystems*, Barcelona, Spain, Jun. 16-20, 2013, pp. 2181-2184.

Tost et al. (2003) "Analysis and quantification of multiple methylation variable positions in CpG islands by Pyrosequencing™" *BioTechniques* 35(1): 152-156.

Uccella et al. (2009) "MGMT methylation in diffuse large B-cell lymphoma: validation of quantitative methylation-specific PCR and comparison with MGMT protein expression" *J Clin Pathol*, 62:715-723.

Warnecke et al. (1997) "Detection and measurement of PCR bias in quantitative methylation analysis of bisulphite-treated DNA." *Nucleic Acids Res.*, 25(21): 4422-4426.

Watts et al. (1997) "Methylation of Discrete Regions of the $O^6$-Methylguanine DNA Methyltransferase (MGMT) CpG Island Is Associated with Heterochromatinization of the MGMT Transcription Start Site and Silencing of the Gene" *Molecular and Cellular Biology*, 17(9): 5612-5619.

Wojdacz and Dobrovic (2007) "Methylation-sensitive high resolution melting (MS-HRM): a new approach for sensitive and high-throughput assessment of methylation" *Nucleic Acids Res.* 35(6): e41 (7 pages).

PCT Invitation to pay additional fees dated Oct. 4, 2016 issued in PCT/US2016/037422.

PCT International Search Report and Written Opinion dated Apr. 3, 2018 issued in PCT/US2017/065905.

PCT International Preliminary Report on Patentability dated Jun. 18, 2019 issued in PCT/US2017/065905.

EP Office Action dated May 21, 2019 issued in EP 16732159.5.

U.S. Office Action dated Oct. 23, 2020 issued in U.S. Appl. No. 15/839,731.

(56) References Cited

OTHER PUBLICATIONS

JP Office Action dated Jul. 13, 2020 issued in JP 2017-564901.
EP Office Action dated Nov. 15, 2020 issued in EP 17822953.0.
Roche Diagnostics K.K, (Jan. 2005) "High Pure PCR Product Purification Kit," 3 pages.
AU First Office Action dated Aug. 26, 2021 issued in AU 2016277943.
EP Extended Search Report dated May 27, 2021 issued in EP 20202659.7.
U.S. Notice of Allowance dated Jun. 21, 2021 issued in U.S. Appl. No. 15/839,731.
CN First Office Action with Search Report dated Jan. 14, 2021 issued in CN 201680048155.X.
JP Final Office Action dated Jun. 21, 2021 issued in JP 2017-564901.
BR Office Action dated Aug. 3, 2021 issued in BR 112019011670-2.
CN First Office Action with Search Report dated Mar. 12, 2021 issued in CN 201780085871.X.
RU Office Action dated May 7, 2021 issued in RU 2019119086.
Athamanolap et al. (2014) "Droplet Array Platform for High-Resolution Melt Analysis of DNA Methylation Density" *Journal of Laboratory Automation* 19(3): 304-312.
AU Office Action dated Feb. 1, 2022 in Application No. AU2017376118.
CN Office Action dated Feb. 8, 2022, in Application No. CN201780085871.X with English translation.
CN Office Action dated Nov. 26, 2021, in Application No. CN201680048155.X with English translation.
Co-pending U.S. Appl. No. 17/586,645, filed Jan. 27, 2022.
IN Office Action dated Dec. 10, 2021, in Application No. IN201817001016.
JP Office Action dated Dec. 6, 2021, in Application No. JP2019-531197 with English translation.
KR Office action dated Mar. 28, 2022 in Application No. KR20197019958 with translation.
Notice of Allowance dated Oct. 29, 2021 in U.S. Appl. No. 15/839,731.
RU Office Action dated Dec. 8, 2021, in Application No. RU20190119086 with English Translation.
U.S. Corrected Notice of Allowability dated Sep. 24, 2021, in U.S. Appl. No. 15/839,731.
AU Office Action dated Jul. 8, 2022, in Application No. AU20160277943.
CA Office Action dated Jul. 28, 2022 in Application No. CA20162989573.
CN Office Action dated May 25, 2022 in Application No. CN20168048155.X with English Translation.
EP Office Action dated Mar. 23, 2022, in Application No. EP17822953.

* cited by examiner

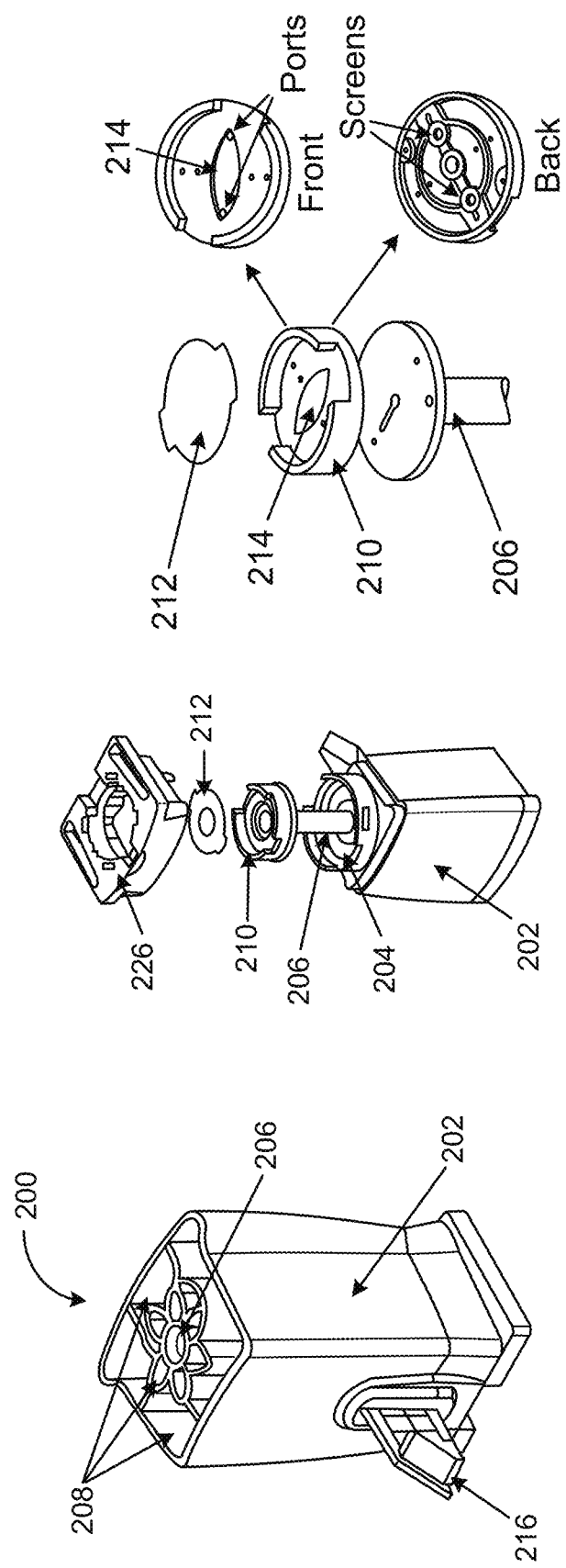

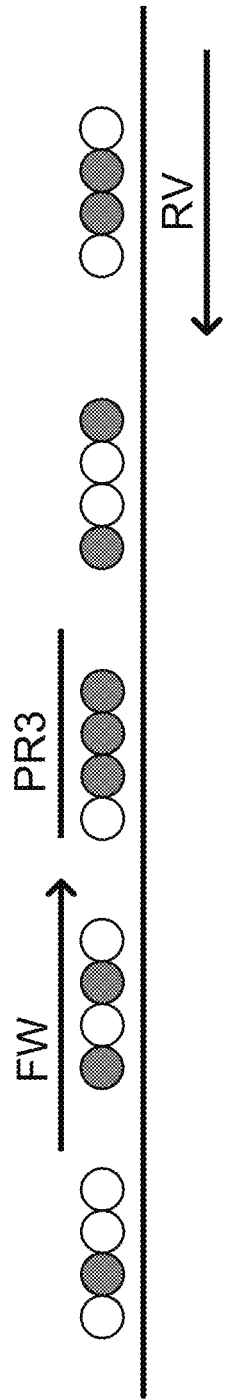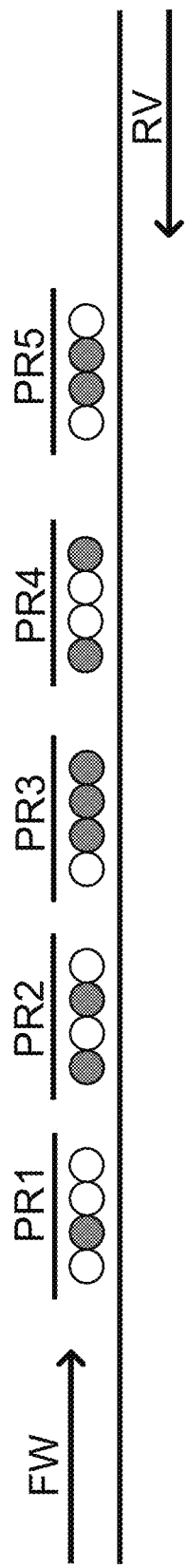

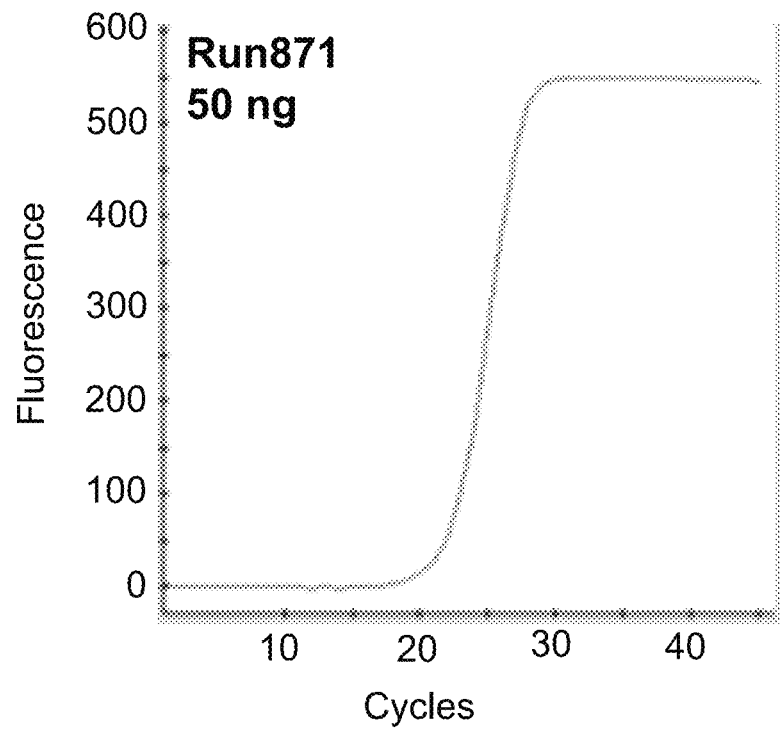
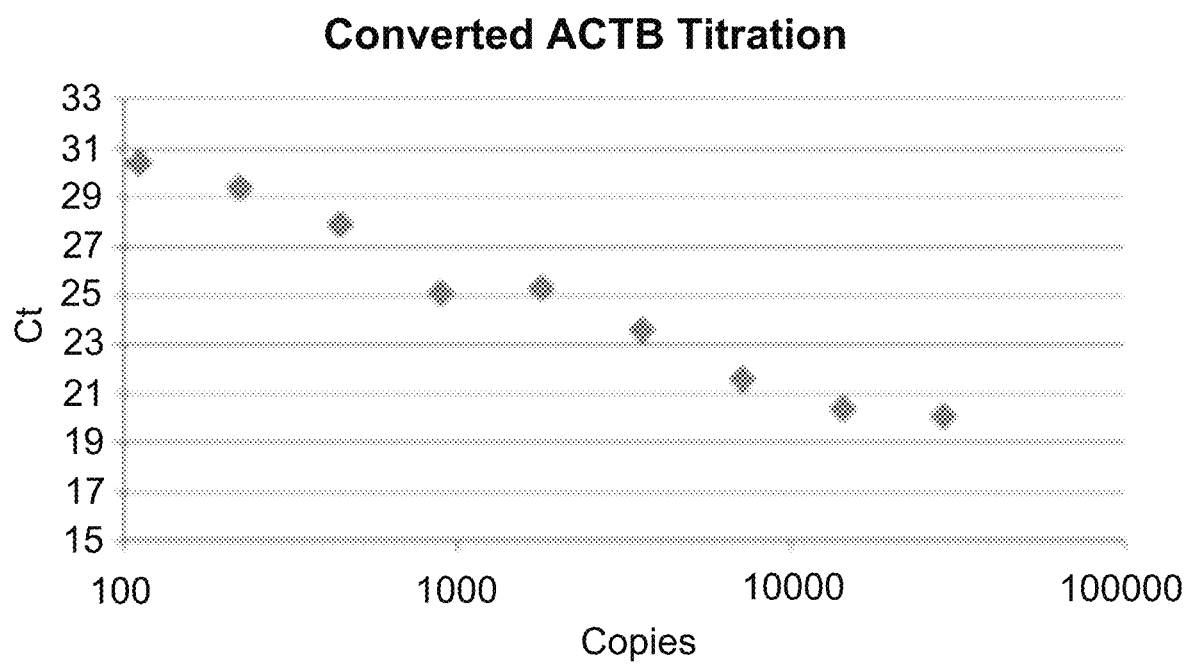
FIG. 6A

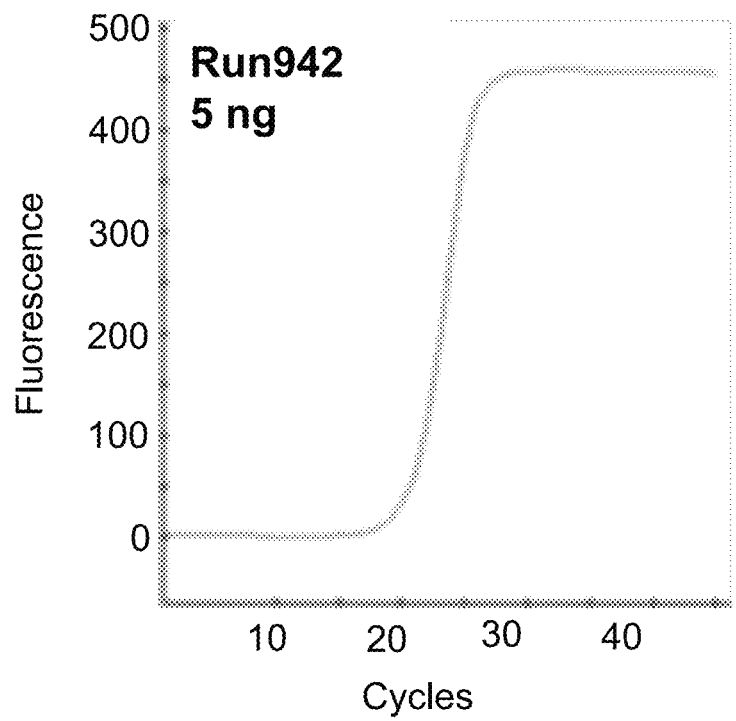
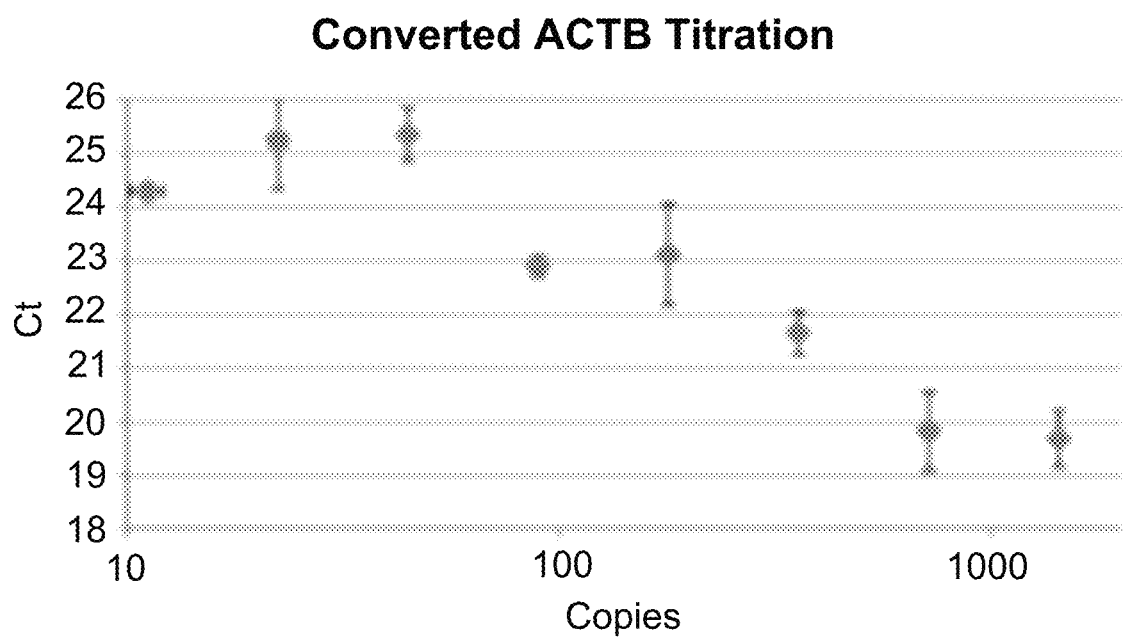
*FIG. 6B*

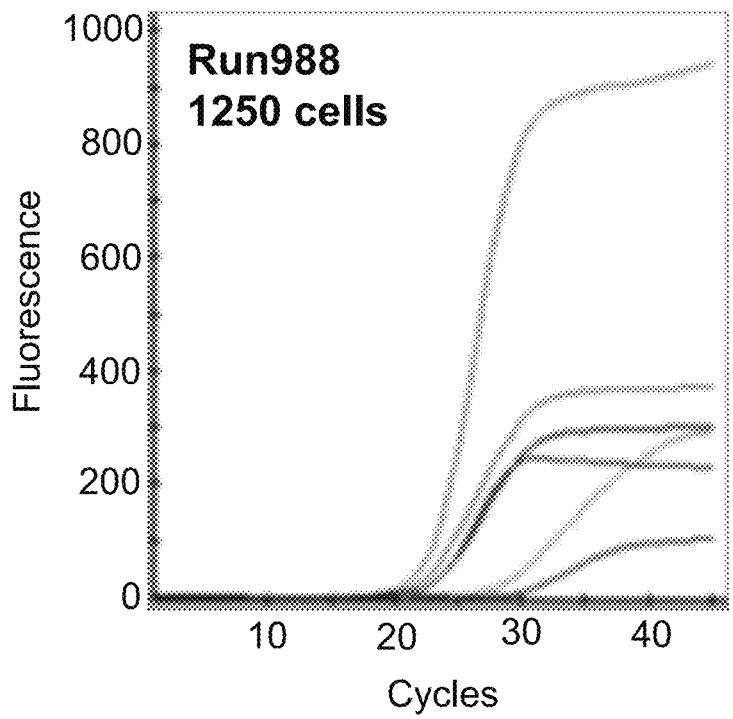
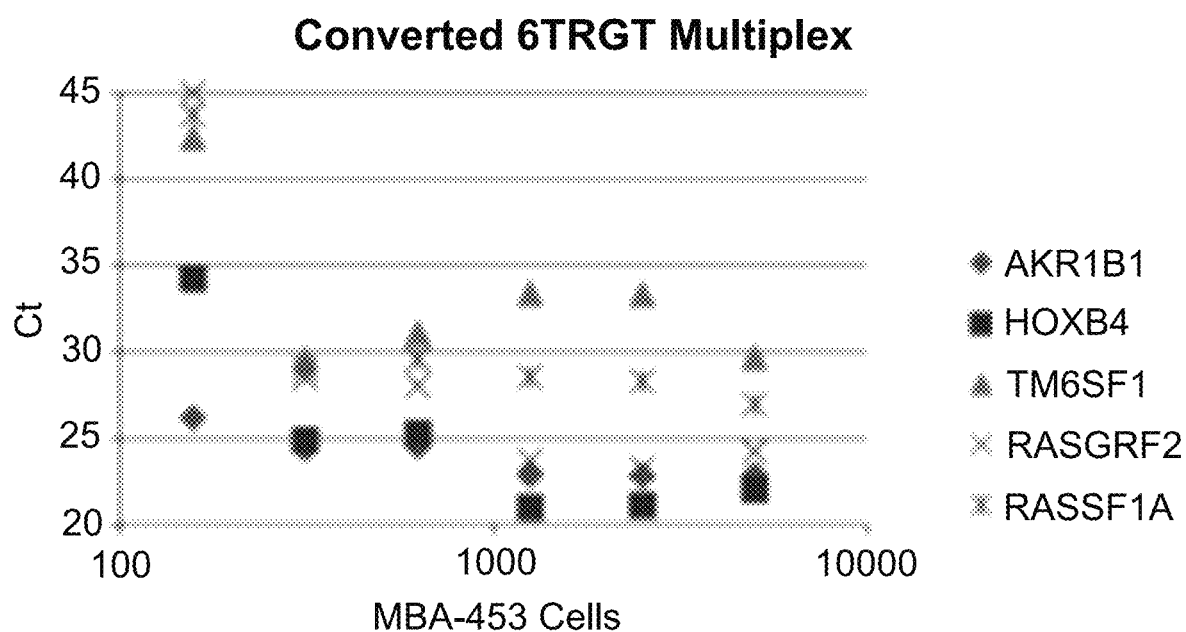
FIG. 7B

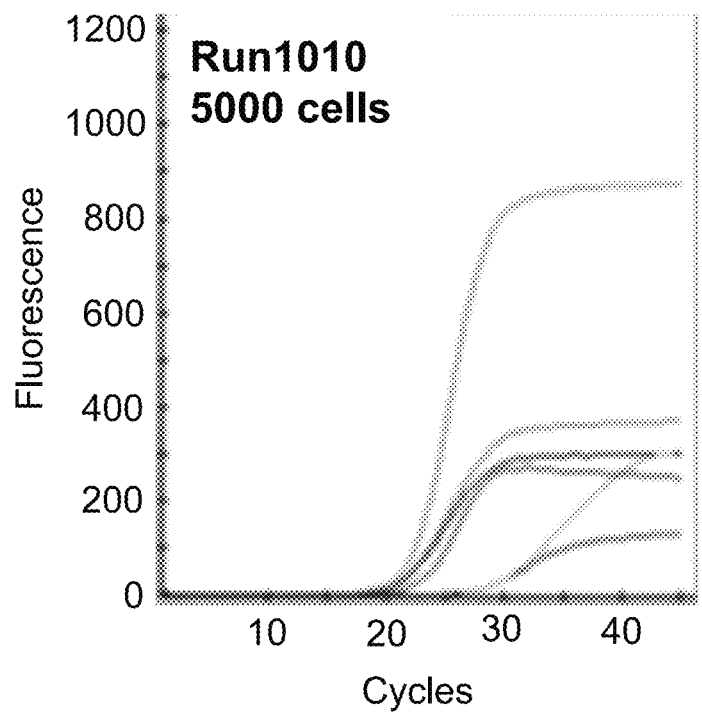
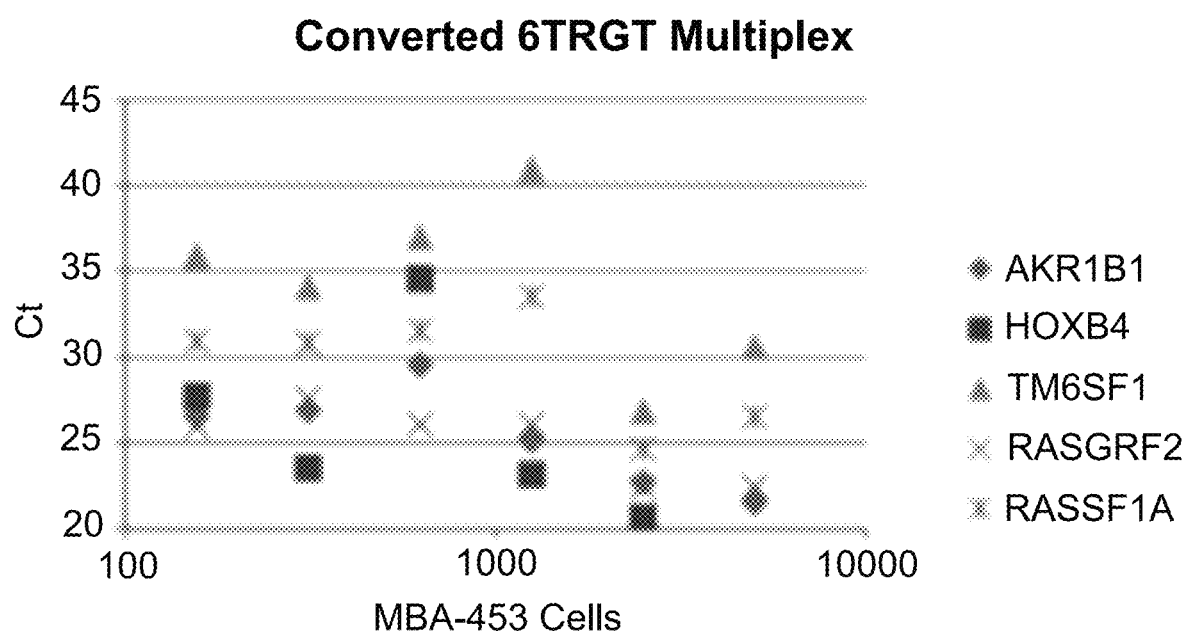
FIG. 7C

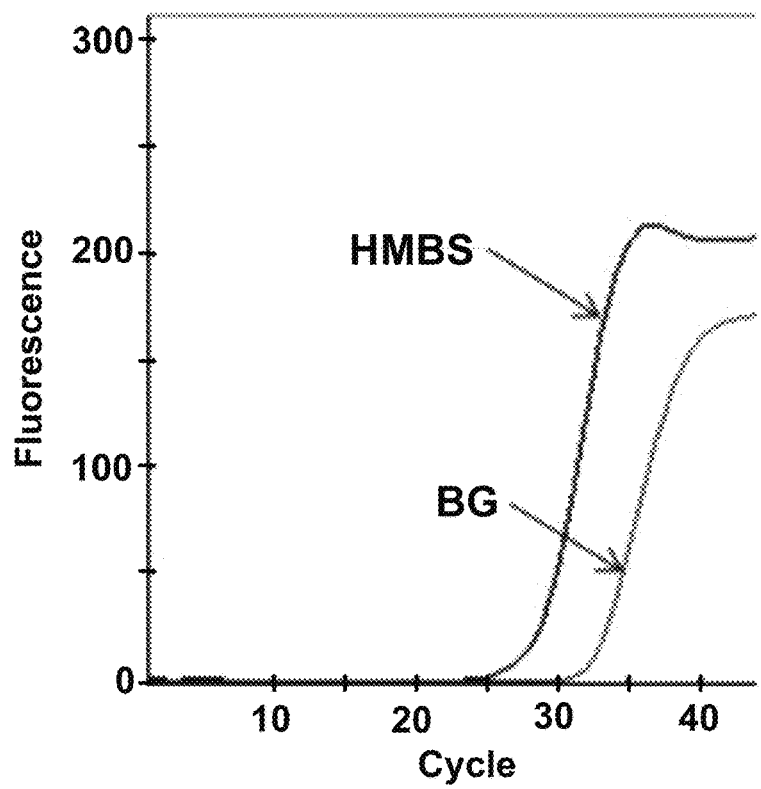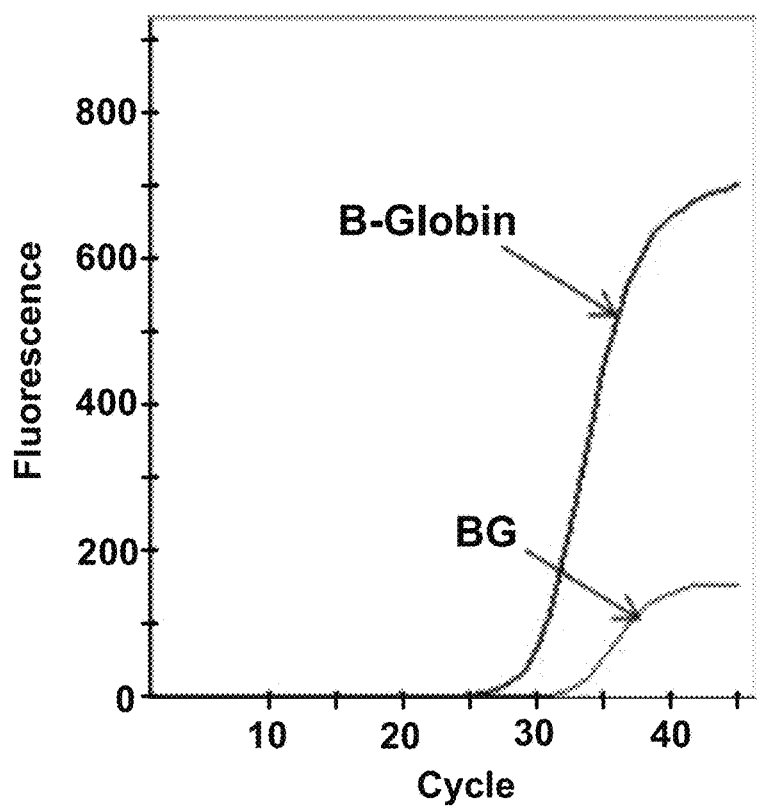
FIG. 18

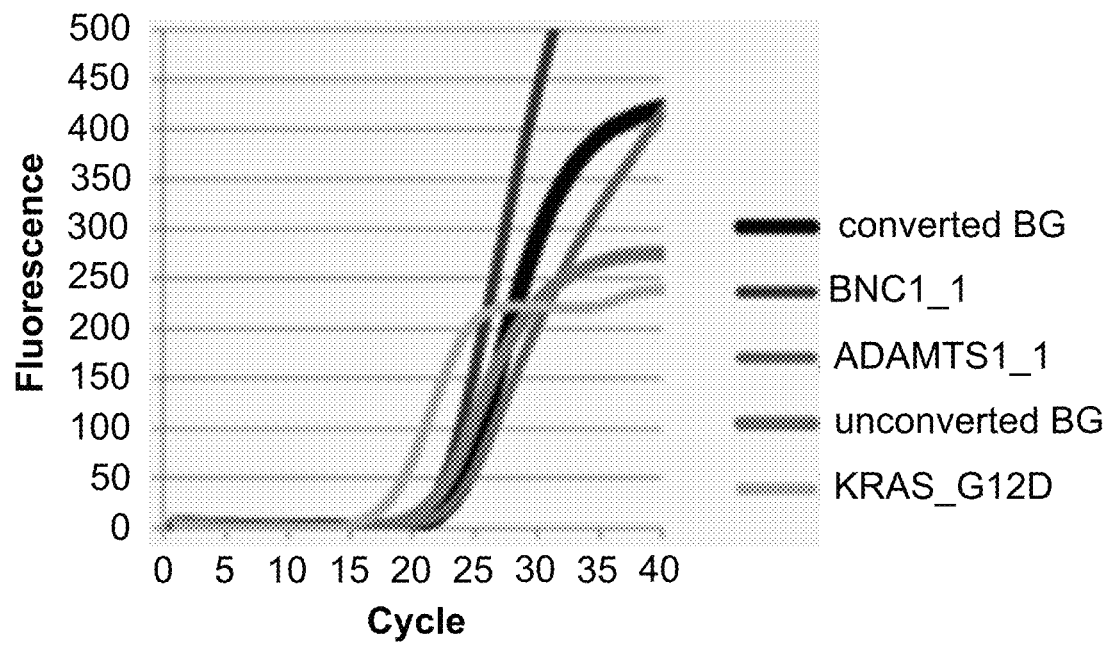
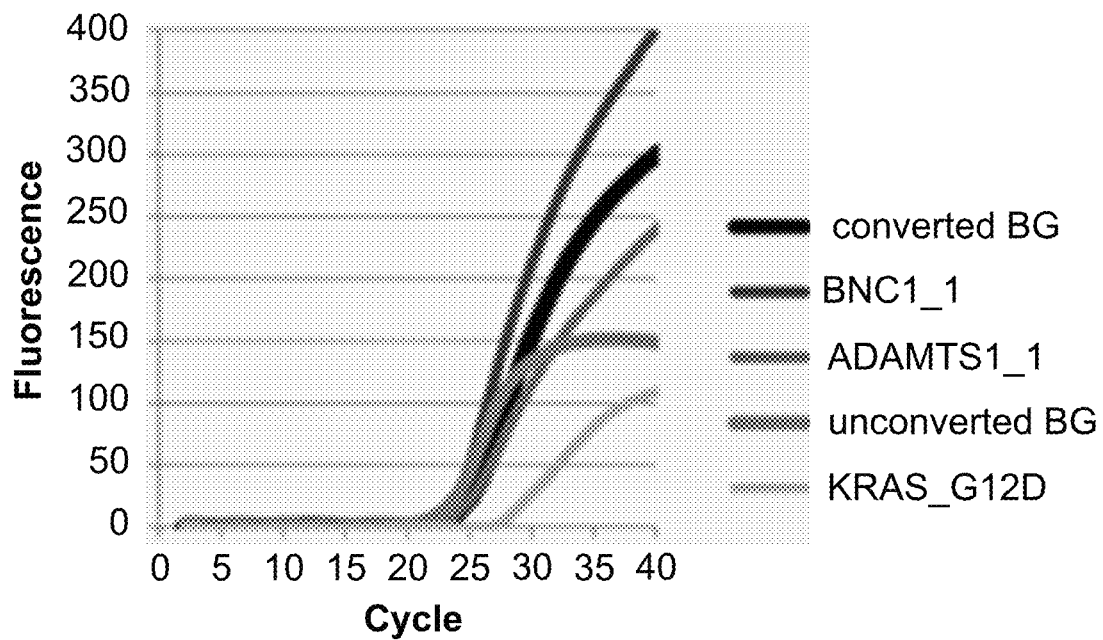
FIG. 27A

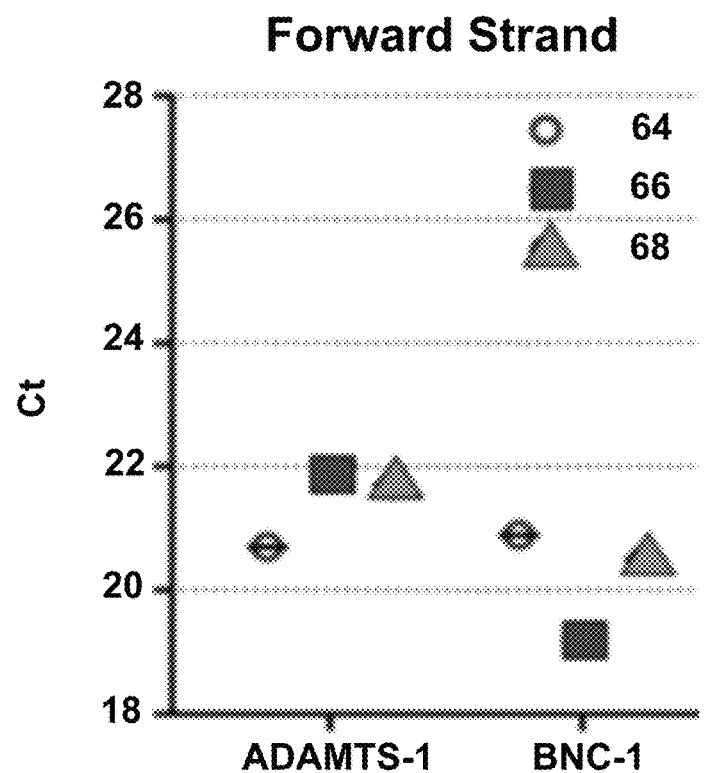
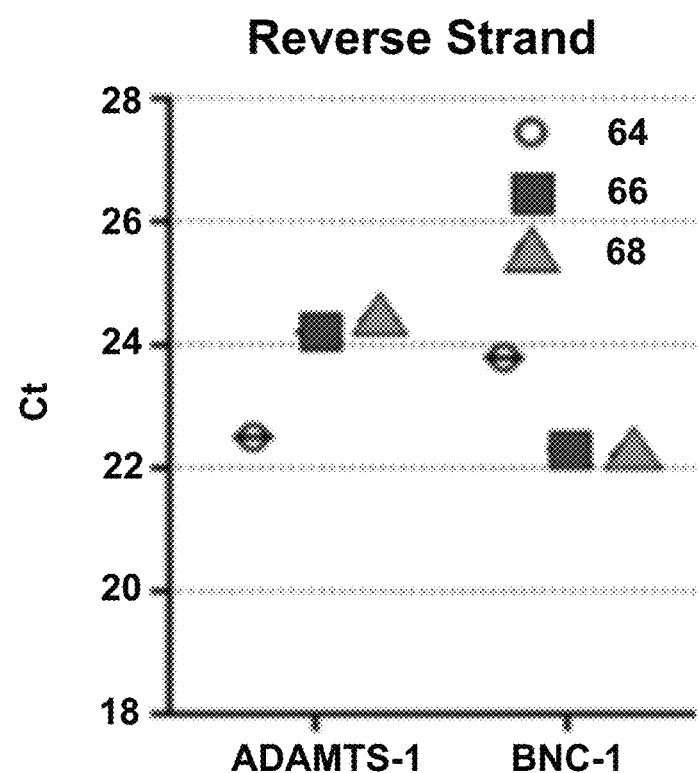
FIG. 28

```
                        SEQUENCE LISTING

<160> NUMBER OF SEQ ID NOS: 390

<210> SEQ ID NO 1
<211> LENGTH: 162
<212> TYPE: DNA
<213> ORGANISM: Homo sapiens

<400> SEQUENCE: 1
cgcgtttcgg atatgttggg atagttcgcg tttttagaac gttttgcgtt tcgacgttcg      60
taggttttcg cggtgcgtat cgtttgctat ttggtgagtg tttgggtcgt ttcgttttcg     120
gaagagtgcg gagtttttttt tcgggacggt ggtagtttcg ag                        162

<210> SEQ ID NO 2
<211> LENGTH: 18
<212> TYPE: DNA
<213> ORGANISM: Artificial
<220> FEATURE:
<223> OTHER INFORMATION: Synthetic oligonucleotide PCR primer

<400> SEQUENCE: 2
gcgttgaagt cggggttc                                                    18

<210> SEQ ID NO 3
<211> LENGTH: 24
<212> TYPE: DNA
<213> ORGANISM: Artificial
<220> FEATURE:
<223> OTHER INFORMATION: Synthetic oligonucleotide PCR primer

<400> SEQUENCE: 3
cccgtacttc gctaacttta aacg                                             24

<210> SEQ ID NO 4
<211> LENGTH: 24
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (24)..(24)
<223> OTHER INFORMATION: 3' quencher and/or blocker

<400> SEQUENCE: 4
acaaacgcga accgaacgaa acca                                             24

<210> SEQ ID NO 5
```

```
<211> LENGTH: 23
<212> TYPE: DNA
<213> ORGANISM: Artificial
<220> FEATURE:
<223> OTHER INFORMATION: Synthetic oligonucleotide PCR primer

<400> SEQUENCE: 5
ttagggtaga ttgtggatat tag                                          23

<210> SEQ ID NO 6
<211> LENGTH: 24
<212> TYPE: DNA
<213> ORGANISM: Artificial
<220> FEATURE:
<223> OTHER INFORMATION: Synthetic oligonucleotide PCR primer

<400> SEQUENCE: 6
atactaacaa ctatccaata caac                                         24

<210> SEQ ID NO 7
<211> LENGTH: 34
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Substituted cytosine coupled to fluor
<220> FEATURE:
<221> NAME/KEY: misc_feature
<222> LOCATION: (15)..(15)
<223> OTHER INFORMATION: Conjugated to quencher

<400> SEQUENCE: 7
caggttgaaa ttagtatgtg ttattttggt atgg                              34

<210> SEQ ID NO 8
<211> LENGTH: 23
<212> TYPE: DNA
<213> ORGANISM: Artificial
<220> FEATURE:
<223> OTHER INFORMATION: Synthetic oligonucleotide PCR primer

<400> SEQUENCE: 8
aatagttcgt aagtttatcg gcg                                          23

<210> SEQ ID NO 9
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 9
cttcacgcca ccgataaccg a                                            21

<210> SEQ ID NO 10
<211> LENGTH: 25
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
```

```
<222> LOCATION: (25)..(25)
<223> OTHER INFORMATION: 3' quencher and/or blocker

<400> SEQUENCE: 10
tacttacgcg aaactttacc gccga                                         25

<210> SEQ ID NO 11
<211> LENGTH: 23
<212> TYPE: DNA
<213> ORGANISM: Artificial
<220> FEATURE:
<223> OTHER INFORMATION: Synthetic oligonucleotide PCR primer

<400> SEQUENCE: 11
gatttagagt tggatgtgtg gat                                           23

<210> SEQ ID NO 12
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 12
accaccatac taataatcaa atcta                                         25

<210> SEQ ID NO 13
<211> LENGTH: 29
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (29)..(29)
<223> OTHER INFORMATION: 3' quencher and/or blocker

<400> SEQUENCE: 13
aaatatcact catcaccaaa taaatccaa                                     29

<210> SEQ ID NO 14
<211> LENGTH: 20
<212> TYPE: DNA
<213> ORGANISM: Artificial
<220> FEATURE:
<223> OTHER INFORMATION: Synthetic oligonucleotide PCR primer

<400> SEQUENCE: 14
gtaagaagac ggtcgaggcg                                               20

<210> SEQ ID NO 15
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 15
acaactctac tcgccctcga a                                             21

<210> SEQ ID NO 16
<211> LENGTH: 25
<212> TYPE: DNA
```

-continued

```
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (25)..(25)
<223> OTHER INFORMATION: 3' quencher and/or blocker

<400> SEQUENCE: 16
aacgaaccac ttctcgtacc aacga                                         25

<210> SEQ ID NO 17
<211> LENGTH: 24
<212> TYPE: DNA
<213> ORGANISM: Artificial
<220> FEATURE:
<223> OTHER INFORMATION: Synthetic oligonucleotide PCR primer

<400> SEQUENCE: 17
tgtatgagtt tgtggtgaat aatg                                          24

<210> SEQ ID NO 18
<211> LENGTH: 23
<212> TYPE: DNA
<213> ORGANISM: Artificial
<220> FEATURE:
<223> OTHER INFORMATION: Synthetic oligonucleotide PCR primer

<400> SEQUENCE: 18
aactcaccat caaacacttt ccc                                           23

<210> SEQ ID NO 19
<211> LENGTH: 27
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (27)..(27)
<223> OTHER INFORMATION: 3' quencher and/or blocker

<400> SEQUENCE: 19
tacaaaccca acatcctcta tctattc                                       27

<210> SEQ ID NO 20
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 20
gcgcgttaat cgtaggcgtt t                                             21

<210> SEQ ID NO 21
<211> LENGTH: 22
<212> TYPE: DNA
<213> ORGANISM: Artificial
<220> FEATURE:
<223> OTHER INFORMATION: Synthetic oligonucleotide PCR primer
```

<400> SEQUENCE: 21
cccaatacga tacgacctta ac                                           22

<210> SEQ ID NO 22
<211> LENGTH: 28
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (28)..(28)
<223> OTHER INFORMATION: 3' quencher and/or blocker

<400> SEQUENCE: 22 cgtacctttaa ataacccgt aaaatcga                                     28

<210> SEQ ID NO 23
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 23
tttgttgatg ttttgtggaa gtaag                                        25

<210> SEQ ID NO 24
<211> LENGTH: 26
<212> TYPE: DNA
<213> ORGANISM: Artificial
<220> FEATURE:
<223> OTHER INFORMATION: Synthetic oligonucleotide PCR primer

<400> SEQUENCE: 24
attcatcaat actttcaaat aacaca                                       26

<210> SEQ ID NO 25
<211> LENGTH: 30
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Substituted cytosine coupled to fluor
<220> FEATURE:
<221> NAME/KEY: misc_feature
<222> LOCATION: (15)..(15)
<223> OTHER INFORMATION: Conjugated to quencher

<400> SEQUENCE: 25
caaatacatt atcctaccac taacaataca                                   30

<210> SEQ ID NO 26
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 26
cgggattttg ggttttcgtc g        21

<210> SEQ ID NO 27
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 27
cgacgaataa cgacgcaaaa ac       22

<210> SEQ ID NO 28
<211> LENGTH: 26
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (26)..(26)
<223> OTHER INFORMATION: 3' quencher and/or blocker

<400> SEQUENCE: 28
aaccgaacga taacgaaaac gacgaa   26

<210> SEQ ID NO 29
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 29
gttagttttg tagtgtattg agtat    25

<210> SEQ ID NO 30
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 30
catcttccac aataaacttc caatt    25

<210> SEQ ID NO 31
<211> LENGTH: 27
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (27)..(27)
<223> OTHER INFORMATION: 3' quencher and/or blocker

<400> SEQUENCE: 31
taactccacc tattctacct accattt   27

```
<210> SEQ ID NO 32
<211> LENGTH: 20
<212> TYPE: DNA
<213> ORGANISM: Artificial
<220> FEATURE:
<223> OTHER INFORMATION: Synthetic oligonucleotide PCR primer

<400> SEQUENCE: 32
cgtttagcgg gatgcggtga                                                  20

<210> SEQ ID NO 33
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 33
acacgaaaac cccgataacc g                                                21

<210> SEQ ID NO 34
<211> LENGTH: 23
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (23)..(23)
<223> OTHER INFORMATION: 3' quencher and/or blocker

<400> SEQUENCE: 34
aaacactcat cgcaaccgcc gcg                                              23

<210> SEQ ID NO 35
<211> LENGTH: 24
<212> TYPE: DNA
<213> ORGANISM: Artificial
<220> FEATURE:
<223> OTHER INFORMATION: Synthetic oligonucleotide PCR primer

<400> SEQUENCE: 35
ttagatgttg attggttgtg tttg                                             24

<210> SEQ ID NO 36
<211> LENGTH: 26
<212> TYPE: DNA
<213> ORGANISM: Artificial
<220> FEATURE:
<223> OTHER INFORMATION: Synthetic oligonucleotide PCR primer

<400> SEQUENCE: 36
atcatcataa aactcaacaa tcaatt                                           26

<210> SEQ ID NO 37
<211> LENGTH: 29
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
```

```
<221> NAME/KEY: misc_feature
<222> LOCATION: (29)..(29)
<223> OTHER INFORMATION: 3' quencher and/or blocker

<400> SEQUENCE: 37
ccaaacatca aatctttaac ttttaccaa                                    29

<210> SEQ ID NO 38
<211> LENGTH: 33
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (18)..(18)
<223> OTHER INFORMATION: Conjugated to quencher
<220> FEATURE:
<221> NAME/KEY: misc_feature
<222> LOCATION: (33)..(33)
<223> OTHER INFORMATION: 3' quencher and/or blocker

<400> SEQUENCE: 38
aggttgaaat tagtatgtgt tattttggta tgg                               33

<210> SEQ ID NO 39
<211> LENGTH: 33
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (21)..(21)
<223> OTHER INFORMATION: Conjugated to quencher
<220> FEATURE:
<221> NAME/KEY: misc_feature
<222> LOCATION: (33)..(33)
<223> OTHER INFORMATION: 3' quencher and/or blocker

<400> SEQUENCE: 39
aggttgaaat tagtatgtgt tattttggta tgg                               33

<210> SEQ ID NO 40
<211> LENGTH: 33
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (23)..(23)
<223> OTHER INFORMATION: Conjugated to quencher
<220> FEATURE:
<221> NAME/KEY: misc_feature
<222> LOCATION: (33)..(33)
<223> OTHER INFORMATION: 3' quencher and/or blocker

<400> SEQUENCE: 40
aggttgaaat tagtatgtgt tattttggta tgg                               33
```

```
<210> SEQ ID NO 41
<211> LENGTH: 23
<212> TYPE: DNA
<213> ORGANISM: Artificial
<220> FEATURE:
<223> OTHER INFORMATION: Synthetic oligonucleotide PCR primer

<400> SEQUENCE: 41
gttttatagt ttttgtattt agg                                          23

<210> SEQ ID NO 42
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 42
aactcaataa actcaaactc cc                                           22

<210> SEQ ID NO 43
<211> LENGTH: 23
<212> TYPE: DNA
<213> ORGANISM: Artificial
<220> FEATURE:
<223> OTHER INFORMATION: Synthetic oligonucleotide PCR primer

<400> SEQUENCE: 43
gtgtgtgttt ttattgtaaa tgg                                          23

<210> SEQ ID NO 44
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 44
ataaaatttc ttcacrccac c                                            21

<210> SEQ ID NO 45
<211> LENGTH: 20
<212> TYPE: DNA
<213> ORGANISM: Artificial
<220> FEATURE:
<223> OTHER INFORMATION: Synthetic oligonucleotide PCR primer

<400> SEQUENCE: 45
gagggagtta gttgggttat                                              20

<210> SEQ ID NO 46
<211> LENGTH: 20
<212> TYPE: DNA
<213> ORGANISM: Artificial
<220> FEATURE:
<223> OTHER INFORMATION: Synthetic oligonucleotide PCR primer

<400> SEQUENCE: 46
cctccaaaaa atacataccc                                              20

<210> SEQ ID NO 47
<211> LENGTH: 24
<212> TYPE: DNA
<213> ORGANISM: Artificial
<220> FEATURE:
```

<223> OTHER INFORMATION: Synthetic oligonucleotide PCR primer

<400> SEQUENCE: 47
gtgtaattaa ttagaaggtt tttt                                              24

<210> SEQ ID NO 48
<211> LENGTH: 20
<212> TYPE: DNA
<213> ORGANISM: Artificial
<220> FEATURE:
<223> OTHER INFORMATION: Synthetic oligonucleotide PCR primer

<400> SEQUENCE: 48
aacacctacc ttccaaatac                                                   20

<210> SEQ ID NO 49
<211> LENGTH: 20
<212> TYPE: DNA
<213> ORGANISM: Artificial
<220> FEATURE:
<223> OTHER INFORMATION: Synthetic oligonucleotide PCR primer

<400> SEQUENCE: 49
ttagaggyga gagagtagtt                                                   20

<210> SEQ ID NO 50
<211> LENGTH: 20
<212> TYPE: DNA
<213> ORGANISM: Artificial
<220> FEATURE:
<223> OTHER INFORMATION: Synthetic oligonucleotide PCR primer

<400> SEQUENCE: 50
aaactactac taaccrcctc                                                   20

<210> SEQ ID NO 51
<211> LENGTH: 20
<212> TYPE: DNA
<213> ORGANISM: Artificial
<220> FEATURE:
<223> OTHER INFORMATION: Synthetic oligonucleotide PCR primer

<400> SEQUENCE: 51
aggagataty gttgagggga                                                   20

<210> SEQ ID NO 52
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 52
tcactcatac taaaccrcca a                                                 21

<210> SEQ ID NO 53
<211> LENGTH: 28
<212> TYPE: DNA
<213> ORGANISM: Artificial
<220> FEATURE:
<223> OTHER INFORMATION: Synthetic oligonucleotide PCR primer

<400> SEQUENCE: 53
ttagggtaga ttgtggatat tagatagg                                          28

```
<210> SEQ ID NO 54
<211> LENGTH: 28
<212> TYPE: DNA
<213> ORGANISM: Artificial
<220> FEATURE:
<223> OTHER INFORMATION: Synthetic oligonucleotide PCR primer

<400> SEQUENCE: 54
taatactaac aactatccaa tacaacac                                28

<210> SEQ ID NO 55
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 55
ccgataaccg aaacgctctt ac                                     22

<210> SEQ ID NO 56
<211> LENGTH: 19
<212> TYPE: DNA
<213> ORGANISM: Artificial
<220> FEATURE:
<223> OTHER INFORMATION: Synthetic oligonucleotide PCR primer

<400> SEQUENCE: 56
gcgttaatcg taggcgttt                                         19

<210> SEQ ID NO 57
<211> LENGTH: 18
<212> TYPE: DNA
<213> ORGANISM: Artificial
<220> FEATURE:
<223> OTHER INFORMATION: Synthetic oligonucleotide PCR primer

<400> SEQUENCE: 57
gtttagcggg atgcggtg                                          18

<210> SEQ ID NO 58
<211> LENGTH: 19
<212> TYPE: DNA
<213> ORGANISM: Artificial
<220> FEATURE:
<223> OTHER INFORMATION: Synthetic oligonucleotide PCR primer

<400> SEQUENCE: 58
acacgaaaac cccgataac                                         19

<210> SEQ ID NO 59
<211> LENGTH: 24
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (12)..(12)
<223> OTHER INFORMATION: Substituted thymine

<400> SEQUENCE: 59
gygtaattaa ttagaaggtt tttt                                   24

<210> SEQ ID NO 60
<211> LENGTH: 25
<212> TYPE: DNA
```

<213> ORGANISM: Artificial
<220> FEATURE:
<223> OTHER INFORMATION: Synthetic oligonucleotide PCR primer

<400> SEQUENCE: 60
tcgtacgaag taaatagttc gtaag                                   25

<210> SEQ ID NO 61
<211> LENGTH: 30
<212> TYPE: DNA
<213> ORGANISM: Artificial
<220> FEATURE:
<223> OTHER INFORMATION: Synthetic oligonucleotide PCR primer

<400> SEQUENCE: 61
ggatttttga aatattatag gattaattag                              30

<210> SEQ ID NO 62
<211> LENGTH: 23
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (12)..(12)
<223> OTHER INFORMATION: Substituted thymine

<400> SEQUENCE: 62
gttttatagt ttttgtattt agg                                     23

<210> SEQ ID NO 63
<211> LENGTH: 25
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (11)..(11)
<223> OTHER INFORMATION: a, c, g, or t conjugated to a quencher
<220> FEATURE:
<221> NAME/KEY: misc_feature
<222> LOCATION: (18)..(18)
<223> OTHER INFORMATION: Substituted cytosine
<220> FEATURE:
<221> NAME/KEY: misc_feature
<222> LOCATION: (25)..(25)
<223> OTHER INFORMATION: 3' quencher and/or blocker

<400> SEQUENCE: 63
acaaacgcga naccgaacga aacca                                   25

<210> SEQ ID NO 64
<211> LENGTH: 20
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor and Substituted cytosine
<220> FEATURE:
<221> NAME/KEY: misc_feature
<222> LOCATION: (11)..(11)
<223> OTHER INFORMATION: Conugated to a quencher

```
<220> FEATURE:
<221> NAME/KEY: misc_feature
<222> LOCATION: (16)..(16)
<223> OTHER INFORMATION: Substituted thymine
<220> FEATURE:
<221> NAME/KEY: misc_feature
<222> LOCATION: (20)..(20)
<223> OTHER INFORMATION: 3' quencher and/or blocker

<400> SEQUENCE: 64
ctggtttcgt tcggttcgcg                                                        20

<210> SEQ ID NO 65
<211> LENGTH: 34
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor and Substituted cytosine
<220> FEATURE:
<221> NAME/KEY: misc_feature
<222> LOCATION: (25)..(25)
<223> OTHER INFORMATION: Conjugated to a quencher
<220> FEATURE:
<221> NAME/KEY: misc_feature
<222> LOCATION: (30)..(30)
<223> OTHER INFORMATION: Conjugated to a quencher
<220> FEATURE:
<221> NAME/KEY: misc_feature
<222> LOCATION: (34)..(34)
<223> OTHER INFORMATION: 3' quencher and/or blocker

<400> SEQUENCE: 65
caggttgaaa ttagtatgtg ttattttggt atgg                                        34

<210> SEQ ID NO 66
<211> LENGTH: 28
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (22)..(22)
<223> OTHER INFORMATION: Substituted thymine
<220> FEATURE:
<221> NAME/KEY: misc_feature
<222> LOCATION: (28)..(28)
<223> OTHER INFORMATION: 3' quencher and/or blocker

<400> SEQUENCE: 66
caaactactt acgcgaaact ttaccgcc                                               28

<210> SEQ ID NO 67
<211> LENGTH: 30
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (13)..(13)
```

```
<223> OTHER INFORMATION: Substituted thymine
<220> FEATURE:
<221> NAME/KEY: misc_feature
<222> LOCATION: (21)..(21)
<223> OTHER INFORMATION: a, c, g, or t conjugated to a quencher
<220> FEATURE:
<221> NAME/KEY: misc_feature
<222> LOCATION: (26)..(26)
<223> OTHER INFORMATION: Substituted thymine
<220> FEATURE:
<221> NAME/KEY: misc_feature
<222> LOCATION: (30)..(30)
<223> OTHER INFORMATION: 3' quencher and/or blocker

<400> SEQUENCE: 67
aaatatcact catcaccaaa ntaaatccaa                                       30

<210> SEQ ID NO 68
<211> LENGTH: 27
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (27)..(27)
<223> OTHER INFORMATION: 3' quencher and/or blocker
<220> FEATURE:
<221> NAME/KEY: misc_feature
<222> LOCATION: (28)..(28)
<223> OTHER INFORMATION: Substituted thymine

<400> SEQUENCE: 68
aaacgaacca cttctcgtac caacgac                                         27

<210> SEQ ID NO 69
<211> LENGTH: 25
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (17)..(17)
<223> OTHER INFORMATION: Substituted thymine
<220> FEATURE:
<221> NAME/KEY: misc_feature
<222> LOCATION: (21)..(21)
<223> OTHER INFORMATION: Substituted thymine
<220> FEATURE:
<221> NAME/KEY: misc_feature
<222> LOCATION: (25)..(25)
<223> OTHER INFORMATION: 3' quencher and/or blocker

<400> SEQUENCE: 69
caaacccaac atcctctatc tattc                                           25

<210> SEQ ID NO 70
<211> LENGTH: 31
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
```

```
<222> LOCATION: (1)..(1)
<223> OTHER INFORMATION: Conjugated to a fluor
<220> FEATURE:
<221> NAME/KEY: misc_feature
<222> LOCATION: (2)..(2)
<223> OTHER INFORMATION: Substituted cytosine
<220> FEATURE:
<221> NAME/KEY: misc_feature
<222> LOCATION: (13)..(13)
<223> OTHER INFORMATION: a, c, g, or t conjugated to a quencher
<220> FEATURE:
<221> NAME/KEY: misc_feature
<222> LOCATION: (17)..(17)
<223> OTHER INFORMATION: Substituted thymine
<220> FEATURE:
<221> NAME/KEY: misc_feature
<222> LOCATION: (24)..(24)
<223> OTHER INFORMATION: Substituted thymine
<220> FEATURE:
<221> NAME/KEY: misc_feature
<222> LOCATION: (31)..(31)
<223> OTHER INFORMATION: 3' quencher and/or blocker

<400> SEQUENCE: 70
acgcgtacct ttnaaataac ccgtaaaatc g                               31

<210> SEQ ID NO 71
<211> LENGTH: 30
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Substituted cytosine coupled to fluor
<220> FEATURE:
<221> NAME/KEY: misc_feature
<222> LOCATION: (12)..(12)
<223> OTHER INFORMATION: Conjugated to a quencher
<220> FEATURE:
<221> NAME/KEY: misc_feature
<222> LOCATION: (16)..(16)
<223> OTHER INFORMATION: Substituted thymine
<220> FEATURE:
<221> NAME/KEY: misc_feature
<222> LOCATION: (23)..(23)
<223> OTHER INFORMATION: Substituted thymine
<220> FEATURE:
<221> NAME/KEY: misc_feature
<222> LOCATION: (30)..(30)
<223> OTHER INFORMATION: 3' quencher and/or blocker

<400> SEQUENCE: 71
acgcgtacct ttaaataacc cgtaaaatcg                                 30

<210> SEQ ID NO 72
<211> LENGTH: 30
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Substituted cytosine coupled to fluor
<220> FEATURE:
<221> NAME/KEY: misc_feature
<222> LOCATION: (21)..(21)
<223> OTHER INFORMATION: Substituted thymine
<220> FEATURE:
<221> NAME/KEY: misc_feature
<222> LOCATION: (27)..(27)
<223> OTHER INFORMATION: Substituted thymine
<220> FEATURE:
```

```
<221> NAME/KEY: misc_feature
<222> LOCATION: (30)..(30)
<223> OTHER INFORMATION: 3' quencher and/or blocker

<400> SEQUENCE: 72
caaatacatt atcctaccac taacaataca                                          30

<210> SEQ ID NO 73
<211> LENGTH: 25
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (20)..(20)
<223> OTHER INFORMATION: Substituted cytosine
<220> FEATURE:
<221> NAME/KEY: misc_feature
<222> LOCATION: (25)..(25)
<223> OTHER INFORMATION: 3' quencher and/or blocker

<400> SEQUENCE: 73
aaccgaacga taacgaaaac gacga                                               25

<210> SEQ ID NO 74
<211> LENGTH: 28
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (16)..(16)
<223> OTHER INFORMATION: a, c, g, or t conjugated to a quencher
<220> FEATURE:
<221> NAME/KEY: misc_feature
<222> LOCATION: (21)..(21)
<223> OTHER INFORMATION: a, c, g, or t conjugated to a quencher
<220> FEATURE:
<221> NAME/KEY: misc_feature
<222> LOCATION: (25)..(25)
<223> OTHER INFORMATION: a, c, g, or t conjugated to a quencher
<220> FEATURE:
<221> NAME/KEY: misc_feature
<222> LOCATION: (28)..(28)
<223> OTHER INFORMATION: 3' quencher and/or blocker

<400> SEQUENCE: 74
taactccacc tattctacct naccattt                                            28

<210> SEQ ID NO 75
<211> LENGTH: 25
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (15)..(15)
<223> OTHER INFORMATION: a, c, g, or t conjugated to a quencher
```

```
<220> FEATURE:
<221> NAME/KEY: misc_feature
<222> LOCATION: (20)..(20)
<223> OTHER INFORMATION: a, c, g, or t conjugated to a quencher
<220> FEATURE:
<221> NAME/KEY: misc_feature
<222> LOCATION: (23)..(23)
<223> OTHER INFORMATION: a, c, g, or t conjugated to a quencher
<220> FEATURE:
<221> NAME/KEY: misc_feature
<222> LOCATION: (25)..(25)
<223> OTHER INFORMATION: 3' quencher and/or blocker

<400> SEQUENCE: 75
caaacatcaa atctttaact tttac                                            25

<210> SEQ ID NO 76
<211> LENGTH: 31
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Substituted cytosine coupled to fluor
<220> FEATURE:
<221> NAME/KEY: misc_feature
<222> LOCATION: (3)..(3)
<223> OTHER INFORMATION: Substituted cytosine
<220> FEATURE:
<221> NAME/KEY: misc_feature
<222> LOCATION: (12)..(12)
<223> OTHER INFORMATION: a, c, g, or t conjugated to a quencher
<220> FEATURE:
<221> NAME/KEY: misc_feature
<222> LOCATION: (17)..(17)
<223> OTHER INFORMATION: Substituted thymine
<220> FEATURE:
<221> NAME/KEY: misc_feature
<222> LOCATION: (29)..(29)
<223> OTHER INFORMATION: Substituted thymine
<220> FEATURE:
<221> NAME/KEY: misc_feature
<222> LOCATION: (31)..(31)
<223> OTHER INFORMATION: 3' quencher and/or blocker

<400> SEQUENCE: 76
cacgcgtacc tttaaataac ccgtaaaatc g                                     31

<210> SEQ ID NO 77
<211> LENGTH: 27
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (11)..(11)
<223> OTHER INFORMATION: Substituted thymine
<220> FEATURE:
<221> NAME/KEY: misc_feature
<222> LOCATION: (19)..(19)
<223> OTHER INFORMATION: a, c, g, or t conjugated to a quencher
<220> FEATURE:
<221> NAME/KEY: misc_feature
<222> LOCATION: (27)..(27)
<223> OTHER INFORMATION: 3' quencher and/or blocker

<400> SEQUENCE: 77
```
aaccgaacga taacgaaana cgacgaa                                        27

<210> SEQ ID NO 78
<211> LENGTH: 23
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (23)..(23)
<223> OTHER INFORMATION: 3' quencher and/or blocker

<400> SEQUENCE: 78
aaacactcat cgcaaccgcc gcg                                            23

<210> SEQ ID NO 79
<211> LENGTH: 25
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (19)..(19)
<223> OTHER INFORMATION: Substituted cytosine
<220> FEATURE:
<221> NAME/KEY: misc_feature
<222> LOCATION: (25)..(25)
<223> OTHER INFORMATION: 3' quencher and/or blocker

<400> SEQUENCE: 79
taaccaccac ccaacacaca ataac                                          25

<210> SEQ ID NO 80
<211> LENGTH: 24
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (10)..(10)
<223> OTHER INFORMATION: Substituted thymine
<220> FEATURE:
<221> NAME/KEY: misc_feature
<222> LOCATION: (19)..(19)
<223> OTHER INFORMATION: Substituted thymine
<220> FEATURE:
<221> NAME/KEY: misc_feature
<222> LOCATION: (24)..(24)
<223> OTHER INFORMATION: 3' quencher and/or blocker

<400> SEQUENCE: 80
cccaactact taaaaaacta aaac                                           24

<210> SEQ ID NO 81
<211> LENGTH: 25
<212> TYPE: DNA
<213> ORGANISM: Artificial

```
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (10)..(10)
<223> OTHER INFORMATION: Substituted thymine
<220> FEATURE:
<221> NAME/KEY: misc_feature
<222> LOCATION: (19)..(19)
<223> OTHER INFORMATION: Substituted thymine
<220> FEATURE:
<221> NAME/KEY: misc_feature
<222> LOCATION: (25)..(25)
<223> OTHER INFORMATION: 3' quencher and/or blocker

<400> SEQUENCE: 81
cacctaaaat caaaaattta aaacc                                         25

<210> SEQ ID NO 82
<211> LENGTH: 25
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (11)..(11)
<223> OTHER INFORMATION: Substituted thymine
<220> FEATURE:
<221> NAME/KEY: misc_feature
<222> LOCATION: (24)..(24)
<223> OTHER INFORMATION: Substituted thymine
<220> FEATURE:
<221> NAME/KEY: misc_feature
<222> LOCATION: (25)..(25)
<223> OTHER INFORMATION: 3' quencher and/or blocker

<400> SEQUENCE: 82
caaataattc tcctacctca acctc                                         25

<210> SEQ ID NO 83
<211> LENGTH: 23
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (11)..(11)
<223> OTHER INFORMATION: Substituted thymine
<220> FEATURE:
<221> NAME/KEY: misc_feature
<222> LOCATION: (20)..(20)
<223> OTHER INFORMATION: Substituted thymine
<220> FEATURE:
<221> NAME/KEY: misc_feature
<222> LOCATION: (23)..(23)
<223> OTHER INFORMATION: 3' quencher and/or blocker

<400> SEQUENCE: 83
cttaactcac tacaacctct acc                                           23
```

-continued

<210> SEQ ID NO 84
<211> LENGTH: 25
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (25)..(25)
<223> OTHER INFORMATION: 3' quencher and/or blocker

<400> SEQUENCE: 84
caaaccgaac gacgcgcaca aacac                                          25

<210> SEQ ID NO 85
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 85
gtatataggt tggggaagtt tg                                             22

<210> SEQ ID NO 86
<211> LENGTH: 23
<212> TYPE: DNA
<213> ORGANISM: Artificial
<220> FEATURE:
<223> OTHER INFORMATION: Synthetic oligonucleotide PCR primer

<400> SEQUENCE: 86
aactatactc aaccaataaa acc                                            23

<210> SEQ ID NO 87
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 87
tgttatttag gttggagtgt ag                                             22

<210> SEQ ID NO 88
<211> LENGTH: 23
<212> TYPE: DNA
<213> ORGANISM: Artificial
<220> FEATURE:
<223> OTHER INFORMATION: Synthetic oligonucleotide PCR primer

<400> SEQUENCE: 88
taataactca tacctataat ccc                                            23

<210> SEQ ID NO 89
<211> LENGTH: 27
<212> TYPE: DNA
<213> ORGANISM: Artificial
<220> FEATURE:
<223> OTHER INFORMATION: Synthetic oligonucleotide PCR primer

<400> SEQUENCE: 89
ggttggagtg tagtggtata attttag                                        27

<210> SEQ ID NO 90
<211> LENGTH: 28
<212> TYPE: DNA
<213> ORGANISM: Artificial
<220> FEATURE:
<223> OTHER INFORMATION: Synthetic oligonucleotide PCR primer

<400> SEQUENCE: 90
taataactca tacctataat cccaacac                              28

<210> SEQ ID NO 91
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 91
gtagagatag ggttttatta tgttg                                 25

<210> SEQ ID NO 92
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 92
ggttttatta tgttggttag gttgg                                 25

<210> SEQ ID NO 93
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 93
gtattttggg aggttaaggt ag                                    22

<210> SEQ ID NO 94
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 94
atcttactct tattacccaa ac                                    22

<210> SEQ ID NO 95
<211> LENGTH: 26
<212> TYPE: DNA
<213> ORGANISM: Artificial
<220> FEATURE:
<223> OTHER INFORMATION: Synthetic oligonucleotide PCR primer

<400> SEQUENCE: 95
ggttaaggta ggtagattat ttgagg                                26

<210> SEQ ID NO 96
<211> LENGTH: 30
<212> TYPE: DNA
<213> ORGANISM: Artificial
<220> FEATURE:

<223> OTHER INFORMATION: Synthetic oligonucleotide PCR primer

<400> SEQUENCE: 96
atcttactct tattacccaa actaaaatac                              30

<210> SEQ ID NO 97
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 97
gttatttagg aggttgaggt ag                                      22

<210> SEQ ID NO 98
<211> LENGTH: 27
<212> TYPE: DNA
<213> ORGANISM: Artificial
<220> FEATURE:
<223> OTHER INFORMATION: Synthetic oligonucleotide PCR primer

<400> SEQUENCE: 98
gaggtaggag aattatttga atttagg                                 27

<210> SEQ ID NO 99
<211> LENGTH: 20
<212> TYPE: DNA
<213> ORGANISM: Artificial
<220> FEATURE:
<223> OTHER INFORMATION: Synthetic oligonucleotide PCR primer

<400> SEQUENCE: 99
atttgagatt tttgagttgg                                         20

<210> SEQ ID NO 100
<211> LENGTH: 20
<212> TYPE: DNA
<213> ORGANISM: Artificial
<220> FEATURE:
<223> OTHER INFORMATION: Synthetic oligonucleotide PCR primer

<400> SEQUENCE: 100
aaccctactc cctatctacg                                         20

<210> SEQ ID NO 101
<211> LENGTH: 20
<212> TYPE: DNA
<213> ORGANISM: Artificial
<220> FEATURE:
<223> OTHER INFORMATION: Synthetic oligonucleotide PCR primer

<400> SEQUENCE: 101
gcgcgcgttt tttttgaag                                          20

<210> SEQ ID NO 102
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 102
ggcgtagata gggagtaggg tt                                      22

```
<210> SEQ ID NO 103
<211> LENGTH: 24
<212> TYPE: DNA
<213> ORGANISM: Artificial
<220> FEATURE:
<223> OTHER INFORMATION: Synthetic oligonucleotide PCR primer

<400> SEQUENCE: 103
gtgatggagg aggtttagta agtt                                              24

<210> SEQ ID NO 104
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 104
ccaataaaac ctactcctcc cttaa                                             25

<210> SEQ ID NO 105
<211> LENGTH: 32
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor cytosine Substituted
<220> FEATURE:
<221> NAME/KEY: misc_feature
<222> LOCATION: (2)..(2)
<223> OTHER INFORMATION: Substituted cytosine
<220> FEATURE:
<221> NAME/KEY: misc_feature
<222> LOCATION: (12)..(12)
<223> OTHER INFORMATION: a, c, g, or t conjugated to a quencher
<220> FEATURE:
<221> NAME/KEY: misc_feature
<222> LOCATION: (19)..(19)
<223> OTHER INFORMATION: Substituted thymine
<220> FEATURE:
<221> NAME/KEY: misc_feature
<222> LOCATION: (25)..(25)
<223> OTHER INFORMATION: Substituted thymine
<220> FEATURE:
<221> NAME/KEY: misc_feature
<222> LOCATION: (32)..(32)
<223> OTHER INFORMATION: 3' quencher and/or blocker

<400> SEQUENCE: 105
ccataccaaa ataacacatc taatttcaac ct                                     32

<210> SEQ ID NO 106
<211> LENGTH: 30
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor cytosine Substituted
<220> FEATURE:
<221> NAME/KEY: misc_feature
<222> LOCATION: (10)..(10)
<223> OTHER INFORMATION: Substituted thymine
<220> FEATURE:
<221> NAME/KEY: misc_feature
<222> LOCATION: (15)..(15)
<223> OTHER INFORMATION: a, c, g, or t conjugated to a quencher
<220> FEATURE:
```

```
<221> NAME/KEY: misc_feature
<222> LOCATION: (21)..(21)
<223> OTHER INFORMATION: Substituted thymine
<220> FEATURE:
<221> NAME/KEY: misc_feature
<222> LOCATION: (27)..(27)
<223> OTHER INFORMATION: Substituted thymine
<220> FEATURE:
<221> NAME/KEY: misc_feature
<222> LOCATION: (30)..(30)
<223> OTHER INFORMATION: 3' quencher and/or blocker

<400> SEQUENCE: 106
caaatacatt atcctaccac taacaataca                                30

<210> SEQ ID NO 107
<211> LENGTH: 31
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor cytosine Substituted
<220> FEATURE:
<221> NAME/KEY: misc_feature
<222> LOCATION: (13)..(13)
<223> OTHER INFORMATION: Optiionally conjugated to a quencher
<220> FEATURE:
<221> NAME/KEY: misc_feature
<222> LOCATION: (17)..(17)
<223> OTHER INFORMATION: Substituted thymine
<220> FEATURE:
<221> NAME/KEY: misc_feature
<222> LOCATION: (24)..(24)
<223> OTHER INFORMATION: Substituted thymine
<220> FEATURE:
<221> NAME/KEY: misc_feature
<222> LOCATION: (31)..(31)
<223> OTHER INFORMATION: 3' quencher and/or blocker

<400> SEQUENCE: 107
cacgcgtacc tttaaataac ccgtaaaatc g                              31

<210> SEQ ID NO 108
<211> LENGTH: 31
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor cytosine Substituted
<220> FEATURE:
<221> NAME/KEY: misc_feature
<222> LOCATION: (13)..(13)
<223> OTHER INFORMATION: Substituted thymine
<220> FEATURE:
<221> NAME/KEY: misc_feature
<222> LOCATION: (17)..(17)
<223> OTHER INFORMATION: a, c, g, or t conjugated to a quencher
<220> FEATURE:
<221> NAME/KEY: misc_feature
<222> LOCATION: (24)..(24)
<223> OTHER INFORMATION: Substituted thymine
<220> FEATURE:
<221> NAME/KEY: misc_feature
<222> LOCATION: (31)..(31)
<223> OTHER INFORMATION: 3' quencher and/or blocker

<400> SEQUENCE: 108
cacgcgtacc tttaaataac ccgtaaaatc g                              31
```

```
<210> SEQ ID NO 109
<211> LENGTH: 27
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (11)..(11)
<223> OTHER INFORMATION: a, c, g, or t conjugated to a quencher
<220> FEATURE:
<221> NAME/KEY: misc_feature
<222> LOCATION: (15)..(15)
<223> OTHER INFORMATION: Substituted cytosine
<220> FEATURE:
<221> NAME/KEY: misc_feature
<222> LOCATION: (20)..(20)
<223> OTHER INFORMATION: Substituted cytosine
<220> FEATURE:
<221> NAME/KEY: misc_feature
<222> LOCATION: (27)..(27)
<223> OTHER INFORMATION: 3' quencher and/or blocker

<400> SEQUENCE: 109
ctaacaaaca caaaccaaac aaaacca                                       27

<210> SEQ ID NO 110
<211> LENGTH: 27
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (11)..(11)
<223> OTHER INFORMATION: Substituted cytosine
<220> FEATURE:
<221> NAME/KEY: misc_feature
<222> LOCATION: (15)..(15)
<223> OTHER INFORMATION: a, c, g, or t conjugated to a quencher
<220> FEATURE:
<221> NAME/KEY: misc_feature
<222> LOCATION: (20)..(20)
<223> OTHER INFORMATION: Substituted cytosine
<220> FEATURE:
<221> NAME/KEY: misc_feature
<222> LOCATION: (27)..(27)
<223> OTHER INFORMATION: 3' quencher and/or blocker

<400> SEQUENCE: 110
ctaacaaaca caaaccaaac aaaacca                                       27

<210> SEQ ID NO 111
<211> LENGTH: 29
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (12)..(12)
```

```
<223> OTHER INFORMATION: Substituted cytosine
<220> FEATURE:
<221> NAME/KEY: misc_feature
<222> LOCATION: (20)..(20)
<223> OTHER INFORMATION: a, c, g, or t conjugated to a quencher
<220> FEATURE:
<221> NAME/KEY: misc_feature
<222> LOCATION: (24)..(24)
<223> OTHER INFORMATION: Substituted cytosine
<220> FEATURE:
<221> NAME/KEY: misc_feature
<222> LOCATION: (29)..(29)
<223> OTHER INFORMATION: 3' quencher and/or blocker

<400> SEQUENCE: 111
aactacttac acaaaacttn taccaccaa                                          29

<210> SEQ ID NO 112
<211> LENGTH: 25
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (10)..(10)
<223> OTHER INFORMATION: Substituted cytosine
<220> FEATURE:
<221> NAME/KEY: misc_feature
<222> LOCATION: (17)..(17)
<223> OTHER INFORMATION: Substituted cytosine
<220> FEATURE:
<221> NAME/KEY: misc_feature
<222> LOCATION: (25)..(25)
<223> OTHER INFORMATION: 3' quencher and/or blocker

<400> SEQUENCE: 112
aactacttac acaaaacttt accac                                              25

<210> SEQ ID NO 113
<211> LENGTH: 27
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (12)..(12)
<223> OTHER INFORMATION: Substituted thymine
<220> FEATURE:
<221> NAME/KEY: misc_feature
<222> LOCATION: (18)..(18)
<223> OTHER INFORMATION: Substituted thymine
<220> FEATURE:
<221> NAME/KEY: misc_feature
<222> LOCATION: (27)..(27)
<223> OTHER INFORMATION: 3' quencher and/or blocker

<400> SEQUENCE: 113
aaacaaacca cttctcatac caacaac                                            27

<210> SEQ ID NO 114
<211> LENGTH: 31
<212> TYPE: DNA
<213> ORGANISM: Artificial
```

```
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor cytosine Substituted
<220> FEATURE:
<221> NAME/KEY: misc_feature
<222> LOCATION: (15)..(15)
<223> OTHER INFORMATION: a, c, g, or t conjugated to a quencher
<220> FEATURE:
<221> NAME/KEY: misc_feature
<222> LOCATION: (22)..(22)
<223> OTHER INFORMATION: Substituted thymine
<220> FEATURE:
<221> NAME/KEY: misc_feature
<222> LOCATION: (27)..(27)
<223> OTHER INFORMATION: Substituted thymine
<220> FEATURE:
<221> NAME/KEY: misc_feature
<222> LOCATION: (31)..(31)
<223> OTHER INFORMATION: 3' quencher and/or blocker

<400> SEQUENCE: 114
cacatacctt taaataaccc ataaaatcaa c                                 31

<210> SEQ ID NO 115
<211> LENGTH: 31
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor cytosine Substituted
<220> FEATURE:
<221> NAME/KEY: misc_feature
<222> LOCATION: (11)..(11)
<223> OTHER INFORMATION: a, c, g, or t conjugated to a quencher
<220> FEATURE:
<221> NAME/KEY: misc_feature
<222> LOCATION: (15)..(15)
<223> OTHER INFORMATION: Substituted thymine
<220> FEATURE:
<221> NAME/KEY: misc_feature
<222> LOCATION: (22)..(22)
<223> OTHER INFORMATION: Substituted thymine
<220> FEATURE:
<221> NAME/KEY: misc_feature
<222> LOCATION: (31)..(31)
<223> OTHER INFORMATION: 3' quencher and/or blocker

<400> SEQUENCE: 115
cacatacctt taaataaccc ataaaatcaa c                                 31

<210> SEQ ID NO 116
<211> LENGTH: 32
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (17)..(17)
<223> OTHER INFORMATION: Substituted thymine
<220> FEATURE:
<221> NAME/KEY: misc_feature
<222> LOCATION: (24)..(24)
<223> OTHER INFORMATION: a, c, g, or t conjugated to a quencher
<220> FEATURE:
```

```
<221> NAME/KEY: misc_feature
<222> LOCATION: (32)..(32)
<223> OTHER INFORMATION: 3' quencher and/or blocker

<400> SEQUENCE: 116
caacaaaaac ccaaaatccc aacnaaacca ca                                    32

<210> SEQ ID NO 117
<211> LENGTH: 25
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (12)..(12)
<223> OTHER INFORMATION: Substituted cytosine
<220> FEATURE:
<221> NAME/KEY: misc_feature
<222> LOCATION: (19)..(19)
<223> OTHER INFORMATION: Substituted cytosine
<220> FEATURE:
<221> NAME/KEY: misc_feature
<222> LOCATION: (25)..(25)
<223> OTHER INFORMATION: 3' quencher and/or blocker

<400> SEQUENCE: 117
caaaatccca acaaaccaca taaca                                            25

<210> SEQ ID NO 118
<211> LENGTH: 25
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (19)..(19)
<223> OTHER INFORMATION: Substituted cytosine
<220> FEATURE:
<221> NAME/KEY: misc_feature
<222> LOCATION: (25)..(25)
<223> OTHER INFORMATION: 3' quencher and/or blocker

<400> SEQUENCE: 118
aaacactcat cacaaccacc acacc                                            25

<210> SEQ ID NO 119
<211> LENGTH: 24
<212> TYPE: DNA
<213> ORGANISM: Artificial
<220> FEATURE:
<223> OTHER INFORMATION: Synthetic oligonucleotide PCR primer

<400> SEQUENCE: 119
tggtgtgtta attgtaggtg tttt                                             24

<210> SEQ ID NO 120
<211> LENGTH: 23
<212> TYPE: DNA
<213> ORGANISM: Artificial
<220> FEATURE:
<223> OTHER INFORMATION: Synthetic oligonucleotide PCR primer
```

<400> SEQUENCE: 120
cccaatacaa tacaacctta acc						23

<210> SEQ ID NO 121
<211> LENGTH: 23
<212> TYPE: DNA
<213> ORGANISM: Artificial
<220> FEATURE:
<223> OTHER INFORMATION: Synthetic oligonucleotide PCR primer

<400> SEQUENCE: 121
gtggtgtgta ttgtgtagtg tta						23

<210> SEQ ID NO 122
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 122
caaaccaaac aataacaaaa acaac						25

<210> SEQ ID NO 123
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 123
tgtttagtgg gatgtggtga ag						22

<210> SEQ ID NO 124
<211> LENGTH: 23
<212> TYPE: DNA
<213> ORGANISM: Artificial
<220> FEATURE:
<223> OTHER INFORMATION: Synthetic oligonucleotide PCR primer

<400> SEQUENCE: 124
acacaaaaac cccaataacc aca						23

<210> SEQ ID NO 125
<211> LENGTH: 26
<212> TYPE: DNA
<213> ORGANISM: Artificial
<220> FEATURE:
<223> OTHER INFORMATION: Synthetic oligonucleotide PCR primer

<400> SEQUENCE: 125
gtttaaagtt agtgaagtat gggttt						26

<210> SEQ ID NO 126
<211> LENGTH: 32
<212> TYPE: DNA
<213> ORGANISM: Artificial
<220> FEATURE:
<223> OTHER INFORMATION: Synthetic oligonucleotide PCR primer

<400> SEQUENCE: 126
tgtatgaagt aaatagtttg taagtttatt gg						32

<210> SEQ ID NO 127

```
<211> LENGTH: 25
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (22)..(22)
<223> OTHER INFORMATION: Substituted thymine

<400> SEQUENCE: 127
tttgttgatg ttttgtggaa gtaag                                              25

<210> SEQ ID NO 128
<211> LENGTH: 26
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (20)..(20)
<223> OTHER INFORMATION: Substituted thymine

<400> SEQUENCE: 128
attcatcaat actttcaaat aacaca                                             26

<210> SEQ ID NO 129
<211> LENGTH: 27
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (18)..(18)
<223> OTHER INFORMATION: Substituted thymine
<220> FEATURE:
<221> NAME/KEY: misc_feature
<222> LOCATION: (27)..(27)
<223> OTHER INFORMATION: 3' quencher and/or blocker

<400> SEQUENCE: 129
aaacgaacca cttctcgtac caacgac                                            27

<210> SEQ ID NO 130
<211> LENGTH: 25
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (17)..(17)
<223> OTHER INFORMATION: Substituted thymine
<220> FEATURE:
<221> NAME/KEY: misc_feature
<222> LOCATION: (21)..(21)
<223> OTHER INFORMATION: Substituted thymine
<220> FEATURE:
<221> NAME/KEY: misc_feature
<222> LOCATION: (25)..(25)
<223> OTHER INFORMATION: 3' quencher and/or blocker

<400> SEQUENCE: 130
```
caaacccaac atcctctatc tattc                                              25

<210> SEQ ID NO 131
<211> LENGTH: 23
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (23)..(23)
<223> OTHER INFORMATION: 3' quencher and/or blocker

<400> SEQUENCE: 131
aaacactcat cgcaaccgcc gcg                                                23

<210> SEQ ID NO 132
<211> LENGTH: 29
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (16)..(16)
<223> OTHER INFORMATION: Substituted thymine
<220> FEATURE:
<221> NAME/KEY: misc_feature
<222> LOCATION: (23)..(23)
<223> OTHER INFORMATION: Substituted thymine
<220> FEATURE:
<221> NAME/KEY: misc_feature
<222> LOCATION: (29)..(29)
<223> OTHER INFORMATION: 3' quencher and/or blocker

<400> SEQUENCE: 132
ccaaacatca aatctttaac ttttaccaa                                          29

<210> SEQ ID NO 133
<211> LENGTH: 23
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (23)..(23)
<223> OTHER INFORMATION: 3' quencher and/or blocker

<400> SEQUENCE: 133
aaacactcat cgcaaccgcc gcg                                                23

<210> SEQ ID NO 134
<211> LENGTH: 20
<212> TYPE: DNA
<213> ORGANISM: Artificial
<220> FEATURE:
<223> OTHER INFORMATION: Synthetic oligonucleotide PCR primer

<400> SEQUENCE: 134
ggtgttgaag ttggggtttg                                              20

<210> SEQ ID NO 135
<211> LENGTH: 23
<212> TYPE: DNA
<213> ORGANISM: Artificial
<220> FEATURE:
<223> OTHER INFORMATION: Synthetic oligonucleotide PCR primer

<400> SEQUENCE: 135
cccatacttc actaacttta aac                                          23

<210> SEQ ID NO 136
<211> LENGTH: 26
<212> TYPE: DNA
<213> ORGANISM: Artificial
<220> FEATURE:
<223> OTHER INFORMATION: Synthetic oligonucleotide PCR primer

<400> SEQUENCE: 136
gtaaatagtt tgtaagttta ttggtg                                       26

<210> SEQ ID NO 137
<211> LENGTH: 24
<212> TYPE: DNA
<213> ORGANISM: Artificial
<220> FEATURE:
<223> OTHER INFORMATION: Synthetic oligonucleotide PCR primer

<400> SEQUENCE: 137
tttcttcaca ccaccaataa ccaa                                         24

<210> SEQ ID NO 138
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 138
gagtaagaag atggttgagg tg                                           22

<210> SEQ ID NO 139
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 139
caacaactct actcaccctc aa                                           22

<210> SEQ ID NO 140
<211> LENGTH: 25
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (12)..(12)
<223> OTHER INFORMATION: Substituted thymine

```
<220> FEATURE:
<221> NAME/KEY: misc_feature
<222> LOCATION: (20)..(20)
<223> OTHER INFORMATION: Substituted thymine
<220> FEATURE:
<221> NAME/KEY: misc_feature
<222> LOCATION: (25)..(25)
<223> OTHER INFORMATION: 3' quencher and/or blocker

<400> SEQUENCE: 140
tcccaactac ttaaaaaact aaaac                                              25

<210> SEQ ID NO 141
<211> LENGTH: 25
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (12)..(12)
<223> OTHER INFORMATION: Substituted thymine
<220> FEATURE:
<221> NAME/KEY: misc_feature
<222> LOCATION: (20)..(20)
<223> OTHER INFORMATION: Substituted thymine
<220> FEATURE:
<221> NAME/KEY: misc_feature
<222> LOCATION: (25)..(25)
<223> OTHER INFORMATION: 3' quencher and/or blocker

<400> SEQUENCE: 141
tcccaactac ttaaaaaact aaaac                                              25

<210> SEQ ID NO 142
<211> LENGTH: 25
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (12)..(12)
<223> OTHER INFORMATION: Substituted thymine
<220> FEATURE:
<221> NAME/KEY: misc_feature
<222> LOCATION: (20)..(20)
<223> OTHER INFORMATION: Substituted thymine
<220> FEATURE:
<221> NAME/KEY: misc_feature
<222> LOCATION: (25)..(25)
<223> OTHER INFORMATION: 3' quencher and/or blocker

<400> SEQUENCE: 142
tcccaactac ttaaaaaact aaaac                                              25

<210> SEQ ID NO 143
<211> LENGTH: 25
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
```

<223> OTHER INFORMATION: Conjugated to a fluor
<220> FEATURE:
<221> NAME/KEY: misc_feature
<222> LOCATION: (12)..(12)
<223> OTHER INFORMATION: Substituted thymine
<220> FEATURE:
<221> NAME/KEY: misc_feature
<222> LOCATION: (20)..(20)
<223> OTHER INFORMATION: Substituted thymine
<220> FEATURE:
<221> NAME/KEY: misc_feature
<222> LOCATION: (25)..(25)
<223> OTHER INFORMATION: 3' quencher and/or blocker

<400> SEQUENCE: 143
tcccaactac ttaaaaaact aaaac                                    25

<210> SEQ ID NO 144
<211> LENGTH: 25
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (12)..(12)
<223> OTHER INFORMATION: Substituted thymine
<220> FEATURE:
<221> NAME/KEY: misc_feature
<222> LOCATION: (20)..(20)
<223> OTHER INFORMATION: Substituted thymine
<220> FEATURE:
<221> NAME/KEY: misc_feature
<222> LOCATION: (25)..(25)
<223> OTHER INFORMATION: 3' quencher and/or blocker

<400> SEQUENCE: 144
tcccaactac ttaaaaaact aaaac                                    25

<210> SEQ ID NO 145
<211> LENGTH: 32
<212> TYPE: DNA
<213> ORGANISM: Artificial
<220> FEATURE:
<223> OTHER INFORMATION: Synthetic oligonucleotide PCR primer

<400> SEQUENCE: 145
ggataagatt tttgatattg tattttttaa gg                            32

<210> SEQ ID NO 146
<211> LENGTH: 34
<212> TYPE: DNA
<213> ORGANISM: Artificial
<220> FEATURE:
<223> OTHER INFORMATION: Synthetic oligonucleotide PCR primer

<400> SEQUENCE: 146
catattcaaa ctccttaata aacaaacttt tctc                          34

<210> SEQ ID NO 147
<211> LENGTH: 31
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature

```
<222> LOCATION: (1)..(1)
<223> OTHER INFORMATION: Conjugated to a fluor
<220> FEATURE:
<221> NAME/KEY: misc_feature
<222> LOCATION: (21)..(21)
<223> OTHER INFORMATION: Substituted thymine
<220> FEATURE:
<221> NAME/KEY: misc_feature
<222> LOCATION: (29)..(29)
<223> OTHER INFORMATION: Substituted thymine
<220> FEATURE:
<221> NAME/KEY: misc_feature
<222> LOCATION: (31)..(31)
<223> OTHER INFORMATION: 3' quencher and/or blocker

<400> SEQUENCE: 147
ccgaacaaaa aaaacctaaa taaatccctt c                               31

<210> SEQ ID NO 148
<211> LENGTH: 28
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (19)..(19)
<223> OTHER INFORMATION: Substituted thymine
<220> FEATURE:
<221> NAME/KEY: misc_feature
<222> LOCATION: (28)..(28)
<223> OTHER INFORMATION: 3' quencher and/or blocker

<400> SEQUENCE: 148
ccaccaccca acacacaata acaaacac                                  28

<210> SEQ ID NO 149
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 149
ggtttagtaa gtttttttgga ttgtg                                    25

<210> SEQ ID NO 150
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 150
ccttaaaaat tacaaaaacc acaac                                     25

<210> SEQ ID NO 151
<211> LENGTH: 28
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
```

<220> FEATURE:
<221> NAME/KEY: misc_feature
<222> LOCATION: (14)..(14)
<223> OTHER INFORMATION: Optinally conjugated to a quencher
<220> FEATURE:
<221> NAME/KEY: misc_feature
<222> LOCATION: (19)..(19)
<223> OTHER INFORMATION: Substituted thymine
<220> FEATURE:
<221> NAME/KEY: misc_feature
<222> LOCATION: (28)..(28)
<223> OTHER INFORMATION: 3' quencher and/or blocker

<400> SEQUENCE: 151
ccaccaccca acacacaata acaaacac                                   28

<210> SEQ ID NO 152
<211> LENGTH: 29
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (13)..(13)
<223> OTHER INFORMATION: a, c, g, or t conjugated to a quencher
<220> FEATURE:
<221> NAME/KEY: misc_feature
<222> LOCATION: (17)..(17)
<223> OTHER INFORMATION: Substituted cytosine
<220> FEATURE:
<221> NAME/KEY: misc_feature
<222> LOCATION: (23)..(23)
<223> OTHER INFORMATION: Substituted cytosine
<220> FEATURE:
<221> NAME/KEY: misc_feature
<222> LOCATION: (29)..(29)
<223> OTHER INFORMATION: 3' quencher and/or blocker

<400> SEQUENCE: 152
ccaccaccca acnacacaat aacaaacac                                  29

<210> SEQ ID NO 153
<211> LENGTH: 29
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (16)..(16)
<223> OTHER INFORMATION: a, c, g, or t conjugated to a quencher
<220> FEATURE:
<221> NAME/KEY: misc_feature
<222> LOCATION: (20)..(20)
<223> OTHER INFORMATION: Substituted thymine
<220> FEATURE:
<221> NAME/KEY: misc_feature
<222> LOCATION: (29)..(29)
<223> OTHER INFORMATION: 3' quencher and/or blocker

<400> SEQUENCE: 153
ccaccaccca acacancaat aacaaacac                                  29

<210> SEQ ID NO 154
<211> LENGTH: 23

```
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (23)..(23)
<223> OTHER INFORMATION: 3' quencher and/or blocker

<400> SEQUENCE: 154
ttcagtgccg gttggtaatg taa                                          23

<210> SEQ ID NO 155
<211> LENGTH: 27
<212> TYPE: DNA
<213> ORGANISM: Artificial
<220> FEATURE:
<223> OTHER INFORMATION: Synthetic oligonucleotide PCR primer

<400> SEQUENCE: 155
caacaacttt aatacctgtt tcaagga                                      27

<210> SEQ ID NO 156
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 156
ggtatttttg tatttgttgg tgttg                                        25

<210> SEQ ID NO 157
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 157
catacataca ccaaacaatt cattc                                        25

<210> SEQ ID NO 158
<211> LENGTH: 26
<212> TYPE: DNA
<213> ORGANISM: Artificial
<220> FEATURE:
<223> OTHER INFORMATION: Synthetic oligonucleotide PCR primer

<400> SEQUENCE: 158
gtatggtggt attttgtat ttgttg                                        26

<210> SEQ ID NO 159
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 159
cacacataca tacaccaaac aattc                                        25

<210> SEQ ID NO 160
<211> LENGTH: 30
<212> TYPE: DNA
<213> ORGANISM: Artificial
<220> FEATURE:
```

<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (18)..(18)
<223> OTHER INFORMATION: a, c, g, or t conjugated to a quencher
<220> FEATURE:
<221> NAME/KEY: misc_feature
<222> LOCATION: (30)..(30)
<223> OTHER INFORMATION: 3' quencher and/or blocker

<400> SEQUENCE: 160
aagatccgat tcacaganca agctccgtca                               30

<210> SEQ ID NO 161
<211> LENGTH: 30
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (18)..(18)
<223> OTHER INFORMATION: a, c, g, or t conjugated to a quencher
<220> FEATURE:
<221> NAME/KEY: misc_feature
<222> LOCATION: (30)..(30)
<223> OTHER INFORMATION: 3' quencher and/or blocker

<400> SEQUENCE: 161
aagatccgat tcacaganca agctccgtca                               30

<210> SEQ ID NO 162
<211> LENGTH: 28
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (12)..(12)
<223> OTHER INFORMATION: a, c, g, or t conjugated to a quencher
<220> FEATURE:
<221> NAME/KEY: misc_feature
<222> LOCATION: (16)..(16)
<223> OTHER INFORMATION: Substituted cytosine
<220> FEATURE:
<221> NAME/KEY: misc_feature
<222> LOCATION: (24)..(24)
<223> OTHER INFORMATION: Substituted cytosine
<220> FEATURE:
<221> NAME/KEY: misc_feature
<222> LOCATION: (28)..(28)
<223> OTHER INFORMATION: 3' quencher and/or blocker

<400> SEQUENCE: 162
caaaatcatt tccttcacaa atacactc                                 28

<210> SEQ ID NO 163
<211> LENGTH: 31
<212> TYPE: DNA
<213> ORGANISM: Artificial

```
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (11)..(11)
<223> OTHER INFORMATION: a, c, g, or t conjugated to a quencher
<220> FEATURE:
<221> NAME/KEY: misc_feature
<222> LOCATION: (17)..(17)
<223> OTHER INFORMATION: Substituted thymine
<220> FEATURE:
<221> NAME/KEY: misc_feature
<222> LOCATION: (26)..(26)
<223> OTHER INFORMATION: Substituted thymine
<220> FEATURE:
<221> NAME/KEY: misc_feature
<222> LOCATION: (31)..(31)
<223> OTHER INFORMATION: 3' quencher and/or blocker

<400> SEQUENCE: 163
ccaaatacca taaccatttt attaataaca c                                          31

<210> SEQ ID NO 164
<211> LENGTH: 28
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (15)..(15)
<223> OTHER INFORMATION: Substituted cytosine
<220> FEATURE:
<221> NAME/KEY: misc_feature
<222> LOCATION: (19)..(19)
<223> OTHER INFORMATION: a, c, g, or t conjugated to a quencher
<220> FEATURE:
<221> NAME/KEY: misc_feature
<222> LOCATION: (24)..(24)
<223> OTHER INFORMATION: Substituted cytosine
<220> FEATURE:
<221> NAME/KEY: misc_feature
<222> LOCATION: (28)..(28)
<223> OTHER INFORMATION: 3' quencher and/or blocker

<400> SEQUENCE: 164
aaaatcattt ccttcacana atacactc                                              28

<210> SEQ ID NO 165
<211> LENGTH: 32
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (11)..(11)
<223> OTHER INFORMATION: Substituted thymine
<220> FEATURE:
<221> NAME/KEY: misc_feature
<222> LOCATION: (18)..(18)
<223> OTHER INFORMATION: Optionally conjugated to a quencher
<220> FEATURE:
```

-continued

```
<221> NAME/KEY: misc_feature
<222> LOCATION: (27)..(27)
<223> OTHER INFORMATION: Substituted thymine
<220> FEATURE:
<221> NAME/KEY: misc_feature
<222> LOCATION: (32)..(32)
<223> OTHER INFORMATION: 3' quencher and/or blocker

<400> SEQUENCE: 165
ccaaatacca taaccatntt tattaataac ac                                32

<210> SEQ ID NO 166
<211> LENGTH: 28
<212> TYPE: DNA
<213> ORGANISM: Artificial
<220> FEATURE:
<223> OTHER INFORMATION: Synthetic oligonucleotide PCR primer

<400> SEQUENCE: 166
ccctagtatg ctaggtctct tgctggga                                    28

<210> SEQ ID NO 167
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 167
cagcctctct gagggtttaa gccca                                       25

<210> SEQ ID NO 168
<211> LENGTH: 22
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (7)..(7)
<223> OTHER INFORMATION: Substituted thymine
<220> FEATURE:
<221> NAME/KEY: misc_feature
<222> LOCATION: (11)..(11)
<223> OTHER INFORMATION: Substituted thymine
<220> FEATURE:
<221> NAME/KEY: misc_feature
<222> LOCATION: (22)..(22)
<223> OTHER INFORMATION: 3' quencher and/or blocker

<400> SEQUENCE: 168
tcagcctatc tgacaccccg gg                                          22

<210> SEQ ID NO 169
<211> LENGTH: 26
<212> TYPE: DNA
<213> ORGANISM: Artificial
<220> FEATURE:
<223> OTHER INFORMATION: Synthetic oligonucleotide PCR primer

<400> SEQUENCE: 169
gactcctgag gagaagtctg ccgtta                                      26

<210> SEQ ID NO 170
<211> LENGTH: 23
```

```
<212> TYPE: DNA
<213> ORGANISM: Artificial
<220> FEATURE:
<223> OTHER INFORMATION: Synthetic oligonucleotide PCR primer

<400> SEQUENCE: 170
ccttgatacc aacctgccca ggg                                          23

<210> SEQ ID NO 171
<211> LENGTH: 27
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (10)..(10)
<223> OTHER INFORMATION: Substituted thymine
<220> FEATURE:
<221> NAME/KEY: misc_feature
<222> LOCATION: (20)..(20)
<223> OTHER INFORMATION: Substituted thymine
<220> FEATURE:
<221> NAME/KEY: misc_feature
<222> LOCATION: (27)..(27)
<223> OTHER INFORMATION: 3' quencher and/or blocker

<400> SEQUENCE: 171
aggtgaacgt ggatgaagtt ggtggtg                                      27

<210> SEQ ID NO 172
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 172
caacatcgcg caagagcacg g                                            21

<210> SEQ ID NO 173
<211> LENGTH: 27
<212> TYPE: DNA
<213> ORGANISM: Artificial
<220> FEATURE:
<223> OTHER INFORMATION: Synthetic oligonucleotide PCR primer

<400> SEQUENCE: 173
cgtttccttc acgagtacgc tctccga                                      27

<210> SEQ ID NO 174
<211> LENGTH: 22
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (10)..(10)
<223> OTHER INFORMATION: Substituted thymine
<220> FEATURE:
<221> NAME/KEY: misc_feature
<222> LOCATION: (18)..(18)
```

-continued

```
<223> OTHER INFORMATION: Substituted thymine
<220> FEATURE:
<221> NAME/KEY: misc_feature
<222> LOCATION: (22)..(22)
<223> OTHER INFORMATION: 3' quencher and/or blocker

<400> SEQUENCE: 174
accggcgaat acagagatac cg                                              22

<210> SEQ ID NO 175
<211> LENGTH: 29
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (3)..(3)
<223> OTHER INFORMATION: Substituted adenine
<220> FEATURE:
<221> NAME/KEY: misc_feature
<222> LOCATION: (6)..(6)
<223> OTHER INFORMATION: Substituted adenine
<220> FEATURE:
<221> NAME/KEY: misc_feature
<222> LOCATION: (13)..(13)
<223> OTHER INFORMATION: a, c, g, or t conjugated to a quencher
<220> FEATURE:
<221> NAME/KEY: misc_feature
<222> LOCATION: (17)..(17)
<223> OTHER INFORMATION: Substituted cytosine
<220> FEATURE:
<221> NAME/KEY: misc_feature
<222> LOCATION: (23)..(23)
<223> OTHER INFORMATION: Substituted cytosine
<220> FEATURE:
<221> NAME/KEY: misc_feature
<222> LOCATION: (29)..(29)
<223> OTHER INFORMATION: 3' quencher and/or blocker

<400> SEQUENCE: 175
ccaccaccca acnacacaat aacaaacac                                       29

<210> SEQ ID NO 176
<211> LENGTH: 23
<212> TYPE: DNA
<213> ORGANISM: Artificial
<220> FEATURE:
<223> OTHER INFORMATION: Synthetic oligonucleotide PCR primer

<400> SEQUENCE: 176
gttggtgttg gagagtgtat ttg                                             23

<210> SEQ ID NO 177
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 177
ggagagtgta tttgtgaagg aaatg                                           25

<210> SEQ ID NO 178
<211> LENGTH: 28
<212> TYPE: DNA
<213> ORGANISM: Artificial
```

```
<220> FEATURE:
<223> OTHER INFORMATION: Synthetic oligonucleotide PCR primer

<400> SEQUENCE: 178
ggaaatgatt tttttatga gatgagtg                                              28

<210> SEQ ID NO 179
<211> LENGTH: 29
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (20)..(20)
<223> OTHER INFORMATION: Substituted thymine
<220> FEATURE:
<221> NAME/KEY: misc_feature
<222> LOCATION: (29)..(29)
<223> OTHER INFORMATION: 3' quencher and/or blocker

<400> SEQUENCE: 179
ccaccaccca acacancaat aacaaacac                                            29

<210> SEQ ID NO 180
<211> LENGTH: 29
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (20)..(20)
<223> OTHER INFORMATION: Substituted thymine
<220> FEATURE:
<221> NAME/KEY: misc_feature
<222> LOCATION: (29)..(29)
<223> OTHER INFORMATION: 3' quencher and/or blocker

<400> SEQUENCE: 180
ccaccaccca acacancaat aacaaacac                                            29

<210> SEQ ID NO 181
<211> LENGTH: 28
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (19)..(19)
<223> OTHER INFORMATION: Substituted thymine
<220> FEATURE:
```

```
<221> NAME/KEY: misc_feature
<222> LOCATION: (28)..(28)
<223> OTHER INFORMATION: 3' quencher and/or blocker

<400> SEQUENCE: 181
ccaccaccca acacacaata acaaacac                                               28

<210> SEQ ID NO 182
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 182
gatggaggag gtttagtaag ttttt                                                  25

<210> SEQ ID NO 183
<211> LENGTH: 26
<212> TYPE: DNA
<213> ORGANISM: Artificial
<220> FEATURE:
<223> OTHER INFORMATION: Synthetic oligonucleotide PCR primer

<400> SEQUENCE: 183
aataaaacct actcctccct taaaaa                                                 26

<210> SEQ ID NO 184
<211> LENGTH: 22
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (18)..(18)
<223> OTHER INFORMATION: Universal purine

<400> SEQUENCE: 184
cttaccataa ctactacrct cc                                                     22

<210> SEQ ID NO 185
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 185
cttaccataa ctactacrct cc                                                     22

<210> SEQ ID NO 186
<211> LENGTH: 24
<212> TYPE: DNA
<213> ORGANISM: Artificial
<220> FEATURE:
<223> OTHER INFORMATION: Synthetic oligonucleotide PCR primer

<400> SEQUENCE: 186
gtgtgtgttt ttattgtaaa tggt                                                   24

<210> SEQ ID NO 187
<211> LENGTH: 25
<212> TYPE: DNA
<213> ORGANISM: Artificial
<220> FEATURE:
<223> OTHER INFORMATION: Synthetic oligonucleotide PCR primer
```

```
<220> FEATURE:
<221> NAME/KEY: misc_feature
<222> LOCATION: (4)..(4)
<223> OTHER INFORMATION: Universal purine
<220> FEATURE:
<221> NAME/KEY: misc_feature
<222> LOCATION: (10)..(10)
<223> OTHER INFORMATION: Universal purine

<400> SEQUENCE: 187
aacrataacr ataaaatttc ttcac                                          25

<210> SEQ ID NO 188
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 188
aacrataacr ataaaatttc ttcac                                          25

<210> SEQ ID NO 189
<211> LENGTH: 19
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (7)..(7)
<223> OTHER INFORMATION: Universal pyrimidine

<400> SEQUENCE: 189
gtttgtyggg attttgggt                                                 19

<210> SEQ ID NO 190
<211> LENGTH: 19
<212> TYPE: DNA
<213> ORGANISM: Artificial
<220> FEATURE:
<223> OTHER INFORMATION: Synthetic oligonucleotide PCR primer

<400> SEQUENCE: 190
gtttgtyggg attttgggt                                                 19

<210> SEQ ID NO 191
<211> LENGTH: 21
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (3)..(3)
<223> OTHER INFORMATION: Universal purine
<220> FEATURE:
<221> NAME/KEY: misc_feature
<222> LOCATION: (10)..(10)
<223> OTHER INFORMATION: Universal purine

<400> SEQUENCE: 191
ccraactccr aaaaaaaaac c                                              21

<210> SEQ ID NO 192
<211> LENGTH: 21
<212> TYPE: DNA
<213> ORGANISM: Artificial
<220> FEATURE:
```

<223> OTHER INFORMATION: Synthetic oligonucleotide PCR primer

<400> SEQUENCE: 192
ccraactccr aaaaaaaaac c					21

<210> SEQ ID NO 193
<211> LENGTH: 21
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (10)..(10)
<223> OTHER INFORMATION: Universal pyrimidine
<220> FEATURE:
<221> NAME/KEY: misc_feature
<222> LOCATION: (12)..(12)
<223> OTHER INFORMATION: Universal pyrimidine

<400> SEQUENCE: 193
ggtattaagy gyggttttttt g					21

<210> SEQ ID NO 194
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 194
ggtattaagy gyggttttttt g					21

<210> SEQ ID NO 195
<211> LENGTH: 21
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (3)..(3)
<223> OTHER INFORMATION: Universal pyrimidine

<400> SEQUENCE: 195
gtygtttagt ttggatttttg g					21

<210> SEQ ID NO 196
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 196
gtygtttagt ttggatttttg g					21

<210> SEQ ID NO 197
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 197
tttcgaaggg taagcgttaa g					21

```
<210> SEQ ID NO 198
<211> LENGTH: 22
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (14)..(14)
<223> OTHER INFORMATION: Universal purine
<220> FEATURE:
<221> NAME/KEY: misc_feature
<222> LOCATION: (17)..(17)
<223> OTHER INFORMATION: Substituted thymine

<400> SEQUENCE: 198
aacataaata accraaataa cc                                              22

<210> SEQ ID NO 199
<211> LENGTH: 22
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (18)..(18)
<223> OTHER INFORMATION: Substituted thymine

<400> SEQUENCE: 199
aacataaata accraaataa cc                                              22

<210> SEQ ID NO 200
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 200
cggttttttg agtaagaaga cggtc                                           25

<210> SEQ ID NO 201
<211> LENGTH: 29
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (17)..(17)
<223> OTHER INFORMATION: Universal purine
<220> FEATURE:
<221> NAME/KEY: misc_feature
<222> LOCATION: (18)..(18)
<223> OTHER INFORMATION: Substituted thymine
<220> FEATURE:
<221> NAME/KEY: misc_feature
<222> LOCATION: (23)..(23)
<223> OTHER INFORMATION: Substituted thymine
<220> FEATURE:
<221> NAME/KEY: misc_feature
<222> LOCATION: (29)..(29)
<223> OTHER INFORMATION: 3' quencher and/or blocker

<400> SEQUENCE: 201
tacctttaaa taaccrtaa aatcgacaa                                        29
```

```
<210> SEQ ID NO 202
<211> LENGTH: 29
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (11)..(11)
<223> OTHER INFORMATION: a, c, g, or t conjugated to a quencher
<220> FEATURE:
<221> NAME/KEY: misc_feature
<222> LOCATION: (18)..(18)
<223> OTHER INFORMATION: Substituted thymine
<220> FEATURE:
<221> NAME/KEY: misc_feature
<222> LOCATION: (23)..(23)
<223> OTHER INFORMATION: Substituted thymine
<220> FEATURE:
<221> NAME/KEY: misc_feature
<222> LOCATION: (29)..(29)
<223> OTHER INFORMATION: 3' quencher and/or blocker

<400> SEQUENCE: 202
tacctttaaa taacccrtaa aatcgacaa                                    29

<210> SEQ ID NO 203
<211> LENGTH: 28
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (14)..(14)
<223> OTHER INFORMATION: Substituted thymine
<220> FEATURE:
<221> NAME/KEY: misc_feature
<222> LOCATION: (17)..(17)
<223> OTHER INFORMATION: Universal purine
<220> FEATURE:
<221> NAME/KEY: misc_feature
<222> LOCATION: (24)..(24)
<223> OTHER INFORMATION: Substituted thymine
<220> FEATURE:
<221> NAME/KEY: misc_feature
<222> LOCATION: (28)..(28)
<223> OTHER INFORMATION: 3' quencher and/or blocker

<400> SEQUENCE: 203
ataacaaact acttacrcga aactttac                                     28

<210> SEQ ID NO 204
<211> LENGTH: 28
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (14)..(14)
<223> OTHER INFORMATION: Substituted thymine
```

```
<220> FEATURE:
<221> NAME/KEY: misc_feature
<222> LOCATION: (24)..(24)
<223> OTHER INFORMATION: Substituted thymine
<220> FEATURE:
<221> NAME/KEY: misc_feature
<222> LOCATION: (28)..(28)
<223> OTHER INFORMATION: 3' quencher and/or blocker

<400> SEQUENCE: 204
ataacaaact acttacrcga aactttac                                              28

<210> SEQ ID NO 205
<211> LENGTH: 24
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (9)..(9)
<223> OTHER INFORMATION: Universal purine
<220> FEATURE:
<221> NAME/KEY: misc_feature
<222> LOCATION: (12)..(12)
<223> OTHER INFORMATION: Substituted cytosine
<220> FEATURE:
<221> NAME/KEY: misc_feature
<222> LOCATION: (15)..(15)
<223> OTHER INFORMATION: Substituted thymine
<220> FEATURE:
<221> NAME/KEY: misc_feature
<222> LOCATION: (19)..(19)
<223> OTHER INFORMATION: a, c, g, or t conjugated to a quencher
<220> FEATURE:
<221> NAME/KEY: misc_feature
<222> LOCATION: (24)..(24)
<223> OTHER INFORMATION: 3' quencher and/or blocker

<400> SEQUENCE: 205
aacaaaccra acgataacna aaac                                                  24

<210> SEQ ID NO 206
<211> LENGTH: 24
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (12)..(12)
<223> OTHER INFORMATION: Substituted cytosine
<220> FEATURE:
<221> NAME/KEY: misc_feature
<222> LOCATION: (15)..(15)
<223> OTHER INFORMATION: Substituted thymine
<220> FEATURE:
<221> NAME/KEY: misc_feature
<222> LOCATION: (19)..(19)
<223> OTHER INFORMATION: a, c, g, or t conjugated to a quencher
<220> FEATURE:
<221> NAME/KEY: misc_feature
<222> LOCATION: (24)..(24)
<223> OTHER INFORMATION: Conjugated to a fluor

<400> SEQUENCE: 206
```
aacaaaccra acgataacna aaac                                              24

<210> SEQ ID NO 207
<211> LENGTH: 28
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (11)..(11)
<223> OTHER INFORMATION: Substituted thymine
<220> FEATURE:
<221> NAME/KEY: misc_feature
<222> LOCATION: (19)..(19)
<223> OTHER INFORMATION: a, c, g, or t optinally conjugated to a
      quencher
<220> FEATURE:
<221> NAME/KEY: misc_feature
<222> LOCATION: (26)..(26)
<223> OTHER INFORMATION: Substituted thymine
<220> FEATURE:
<221> NAME/KEY: misc_feature
<222> LOCATION: (28)..(28)
<223> OTHER INFORMATION: 3' quencher and/or blocker

<400> SEQUENCE: 207
cacattctaa taaaaaacna accacttc                                          28

<210> SEQ ID NO 208
<211> LENGTH: 21
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (5)..(5)
<223> OTHER INFORMATION: Universal purine
<220> FEATURE:
<221> NAME/KEY: misc_feature
<222> LOCATION: (8)..(8)
<223> OTHER INFORMATION: Substituted cytosine
<220> FEATURE:
<221> NAME/KEY: misc_feature
<222> LOCATION: (13)..(13)
<223> OTHER INFORMATION: Optinally conjugated to a quencher
<220> FEATURE:
<221> NAME/KEY: misc_feature
<222> LOCATION: (16)..(16)
<223> OTHER INFORMATION: Substituted cytosine
<220> FEATURE:
<221> NAME/KEY: misc_feature
<222> LOCATION: (21)..(21)
<223> OTHER INFORMATION: 3' quencher and/or blocker

<400> SEQUENCE: 208
aaccraacga aaccacaaaa c                                                 21

<210> SEQ ID NO 209
<211> LENGTH: 21
<212> TYPE: DNA
<213> ORGANISM: Artificial
<220> FEATURE:
<223> OTHER INFORMATION: Synthetic oligonucleotide PCR probe
<220> FEATURE:

```
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (8)..(8)
<223> OTHER INFORMATION: Substituted cytosine
<220> FEATURE:
<221> NAME/KEY: misc_feature
<222> LOCATION: (13)..(13)
<223> OTHER INFORMATION: Conjugated to a quencher
<220> FEATURE:
<221> NAME/KEY: misc_feature
<222> LOCATION: (16)..(16)
<223> OTHER INFORMATION: Substituted cytosine
<220> FEATURE:
<221> NAME/KEY: misc_feature
<222> LOCATION: (21)..(21)
<223> OTHER INFORMATION: 3' quencher and/or blocker

<400> SEQUENCE: 209
aaccraacga aaccacaaaa c                                             21

<210> SEQ ID NO 210
<211> LENGTH: 23
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (10)..(10)
<223> OTHER INFORMATION: Substituted thymine
<220> FEATURE:
<221> NAME/KEY: misc_feature
<222> LOCATION: (15)..(14)
<223> OTHER INFORMATION: a, c, g, or t conjugated to a quencher
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (23)..(23)
<223> OTHER INFORMATION: 3' quencher and/or blocker

<400> SEQUENCE: 210
caaaaacact catcncaacc gcc                                           23

<210> SEQ ID NO 211
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 211
acaaccctcc aaaaaataca ta                                            22

<210> SEQ ID NO 212
<211> LENGTH: 31
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (1)..(1)
<223> OTHER INFORMATION: Conjugated to a fluor
```

```
<220> FEATURE:
<221> NAME/KEY: misc_feature
<222> LOCATION: (17)..(17)
<223> OTHER INFORMATION: Substituted thymine
<220> FEATURE:
<221> NAME/KEY: misc_feature
<222> LOCATION: (26)..(26)
<223> OTHER INFORMATION: Substituted thymine
<220> FEATURE:
<221> NAME/KEY: misc_feature
<222> LOCATION: (31)..(31)
<223> OTHER INFORMATION: 3' quencher and/or blocker

<400> SEQUENCE: 212
ccaaatacca taaccatttt attaataaca c                                31

<210> SEQ ID NO 213
<211> LENGTH: 31
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (17)..(17)
<223> OTHER INFORMATION: Substituted thymine
<220> FEATURE:
<221> NAME/KEY: misc_feature
<222> LOCATION: (26)..(26)
<223> OTHER INFORMATION: Substituted thymine
<220> FEATURE:
<221> NAME/KEY: misc_feature
<222> LOCATION: (31)..(31)
<223> OTHER INFORMATION: 3' quencher and/or blocker

<400> SEQUENCE: 213
ccaaatacca taaccatttt attaataaca c                                31

<210> SEQ ID NO 214
<211> LENGTH: 21
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (4)..(4)
<223> OTHER INFORMATION: Universal pyrimidine
<220> FEATURE:
<221> NAME/KEY: misc_feature
<222> LOCATION: (15)..(15)
<223> OTHER INFORMATION: Universal pyrimidine

<400> SEQUENCE: 214
tttygaaggg taagygttaa g                                           21

<210> SEQ ID NO 215
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 215
tttygaaggg taagygttaa g                                           21

<210> SEQ ID NO 216
```

```
<211> LENGTH: 19
<212> TYPE: DNA
<213> ORGANISM: Artificial
<220> FEATURE:
<223> OTHER INFORMATION: Synthetic oligonucleotide PCR primer

<400> SEQUENCE: 216
caacacraaa accccrata                                                  19

<210> SEQ ID NO 217
<211> LENGTH: 19
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (7)..(7)
<223> OTHER INFORMATION: Universal purine
<220> FEATURE:
<221> NAME/KEY: misc_feature
<222> LOCATION: (16)..(16)
<223> OTHER INFORMATION: Universal purine

<400> SEQUENCE: 217
caacacraaa accccrata                                                  19

<210> SEQ ID NO 218
<211> LENGTH: 51
<212> TYPE: DNA
<213> ORGANISM: Artificial
<220> FEATURE:
<223> OTHER INFORMATION: Synthetic oligonucleotide PCR primer

<400> SEQUENCE: 218
cctgctgaaa atgactgaat ataaccgcta agaacctctc ggtcagctga t              51

<210> SEQ ID NO 219
<211> LENGTH: 51
<212> TYPE: DNA
<213> ORGANISM: Artificial
<220> FEATURE:
<223> OTHER INFORMATION: Synthetic oligonucleotide PCR primer

<400> SEQUENCE: 219
cctgctgaaa atgactgaat ataaagtctc attataatcg ttcgagctgt t              51

<210> SEQ ID NO 220
<211> LENGTH: 51
<212> TYPE: DNA
<213> ORGANISM: Artificial
<220> FEATURE:
<223> OTHER INFORMATION: Synthetic oligonucleotide PCR primer

<400> SEQUENCE: 220
cctgctgaaa atgactgaat ataagcagac ttggcggtag gtccgagctt g              51

<210> SEQ ID NO 221
<211> LENGTH: 51
<212> TYPE: DNA
<213> ORGANISM: Artificial
<220> FEATURE:
<223> OTHER INFORMATION: Synthetic oligonucleotide PCR primer

<400> SEQUENCE: 221
cctgctgaaa atgactgaat ataagtatcc tgagcacggt tgcgagctgc t              51
```

-continued

```
<210> SEQ ID NO 222
<211> LENGTH: 35
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (15)..(15)
<223> OTHER INFORMATION: a, c, g, or t conjugated to a quencher

<400> SEQUENCE: 222
ctcttgccta cgccnccgct aagaacctct cggtc                               35

<210> SEQ ID NO 223
<211> LENGTH: 35
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (15)..(15)
<223> OTHER INFORMATION: a, c, g, or t conjugated to a quencher

<400> SEQUENCE: 223
ctcttgccta cgccnagtct cattataatc gttcg                               35

<210> SEQ ID NO 224
<211> LENGTH: 35
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (15)..(15)
<223> OTHER INFORMATION: a, c, g, or t conjugated to a quencher

<400> SEQUENCE: 224
ctcttgccta cgccngcaga cttggcggta ggtcc                               35

<210> SEQ ID NO 225
<211> LENGTH: 35
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (15)..(15)
<223> OTHER INFORMATION: a, c, g, or t conjugated to a quencher

<400> SEQUENCE: 225
ctcttgccta cgccngtatc ctgagcacgg ttgcg                               35

<210> SEQ ID NO 226
<211> LENGTH: 28
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (19)..(19)
<223> OTHER INFORMATION: Substituted thymine
<220> FEATURE:
```

<221> NAME/KEY: misc_feature
<222> LOCATION: (28)..(28)
<223> OTHER INFORMATION: 3' quencher and/or blocker

<400> SEQUENCE: 226
ccaccaccca acacacaata acaaacac                                              28

<210> SEQ ID NO 227
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 227
cccrcaaacc rcgaaaacct c                                                     21

<210> SEQ ID NO 228
<211> LENGTH: 24
<212> TYPE: DNA
<213> ORGANISM: Artificial
<220> FEATURE:
<223> OTHER INFORMATION: Synthetic oligonucleotide PCR primer

<400> SEQUENCE: 228 gttttttttty gggagaggta aata                                                 24

<210> SEQ ID NO 229
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 229
crcctccraa actaaaacaa c                                                     21

<210> SEQ ID NO 230
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 230
gggttattgt aaagttaggg tg                                                    22

<210> SEQ ID NO 231
<211> LENGTH: 21
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (6)..(6)
<223> OTHER INFORMATION: Universal pyrimidine
<220> FEATURE:
<221> NAME/KEY: misc_feature
<222> LOCATION: (15)..(15)
<223> OTHER INFORMATION: Universal pyrimidine

<400> SEQUENCE: 231
gaggtygtgg ttttygtaga t                                                     21

<210> SEQ ID NO 232
<211> LENGTH: 22

```
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (5)..(5)
<223> OTHER INFORMATION: Universal purine

<400> SEQUENCE: 232
aaacrccaaa aaacttcaaa ac                                             22

<210> SEQ ID NO 233
<211> LENGTH: 23
<212> TYPE: DNA
<213> ORGANISM: Artificial
<220> FEATURE:
<223> OTHER INFORMATION: Synthetic oligonucleotide PCR primer

<400> SEQUENCE: 233
ttttgttggg ataagaagyg ttt                                            23

<210> SEQ ID NO 234
<211> LENGTH: 24
<212> TYPE: DNA
<213> ORGANISM: Artificial
<220> FEATURE:
<223> OTHER INFORMATION: Synthetic oligonucleotide PCR primer

<400> SEQUENCE: 234
accaaaaact attacaaaac caaa                                           24

<210> SEQ ID NO 235
<211> LENGTH: 13
<212> TYPE: DNA
<213> ORGANISM: Artificial
<220> FEATURE:
<223> OTHER INFORMATION: Synthetic oligonucleotide PCR primer

<400> SEQUENCE: 235
ccgacgaccg acg                                                       13

<210> SEQ ID NO 236
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 236
gggagaggta aatatcgata c                                              21

<210> SEQ ID NO 237
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 237
cgcgaaaatt aatacctaac g                                              21

<210> SEQ ID NO 238
<211> LENGTH: 19
<212> TYPE: DNA
<213> ORGANISM: Artificial
<220> FEATURE:
```

```
<223> OTHER INFORMATION: Synthetic oligonucleotide PCR primer

<400> SEQUENCE: 238
ttagggtgcg ttatcggac                                              19

<210> SEQ ID NO 239
<211> LENGTH: 20
<212> TYPE: DNA
<213> ORGANISM: Artificial
<220> FEATURE:
<223> OTHER INFORMATION: Synthetic oligonucleotide PCR primer

<400> SEQUENCE: 239
cggaggtgtt tgttttcgtc                                             20

<210> SEQ ID NO 240
<211> LENGTH: 23
<212> TYPE: DNA
<213> ORGANISM: Artificial
<220> FEATURE:
<223> OTHER INFORMATION: Synthetic oligonucleotide PCR primer

<400> SEQUENCE: 240
cgaaaaaaac aaacaccgac acg                                         23

<210> SEQ ID NO 241
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 241
cgttttcggg gttgaggtaa c                                           21

<210> SEQ ID NO 242
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 242
ccaaaatacg ctaccgaacg a                                           21

<210> SEQ ID NO 243
<211> LENGTH: 18
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (6)..(6)
<223> OTHER INFORMATION: Substituted adenine
<220> FEATURE:
<221> NAME/KEY: misc_feature
<222> LOCATION: (10)..(10)
<223> OTHER INFORMATION: Substituted adenine
<220> FEATURE:
<221> NAME/KEY: misc_feature
<222> LOCATION: (11)..(11)
<223> OTHER INFORMATION: Substituted cytosine
<220> FEATURE:
<221> NAME/KEY: misc_feature
```

```
<222> LOCATION: (15)..(15)
<223> OTHER INFORMATION: Substituted cytosine
<220> FEATURE:
<221> NAME/KEY: misc_feature
<222> LOCATION: (18)..(18)
<223> OTHER INFORMATION: Universal purine
<220> FEATURE:
<221> NAME/KEY: misc_feature
<222> LOCATION: (18)..(18)
<223> OTHER INFORMATION: 3' quencher and/or blocker

<400> SEQUENCE: 243
aaaatatcta cccccrcc                                                     18

<210> SEQ ID NO 244
<211> LENGTH: 27
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (16)..(16)
<223> OTHER INFORMATION: Substituted thymine
<220> FEATURE:
<221> NAME/KEY: misc_feature
<222> LOCATION: (23)..(23)
<223> OTHER INFORMATION: Substituted thymine
<220> FEATURE:
<221> NAME/KEY: misc_feature
<222> LOCATION: (27)..(27)
<223> OTHER INFORMATION: 3' quencher and/or blocker

<400> SEQUENCE: 244
tattactcac tctactcaaa actctcc                                           27

<210> SEQ ID NO 245
<211> LENGTH: 28
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (19)..(19)
<223> OTHER INFORMATION: Substituted thymine
<220> FEATURE:
<221> NAME/KEY: misc_feature
<222> LOCATION: (24)..(24)
<223> OTHER INFORMATION: Substituted thymine
<220> FEATURE:
<221> NAME/KEY: misc_feature
<222> LOCATION: (28)..(28)
<223> OTHER INFORMATION: 3' quencher and/or blocker

<400> SEQUENCE: 245 atatcttta ccaacaaata ccttcaaa                                           28

<210> SEQ ID NO 246
<211> LENGTH: 25
<212> TYPE: DNA
<213> ORGANISM: Artificial
<220> FEATURE:
<223> OTHER INFORMATION: Synthetic oligonucleotide PCR probe
<220> FEATURE:
```

```
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (6)..(6)
<223> OTHER INFORMATION: Universal pyrimidine
<220> FEATURE:
<221> NAME/KEY: misc_feature
<222> LOCATION: (20)..(20)
<223> OTHER INFORMATION: Substituted thymine
<220> FEATURE:
<221> NAME/KEY: misc_feature
<222> LOCATION: (25)..(25)
<223> OTHER INFORMATION: 3' quencher and/or blocker

<400> SEQUENCE: 246
gttttygttt tggttgcgat gttgt                                    25

<210> SEQ ID NO 247
<211> LENGTH: 21
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (18)..(18)
<223> OTHER INFORMATION: Universal pyrimidine

<400> SEQUENCE: 247
gggatttttt agaagagygg t                                        21

<210> SEQ ID NO 248
<211> LENGTH: 23
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (15)..(15)
<223> OTHER INFORMATION: Universal pyrimidine
<220> FEATURE:
<221> NAME/KEY: misc_feature
<222> LOCATION: (21)..(21)
<223> OTHER INFORMATION: Substituted thymine

<400> SEQUENCE: 248
tactcactaa taacraaaac tac                                      23

<210> SEQ ID NO 249
<211> LENGTH: 22
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (18)..(18)
<223> OTHER INFORMATION: Universal pyrimidine

<400> SEQUENCE: 249
ggttttgtgt tttattgygg ag                                       22

<210> SEQ ID NO 250
<211> LENGTH: 23
<212> TYPE: DNA
<213> ORGANISM: Artificial
<220> FEATURE:
<223> OTHER INFORMATION: Synthetic oligonucleotide PCR primer
```

-continued

```
<220> FEATURE:
<221> NAME/KEY: misc_feature
<222> LOCATION: (7)..(7)
<223> OTHER INFORMATION: Universal purine

<400> SEQUENCE: 250
cctaacraac tacaccaata caa                                          23

<210> SEQ ID NO 251
<211> LENGTH: 21
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (17)..(17)
<223> OTHER INFORMATION: Universal pyrimidine

<400> SEQUENCE: 251 gagagggat tttttgygtt t                                             21

<210> SEQ ID NO 252
<211> LENGTH: 24
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (3)..(3)
<223> OTHER INFORMATION: Universal purine

<400> SEQUENCE: 252
ccraaaacca attctaaact aatc                                         24

<210> SEQ ID NO 253
<211> LENGTH: 20
<212> TYPE: DNA
<213> ORGANISM: Artificial
<220> FEATURE:
<223> OTHER INFORMATION: Synthetic oligonucleotide PCR primer

<400> SEQUENCE: 253
tttttagaag agcggtcggc                                              20

<210> SEQ ID NO 254
<211> LENGTH: 24
<212> TYPE: DNA
<213> ORGANISM: Artificial
<220> FEATURE:
<223> OTHER INFORMATION: Synthetic oligonucleotide PCR primer

<400> SEQUENCE: 254
ctaataacga aaactacgac gacg                                         24

<210> SEQ ID NO 255
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 255
ttgtgtttta ttgcggagtg c                                            21

<210> SEQ ID NO 256
```

```
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 256
aaccacatat cgatcacgta cg                                              22

<210> SEQ ID NO 257
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 257
gcgttttcgg attttagggt c                                               21

<210> SEQ ID NO 258
<211> LENGTH: 26
<212> TYPE: DNA
<213> ORGANISM: Artificial
<220> FEATURE:
<223> OTHER INFORMATION: Synthetic oligonucleotide PCR primer

<400> SEQUENCE: 258
aactaatcgc cttaaataaa ataccg                                          26

<210> SEQ ID NO 259
<211> LENGTH: 27
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (6)..(6)
<223> OTHER INFORMATION: Universal purine
<220> FEATURE:
<221> NAME/KEY: misc_feature
<222> LOCATION: (14)..(14)
<223> OTHER INFORMATION: Substituted thymine
<220> FEATURE:
<221> NAME/KEY: misc_feature
<222> LOCATION: (17)..(17)
<223> OTHER INFORMATION: a, c, g, or t conjugated to a quencher
<220> FEATURE:
<221> NAME/KEY: misc_feature
<222> LOCATION: (21)..(21)
<223> OTHER INFORMATION: Substituted thymine
<220> FEATURE:
<221> NAME/KEY: misc_feature
<222> LOCATION: (27)..(27)
<223> OTHER INFORMATION: 3' quencher and/or blocker

<400> SEQUENCE: 259
cctccraacc ttataanaaa taatccc                                         27

<210> SEQ ID NO 260
<211> LENGTH: 25
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
```

```
<222> LOCATION: (1)..(1)
<223> OTHER INFORMATION: Conjugated to a fluor
<220> FEATURE:
<221> NAME/KEY: misc_feature
<222> LOCATION: (7)..(7)
<223> OTHER INFORMATION: Universal purine
<220> FEATURE:
<221> NAME/KEY: misc_feature
<222> LOCATION: (17)..(17)
<223> OTHER INFORMATION: a, c, g, or t conjugated to a quencher
<220> FEATURE:
<221> NAME/KEY: misc_feature
<222> LOCATION: (20)..(20)
<223> OTHER INFORMATION: Substituted thymine
<220> FEATURE:
<221> NAME/KEY: misc_feature
<222> LOCATION: (25)..(25)
<223> OTHER INFORMATION: 3' quencher and/or blocker

<400> SEQUENCE: 260
aaaaacrccc taatccncat ccaac                                          25

<210> SEQ ID NO 261
<211> LENGTH: 29
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (15)..(15)
<223> OTHER INFORMATION: Substituted thymine
<220> FEATURE:
<221> NAME/KEY: misc_feature
<222> LOCATION: (25)..(25)
<223> OTHER INFORMATION: Substituted thymine
<220> FEATURE:
<221> NAME/KEY: misc_feature
<222> LOCATION: (29)..(29)
<223> OTHER INFORMATION: 3' quencher and/or blocker

<400> SEQUENCE: 261
cacttaactt cctctccaaa aatctaaac                                      29

<210> SEQ ID NO 262
<211> LENGTH: 22
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (6)..(6)
<223> OTHER INFORMATION: Substituted thymine
<220> FEATURE:
<221> NAME/KEY: misc_feature
<222> LOCATION: (11)..(11)
<223> OTHER INFORMATION: Universal pyrimidine
<220> FEATURE:
<221> NAME/KEY: misc_feature
<222> LOCATION: (13)..(13)
<223> OTHER INFORMATION: Substituted thymine
<220> FEATURE:
<221> NAME/KEY: misc_feature
<222> LOCATION: (18)..(18)
<223> OTHER INFORMATION: Universal pyrimidine

<400> SEQUENCE: 262
gtttttagaa ygtttttgygt tt                                            22
```

<210> SEQ ID NO 263
<211> LENGTH: 22
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (6)..(6)
<223> OTHER INFORMATION: Substituted thymine
<220> FEATURE:
<221> NAME/KEY: misc_feature
<222> LOCATION: (13)..(13)
<223> OTHER INFORMATION: Substituted thymine

<400> SEQUENCE: 263
gtttttagaa ygttttgygt tt                                              22

<210> SEQ ID NO 264
<211> LENGTH: 20
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (8)..(8)
<223> OTHER INFORMATION: Substituted thymine
<220> FEATURE:
<221> NAME/KEY: misc_feature
<222> LOCATION: (11)..(11)
<223> OTHER INFORMATION: Universal purine

<400> SEQUENCE: 264
aaaaaactcc rcactcttcc                                                 20

<210> SEQ ID NO 265
<211> LENGTH: 20
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (8)..(8)
<223> OTHER INFORMATION: Substituted thymine

<400> SEQUENCE: 265
aaaaaactcc rcactcttcc                                                 20

<210> SEQ ID NO 266
<211> LENGTH: 23
<212> TYPE: DNA
<213> ORGANISM: Artificial
<220> FEATURE:
<223> OTHER INFORMATION: Synthetic oligonucleotide PCR primer

<400> SEQUENCE: 266
tttcgacgtt cgtaggtttt cgc                                             23

<210> SEQ ID NO 267
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 267
gcactcttcc gaaaacgaaa cg                                              22

```
<210> SEQ ID NO 268
<211> LENGTH: 24
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (9)..(9)
<223> OTHER INFORMATION: Substituted thymine
<220> FEATURE:
<221> NAME/KEY: misc_feature
<222> LOCATION: (19)..(19)
<223> OTHER INFORMATION: a, c, g, or t conjugated to a quencher
<220> FEATURE:
<221> NAME/KEY: misc_feature
<222> LOCATION: (24)..(24)
<223> OTHER INFORMATION: 3' quencher and/or blocker

<400> SEQUENCE: 268
ccaaacactc accaaatcnc aaac                                              24

<210> SEQ ID NO 269
<211> LENGTH: 24
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (9)..(9)
<223> OTHER INFORMATION: Substituted thymine
<220> FEATURE:
<221> NAME/KEY: misc_feature
<222> LOCATION: (19)..(19)
<223> OTHER INFORMATION: a, c, g, or t conjugated to a quencher
<220> FEATURE:
<221> NAME/KEY: misc_feature
<222> LOCATION: (24)..(24)
<223> OTHER INFORMATION: 3' quencher and/or blocker

<400> SEQUENCE: 269
ccaaacactc accaaatcnc aaac                                              24

<210> SEQ ID NO 270
<211> LENGTH: 28
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (15)..(15)
<223> OTHER INFORMATION: a, c, g, or t conjugated to a quencher
<220> FEATURE:
<221> NAME/KEY: misc_feature
<222> LOCATION: (19)..(19)
<223> OTHER INFORMATION: Substituted thymine
<220> FEATURE:
<221> NAME/KEY: misc_feature
<222> LOCATION: (24)..(24)
```

<223> OTHER INFORMATION: Substituted thymine
<220> FEATURE:
<221> NAME/KEY: misc_feature
<222> LOCATION: (28)..(28)
<223> OTHER INFORMATION: 3' quencher and/or blocker

<400> SEQUENCE: 270
atatctttta ccaacaaata ccttcaaa                                    28

<210> SEQ ID NO 271
<211> LENGTH: 25
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (6)..(6)
<223> OTHER INFORMATION: Universal pyrimidine
<220> FEATURE:
<221> NAME/KEY: misc_feature
<222> LOCATION: (20)..(20)
<223> OTHER INFORMATION: Substituted thymine
<220> FEATURE:
<221> NAME/KEY: misc_feature
<222> LOCATION: (25)..(25)
<223> OTHER INFORMATION: 3' quencher and/or blocker

<400> SEQUENCE: 271
gttttygttt tggttgcgat gttgt                                       25

<210> SEQ ID NO 272
<211> LENGTH: 20
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (9)..(9)
<223> OTHER INFORMATION: Universal pyrimidine

<400> SEQUENCE: 272
ggagataayg gggtttttgg                                             20

<210> SEQ ID NO 273
<211> LENGTH: 22
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (19)..(19)
<223> OTHER INFORMATION: Universal purine

<400> SEQUENCE: 273
cactaaaaat ataccaacra cc                                          22

<210> SEQ ID NO 274
<211> LENGTH: 23
<212> TYPE: DNA
<213> ORGANISM: Artificial
<220> FEATURE:
<223> OTHER INFORMATION: Synthetic oligonucleotide PCR primer

<400> SEQUENCE: 274
ggagagttat ttaagaaagg tgg                                            23

<210> SEQ ID NO 275
<211> LENGTH: 19
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (9)..(9)
<223> OTHER INFORMATION: Universal purine
<220> FEATURE:
<221> NAME/KEY: misc_feature
<222> LOCATION: (11)..(11)
<223> OTHER INFORMATION: Universal purine

<400> SEQUENCE: 275
aaaattacrc raaacccac                                                 19

<210> SEQ ID NO 276
<211> LENGTH: 26
<212> TYPE: DNA
<213> ORGANISM: Artificial
<220> FEATURE:
<223> OTHER INFORMATION: Synthetic oligonucleotide PCR primer

<400> SEQUENCE: 276
cgtgttcgta gggttttttc gttttc                                         26

<210> SEQ ID NO 277
<211> LENGTH: 24
<212> TYPE: DNA
<213> ORGANISM: Artificial
<220> FEATURE:
<223> OTHER INFORMATION: Synthetic oligonucleotide PCR primer

<400> SEQUENCE: 277
ccaacgaccc tcgaaaaaaa aacg                                           24

<210> SEQ ID NO 278
<211> LENGTH: 23
<212> TYPE: DNA
<213> ORGANISM: Artificial
<220> FEATURE:
<223> OTHER INFORMATION: Synthetic oligonucleotide PCR primer

<400> SEQUENCE: 278
gattttgcgg gtacggttta cgc                                            23

<210> SEQ ID NO 279
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 279
gatccctaaa acgccgaaaa caacg                                          25

<210> SEQ ID NO 280
<211> LENGTH: 26
<212> TYPE: DNA
<213> ORGANISM: Artificial
<220> FEATURE:
<223> OTHER INFORMATION: Synthetic oligonucleotide PCR probe
<220> FEATURE:

<221> NAME/KEY: misc_feature
<222> LOCATION: (1)..(1)
<223> OTHER INFORMATION: Conjugated to a fluor cytosine Substituted
<220> FEATURE:
<221> NAME/KEY: misc_feature
<222> LOCATION: (11)..(11)
<223> OTHER INFORMATION: a, c, g, or t conjugated to a quencher
<220> FEATURE:
<221> NAME/KEY: misc_feature
<222> LOCATION: (17)..(17)
<223> OTHER INFORMATION: Substituted thymine
<220> FEATURE:
<221> NAME/KEY: misc_feature
<222> LOCATION: (22)..(22)
<223> OTHER INFORMATION: Substituted thymine
<220> FEATURE:
<221> NAME/KEY: misc_feature
<222> LOCATION: (26)..(26)
<223> OTHER INFORMATION: 3' quencher and/or blocker

<400> SEQUENCE: 280
cgttattttt tttgggtggt ttttcg       26

<210> SEQ ID NO 281
<211> LENGTH: 25
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (13)..(13)
<223> OTHER INFORMATION: a, c, g, or t conjugated to a quencher
<220> FEATURE:
<221> NAME/KEY: misc_feature
<222> LOCATION: (22)..(22)
<223> OTHER INFORMATION: Substituted thymine
<220> FEATURE:
<221> NAME/KEY: misc_feature
<222> LOCATION: (25)..(25)
<223> OTHER INFORMATION: 3' quencher and/or blocker

<400> SEQUENCE: 281
craaaaacca cccaaaaaaa ataac       25

<210> SEQ ID NO 282
<211> LENGTH: 24
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (11)..(11)
<223> OTHER INFORMATION: Universal pyrimidine

<400> SEQUENCE: 282
ggataaatat ygtaaggtat tgag       24

<210> SEQ ID NO 283
<211> LENGTH: 27
<212> TYPE: DNA
<213> ORGANISM: Artificial
<220> FEATURE:
<223> OTHER INFORMATION: Synthetic oligonucleotide PCR primer

<400> SEQUENCE: 283
cgaaatacta aatttctcta attcctc       27

```
<210> SEQ ID NO 284
<211> LENGTH: 22
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (19)..(19)
<223> OTHER INFORMATION: Universal pyrimidine

<400> SEQUENCE: 284
gagttttttt ggttttttyg ag                                              22

<210> SEQ ID NO 285
<211> LENGTH: 23
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (15)..(15)
<223> OTHER INFORMATION: Universal purine

<400> SEQUENCE: 285
ctaaaataaa taccrcaaaa cac                                             23

<210> SEQ ID NO 286
<211> LENGTH: 23
<212> TYPE: DNA
<213> ORGANISM: Artificial
<220> FEATURE:
<223> OTHER INFORMATION: Synthetic oligonucleotide PCR primer

<400> SEQUENCE: 286
cgcgttcgga ttttttttc ggc                                              23

<210> SEQ ID NO 287
<211> LENGTH: 28
<212> TYPE: DNA
<213> ORGANISM: Artificial
<220> FEATURE:
<223> OTHER INFORMATION: Synthetic oligonucleotide PCR primer

<400> SEQUENCE: 287
aaatttctct aattcctccg aacgcacg                                        28

<210> SEQ ID NO 288
<211> LENGTH: 26
<212> TYPE: DNA
<213> ORGANISM: Artificial
<220> FEATURE:
<223> OTHER INFORMATION: Synthetic oligonucleotide PCR primer

<400> SEQUENCE: 288
gcgtacgttg gtcgtttcgt attttc                                          26

<210> SEQ ID NO 289
<211> LENGTH: 29
<212> TYPE: DNA
<213> ORGANISM: Artificial
<220> FEATURE:
<223> OTHER INFORMATION: Synthetic oligonucleotide PCR primer

<400> SEQUENCE: 289
```
gcaaaacact aaacaaacga aaaaacgcg                                                29

<210> SEQ ID NO 290
<211> LENGTH: 28
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (9)..(9)
<223> OTHER INFORMATION: Universal pyrimidine
<220> FEATURE:
<221> NAME/KEY: misc_feature
<222> LOCATION: (15)..(15)
<223> OTHER INFORMATION: Substituted thymine
<220> FEATURE:
<221> NAME/KEY: misc_feature
<222> LOCATION: (17)..(17)
<223> OTHER INFORMATION: a, c, g, or t conjugated to a quencher
<220> FEATURE:
<221> NAME/KEY: misc_feature
<222> LOCATION: (25)..(25)
<223> OTHER INFORMATION: Substituted thymine
<220> FEATURE:
<221> NAME/KEY: misc_feature
<222> LOCATION: (28)..(28)
<223> OTHER INFORMATION: 3' quencher and/or blocker

<400> SEQUENCE: 290
gtagttatyg agagtgngga gcgattag                                                 28

<210> SEQ ID NO 291
<211> LENGTH: 28
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (7)..(7)
<223> OTHER INFORMATION: Universal purine
<220> FEATURE:
<221> NAME/KEY: misc_feature
<222> LOCATION: (16)..(16)
<223> OTHER INFORMATION: Substituted thymine
<220> FEATURE:
<221> NAME/KEY: misc_feature
<222> LOCATION: (20)..(20)
<223> OTHER INFORMATION: a, c, g, or t conjugated to a quencher
<220> FEATURE:
<221> NAME/KEY: misc_feature
<222> LOCATION: (21)..(21)
<223> OTHER INFORMATION: Substituted thymine
<220> FEATURE:
<221> NAME/KEY: misc_feature
<222> LOCATION: (28)..(28)
<223> OTHER INFORMATION: 3' quencher and/or blocker

<400> SEQUENCE: 291
ctaatcrctc cgcactctcn ataactac                                                 28

<210> SEQ ID NO 292
<211> LENGTH: 20
<212> TYPE: DNA
<213> ORGANISM: Artificial

```
<220> FEATURE:
<223> OTHER INFORMATION: Synthetic oligonucleotide PCR primer
<220> FEATURE:
<221> NAME/KEY: misc_feature
<222> LOCATION: (9)..(9)
<223> OTHER INFORMATION: Universal pyrimidine

<400> SEQUENCE: 292
gtttggagyg ttatgagtag                                              20

<210> SEQ ID NO 293
<211> LENGTH: 22
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (13)..(13)
<223> OTHER INFORMATION: Universal purine

<400> SEQUENCE: 293
cttcatatcc ccrataaaac tc                                           22

<210> SEQ ID NO 294
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 294
gggtttttag tcggtttagt g                                            21

<210> SEQ ID NO 295
<211> LENGTH: 21
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (8)..(8)
<223> OTHER INFORMATION: Universal purine
<220> FEATURE:
<221> NAME/KEY: misc_feature
<222> LOCATION: (17)..(17)
<223> OTHER INFORMATION: Universal purine

<400> SEQUENCE: 295
ctaaaacrta aaactcraac c                                            21

<210> SEQ ID NO 296
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 296
gatttagagc gcgttgttcg c                                            21

<210> SEQ ID NO 297
<211> LENGTH: 28
<212> TYPE: DNA
<213> ORGANISM: Artificial
<220> FEATURE:
<223> OTHER INFORMATION: Synthetic oligonucleotide PCR primer
```

-continued

```
<400> SEQUENCE: 297
catatccccg ataaaactca acgactcg                                              28

<210> SEQ ID NO 298
<211> LENGTH: 23
<212> TYPE: DNA
<213> ORGANISM: Artificial
<220> FEATURE:
<223> OTHER INFORMATION: Synthetic oligonucleotide PCR primer

<400> SEQUENCE: 298
gtcggtttag tgatattgcg ggc                                                   23

<210> SEQ ID NO 299
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 299
ccacgaccta aacgtaaacc taacg                                                 25

<210> SEQ ID NO 300
<211> LENGTH: 28
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (7)..(7)
<223> OTHER INFORMATION: Universal pyrimidine
<220> FEATURE:
<221> NAME/KEY: misc_feature
<222> LOCATION: (18)..(18)
<223> OTHER INFORMATION: Substituted thymine
<220> FEATURE:
<221> NAME/KEY: misc_feature
<222> LOCATION: (28)..(28)
<223> OTHER INFORMATION: 3' quencher and/or blocker

<400> SEQUENCE: 300
gatggtyggg ttgggttttt gttttttgg                                             28

<210> SEQ ID NO 301
<211> LENGTH: 28
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (19)..(19)
<223> OTHER INFORMATION: Substituted cytosine
<220> FEATURE:
<221> NAME/KEY: misc_feature
<222> LOCATION: (28)..(28)
<223> OTHER INFORMATION: 3' quencher and/or blocker

<400> SEQUENCE: 301
ccaaaaacaa aaacccaacc cgaccatc                                              28
```

```
<210> SEQ ID NO 302
<211> LENGTH: 28
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor cytosine Substituted
<220> FEATURE:
<221> NAME/KEY: misc_feature
<222> LOCATION: (11)..(11)
<223> OTHER INFORMATION: Universal pyrimidine
<220> FEATURE:
<221> NAME/KEY: misc_feature
<222> LOCATION: (16)..(16)
<223> OTHER INFORMATION: Substituted thymine
<220> FEATURE:
<221> NAME/KEY: misc_feature
<222> LOCATION: (20)..(20)
<223> OTHER INFORMATION: a, c, g, or t conjugated to a quencher
<220> FEATURE:
<221> NAME/KEY: misc_feature
<222> LOCATION: (25)..(25)
<223> OTHER INFORMATION: Substituted thymine
<220> FEATURE:
<221> NAME/KEY: misc_feature
<222> LOCATION: (28)..(28)
<223> OTHER INFORMATION: 3' quencher and/or blocker

<400> SEQUENCE: 302
cgtatatttt yggttttttn gggtttcg                                          28

<210> SEQ ID NO 303
<211> LENGTH: 27
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (2)..(2)
<223> OTHER INFORMATION: Universal purine
<220> FEATURE:
<221> NAME/KEY: misc_feature
<222> LOCATION: (8)..(8)
<223> OTHER INFORMATION: Substituted cytosine
<220> FEATURE:
<221> NAME/KEY: misc_feature
<222> LOCATION: (16)..(16)
<223> OTHER INFORMATION: Substituted cytosine
<220> FEATURE:
<221> NAME/KEY: misc_feature
<222> LOCATION: (18)..(18)
<223> OTHER INFORMATION: a, c, g, or t conjugated to a quencher
<220> FEATURE:
<221> NAME/KEY: misc_feature
<222> LOCATION: (27)..(27)
<223> OTHER INFORMATION: 3' quencher and/or blocker

<400> SEQUENCE: 303
craaacccga aaaaccnaa aatatac                                            27

<210> SEQ ID NO 304
<211> LENGTH: 27
<212> TYPE: DNA
<213> ORGANISM: Artificial
<220> FEATURE:
```

<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (10)..(10)
<223> OTHER INFORMATION: Universal pyrimidine
<220> FEATURE:
<221> NAME/KEY: misc_feature
<222> LOCATION: (12)..(12)
<223> OTHER INFORMATION: Substituted thymine
<220> FEATURE:
<221> NAME/KEY: misc_feature
<222> LOCATION: (27)..(27)
<223> OTHER INFORMATION: 3' quencher and/or blocker

<400> SEQUENCE: 304
ggtagttgty gtcgggaagg aggttcg        27

<210> SEQ ID NO 305
<211> LENGTH: 27
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (2)..(2)
<223> OTHER INFORMATION: Universal purine
<220> FEATURE:
<221> NAME/KEY: misc_feature
<222> LOCATION: (18)..(18)
<223> OTHER INFORMATION: a, c, g, or t conjugated to a quencher
<220> FEATURE:
<221> NAME/KEY: misc_feature
<222> LOCATION: (24)..(24)
<223> OTHER INFORMATION: Substituted thymine
<220> FEATURE:
<221> NAME/KEY: misc_feature
<222> LOCATION: (27)..(27)
<223> OTHER INFORMATION: 3' quencher and/or blocker

<400> SEQUENCE: 305
craacctcct tcccgacnac aactacc        27

<210> SEQ ID NO 306
<211> LENGTH: 29
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (14)..(14)
<223> OTHER INFORMATION: Substituted thymine
<220> FEATURE:
<221> NAME/KEY: misc_feature
<222> LOCATION: (24)..(24)
<223> OTHER INFORMATION: Substituted thymine
<220> FEATURE:
<221> NAME/KEY: misc_feature
<222> LOCATION: (29)..(29)
<223> OTHER INFORMATION: 3' quencher and/or blocker

<400> SEQUENCE: 306
ggtttttttt gtatagatgt ggttaatgg                    29

<210> SEQ ID NO 307
<211> LENGTH: 29
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (13)..(13)
<223> OTHER INFORMATION: Substituted thymine
<220> FEATURE:
<221> NAME/KEY: misc_feature
<222> LOCATION: (17)..(17)
<223> OTHER INFORMATION: Substituted thymine
<220> FEATURE:
<221> NAME/KEY: misc_feature
<222> LOCATION: (29)..(29)
<223> OTHER INFORMATION: 3' quencher and/or blocker

<400> SEQUENCE: 307
ccattaacca catctataca aaaaaaacc                    29

<210> SEQ ID NO 308
<211> LENGTH: 24
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (15)..(15)
<223> OTHER INFORMATION: Universal pyrimidine

<400> SEQUENCE: 308
ggtttggttt atagygtatt tagg                         24

<210> SEQ ID NO 309
<211> LENGTH: 27
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (10)..(10)
<223> OTHER INFORMATION: Substituted thymine

<400> SEQUENCE: 309
gaggtttagt aagtttttg gattgtg                       27

<210> SEQ ID NO 310
<211> LENGTH: 26
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (12)..(12)
<223> OTHER INFORMATION: Substituted thymine

<400> SEQUENCE: 310
cccttaaaaa ttacaaaaac cacaac                       26

<210> SEQ ID NO 311
<211> LENGTH: 24
<212> TYPE: DNA
<213> ORGANISM: Artificial
<220> FEATURE:
<223> OTHER INFORMATION: Synthetic oligonucleotide PCR primer

<400> SEQUENCE: 311
gtagattggg tggttaatttt agag        24

<210> SEQ ID NO 312
<211> LENGTH: 20
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (12)..(12)
<223> OTHER INFORMATION: Universal purine
<220> FEATURE:
<221> NAME/KEY: misc_feature
<222> LOCATION: (14)..(14)
<223> OTHER INFORMATION: Universal purine

<400> SEQUENCE: 312
ctataattcc crcrcttttc        20

<210> SEQ ID NO 313
<211> LENGTH: 27
<212> TYPE: DNA
<213> ORGANISM: Artificial
<220> FEATURE:
<223> OTHER INFORMATION: Synthetic oligonucleotide PCR primer

<400> SEQUENCE: 313
ggtggttaat ttagagtttc gagagac        27

<210> SEQ ID NO 314
<211> LENGTH: 28
<212> TYPE: DNA
<213> ORGANISM: Artificial
<220> FEATURE:
<223> OTHER INFORMATION: Synthetic oligonucleotide PCR primer

<400> SEQUENCE: 314
cgttaccacg aaaaccaaaa aactaccg        28

<210> SEQ ID NO 315
<211> LENGTH: 30
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (13)..(13)
<223> OTHER INFORMATION: Substituted thymine
<220> FEATURE:
<221> NAME/KEY: misc_feature
<222> LOCATION: (20)..(20)
<223> OTHER INFORMATION: Substituted thymine
<220> FEATURE:
<221> NAME/KEY: misc_feature
<222> LOCATION: (30)..(30)
<223> OTHER INFORMATION: 3' quencher and/or blocker

<400> SEQUENCE: 315
gatttcgtat tttgagaggt tgttgtttag							30

<210> SEQ ID NO 316
<211> LENGTH: 30
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (14)..(14)
<223> OTHER INFORMATION: Substituted thymine
<220> FEATURE:
<221> NAME/KEY: misc_feature
<222> LOCATION: (22)..(22)
<223> OTHER INFORMATION: Substituted thymine
<220> FEATURE:
<221> NAME/KEY: misc_feature
<222> LOCATION: (30)..(30)
<223> OTHER INFORMATION: 3' quencher and/or blocker

<400> SEQUENCE: 316
ctaaacaaca acctctcaaa atacgaaatc						30

<210> SEQ ID NO 317
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 317
ggtagattgg gtggttaatt tagag							25

<210> SEQ ID NO 318
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 318
ccaaaaaatc tcaacraact c								21

<210> SEQ ID NO 319
<211> LENGTH: 28
<212> TYPE: DNA
<213> ORGANISM: Artificial
<220> FEATURE:
<223> OTHER INFORMATION: Synthetic oligonucleotide PCR primer

<400> SEQUENCE: 319
gggtggttaa tttagagttt cgagagac						28

<210> SEQ ID NO 320
<211> LENGTH: 24
<212> TYPE: DNA
<213> ORGANISM: Artificial
<220> FEATURE:
<223> OTHER INFORMATION: Synthetic oligonucleotide PCR primer

<400> SEQUENCE: 320
accacgaaaa ccaaaaaact accg                                              24

<210> SEQ ID NO 321
<211> LENGTH: 26
<212> TYPE: DNA
<213> ORGANISM: Artificial
<220> FEATURE:
<223> OTHER INFORMATION: Synthetic oligonucleotide PCR primer

<400> SEQUENCE: 321
gggattttgt ttaagtatgt taaagg                                            26

<210> SEQ ID NO 322
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 322
cctaccttac ctctaaatac caacc                                             25

<210> SEQ ID NO 323
<211> LENGTH: 29
<212> TYPE: DNA
<213> ORGANISM: Artificial
<220> FEATURE:
<223> OTHER INFORMATION: Synthetic oligonucleotide PCR primer

<400> SEQUENCE: 323
gtatgttaaa gggttgttgt aagttaagg                                         29

<210> SEQ ID NO 324
<211> LENGTH: 23
<212> TYPE: DNA
<213> ORGANISM: Artificial
<220> FEATURE:
<223> OTHER INFORMATION: Synthetic oligonucleotide PCR primer

<400> SEQUENCE: 324
cctctaaata caaccccaa acc                                                23

<210> SEQ ID NO 325
<211> LENGTH: 29
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (11)..(11)
<223> OTHER INFORMATION: a, c, g, or t conjugated to a quencher
<220> FEATURE:
<221> NAME/KEY: misc_feature
<222> LOCATION: (29)..(29)
<223> OTHER INFORMATION: 3' quencher and/or blocker

<400> SEQUENCE: 325
ccaactactc caaaaaactt ccaaaaacc                                         29

<210> SEQ ID NO 326
<211> LENGTH: 29
<212> TYPE: DNA
<213> ORGANISM: Artificial

```
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (6)..(6)
<223> OTHER INFORMATION: Substituted thymine
<220> FEATURE:
<221> NAME/KEY: misc_feature
<222> LOCATION: (19)..(19)
<223> OTHER INFORMATION: Substituted thymine
<220> FEATURE:
<221> NAME/KEY: misc_feature
<222> LOCATION: (29)..(29)
<223> OTHER INFORMATION: 3' quencher and/or blocker

<400> SEQUENCE: 326
ccaactactc caaaaaactt ccaaaaacc                                    29

<210> SEQ ID NO 327
<211> LENGTH: 29
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (18)..(18)
<223> OTHER INFORMATION: Substituted thymine

<400> SEQUENCE: 327
gtatgttaaa gggttgttgt aagttaagg                                    29

<210> SEQ ID NO 328
<211> LENGTH: 23
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (15)..(15)
<223> OTHER INFORMATION: Substituted cytosine

<400> SEQUENCE: 328
cctctaaata ccaccccaa acc                                           23

<210> SEQ ID NO 329
<211> LENGTH: 28
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (19)..(19)
<223> OTHER INFORMATION: Substituted thymine
<220> FEATURE:
<221> NAME/KEY: misc_feature
<222> LOCATION: (28)..(28)
<223> OTHER INFORMATION: 3' quencher and/or blocker

<400> SEQUENCE: 329
ccaccaccca acacacaata acaaacac                                     28
```

<210> SEQ ID NO 330
<211> LENGTH: 28
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (19)..(19)
<223> OTHER INFORMATION: Substituted thymine
<220> FEATURE:
<221> NAME/KEY: misc_feature
<222> LOCATION: (28)..(28)
<223> OTHER INFORMATION: 3' quencher and/or blocker

<400> SEQUENCE: 330
ccaccaccca acacacaata acaaacac                                          28

<210> SEQ ID NO 331
<211> LENGTH: 20
<212> TYPE: DNA
<213> ORGANISM: Artificial
<220> FEATURE:
<223> OTHER INFORMATION: Synthetic oligonucleotide PCR primer

<400> SEQUENCE: 331
atttagagcg cgttgttcgc                                                   20

<210> SEQ ID NO 332
<211> LENGTH: 27
<212> TYPE: DNA
<213> ORGANISM: Artificial
<220> FEATURE:
<223> OTHER INFORMATION: Synthetic oligonucleotide PCR primer

<400> SEQUENCE: 332
atatccccga taaaactcaa cgactcg                                           27

<210> SEQ ID NO 333
<211> LENGTH: 26
<212> TYPE: DNA
<213> ORGANISM: Artificial
<220> FEATURE:
<223> OTHER INFORMATION: Synthetic oligonucleotide PCR primer

<400> SEQUENCE: 333
tatccccgat aaaactcaac gactcg                                            26

<210> SEQ ID NO 334
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 334
atccccgata aaactcaacg actcg                                             25

<210> SEQ ID NO 335
<211> LENGTH: 22
<212> TYPE: DNA
<213> ORGANISM: Artificial
<220> FEATURE:
<223> OTHER INFORMATION: Synthetic oligonucleotide PCR primer

```
<400> SEQUENCE: 335
gcgttcggat tttttttttcg gc                                          22

<210> SEQ ID NO 336
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 336
tttctctaat tcctccgaac gcacg                                        25

<210> SEQ ID NO 337
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 337
ctctaattcc tccgaacgca cg                                           22

<210> SEQ ID NO 338
<211> LENGTH: 28
<212> TYPE: DNA
<213> ORGANISM: Artificial
<220> FEATURE:
<223> OTHER INFORMATION: Synthetic oligonucleotide PCR primer

<400> SEQUENCE: 338
gtgacgatta gagttagatt tagagcgc                                     28

<210> SEQ ID NO 339
<211> LENGTH: 28
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (15)..(15)
<223> OTHER INFORMATION: Substituted thymine
<220> FEATURE:
<221> NAME/KEY: misc_feature
<222> LOCATION: (25)..(25)
<223> OTHER INFORMATION: Substituted thymine
<220> FEATURE:
<221> NAME/KEY: misc_feature
<222> LOCATION: (28)..(28)
<223> OTHER INFORMATION: 3' quencher and/or blocker

<400> SEQUENCE: 339
gtagttatcg agagtgcgga gcgattag                                     28

<210> SEQ ID NO 340
<211> LENGTH: 26
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
```

```
<223> OTHER INFORMATION: Conjugated to a fluor
<220> FEATURE:
<221> NAME/KEY: misc_feature
<222> LOCATION: (26)..(26)
<223> OTHER INFORMATION: 3' quencher and/or blocker

<400> SEQUENCE: 340
ccaacccgac catcaccgcg aacaac                                            26

<210> SEQ ID NO 341
<211> LENGTH: 25
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (15)..(15)
<223> OTHER INFORMATION: Substituted thymine

<400> SEQUENCE: 341
ggagagtgta tttgtgaagg aaatg                                             25

<210> SEQ ID NO 342
<211> LENGTH: 25
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (19)..(19)
<223> OTHER INFORMATION: Substituted thymine

<400> SEQUENCE: 342
catacataca ccaaacaatt cattc                                             25

<210> SEQ ID NO 343
<211> LENGTH: 31
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (11)..(11)
<223> OTHER INFORMATION: Conjugated to a fluor
<220> FEATURE:
<221> NAME/KEY: misc_feature
<222> LOCATION: (26)..(26)
<223> OTHER INFORMATION: Conjugated to a fluor
<220> FEATURE:
<221> NAME/KEY: misc_feature
<222> LOCATION: (31)..(31)
<223> OTHER INFORMATION: 3' quencher and/or blocker

<400> SEQUENCE: 343
ccaaatacca taaccatttt attaataaca c                                      31

<210> SEQ ID NO 344
<211> LENGTH: 31
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
```

```
<222> LOCATION: (1)..(1)
<223> OTHER INFORMATION: Conjugated to a fluor
<220> FEATURE:
<221> NAME/KEY: misc_feature
<222> LOCATION: (11)..(11)
<223> OTHER INFORMATION: Conjugated to a fluor
<220> FEATURE:
<221> NAME/KEY: misc_feature
<222> LOCATION: (31)..(31)
<223> OTHER INFORMATION: 3' quencher and/or blocker
<220> FEATURE:
<221> NAME/KEY: misc_feature
<222> LOCATION: (36)..(36)
<223> OTHER INFORMATION: Conjugated to a fluor

<400> SEQUENCE: 344
ccaaatacca taaccatttt attaataaca c                          31

<210> SEQ ID NO 345
<211> LENGTH: 18
<212> TYPE: DNA
<213> ORGANISM: Artificial
<220> FEATURE:
<223> OTHER INFORMATION: Synthetic oligonucleotide PCR primer

<400> SEQUENCE: 345
ggtttygttg gggatttg                                         18

<210> SEQ ID NO 346
<211> LENGTH: 20
<212> TYPE: DNA
<213> ORGANISM: Artificial
<220> FEATURE:
<223> OTHER INFORMATION: Synthetic oligonucleotide PCR primer

<400> SEQUENCE: 346
accrctcttc taaaaaatcc                                       20

<210> SEQ ID NO 347
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 347 aggtttttc ggttagttgc gc                                     22

<210> SEQ ID NO 348
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 348
aacgtcgacc gcaaaaaaac g                                     21

<210> SEQ ID NO 349
<211> LENGTH: 21
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor cytosine Substituted
<220> FEATURE:
```

<221> NAME/KEY: misc_feature
<222> LOCATION: (7)..(7)
<223> OTHER INFORMATION: Substituted thymine
<220> FEATURE:
<221> NAME/KEY: misc_feature
<222> LOCATION: (9)..(9)
<223> OTHER INFORMATION: a, c, g, or t conjugated to a quencher
<220> FEATURE:
<221> NAME/KEY: misc_feature
<222> LOCATION: (15)..(15)
<223> OTHER INFORMATION: Substituted thymine
<220> FEATURE:
<221> NAME/KEY: misc_feature
<222> LOCATION: (17)..(17)
<223> OTHER INFORMATION: Substituted thymine
<220> FEATURE:
<221> NAME/KEY: misc_feature
<222> LOCATION: (21)..(21)
<223> OTHER INFORMATION: 3' quencher and/or blocker

<400> SEQUENCE: 349
cgcgatttcg gggattttag g                                    21

<210> SEQ ID NO 350
<211> LENGTH: 20
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (3)..(3)
<223> OTHER INFORMATION: Substituted thymine
<220> FEATURE:
<221> NAME/KEY: misc_feature
<222> LOCATION: (8)..(8)
<223> OTHER INFORMATION: Conjugated to a fluor
<220> FEATURE:
<221> NAME/KEY: misc_feature
<222> LOCATION: (10)..(10)
<223> OTHER INFORMATION: a, c, g, or t conjugated to a quencher
<220> FEATURE:
<221> NAME/KEY: misc_feature
<222> LOCATION: (17)..(17)
<223> OTHER INFORMATION: Substituted thymine
<220> FEATURE:
<221> NAME/KEY: misc_feature
<222> LOCATION: (20)..(20)
<223> OTHER INFORMATION: 3' quencher and/or blocker

<400> SEQUENCE: 350
cctaaaatcc ccgaaatcgc                                      20

<210> SEQ ID NO 351
<211> LENGTH: 23
<212> TYPE: DNA
<213> ORGANISM: Artificial
<220> FEATURE:
<223> OTHER INFORMATION: Synthetic oligonucleotide PCR primer

<400> SEQUENCE: 351
gaagtagttg tgtaattygt tgg                                  23

<210> SEQ ID NO 352
<211> LENGTH: 19
<212> TYPE: DNA
<213> ORGANISM: Artificial
<220> FEATURE:
<223> OTHER INFORMATION: Synthetic oligonucleotide PCR primer

<400> SEQUENCE: 352
caccctaacr aactacacc                                                19

<210> SEQ ID NO 353
<211> LENGTH: 26
<212> TYPE: DNA
<213> ORGANISM: Artificial
<220> FEATURE:
<223> OTHER INFORMATION: Synthetic oligonucleotide PCR primer

<400> SEQUENCE: 353
tgcggattag ggcgtttttt attttc                                        26

<210> SEQ ID NO 354
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 354
tacaaccaca tatcgatcac gtacg                                         25

<210> SEQ ID NO 355
<211> LENGTH: 21
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (13)..(13)
<223> OTHER INFORMATION: Substituted thymine
<220> FEATURE:
<221> NAME/KEY: misc_feature
<222> LOCATION: (17)..(17)
<223> OTHER INFORMATION: Substituted thymine
<220> FEATURE:
<221> NAME/KEY: misc_feature
<222> LOCATION: (21)..(21)
<223> OTHER INFORMATION: 3' quencher and/or blocker

<400> SEQUENCE: 355
ggagttcgtc gattggttgg g                                             21

<210> SEQ ID NO 356
<211> LENGTH: 21
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (10)..(10)
<223> OTHER INFORMATION: Substituted thymine
<220> FEATURE:
<221> NAME/KEY: misc_feature
<222> LOCATION: (19)..(19)
<223> OTHER INFORMATION: Substituted thymine
<220> FEATURE:
<221> NAME/KEY: misc_feature
<222> LOCATION: (21)..(21)

<223> OTHER INFORMATION: 3' quencher and/or blocker

<400> SEQUENCE: 356
cccaaccaat cgacgaactc c    21

<210> SEQ ID NO 357
<211> LENGTH: 21
<212> TYPE: DNA
<213> ORGANISM: Artificial
<220> FEATURE:
<223> OTHER INFORMATION: Synthetic oligonucleotide PCR primer

<400> SEQUENCE: 357
gagtttttyg gagggttata g    21

<210> SEQ ID NO 358
<211> LENGTH: 24
<212> TYPE: DNA
<213> ORGANISM: Artificial
<220> FEATURE:
<223> OTHER INFORMATION: Synthetic oligonucleotide PCR primer

<400> SEQUENCE: 358
caaactacaa aaacattca atcc    24

<210> SEQ ID NO 359
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 359
gcgtttgggt ttttcggtg tc    22

<210> SEQ ID NO 360
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 360
atcgccgcaa ttaaaaaacc cg    22

<210> SEQ ID NO 361
<211> LENGTH: 27
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (16)..(16)
<223> OTHER INFORMATION: Substituted thymine
<220> FEATURE:
<221> NAME/KEY: misc_feature
<222> LOCATION: (23)..(23)
<223> OTHER INFORMATION: Substituted thymine
<220> FEATURE:
<221> NAME/KEY: misc_feature
<222> LOCATION: (27)..(27)
<223> OTHER INFORMATION: 3' quencher and/or blocker

<400> SEQUENCE: 361
ggttcgcgtt ttaattttta ggtattg                                27

<210> SEQ ID NO 362
<211> LENGTH: 27
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (8)..(8)
<223> OTHER INFORMATION: Substituted thymine
<220> FEATURE:
<221> NAME/KEY: misc_feature
<222> LOCATION: (15)..(15)
<223> OTHER INFORMATION: Substituted thymine
<220> FEATURE:
<221> NAME/KEY: misc_feature
<222> LOCATION: (27)..(27)
<223> OTHER INFORMATION: 3' quencher and/or blocker

<400> SEQUENCE: 362
caatacctaa aaattaaaac gcgaacc                                27

<210> SEQ ID NO 363
<211> LENGTH: 20
<212> TYPE: DNA
<213> ORGANISM: Artificial
<220> FEATURE:
<223> OTHER INFORMATION: Synthetic oligonucleotide PCR primer

<400> SEQUENCE: 363
gttatggatt yggaygttag                                       20

<210> SEQ ID NO 364
<211> LENGTH: 19
<212> TYPE: DNA
<213> ORGANISM: Artificial
<220> FEATURE:
<223> OTHER INFORMATION: Synthetic oligonucleotide PCR primer

<400> SEQUENCE: 364
ctccracraa caatcactc                                        19

<210> SEQ ID NO 365
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 365
gtttggtgtt tagtcgttcg tc                                    22

<210> SEQ ID NO 366
<211> LENGTH: 23
<212> TYPE: DNA
<213> ORGANISM: Artificial
<220> FEATURE:
<223> OTHER INFORMATION: Synthetic oligonucleotide PCR primer

<400> SEQUENCE: 366
cactcgaaat aaacgaaaac acg                                   23

<210> SEQ ID NO 367
<211> LENGTH: 25
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (12)..(12)
<223> OTHER INFORMATION: Substituted thymine
<220> FEATURE:
<221> NAME/KEY: misc_feature
<222> LOCATION: (19)..(19)
<223> OTHER INFORMATION: Substituted thymine
<220> FEATURE:
<221> NAME/KEY: misc_feature
<222> LOCATION: (25)..(25)
<223> OTHER INFORMATION: 3' quencher and/or blocker

<400> SEQUENCE: 367
ggtagtagcg gtagcgtttt tattg                                 25

<210> SEQ ID NO 368
<211> LENGTH: 25
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (13)..(13)
<223> OTHER INFORMATION: Substituted thymine
<220> FEATURE:
<221> NAME/KEY: misc_feature
<222> LOCATION: (19)..(19)
<223> OTHER INFORMATION: Substituted thymine
<220> FEATURE:
<221> NAME/KEY: misc_feature
<222> LOCATION: (25)..(25)
<223> OTHER INFORMATION: 3' quencher and/or blocker

<400> SEQUENCE: 368
caataaaaac gctaccgcta ctacc                                 25

<210> SEQ ID NO 369
<211> LENGTH: 19
<212> TYPE: DNA
<213> ORGANISM: Artificial
<220> FEATURE:
<223> OTHER INFORMATION: Synthetic oligonucleotide PCR primer

<400> SEQUENCE: 369
ggygtagttt atttyggtt                                        19

<210> SEQ ID NO 370
<211> LENGTH: 20
<212> TYPE: DNA
<213> ORGANISM: Artificial
<220> FEATURE:
<223> OTHER INFORMATION: Synthetic oligonucleotide PCR primer

<400> SEQUENCE: 370
atttaaccra ctcraccaac                                       20

<210> SEQ ID NO 371
<211> LENGTH: 24
<212> TYPE: DNA
<213> ORGANISM: Artificial
<220> FEATURE:
<223> OTHER INFORMATION: Synthetic oligonucleotide PCR primer

<400> SEQUENCE: 371
gtatgtttcg cggtttcgta gttc                                          24

<210> SEQ ID NO 372
<211> LENGTH: 22
<212> TYPE: DNA
<213> ORGANISM: Artificial
<220> FEATURE:
<223> OTHER INFORMATION: Synthetic oligonucleotide PCR primer
<220> FEATURE:
<221> NAME/KEY: misc_feature
<222> LOCATION: (14)..(14)
<223> OTHER INFORMATION: Substituted thymine

<400> SEQUENCE: 372
actaaaccta acgttcgaaa cg                                            22

<210> SEQ ID NO 373
<211> LENGTH: 27
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor cytosine Substituted
<220> FEATURE:
<221> NAME/KEY: misc_feature
<222> LOCATION: (12)..(12)
<223> OTHER INFORMATION: a, c, g, or t conjugated to a quencher
<220> FEATURE:
<221> NAME/KEY: misc_feature
<222> LOCATION: (14)..(14)
<223> OTHER INFORMATION: Substituted thymine
<220> FEATURE:
<221> NAME/KEY: misc_feature
<222> LOCATION: (22)..(22)
<223> OTHER INFORMATION: Substituted thymine
<220> FEATURE:
<221> NAME/KEY: misc_feature
<222> LOCATION: (27)..(27)
<223> OTHER INFORMATION: 3' quencher and/or blocker

<400> SEQUENCE: 373
cgttcgttcg gtgtattttt ttttcgg                                       27

<210> SEQ ID NO 374
<211> LENGTH: 26
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (13)..(13)
<223> OTHER INFORMATION: a, c, g, or t conjugated to a quencher
<220> FEATURE:
<221> NAME/KEY: misc_feature
<222> LOCATION: (15)..(15)

```
<223> OTHER INFORMATION: Substituted cytosine
<220> FEATURE:
<221> NAME/KEY: misc_feature
<222> LOCATION: (22)..(22)
<223> OTHER INFORMATION: Substituted cytosine
<220> FEATURE:
<221> NAME/KEY: misc_feature
<222> LOCATION: (26)..(26)
<223> OTHER INFORMATION: 3' quencher and/or blocker

<400> SEQUENCE: 374
ccgaaaaaaa aatacaccga acgaac                                              26

<210> SEQ ID NO 375
<211> LENGTH: 24
<212> TYPE: DNA
<213> ORGANISM: Artificial
<220> FEATURE:
<223> OTHER INFORMATION: Synthetic oligonucleotide PCR primer

<400> SEQUENCE: 375
gtttgagttg ttttgatttt agtg                                                24

<210> SEQ ID NO 376
<211> LENGTH: 20
<212> TYPE: DNA
<213> ORGANISM: Artificial
<220> FEATURE:
<223> OTHER INFORMATION: Synthetic oligonucleotide PCR primer

<400> SEQUENCE: 376
ctccaacctc aactctaaac                                                     20

<210> SEQ ID NO 377
<211> LENGTH: 26
<212> TYPE: DNA
<213> ORGANISM: Artificial
<220> FEATURE:
<223> OTHER INFORMATION: Synthetic oligonucleotide PCR primer

<400> SEQUENCE: 377
gattttagtg tcgcgtattt tggttc                                              26

<210> SEQ ID NO 378
<211> LENGTH: 24
<212> TYPE: DNA
<213> ORGANISM: Artificial
<220> FEATURE:
<223> OTHER INFORMATION: Synthetic oligonucleotide PCR primer

<400> SEQUENCE: 378
ctaaactaaa tcccgcgaac ctcg                                                24

<210> SEQ ID NO 379
<211> LENGTH: 28
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (9)..(9)
<223> OTHER INFORMATION: Substituted thymine
<220> FEATURE:
<221> NAME/KEY: misc_feature
```

<222> LOCATION: (17)..(17)
<223> OTHER INFORMATION: a, c, g, or t conjugated to a quencher
<220> FEATURE:
<221> NAME/KEY: misc_feature
<222> LOCATION: (20)..(20)
<223> OTHER INFORMATION: Substituted thymine
<220> FEATURE:
<221> NAME/KEY: misc_feature
<222> LOCATION: (28)..(28)
<223> OTHER INFORMATION: 3' quencher and/or blocker

<400> SEQUENCE: 379
ggttttattg ggggttnatt tcgggtag                                    28

<210> SEQ ID NO 380
<211> LENGTH: 28
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (17)..(17)
<223> OTHER INFORMATION: Substituted cytosine
<220> FEATURE:
<221> NAME/KEY: misc_feature
<222> LOCATION: (21)..(21)
<223> OTHER INFORMATION: a, c, g, or t conjugated to a quencher
<220> FEATURE:
<221> NAME/KEY: misc_feature
<222> LOCATION: (27)..(27)
<223> OTHER INFORMATION: Substituted cytosine
<220> FEATURE:
<221> NAME/KEY: misc_feature
<222> LOCATION: (28)..(28)
<223> OTHER INFORMATION: 3' quencher and/or blocker

<400> SEQUENCE: 380
ctacccgaaa taaccccaa ntaaaacc                                     28

<210> SEQ ID NO 381
<211> LENGTH: 24
<212> TYPE: DNA
<213> ORGANISM: Artificial
<220> FEATURE:
<223> OTHER INFORMATION: Synthetic oligonucleotide PCR primer

<400> SEQUENCE: 381
ggtttttagt atttttayga aggt                                        24

<210> SEQ ID NO 382
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 382
cratacraaa acctactctc ta                                          22

<210> SEQ ID NO 383
<211> LENGTH: 25
<212> TYPE: DNA
<213> ORGANISM: Artificial
<220> FEATURE:
<223> OTHER INFORMATION: Synthetic oligonucleotide PCR primer

```
<400> SEQUENCE: 383
tttggatttt gttcgtcgtt agtgc                                          25

<210> SEQ ID NO 384
<211> LENGTH: 22
<212> TYPE: DNA
<213> ORGANISM: Artificial
<220> FEATURE:
<223> OTHER INFORMATION: Synthetic oligonucleotide PCR primer

<400> SEQUENCE: 384
ctactctcta aacccgcgaa cg                                             22

<210> SEQ ID NO 385
<211> LENGTH: 24
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (12)..(12)
<223> OTHER INFORMATION: Substituted thymine
<220> FEATURE:
<221> NAME/KEY: misc_feature
<222> LOCATION: (24)..(24)
<223> OTHER INFORMATION: 3' quencher and/or blocker

<400> SEQUENCE: 385
ggttttagtc gtcgcggacg atgt                                           24

<210> SEQ ID NO 386
<211> LENGTH: 24
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (18)..(18)
<223> OTHER INFORMATION: Substituted thymine
<220> FEATURE:
<221> NAME/KEY: misc_feature
<222> LOCATION: (24)..(24)
<223> OTHER INFORMATION: 3' quencher and/or blocker

<400> SEQUENCE: 386
acatcgtccg cgacgactaa aacc                                           24

<210> SEQ ID NO 387
<211> LENGTH: 25
<212> TYPE: DNA
<213> ORGANISM: Artificial
<220> FEATURE:
<223> OTHER INFORMATION: Synthetic oligonucleotide PCR primer

<400> SEQUENCE: 387
gagttagatt tagagcgcgt tgttc                                          25

<210> SEQ ID NO 388
<211> LENGTH: 23
```

```
<212> TYPE: DNA
<213> ORGANISM: Artificial
<220> FEATURE:
<223> OTHER INFORMATION: Synthetic oligonucleotide PCR primer

<400> SEQUENCE: 388
gagcgcgttc ggattttttt ttc                                            23

<210> SEQ ID NO 389
<211> LENGTH: 19
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (10)..(10)
<223> OTHER INFORMATION: Substituted thymine
<220> FEATURE:
<221> NAME/KEY: misc_feature
<222> LOCATION: (14)..(14)
<223> OTHER INFORMATION: Substituted thymine
<220> FEATURE:
<221> NAME/KEY: misc_feature
<222> LOCATION: (19)..(19)
<223> OTHER INFORMATION: 3' quencher and/or blocker

<400> SEQUENCE: 389 tggyggggt agatatttt                                                  19

<210> SEQ ID NO 390
<211> LENGTH: 24
<212> TYPE: DNA
<213> ORGANISM: Artificial
<220> FEATURE:
<223> OTHER INFORMATION: Synthetic oligonucleotide PCR probe
<220> FEATURE:
<221> NAME/KEY: misc_feature
<222> LOCATION: (1)..(1)
<223> OTHER INFORMATION: Conjugated to a fluor
<220> FEATURE:
<221> NAME/KEY: misc_feature
<222> LOCATION: (24)..(24)
<223> OTHER INFORMATION: 3' quencher and/or blocker

<400> SEQUENCE: 390
tctactcaaa actctcccct ctcc                                           24
```

INTEGRATED PURIFICATION AND MEASUREMENT OF DNA METHYLATION AND CO-MEASUREMENT OF MUTATIONS AND/OR MRNA EXPRESSION LEVELS IN AN AUTOMATED REACTION CARTRIDGE

CROSS-REFERENCE TO RELATED APPLICATIONS

This application claims priority to and benefit of U.S. Ser. No. 62/175,916, filed on Jun. 15, 2015, which is incorporated herein by reference in its entirety for all purposes.

INCORPORATION OF SEQUENCE LISTING

Incorporated herein by reference in its entirety is the Sequence Listing for the application. The Sequence Listing is disclosed on a computer-readable ASCII text file titled, "CPHDP008 revised ST25.txt", created on Jan. 31, 2017. The sequence listing text file is 127 kb in size.

STATEMENT OF GOVERNMENTAL SUPPORT

[Not Applicable]

BACKGROUND

The genomes of higher eukaryotes contain the modified nucleoside 5-methyl cytosine (5-meC). This modification is usually found as part of the dinucleotide CpG in which cytosine is converted to 5-methylcytosine in a reaction that involves flipping a target cytosine out of an intact double helix and transfer of a methyl group from S-adenosylmethionine by a methyltransferase enzyme (see, e.g., Klimasauskas et al. (1994) Cell 76: 357-369). This enzymatic conversion is the primary epigenetic modification of DNA known to exist in vertebrates and is essential for normal embryonic development (see, e.g., Bird (1992) Cell 70: 5-8; Laird and Jaenisch (1994) Human Mol. Genet. 3: 1487-1495; and Li et al. (1992) Cell 69: 915-926).

In eukaryotes, DNA methylation regulates normal cellular processes such as genomic imprinting, chromosomal instability, and X-chromosome inactivation. Typically, DNA methylation occurs at the fifth carbon position of cytosine at dinucleotide 5'-CpG-3' sites in or near gene promoters termed CpG islands or shores. Methylation controls gene expression by down-regulating transcription either by directly inhibiting transcriptional machinery or indirectly through the recruitment of chromatin remodeling proteins. Chromosomal methylation patterns change dynamically during embryonic development, and the correct methylation patterns have to be maintained throughout an individual's lifetime. Changes in methylation patterns are linked to aging, and errors in DNA methylation are among the earliest changes that occur during oncogenesis. Thus, the detection of methylation at gene promoters is important, inter alia, for diagnosing and/or monitoring patients with cancer.

Epigenetic alterations, including DNA methylation, interrupt the DNA-RNA-protein axis which describes how genetic information is transcribed into messenger RNAs (mRNAs). The correlation between genomic DNA variation, mRNA copy numbers and protein levels may be described by DNA methylation levels. Thus co-measurement of DNA methylation levels and corresponding down-stream mRNA levels can be important to understanding the mechanism of epigenetic cellular regulation.

Several methods have been developed to detect and quantify methylation efficiently and accurately. The most common technique is the bisulfite conversion method which converts unmethylated cytosines to uracil. Once converted, the methylation profile of DNA can be determined by standard PCR techniques, sequencing methods, and the like.

There are several DNA Methylation kits suitable for bisulfite conversion and DNA cleanup (e.g., EZ DNA Methylation™ kits from Zymo Research). Most kits involve several steps, reagents, and incubation times and often require purified DNA before conversion although some kits can utilize tissue or plasma/serum as starting material.

Typically the bisulfite conversion process requires at least four steps: 1) DNA Denaturation; 2) Bisulfite Incubation; 3) DNA Purification; and 4) Desulphonation. The final desulphonation step can be completed on-column or in solution followed by an ethanol precipitation. There are currently no methylation kits that allow a user to complete the entire process—DNA purification, bisulfite incubation, desulphonation, second DNA purification, and methylation-specific PCR all in one step.

SUMMARY

Various embodiments contemplated herein may comprise, but need not be limited to, one or more of the following:

Various embodiments contemplated herein may include, but need not be limited to, one or more of the following:

Embodiment 1

A method of determining the methylation state of a nucleic acid, said method comprising:
 i) contacting a biological sample comprising a nucleic acid to a first matrix material comprising a first column or filter where said matrix material binds and/or filters nucleic acids in said sample and thereby purifies the DNA;
 ii) eluting the bound DNA from the first matrix material and denaturing the DNA to produce eluted denatured DNA;
 iii) heating the eluted DNA in the presence of a bisulfite reagent to produce a deaminated nucleic acid;
 iv) contacting said deaminated nucleic acid to a second matrix material comprising a second column to bind said deaminated nucleic acid to said second matrix material;
 v) desulfonating the bound deaminated nucleic acid and/or simultaneously eluting and desulfonating the nucleic acid by contacting the deaminated nucleic acid with an alkaline solution to produce a converted (e.g., bisulfite converted) nucleic acid;
 vi) eluting said bisulfite converted nucleic acid from said second matrix material; and
 vii) performing methylation specific PCR and/or nucleic acid sequencing, and/or high resolution melting analysis (HRM) on said converted nucleic acid to determine the methylation of said nucleic acid, wherein at least steps iv) through vi) are performed in a single reaction cartridge.

Embodiment 2

The method of embodiment 1, wherein at least steps iv) through vi) are performed in a single reaction cartridge.

Embodiment 3

The method of embodiment 1, wherein at least steps iii) through vi) are performed in a single reaction cartridge.

Embodiment 4

The method of embodiment 1, wherein at least steps ii) through vi) are performed in a single reaction cartridge.

Embodiment 5

The method of embodiment 1, wherein at least steps i) through vi) are performed in a single reaction cartridge.

Embodiment 6

The method according to any one of embodiments 1-5, wherein step vii is performed in the same reaction cartridge.

Embodiment 7

The method according to any one of embodiments 1-6, wherein said first matrix material and said second matrix material are the same material forming the same column.

Embodiment 8

The method according to any one of embodiments 1-7, wherein said first matrix material and said second matrix material form different columns.

Embodiment 9

The method according to any one of embodiments of embodiment 1-8, wherein said methylation specific PCR, when performed, is performed in said cartridge.

Embodiment 10

The method according to any one of embodiments 1-9, wherein said nucleic acid sequencing, when performed, is performed in said cartridge or in a device coupled to said cartridge.

Embodiment 11

The method according to any one of embodiments 1-10, wherein said cartridge comprises a column comprising said first matrix material, a sample receiving chamber, a temperature controlled channel or chamber, a plurality of chambers containing reagents and/or buffers, and when in use at least one of said chambers contains a desulfonation/elution buffer, and wherein said cartridge optionally comprises a second column comprising said second matrix material.

Embodiment 12

The method of embodiment 11, wherein, when in use, at least one of said chambers contains a reagent that provides bisulfite ions.

Embodiment 13

The method according to any one of embodiments 11-12, wherein said second column is absent.

Embodiment 14

The method according to any one of embodiments 11-13, wherein said second column is present.

Embodiment 15

The method according to any one of embodiments 11-14, wherein said cartridge comprises a thermocycling channel or chamber in addition to said temperature controlled channel or chamber.

Embodiment 16

The method according to any one of embodiments 11-14, wherein said temperature controlled channel or chamber is a thermocycling channel or chamber.

Embodiment 17

The method according to any one of embodiments 11-16, wherein said cartridge comprises one or more chambers containing one or more reagents selected from the group consisting of methylation specific PCR primers, methylation specific PCR probes, PCR enzyme(s), and PCR reaction buffer.

Embodiment 18

The method of embodiment 17, wherein said cartridge comprises one or more chambers containing one or more primers and probes for detection of methylation of a forward strand of a bisulfite-converted DNA.

Embodiment 19

The method according to any one of embodiments 17-18, wherein said cartridge comprises one or more chambers containing one or more primers and probes for detection of methylation of a reverse strand of a bisulfite-converted DNA.

Embodiment 20

The method according to any one of embodiments 11-19, wherein said sample receiving chamber, said column(s), said plurality of chambers, and when present, said temperature controlled channel or chamber and/or thermocycling channel or chamber, are selectively in fluid communication.

Embodiment 21

The method of embodiment 20, wherein said sample receiving chamber, said column(s), said plurality of chambers, and when present, said thermocycling channel or chamber, are selectively in fluid communication by microfluidic channels and valves.

Embodiment 22

The method of embodiment 20, wherein said sample receiving chamber, said column(s), said plurality of chambers, and when present, said thermocycling channel or chamber or a port into said thermocycling channel or chamber, are disposed around a central valve and selectively in fluid communication with a channel in said central valve, wherein said central valve is configured to accommodate a plunger that is capable of drawing fluid into or out of a chamber in fluid communication with said central valve.

Embodiment 23

The method according to any one of embodiments 11-22, wherein said cartridge, when in use, comprises:
  a first chamber containing a sample;
  a second chamber containing a guanidinium thiocyanate-ethanol (GTC-EtOH) solution;
  a third chamber containing a bisulfite reagent;
  a fourth chamber containing a buffer;
  a fifth chamber containing a rinse solution; and
  a sixth chamber containing an elution/desulfonation reagent.

Embodiment 24

The method of embodiment 23, wherein first chamber contains said sample in a GTC-EtOH-Tween extraction/precipitation reagent.

Embodiment 25

The method according to any one of embodiments 23-24, wherein the GTC-ETOH-Tween buffer is added at or near the time the sample is placed into the cartridge.

Embodiment 26

The method according to any one of embodiments 23-25, wherein the bisulfite reagent is added to the cartridge at or near the time the sample is placed in the cartridge.

Embodiment 27

The method of embodiment 23, wherein the GTC-ETOH-Tween buffer is provided as a component of the cartridge.

Embodiment 28

The method according to any one of embodiments 23-25, wherein the bisulfite reagent is provided as a component of the cartridge.

Embodiment 29

The method according to any one of embodiments 11-28, wherein said cartridge comprises a seventh chamber containing PCR primers and/or probes and/or PCR enzymes.

Embodiment 30

The method according to any one of embodiments 11-29, wherein said cartridge comprises an eighth chamber also containing PCR primers and/or probes and/or PCR enzymes.

Embodiment 31

The method of embodiments 29-30, wherein said PCR primers, and/or probes, and/or enzymes are provided as beads.

Embodiment 32

The method according to any one of embodiments 1-31, wherein said biological sample comprises one or more samples selected from the group consisting of a cell, a tissue, and a biological fluid containing a nucleic acid.

Embodiment 33

The method of embodiment 32, wherein said biological sample comprises a biological fluid selected from the group consisting of whole blood, plasma, serum, saliva, mucus, urine, sputum, pancreatic juice, and cerebrospinal fluid.

Embodiment 34

The method of embodiment 32, wherein said biological sample comprises a sample selected from the group consisting of a tissue sample, a formalin fixed paraffin embedded (FFPE) tissue, fresh frozen tissue, fine needle aspirates (FNA), and a core biopsy.

Embodiment 35

The method according to any one of embodiments 1-34, wherein said method comprises contacting said biological sample with a lysis solution.

Embodiment 36

The method of embodiment 35, wherein said method comprises providing said sample in said sample receiving chamber and contacting said sample with an extraction/precipitation solution.

Embodiment 37

The method according to any one of embodiments 1-36, wherein said matrix material comprises a column material selected from the group consisting of glass or silica, an ion exchange resin, cellulose, and hydroxyapatite.

Embodiment 38

The method of embodiment 37, wherein said matrix material comprises glass.

Embodiment 39

The method according to any one of embodiments 1-38, wherein said bisulfite ion is provided as compound selected from the group consisting of ammonium bisulfite, sodium metabisulfite, potassium bisulfite, cesium bisulfite, and DABSO.

Embodiment 40

The method of embodiment 39, wherein said bisulfite ion is provided by ammonium bisulfite.

Embodiment 41

The method according to any one of embodiments 1-40, wherein said bisulfite is provided in a reagent mix comprising scavengers to prevent sulfite oxidation and/or catalysts.

Embodiment 42

The method of embodiment 41, wherein said bisulfite is provided in a reagent mix comprising scavengers selected from the group consisting of Trolox and hydroquinone.

Embodiment 43

The method according to any one of embodiments 41-42, wherein said bisulfite is provided in a reagent mix comprising polyamines as catalysts.

Embodiment 44

The method according to any one of embodiments 1-43, wherein said eluting the bound DNA comprises eluting and denaturing said DNA using a low concentration of potassium hydroxide or other base.

Embodiment 45

The method of embodiment 44, wherein said eluting the bound DNA comprises eluting and denaturing said DNA with an alkaline solution with a pH greater than about pH 10.5.

Embodiment 46

The method of embodiment 44, wherein said eluting the bound DNA comprises eluting and denaturing said DNA with an alkaline solution with a pH greater than about pH 12.

Embodiment 47

The method of embodiments 45-46, wherein said alkaline solution is a 10-15 mM KOH solution.

Embodiment 48

The method according to any one of embodiments 1-47, wherein said incubating the eluted DNA with bisulfite ions to produce a deaminated nucleic acid comprises incubating the DNA in an ammonium bisulfite solution having a concentration that ranges from about 6 M to about 7 M.

Embodiment 49

The method of embodiment 48, wherein said incubating the eluted DNA with bisulfite ions to produce a deaminated nucleic acid comprises incubating the DNA in an ammonium bisulfite solution having a concentration of about 6.5 M.

Embodiment 50

The method of embodiment 49, wherein said incubating comprises transferring the DNA in a concentrated bisulfite solution into a temperature controlled channel or chamber in said cartridge and heating said mixture.

Embodiment 51

The method of embodiment 50, wherein said incubating comprises thermally cycling the concentrated bisulfite solution from a temperature of about 60° C. to about 95° C.

Embodiment 52

The method according to any one of embodiments 1-51, wherein said contacting said deaminated nucleic acid to a second matrix material comprises mixing the DNA-bisulfite solution with fresh GTC-EtOH and dispensing the solution over said second matrix material.

Embodiment 53

The method of embodiment 52, wherein said method comprises washing the DNA in said second matrix material with fresh GTC-EtOH, and then a rinse solution.

Embodiment 54

The method of embodiment 53, wherein said rinse solution comprises PEG200.

Embodiment 55

The method according to any one of embodiments 1-54, wherein said desulfonating the bound deaminated nucleic acid comprises eluting the DNA from said second column with a high pH desulphonation buffer and incubating said solution.

Embodiment 56

The method of embodiment 55, wherein said incubating is for a period of time ranging from about 1 minute to about 1 hour, or from about 5 minutes to about 30 minutes, or from about 10 minutes to about 20 minutes, or for about 15 minutes.

Embodiment 57

The method of embodiments 55-56, wherein said high pH desulphonation/elution buffer comprises KOH.

Embodiment 58

The method according to any one of embodiments 55-57, wherein said incubation is in a chamber that previously held said high pH desulphonation buffer (e.g., chamber 10).

Embodiment 59

The method according to any one of embodiments 1-58, wherein after the incubation with bisulfite ions, a temperature controlled channel or chamber is washed with a buffer to remove the residual bisulfite and neutralize pH.

Embodiment 60

The method according to any one of embodiments 1-59, wherein high resolution melting analysis (FIRM) on said bisulfite-converted nucleic acid is performed to determine the methylation of said nucleic acid.

Embodiment 61

The method according to any one of embodiments 1-60, wherein nucleic acid sequencing of said bisulfite-converted nucleic acid is performed to determine the methylation of said nucleic acid.

Embodiment 62

The method according to any one of embodiments 1-60, wherein methylation specific PCR is performed to determine methylation of target nucleic acid sequences.

Embodiment 63

The method of embodiment 62, wherein said methylation specific PCR (MSP) is performed using primers specific for methylated sequences and/or primers specific for unmethylated sequences.

Embodiment 64

The method of embodiment 62, wherein said methylation specific PCR comprises a MethyLight protocol.

Embodiment 65

The method of embodiment 62, wherein TaqMan PCR reactions are performed with primers specific for bisulfite-converted methylated and/or unmethylated sequences.

Embodiment 66

The method according to any one of embodiments 62-65, wherein said MSP utilizes one or more fluorescent probes that are markers for amplified methylated sequences and/or one or more fluorescent probes that are markers for amplified unmethylated sequences.

Embodiment 67

The method of embodiment 66, wherein said fluorescent probes comprise a fluorescent reporter dye and a quencher dye where the probe provides a signal upon cleavage by 5' to 3' nuclease activity of Taq DNA polymerase.

Embodiment 68

The method according to any one of embodiments 66-67, wherein a methylation signal is determined by the combined signal for a plurality of probes each specific to a different methylated region in an amplified region of interest.

Embodiment 69

The method according to any one of embodiments 66-67, wherein a methylation signal is determined by a plurality of probes specific for the same methylated region in an amplified region of interest.

Embodiment 70

The method according to any one of embodiments 66-67, wherein said plurality of probes comprise 2, 3, 4, 5, 6, 7, 8, 9, 10, or more probes.

Embodiment 71

The method according to any one of embodiments 66-67, wherein a methylation signal is determined by a single probe in the amplified region of interest.

Embodiment 72

The method according to any one of embodiments 66-71, wherein said probes are run in simplex or multiplex.

Embodiment 73

The method according to any one of embodiments 66-71, wherein said probes are run in a multiplex format.

Embodiment 74

The method according to any one of embodiments 66-73, wherein said probes are run as a nested PCR reaction.

Embodiment 75

The method according to any one of embodiments 66-74, wherein said PCR reaction comprises a bisulfite contamination control probe that that undergoes bisulfite-mediated cleavage during PCR if bisulfite is present in the reaction.

Embodiment 76

The method according to any one of embodiments 1-75, wherein PCR is performed for one or more mutated genes.

Embodiment 77

The method according to any one of embodiments 1-76, wherein PCR is performed for unconverted DNA as a control.

Embodiment 78

The method according to any one of embodiments 1-77, wherein PCR is performed for converted DNA as a control.

Embodiment 79

The method of embodiment 77, wherein PCR is performed for unconverted DNA where the unconverted DNA is a target for said method.

Embodiment 80

The method according to any one of embodiments 1-79, wherein a bisulfite reaction and a PCR reaction, or a desulfonation reaction and a PCR reaction, or a bisulfite reaction, a desulfonation reaction and a PCR reaction are all performed in the same reaction tube or chamber.

Embodiment 81

The method according to any one of embodiments 1-80, wherein said contacting a biological sample comprising a nucleic acid to a first matrix material comprises contacting a sample containing RNA to said first matrix material, where said matrix material binds said RNA thereby purifies the RNA.

Embodiment 82

The method of embodiment 81, wherein said method comprises eluting said RNA from said matrix material substantially independently of the DNA.

Embodiment 83

The method of embodiment 82, wherein the RNA is eluted from said first matrix material using a Tris buffered elution.

Embodiment 84

The method according to any one of embodiments 81-83, wherein said RNA is eluted and stored in a chamber.

Embodiment 85

The method according to any one of embodiments 81-84, wherein reverse transcription (RT) is performed on said RNA and qRT-PCR is performed to determine the level of target RNA sequences.

Embodiment 86

The method according to any one of embodiments 82-85, where the RNA fraction is used to elute the bisulfite converted nucleic acid from said second matrix material and mix with the bisulfite-converted DNA, or is mixed with eluted bisulfate-converted DNA.

Embodiment 87

The method of embodiment 86, wherein RT is performed on said RNA prior to, or after, combination with the bisulfite-converted DNA.

Embodiment 88

The method according to any one of embodiments 86-87, wherein qRT-PCR is performed for RT RNA in the mixture to determine the level of target RNA sequences and methylation specific PCR is performed on the mixture to determine methylation of target DNA sequences.

Embodiment 89

The method according to any one of embodiments 1-88, where methylation is determined for a promoter region of a gene selected from the group consisting of MGMT. RASSF1A, ADAMTS1, BNC1, HIST1H3C, HOXB4, RASGRF2, TM6SF1, and AKR1B1.

Embodiment 90

The method according to any one of embodiments 81-89, wherein the expression level of RNA is determined for a methyltransferase.

Embodiment 91

The method of embodiment 90, wherein the expression level of RNA is determined for a methyltransferase selected from the group consisting of DNMT1, DNMT2, DNMT3A, DNMT3B, and TNMT3L.

Embodiment 92

A cartridge for determining the methylation state of a nucleic acid, said cartridge comprising: a column comprising a first matrix material, a sample receiving chamber, a temperature controlled channel or chamber, a plurality of chambers containing reagents and/or buffers, and when in use at least one of said chambers contains a bisulfite reagent, and at least one of said chambers contains a desulphonation/elution buffer, and wherein said cartridge optionally comprises a second column comprising said second matrix material.

Embodiment 93

The cartridge of embodiment 92, wherein said cartridge, when in use, comprises a chamber containing a reagent comprising guanidinium thiocyanate ethanol (GTC-EtOH).

Embodiment 94

The cartridge according to any one of embodiments 92-93, wherein said second column is absent.

Embodiment 95

The cartridge according to any one of embodiments 92-93, wherein said second column is present.

Embodiment 96

The cartridge according to any one of embodiments 92-95, wherein said temperature controlled channel or chamber is a thermocycling channel or chamber.

Embodiment 97

The cartridge according to any one of embodiments 92-96, wherein said cartridge further comprises a second heating channel or chamber.

Embodiment 98

The cartridge according to any one of embodiment 92-97, wherein said bisulfite reagent comprises a compound selected from the group consisting of ammonium bisulfite, sodium metabisulfite, potassium bisulfite, cesium bisulfite, and DABSO.

Embodiment 99

The cartridge of embodiment 98, wherein said bisulfite reagent comprises ammonium bisulfite.

Embodiment 100

The cartridge according to any one of embodiments 92-99, wherein said bisulfite is provided in a reagent mix comprising scavengers to prevent sulfite oxidation and/or catalysts.

Embodiment 101

The cartridge of embodiment 100, wherein said bisulfite is provided in a reagent mix comprising scavengers selected from the group consisting of Trolox and hydroquinone.

Embodiment 102

The cartridge according to any one of embodiments 100-101, wherein said bisulfite is provided in a reagent mix comprising polyamines as catalysts.

Embodiment 103

The cartridge according to any one of embodiments 92-102, wherein said first matrix material and/or said second matrix material, when present, comprises a material is selected from the group consisting of glass or silica, an ion exchange resin, and hydroxyapatite.

Embodiment 104

The cartridge according to any one of embodiments 92-103, wherein said cartridge comprises one or more chambers containing one or more reagents selected from the group consisting of methylation specific PCR primers, methylation specific PCR probes, PCR enzyme(s), and PCR reaction buffer.

Embodiment 105

The cartridge of embodiment 104, wherein said cartridge contains at least two chambers containing one or more reagents selected from the group consisting of methylation specific PCR primers, methylation specific PCR probes, PCR enzyme(s), and PCR reaction buffer.

Embodiment 106

The cartridge according to any one of embodiments 92-105, wherein said cartridge contains at least one chamber containing primers and probes for detection of methylation of a forward strand of a converted DNA.

Embodiment 107

The cartridge according to any one of embodiments 92-106, wherein said cartridge contains at least one chamber containing primers and probes for detection of methylation of a reverse strand of a converted DNA.

Embodiment 108

The cartridge according to any of embodiments 104-107, wherein said PCR primers, and/or probes, and/or enzymes are provided as beads.

Embodiment 109

The cartridge according to any one of embodiments 92-108, wherein said sample receiving chamber, said column(s), said plurality of chambers, and said temperature-controlled heating channel or chamber, are selectively in fluid communication.

Embodiment 110

The cartridge of embodiment 109, wherein said sample receiving chamber, said column(s), said plurality of chambers, and said temperature controlled channel or chamber, are selectively in fluid communication by microfluidic channels and valves.

Embodiment 111

The cartridge of embodiment 109, wherein said sample receiving chamber, said column(s), said plurality of chambers, and said temperature controlled channel or chamber or a port into said temperature controlled channel or chamber, are disposed around a central valve and selectively in fluid communication with a channel in said central valve, wherein said central valve is configured to accommodate a plunger that is capable of drawing fluid into or out of a chamber in fluid communication with said central valve.

Embodiment 112

The cartridge according to any one of embodiments 92-111, wherein said cartridge is configured so that, when in use, said cartridge comprises:

a first chamber containing a sample;
a second chamber containing a guanidinium thiosulfate-ethanol
(GTC-EtOH) solution;
a third chamber containing a bisulfite reagent;
a fourth chamber containing a buffer;
a fifth chamber containing a rinse solution; and
a sixth chamber containing an elution/desulphonation reagent.

Embodiment 113

The cartridge of embodiment 112, wherein said first chamber contains said sample in a GTC-EtOH-Tween extraction/precipitation reagent.

Embodiment 114

The cartridge according to any one of embodiments 92-113, wherein the cartridge is configured for the bisulfite reagent to be added to the cartridge at or near the time the sample is placed in the cartridge.

Embodiment 115

The cartridge according to any one of embodiments 92-113, wherein the bisulfite reagent is provided as a component of the cartridge.

Embodiment 116

The cartridge according to any one of embodiments 92-115, wherein the cartridge is configured for addition of GTC-ETOH-Tween buffer at or near the time the sample is placed into the cartridge.

Embodiment 117

The cartridge according to any one of embodiments 92-115, wherein the GTC-ETOH-Tween buffer is provided as a component of the cartridge.

Embodiment 118

The cartridge according to any one of embodiments 92-117, wherein said cartridge comprises a seventh chamber containing PCR primers and/or probes and/or PCR enzymes.

Embodiment 119

The cartridge according to any one of embodiments 92-118, wherein said cartridge comprises an eighth chamber also containing PCR primers and/or probes and/or PCR enzymes.

Embodiment 120

The cartridge according to any one of embodiments 92-119, wherein said cartridge comprises one or more chambers containing primers specific for bisulfite-converted methylated and/or unmethylated sequences.

Embodiment 121

The cartridge according to any one of embodiments 92-120, wherein said cartridge comprises one or more chambers containing reagents for TaqMan PCR reactions.

Embodiment 122

The cartridge according to any one of embodiments 92-121, wherein said cartridge comprises one or more chambers containing one or more fluorescent probes that are markers for amplified methylated sequences and/or one or more fluorescent probes that are markers for amplified unmethylated sequences.

Embodiment 123

The cartridge of embodiment 122, wherein said probes comprise a fluorescent reporter dye and a quencher dye, where the probes provides a signal upon cleavage by the 5' to 3' nuclease activity of Taq DNA polymerase.

Embodiment 124

The cartridge according to any one of embodiments 122-123, wherein said cartridge comprises a plurality of probes each specific to a different methylated region in an amplified region of interest.

Embodiment 125

The cartridge according to any one of embodiments 122-123, wherein said cartridge comprises a single probe specific to a methylated region in an amplified region of interest.

Embodiment 126

The cartridge according to any one of embodiments 122-123, wherein said cartridge comprises a plurality of probes each specific to the same methylated region in an amplified region of interest.

Embodiment 127

The cartridge according to any one of embodiments 92-126, wherein said cartridge contains primers and/or probes to determine methylation of a promoter region of a gene selected from the group consisting of MGMT, RASSF1A, ADAMTS1, BNC1, HIST1H3C, HOXB4, RASGRF2, TM6SF1, and AKR1B1.

Embodiment 128

The cartridge according to any one of embodiments 92-126, wherein said cartridge contains one or more primers shown in Tables 5, 9, or 10, and/or one or more probes shown in Tables 5, 9, or 10.

Embodiment 129

The cartridge of embodiment 128, wherein said cartridge contains the following probes and primers for determining methylation of MGMT using a nested PCR reaction:
- an external forward primer (248b) comprising the nucleotide sequence GTTTT(T*)AGAAYG(T*)TTTGYGTTT (SEQ ID NO:263);
- an external reverse primer (249b) comprising the nucleotide sequence: AAAAAAC(T*)CCRCACTCTTCC (SEQ ID NO:265);
- an internal forward primer (250) comprising the nucleotide sequence TTTCGACGTTCGTAGGTTTTCGC (SEQ ID NO:266);
- an internal reverse primer (251) comprising the nucleotide sequence GCACTCTTCCGAAAACGAAACG (SEQ ID NO:267); and
- a probe (252a) comprising the nucleotide sequence fluor-CCAAACAC(T*)CACCAAATC(N*)CAAAC-blocker (SEQ ID NO: 268).

Embodiment 130

The cartridge according to any one of embodiments 128-129, wherein said cartridge contains the following probes and primers for determining methylation of ACTB (e.g., as a control) using a nested PCR reaction:
- an external forward primer (102) comprising the nucleotide sequence: GTGATGGAGGAGGTTTAGTAAGTT (SEQ ID NO:103);
- an external reverse primer (103) comprising the nucleotide sequence: CCAATAAAACCTACTCCTCCCTTAA (SEQ ID NO:104);
- an internal forward primer (148) comprising the nucleotide sequence: GGTTTAGTAAGTTTTTTGGATTGTG (SEQ ID NO:149);
- an internal reverse primer (149) comprising the nucleotide sequence: CCTTAAAAATTACAAAAACCACAAC (SEQ ID NO:150); and
- a probe (178) comprising the nucleotide sequence: fluor-CCACCACCCAACACA(N*)CAA(T*)AACAAACAC-blocker (SEQ ID NO:179).

Embodiment 131

The cartridge according to any one of embodiments 92-130, wherein the cartridge is configured for determination of the expression level of RNA for a methyltransferase.

Embodiment 132

The cartridge of embodiment 131, wherein said methyltransferases is selected from the group consisting of DNMT1, DNMT2, DNMT3A, DNMT3B, and TNMT3L.

Embodiment 133

A system for determining the methylation of a nucleic acid in a biological sample, said system comprising: an enclosure configured to contain one or more sample processing modules, each sample processing module configured to hold a removable cartridge according to any one of embodiments 92-132; where said system is configured to operate the sample processing modules to perform sample processing to determine methylation of one or more target nucleic acids and optionally to determine the level of one or more target DNA sequences within a corresponding removable sample cartridge, wherein said processing on a sample within the corresponding removable sample cartridge performs a method according to any one of embodiments 1-91.

Embodiment 134

The system of embodiment 133, wherein said system is configured to contain one sample processing module.

Embodiment 135

The system of embodiment 133, wherein said system is configured to contain at least two sample processing modules, or at least 4 sample processing modules, or at least 8 sample processing modules, or at least 12 sample processing modules, or at least 16 sample processing modules, or at least 20 sample processing modules, or at least 24 sample processing modules, or at least 28 sample processing modules, or at least 32 sample processing modules, or at least 64 sample processing modules, or at least 128 sample processing modules.

Embodiment 136

The system according to any one of embodiments 133-135, wherein said modules comprise one or more heating plates to heat a temperature controlled chamber or channel in said cartridge.

Embodiment 137

The system according to any one of embodiments 133-136, wherein said modules comprise a fan configured to cool a temperature controlled channel or chamber in said cartridge.

Embodiment 138

The system according to any one of embodiments 133-137, wherein said modules comprise circuitry to pass information (e.g., optical information) to a computer for analysis.

Embodiment 139

The system according to any one of embodiments 133-138, wherein said modules comprise optical blocks to provide excitation and/or detection of one or more optical signals produced by reactions in said cartridge.

Embodiment 140

The system according to any one of embodiments 133-139, wherein said system is configured to operate said cartridge to perform a method according to any one of embodiments 1-91.

Embodiment 141

The system according to any one of embodiments 133-139, wherein said system is configured to operate said cartridge to: bind a sample to a column; elute DNA from the column and combine said DNA with a conversion reagent; heat the DNA/conversion reagent solution in a reaction chamber or tube to produce converted DNA; bind the converted DNA to a column; desulphonate and elute the DNA from the column; and perform PCR on the eluted desulphonated DNA in a reaction chamber or tube.

Embodiment 142

The system of embodiment 141, wherein said PCR is performed in the same reaction chamber or tube where the DNA/conversion reagent solution was previously heated.

Embodiment 143

A cartridge for sample preparation, said cartridge comprising: a channel or chamber comprising an affinity matrix that binds DNA, a plurality of chambers disposed around a central valve assembly and selectively in fluid communication with said central valve assembly where said central valve assembly is configured to accommodate a plunger that is capable of drawing fluid into or out of a chamber in fluid communication with said central valve wherein said plurality of chambers comprises: a chamber configured to receive up to about 5 ml or up to about 4 ml of sample solution; a chamber containing PEG; a chamber containing GTC-EtOH; a chamber containing an alkaline solution; and a chamber containing a buffer.

Embodiment 144

The cartridge of embodiment 143, wherein said plurality of chambers further comprises a chamber containing a bisulfite reagent.

Embodiment 145

The cartridge according to any one of embodiments 143-144, wherein said plurality of chambers comprises a chamber containing a GTC-ethanol wash solution.

Embodiment 146

The cartridge of embodiment 145, wherein said GTC-ethanol wash solution comprises 1.25 M guanidinium thiocyanate, 25 mM Tris pH 7.0, and 50% ethanol.

Embodiment 147

The cartridge according to any one of embodiments 143-146, wherein said PEG comprises PEG200.

Embodiment 148

The cartridge according to any one of embodiments 143-147, wherein said alkaline solution comprises KOH.

Embodiment 149

The cartridge according to any one of embodiments 143-148, wherein said buffer comprises Tris.

Embodiment 150

The cartridge according to any one of embodiments 143-149. wherein said plurality of chambers comprises a chamber containing beads comprising one or more PCR primers and/or probes.

Embodiment 151

The cartridge according to any one of embodiments 143-150, wherein said chamber containing PEG contains about 1 ml of PEG.

Embodiment 152

The cartridge according to any one of embodiments 143-151, wherein said chamber containing an alkaline solution contains about 500 µL of solution.

Embodiment 153

The cartridge according to any one of embodiments 143-152, wherein said chamber containing GTC-EtOH contains about 2 ml GTC-EtOH.

Embodiment 154

The cartridge according to any one of embodiments 143-153, wherein said chamber containing a buffer contains about 2 mL of buffer.

Embodiment 155

A high volume sample preparation (HVSP), said cartridge comprising: a channel or chamber comprising an affinity matrix that binds DNA, a plurality of chambers disposed around a central valve assembly and selectively in fluid communication with said central valve assembly where said central valve assembly is configured to accommodate a plunger that is capable of drawing fluid into or out of a chamber in fluid communication with said central valve wherein said plurality of chambers comprises: at least two different chambers each configured to receive up to about 4.5 ml of sample solution; a chamber containing PEG; a chamber containing an alkaline solution; and a chamber containing a buffer.

Embodiment 156

The cartridge of embodiment 155, wherein said plurality of chambers comprises at least three different chambers each configured to receive up to 4 ml of sample solution.

Embodiment 157

The cartridge according to any one of embodiments 155-156, wherein said PEG comprises PEG200.

Embodiment 158

The cartridge according to any one of embodiments 155-157, wherein said basic solution comprises KOH.

Embodiment 159

The cartridge according to any one of embodiments 155-158, wherein said buffer comprises Tris.

Embodiment 160

The cartridge according to any one of embodiments 155-159, wherein said plurality of chambers comprises a chamber containing a wash solution.

Embodiment 161

The cartridge of embodiment 160, wherein said wash solution comprise 1.25 M guanidinium thiocyanate, 25 mM Tris pH 7.0, and 50% ethanol.

Embodiment 162

The cartridge according to any one of embodiments 155-161, wherein said cartridge comprises a chamber configured for removal of a processed sample.

Embodiment 163

The cartridge according to any one of embodiments 155-162, wherein said sample chambers, when in use contain sample solution, GTC and isopropanol.

Embodiment 164

The cartridge of embodiment 163, wherein said sample chambers, when in use contain sample solution, GTC and isopropanol in substantially equal volumes.

Embodiment 165

The cartridge according to any one of embodiments 155-164 wherein said cartridge, when in use, comprises 4 ml of sample solution disposed in each of said chambers configured to receive a sample.

Embodiment 166

The cartridge according to any one of embodiments 155-165, wherein said cartridge provides DNA or RNA recovery that is substantially linear with respect to the sample volume between 0.5 ml and about 4 ml of sample.

Embodiment 167

The cartridge according to any one of embodiments 155-166, wherein said cartridge contains or is configured to receive a conversion reagent.

Embodiment 168

The cartridge of embodiment 167, wherein said cartridge, when in use, performs a bisulfite conversion of DNA.

Embodiment 169

A lysis solution for preparation of a DNA sample from serum or plasma, said lysis solution comprising: GTC, a buffer, a detergent, and optionally an anti-foaming agent.

Embodiment 170

The lysis solution of embodiment 169, wherein said lysis solution for serum or plasma comprises GTC, Tris pH 7.0, Tween 20, and antifoam SE15.

Embodiment 171

The lysis solution of embodiment 170, wherein said lysis solution for serum or plasma comprises about 4.5 M GTC, about 45 mM Tris pH 7.0, about 1% Tween20, and about 0.01% Antifoam SE15.

Embodiment 172

A lysis solution for preparation of a DNA sample from an FFPE sample.

Embodiment 173

The lysis solution of embodiment 172, wherein said lysis solution for FFPE samples comprises a buffer, a detergent, NaCl, $MgCl_2$, a chelating agent, antifoam SE15, and sodium azide.

Embodiment 174

The lysis solution of embodiment 173, wherein said lysis solution for FFPE samples comprises about 1% Tween20, about 400 mM NaCl, about 25 mM EDTA, about 10 mM MgCl$_2$, about 50 mM HEPES pH 7.2, about 0.01% antifoam SE15, and about 0.01% sodium azide.

Embodiment 175

A kit for the determination of DNA methylation, said kit comprising: a container containing a cartridge for determining the methylation state of a nucleic acid according to any one of embodiments 92-136.

Embodiment 176

The kit of embodiment 175, wherein said kit further comprises a container containing a lysis solution.

Embodiment 177

The kit of embodiment 176, wherein said lysis solution is a lysis solution for serum or plasma according to any one of embodiments 169-171.

Embodiment 178

The kit of embodiment 176, wherein said lysis solution is a lysis solution for an FFPE sample according to any one of embodiments 172-174.

Embodiment 179

The kit according to any one of embodiments 175-178, wherein said kit comprises a container containing proteinase K.

Embodiment 180

The kit according to any one of embodiments 175-179, wherein said kit comprises a conversion reagent in said cartridge or in a container separate from the cartridge.

Embodiment 181

The kit of embodiment 180, wherein said kit comprises said conversion reagent in a container separate from the cartridge.

Embodiment 182

The kit of embodiment 180, wherein said kit comprises said conversion reagent is provided in a chamber of the cartridge.

Embodiment 183

The according to any one of embodiments 180-182, wherein said conversion reagent comprises a compound selected from the group consisting of sodium metabisulfite, potassium bisulfite, cesium bisulfite, ammonium bisulfite, and DABSO.

Embodiment 184

The kit of embodiment 183, wherein said conversion reagent comprises ammonium bisulfite.

Embodiment 185

The kit according to any one of embodiments 175-184, wherein said kit comprises a container containing a sample processing reagent.

Embodiment 186

The kit of embodiment 185, wherein said sample processing reagent comprises guanidium thiocyanate.

Embodiment 187

The kit according to any one of embodiments 185-186, wherein said sample processing reagent comprise ethanol.

Embodiment 188

The kit according to any one of embodiments 175-187, wherein said kit comprises a container containing a cartridge for sample preparation according to any one of embodiments 155-166.

Embodiment 189

The kit according to any one of embodiments 175-188, wherein said kit contains instructional materials teaching the use of said cartridge for the determination of DNA methylation.

Embodiment 190

A cartridge for the detection of methylation markers of a cancer, said cartridge comprising: a plurality of chambers and a thermocycling channel or chamber, wherein said plurality of chambers and a port into said thermocycling channel or chamber are disposed around a central valve assembly and selectively in fluid communication with said central valve assembly where said central valve assembly is configured to accommodate a plunger that is capable of drawing fluid into or out of a chamber or port in fluid communication with said central valve wherein said plurality of chambers comprises: a sample receiving chamber; a chamber containing or configured to receive a bisulfite reagent; a chamber containing a wash solution; a chamber containing a Tris buffer; a chamber containing an alkaline solution comprising KOH; a chamber containing beads that provide a PCR master mix; and a chamber containing beads that provide PCR primers and probes to detect methylation of one or more gene promoters whose methylation state is a marker for a cancer.

Embodiment 191

The cartridge of embodiment 190, wherein said plurality of chambers comprises a chamber disposed to receive waste solutions.

Embodiment 192

The cartridge according to any of embodiments 190-191, wherein said bisulfite reagent comprises a compound selected from the group consisting of sodium metabisulfite, potassium bisulfite, cesium bisulfite, ammonium bisulfite, and DABSO.

Embodiment 193

The cartridge of embodiment 192, wherein said bisulfite reagent comprises ammonium bisulfite.

Embodiment 194

The cartridge according to any of embodiments 190-193, wherein said wash solution comprises 1.25 M GTC, 25 mM Tris pH 7.0, and 50% ethanol.

Embodiment 195

The cartridge according to any of embodiments 190-194, wherein said chamber containing beads that provide PCR primers and probes to detect methylation of one or more gene promoters comprises beads that provide PCR primers and probes to detect methylation of one or more gene promoters whose methylation state is a marker for a cancer selected from the group consisting of breast cancer, pancreatic cancer, prostate cancer, brain cancer, and lung cancer.

Embodiment 196

The cartridge of embodiment 195, wherein said chamber containing beads that provide PCR primers and probes to detect methylation of one or more gene promoters comprises beads that provide PCR primers and probes for a nested PCR reaction.

Embodiment 197

The cartridge of embodiment 196, wherein said nested PCR comprises a first PCR reaction specific for converted DNA and a second PCR reaction specific for methylated CpGs.

Embodiment 198

The cartridge according to any one of embodiments 190-197, wherein said chamber containing beads that provide PCR primers and probes chamber contains beads that provide PCR primers and probes to detect methylation of a forward strand of converted DNA.

Embodiment 199

The cartridge according to any one of embodiments 190-198, wherein said chamber containing beads that provide PCR primers and probes chamber contains beads that provide PCR primers and probes to detect methylation of a reverse strand of converted DNA.

Embodiment 200

The cartridge according to any of embodiments 190-197, wherein said chamber containing beads that provide PCR primers and probes to detect methylation of one or more gene promoters comprises beads that provide PCR primers and probes to detect methylation of the promoters of one or more genes selected from the group consisting of RASSF1A, AKR1B1, HOXB4, HIST1H3C, RASGRF2, TM6SF1, BRCA1, BNC1, ADAMTS1, CDO1, SOX17, TAC1, HOXA7, and MGMT.

Embodiment 201

The cartridge according to any of embodiments 190-200, wherein said chamber containing beads that provide PCR primers and probes to detect methylation of one or more gene promoters comprises beads that provide PCR primers and probes to detect methylation of one or more gene promoters whose methylation state is a marker for pancreatic cancer.

Embodiment 202

The cartridge of embodiment 201, wherein said chamber containing beads that provide PCR primers and probes to detect methylation of one or more gene promoters comprises beads that provide PCR primers and probes to detect methylation of the promoters of ADAMTS1, and/or BNC1.

Embodiment 203

The cartridge of embodiment 202, wherein said chamber containing beads that provide PCR primers and probes to detect methylation of one or more gene promoters comprises beads that provide PCR primers and probes to detect methylation of the promoter of ADAMTS1.

Embodiment 204

The cartridge according to any one of embodiments 202-203, wherein said chamber containing beads that provide PCR primers and probes to detect methylation of one or more gene promoters comprises beads that provide PCR primers and probes to detect methylation of the promoter of BNC1.

Embodiment 205

The cartridge of embodiment 202, wherein said chamber containing beads that provide PCR primers and probes to detect methylation of one or more gene promoters comprises beads that provide one or more PCR primers and/or probes for ADAMTS1 and/or BNC1 shown in Tables 5, or 10.

Embodiment 206

The cartridge according to any of embodiments 190-200, wherein said chamber containing beads that provide PCR primers and probes to detect methylation of one or more gene promoters comprises beads that provide PCR primers and probes to detect methylation of one or more gene promoters whose methylation state is a marker for breast cancer.

Embodiment 207

The cartridge of embodiment 206, wherein said chamber containing beads that provide PCR primers and probes to detect methylation of one or more gene promoters comprises beads that provide PCR primers and probes to detect methylation of the promoters of one, two, three, four, five, or all genes selected from the group consisting of BRCA1, RASSF1A, AKR1B1, HOXB4, HIST1H3C, RASGRF2, and TM6SF1.

Embodiment 208

The cartridge of embodiment 207, wherein said chamber containing beads that provide PCR primers and probes to detect methylation of one or more gene promoters comprises beads that provide PCR primers and probes to detect methylation of the promoter of BRCA1.

Embodiment 209

The cartridge according to any one of embodiments 207-208, wherein said chamber containing beads that provide PCR primers and probes to detect methylation of one or more gene promoters comprises beads that provide PCR primers and probes to detect methylation of the promoter of RASSF1A.

Embodiment 210

The cartridge according to any one of embodiments 207-209, wherein said chamber containing beads that provide PCR primers and probes to detect methylation of one or more gene promoters comprises beads that provide PCR primers and probes to detect methylation of the promoter of AKR1B1.

Embodiment 211

The cartridge according to any one of embodiments 207-210, wherein said chamber containing beads that provide PCR primers and probes to detect methylation of one or more gene promoters comprises beads that provide PCR primers and probes to detect methylation of the promoter of HOXB4.

Embodiment 212

The cartridge according to any one of embodiments 207-211, wherein said chamber containing beads that provide PCR primers and probes to detect methylation of one or more gene promoters comprises beads that provide PCR primers and probes to detect methylation of the promoter of HIST1H3C.

Embodiment 213

The cartridge according to any one of embodiments 207-212, wherein said chamber containing beads that provide PCR primers and probes to detect methylation of one or more gene promoters comprises beads that provide PCR primers and probes to detect methylation of the promoter of RASGRF2.

Embodiment 214

The cartridge according to any one of embodiments 207-213, wherein said chamber containing beads that provide PCR primers and probes to detect methylation of one or more gene promoters comprises beads that provide PCR primers and probes to detect methylation of the promoter of TM6SF1.

Embodiment 215

The cartridge according to any one of embodiments 207-214, wherein said chamber containing beads that provide PCR primers and probes to detect methylation of one or more gene promoters comprises beads that provide one or more PCR primers and/or one or more PCR probes shown in Tables 5, or 9.

Embodiment 216

The cartridge of embodiment 206, wherein said chamber containing beads that provide PCR primers and probes to detect methylation of one or more gene promoters comprises beads that provide PCR primers and probes to detect methylation of the promoters of BRCA1.

Embodiment 217

The cartridge according to any of embodiments 190-200, wherein said chamber containing beads that provide PCR primers and probes to detect methylation of one or more gene promoters comprises beads that provide PCR primers and probes to detect methylation of one or more gene promoters whose methylation state is a marker for lung cancer.

Embodiment 218

The cartridge of embodiment 217, wherein said chamber containing beads that provide PCR primers and probes to detect methylation of one or more gene promoters comprises beads that provide PCR primers and probes to detect methylation of the promoters of one, two, three, or all genes selected from the group consisting of CDO1, SOX17, TAC1, and HOXA7.

Embodiment 219

The cartridge of embodiment 218, wherein said chamber containing beads that provide PCR primers and probes to detect methylation of one or more gene promoters comprises beads that provide PCR primers and probes to detect methylation of the promoter of CDO1.

Embodiment 220

The cartridge according to any one of embodiments 218-219, wherein said chamber containing beads that provide PCR primers and probes to detect methylation of one or more gene promoters comprises beads that provide PCR primers and probes to detect methylation of the promoter of SOX17.

Embodiment 221

The cartridge according to any one of embodiments 218-220, wherein said chamber containing beads that provide PCR primers and probes to detect methylation of one or more gene promoters comprises beads that provide PCR primers and probes to detect methylation of the promoter of TAC1.

Embodiment 222

The cartridge according to any one of embodiments 218-221, wherein said chamber containing beads that provide PCR primers and probes to detect methylation of one or more gene promoters comprises beads that provide PCR primers and probes to detect methylation of the promoter of HOXA7.

Embodiment 223

The cartridge according to any of embodiments 190-200, wherein said chamber containing beads that provide PCR primers and probes to detect methylation of one or more gene promoters comprises beads that provide PCR primers and probes to detect methylation of one or more gene promoters whose methylation state is a marker for brain cancer.

Embodiment 224

The cartridge of embodiment 223, wherein said chamber containing beads that provide PCR primers and probes to detect methylation of one or more gene promoters comprises beads that provide PCR primers and probes to detect methylation of the promoter of MGMT.

Embodiment 225

The cartridge of embodiment 224, wherein said chamber containing beads that provide PCR primers and probes to detect methylation of one or more gene promoters comprises beads that provide one or more PCR primers and/or probes for MGMT shown in Tables 5, or 10.

Embodiment 226

The cartridge of embodiment 225, wherein said cartridge contains the following probes and primers for determining methylation of MGMT using a nested PCR reaction:
- an external forward primer (248b) comprising the nucleotide sequence GTTTT(T*)AGAAYG(T*)TTTGYGTTT (SEQ ID NO:263);
- an external reverse primer (249b) comprising the nucleotide sequence AAAAAAC(T*)CCRCACTCTTCC (SEQ ID NO:265);
- an internal forward primer (250) comprising the nucleotide sequence TTTCGACGTTCGTAGGTTTTCGC (SEQ ID NO:266);
- an internal reverse primer (251) comprising the nucleotide sequence GCACTCTTCCGAAAACGAAACG (SEQ ID NO:267); and
- a probe (252a) comprising the nucleotide sequence fluor-CCAAACAC(T*)CACCAAATC(N*)CAAAC-blocker (SEQ ID NO: 268).

Embodiment 227

The cartridge according to any one of embodiments 225-226, wherein said cartridge contains the following probes and primers for determining methylation of ACTB (e.g., as a control) using a nested PCR reaction:
- an external forward primer (102) comprising the nucleotide sequence GTGATGGAGGAGGTTTAGTAAGTT (SEQ ID NO:103);
- an external reverse primer (103) comprising the nucleotide sequence CCAATAAAACCTACTCCTCCCTTAA (SEQ ID NO:104);
- an internal forward primer (148) comprising the nucleotide sequence GGTTTAGTAAGTTTTTTGGATTGTG (SEQ ID NO:149);
- an internal reverse primer (149) comprising the nucleotide sequence CCTTAAAAATTACAAAAACCACAAC (SEQ ID NO:150); and
- a probe (178) comprising the nucleotide sequence fluor-CCACCACCCAACACA(N*)CAA(T*)AACAAACAC-blocker (SEQ ID NO:179).

Embodiment 228

A method of preparing a sample of cfDNA from serum or plasma, said method comprising:
- combining a proteinase K treated sample of serum or plasma with a lysis solution according to any one of embodiments 169-171, and an alcohol to form a sample solution;
- loading said sample solution into a sample receiving chamber in a cartridge according to any one of embodiments 143-154, or into a sample receiving chamber in a cartridge according to any one of embodiments 155-168; and
- operating said cartridge to bind DNA in said sample to said affinity matrix and then to wash and release said DNA from said matrix.

Embodiment 229

The method of embodiment 228, wherein said combining a proteinase K treated sample of serum or plasma comprises combining said sample, lysis solution and alcohol in proportions corresponding to about 1.3 ml proteinase K treated serum or plasma, 2.2 mL lysis solution; and about 1.5 ml alcohol.

Embodiment 230

The method according to any one of embodiments 228-229, wherein said alcohol comprises isopropanol.

Embodiment 231

The method according to any one of embodiments 228-230, wherein said sample comprises serum.

Embodiment 232

The method according to any one of embodiments 228-231, wherein said sample comprises plasma.

Embodiment 233

The method according to any one of embodiments 228-232, wherein said sample comprises serum.

Embodiment 234

The method according to any one of embodiments 228-233, wherein operating said cartridge comprises introducing said cartridge into a sample processing module in a system according to any one of embodiments 133-139.

Embodiment 235

The method according to any one of embodiments 228-234, wherein said method further comprises operating said cartridge to convert said DNA for methylation detection.

Embodiment 236

The method according to any one of embodiments 228-235, wherein said method further comprises operating said cartridge to perform one or more PCR reactions using said DNA or converted DNA a template.

Embodiment 237

The method according to any one of embodiments 228-234, wherein said loading comprises loading said sample solution into one or more sample receiving chambers in a cartridge according to any one of embodiments 155-165.

Embodiment 238

The method of embodiment 237, wherein said method further comprises transferring the released DNA to a second cartridge for methylation detection and/or PCR.

Embodiment 239

The method of embodiment 238, wherein said second cartridge is a cartridge according to any one of embodiments 92-132.

Embodiment 240

The method according to any one of embodiments 238-239, wherein said method further comprises operating said second cartridge to convert said DNA for methylation detection.

Embodiment 241

The method according to any one of embodiments 238-240, wherein said method further comprises operating said second cartridge to perform one or more PCR reactions using said DNA or converted DNA as a template.

Embodiment 242

The method according to any one of embodiments 238-241, wherein said operating said second cartridge comprises introducing said second cartridge into a sample processing module in a system according to any one of embodiments 133-139.

Embodiment 243

A method of preparing a DNA from an FFPE sample, said method comprising:
combining a formalin-fixed paraffin embedded sample with a lysis solution according to any one of embodiments 172-174;
heating said lysis solution containing said sample; adding an alcohol to said sample to form a sample solution; loading said sample solution into a sample receiving chamber in a cartridge according to any one of embodiments 143-154, or into a sample receiving chamber in a cartridge according to any one of embodiments 155-168; and
operating said cartridge to bind DNA in said sample to said affinity matrix and then to wash and release said DNA from said matrix.

Embodiment 244

The method of embodiment 243, wherein said heating comprises adding proteinase K to said sample and heating said sample.

Embodiment 245

The method of embodiment 244, wherein said heating comprises adding about 50 µL proteinase K to about 1.2 mL of FFPE lysis solution containing a FFPE sample.

Embodiment 246

The method according to any one of embodiments 243-245, wherein said heating comprises heating said lysis solution to a temperature ranging from about 50° C. to about 60° C.

Embodiment 247

The method of embodiment 246, wherein said heating comprises heating said lysis solution to a temperature of about 56° C.

Embodiment 248

The method according to any one of embodiments 243-247, wherein said heating is for a period of time ranging up to about 4 hours, or up to about 5 hours, or up to about 6 hours.

Embodiment 249

The method of embodiment 248, wherein said heating is for about 4 hours.

Embodiment 250

The method according to any one of embodiments 243-249, wherein said alcohol comprises ethanol.

Embodiment 251

The method according to any one of embodiments 243-250, wherein said method comprises adding alcohol to said lysis solution in a volume ratio of about 1:1 lysis solution: alcohol.

Embodiment 252

The method according to any one of embodiments 243-251, wherein operating said cartridge comprises introducing said cartridge into a sample processing module in a system according to any one of embodiments 133-139.

Embodiment 253

The method according to any one of embodiments 243-252, wherein said method further comprises operating said cartridge to convert said DNA for methylation detection.

Embodiment 254

The method according to any one of embodiments 243-253, wherein said method further comprises operating said cartridge to perform one or more PCR reactions using said DNA or converted DNA as a template.

Embodiment 255

The method according to any one of embodiments 243-251, wherein said loading comprise loading said sample solution into one or more sample receiving chambers in a cartridge according to any one of embodiments 155-165.

Embodiment 256

The method of embodiment 255, wherein said method further comprises transferring the released DNA to a second cartridge for methylation detection and/or PCR.

Embodiment 257

The method of embodiment 256, wherein said second cartridge is a cartridge according to any one of embodiments 92-132.

Embodiment 258

The method according to any one of embodiments 256-257, wherein said method further comprises operating said second cartridge to convert said DNA for methylation detection.

Embodiment 259

The method according to any one of embodiments 256-258, wherein said method further comprises operating said second cartridge to perform one or more PCR reactions using said DNA or converted DNA as a template.

Embodiment 260

The method according to any one of embodiments 256-259, wherein said operating said second cartridge comprises introducing said second cartridge into a sample processing module in a system according to any one of embodiments 133-139.

Embodiment 261

A method of detecting a cancer, and/or staging a cancer, and/or detecting the predisposition to a cancer in a subject, said method comprising:
providing a biological sample from said subject, wherein said biological sample comprises a DNA;
utilizing a cartridge according to any one of claims 190-225 to detect methylation of one or more gene promoters in said DNA whose methylation state is a marker for a cancer, where an increase in methylation of said one or more gene promoters is indicative of the presence of a cancer or a predisposition to a cancer or a stage of a cancer or precancer.

Embodiment 262

The method of embodiment 261, wherein said subject is a human.

Embodiment 263

The method according to any one of embodiments 261-262, wherein said cancer is a cancer selected from the group consisting of breast cancer, pancreatic cancer, prostate cancer, brain cancer, a lung cancer, a B cell lymphoma, a bronchus cancer, a colorectal cancer, a stomach cancer, an ovarian cancer, a urinary bladder cancer, a brain or central nervous system cancer, a peripheral nervous system cancer, an esophageal cancer, a cervical cancer, a melanoma, a uterine or endometrial cancer, a cancer of the oral cavity or pharynx, a liver cancer, a kidney cancer, a biliary tract cancer, a small bowel or appendix cancer, a salivary gland cancer, a thyroid gland cancer, a adrenal gland cancer, an osteosarcoma, a chondrosarcoma, a liposarcoma, a testes cancer, and a malignant fibrous histiocytoma.

Embodiment 264

The method according to any one of embodiments 261-262, wherein said cancer is a cancer selected from the group consisting of breast cancer, pancreatic cancer, prostate cancer, brain cancer, a lung cancer.

Embodiment 265

The method according to any one of embodiments 261-264, wherein said sample comprise a sample from serum or plasma.

Embodiment 266

The method according to any one of embodiments 261-264, wherein said sample comprise an FFPE sample.

Embodiment 267

The method according to any one of embodiments 261-266, wherein said one or more gene promoters comprise the promoters of one or more genes selected from the group consisting of RASSF1A, AKR1B1, HOXB4, HIST1H3C, RASGRF2, TM6SF1, BRCA1, BNC1, ADAMTS1, CDO1, SOX17, TAC1, HOXA7, and MGMT.

Embodiment 268

The method according to any one of embodiments 261-266, wherein said cancer is pancreatic cancer and said one or more gene promoters comprise the promoters of one, two, three, or four genes selected from the group consisting of ADAMTS1, and BNC1.

Embodiment 269

The method of embodiment 268, wherein said one or more gene promoters comprise the promoter of ADAMTS1.

Embodiment 270

The method according to any one of embodiments 268-269, wherein said one or more gene promoters comprise the promoter of BNC1.

Embodiment 271

The method according to any one of embodiments 261-266, wherein said cancer is breast cancer and said one or more gene promoters comprise the promoters of one, two, three, four, five, or all genes selected from the group consisting of BRCA1, RASSF1A, AKR1B1, HOXB4, HIST1H3C, RASGRF2, and TM6SF1.

Embodiment 272

The method of embodiment 271, wherein said one or more gene promoters comprise the promoter of BRCA1.

Embodiment 273

The method according to any one of embodiments 271-272, wherein said one or more gene promoters comprise the promoter of RASSF1A.

Embodiment 274

The method according to any one of embodiments 271-273, wherein said one or more gene promoters comprise the promoter of AKR1B1.

Embodiment 275

The method according to any one of embodiments 271-274, wherein said one or more gene promoters comprise the promoter of HOXB4.

Embodiment 276

The method according to any one of embodiments 271-275, wherein said one or more gene promoters comprise the promoter of HIST1H3C.

Embodiment 277

The method according to any one of embodiments 271-276, wherein said one or more gene promoters comprise the promoter of RASGRF2.

Embodiment 278

The method according to any one of embodiments 271-277, wherein said one or more gene promoters comprise the promoter of TM6SF1.

Embodiment 279

The method according to any one of embodiments 261-266, wherein said cancer is breast cancer and said one or more gene promoters comprise the promoter of BRCA1.

Embodiment 280

The method according to any one of embodiments 261-266, wherein said cancer is lung cancer and said one or more gene promoters comprise the promoters of one, two, three, for all genes selected from the group consisting of CDO1, SOX17, TAC1, and HOXA7.

Embodiment 281

The method of embodiment 280, wherein said one or more gene promoters comprise the promoter of CDO1.

Embodiment 282

The method according to any one of embodiments 280-281, wherein said one or more gene promoters comprise the promoter of SOX17.

Embodiment 283

The method according to any one of embodiments 280-282, wherein said one or more gene promoters comprise the promoter of TAC1.

Embodiment 284

The method according to any one of embodiments 280-283, wherein said one or more gene promoters comprise the promoter of HOXA7.

Embodiment 285

The method according to any one of embodiments 261-266, wherein said cancer is brain cancer and said one or more gene promoters comprise the promoter of MGMT.

Embodiment 286

A method of converting cytosine residues in a DNA to uracil, while leaving 5-methylcytosine residues substantially unaffected, said method comprising:
  contacting a sample comprising DNA with DABSO to convert said DNA;
  desulfonating the converted DNA, to produce a DNA in which cytosine residues are converted to uracil, but 5-methylcytosine residues substantially unaffected.

Embodiment 287

The method of embodiment 286, wherein said contacting comprises contacting said DNA with DABSO at a concentration ranging from about 2 M up to about 5 M.

Embodiment 288

The method of embodiment 286, wherein said contacting comprises contacting said DNA with DABSO at a concentration of about 2.5 M.

Embodiment 289

The method according to any one of embodiments 286-288, wherein said DABSO is dissolved in an alkaline aqueous solution.

Embodiment 290

The method of embodiment 289, wherein said DABSO is dissolved in a solution comprising KOH.

Embodiment 291

The method according to any one of embodiments 286-290, wherein said contacting comprises heating the DABSO/DNA solution to a temperature ranging from about 55° C. to about 90° C.

Embodiment 292

The method according to any one of embodiments 286-291, wherein said DABSO is reacted with the DNA for a period of time ranging from about 15 minutes up to about 90 minutes.

Embodiment 293

The method according to any one of embodiments 286-292, wherein said desulfonating comprises contacting said converted DNA with an alkaline reagent.

Embodiment 294

The method of embodiment 293, wherein said alkaline reagent comprises KOH.

Embodiment 295

The method according to any one of embodiments 286-294, wherein said conversion and/or desulphonation is performed on the DNA bound to a column.

Embodiment 296

The method according to any one of embodiments 286-294, wherein said conversion and/or desulphonation is performed on the DNA in solution.

Embodiment 297

A method of analyzing DNA methylation, said method comprising:
 providing a DNA sample;
 converting DNA in said sample according to the method of any one of embodiments 286-296; and
 performing methylation specific PCR and/or nucleic acid sequencing, and/or high resolution melting analysis (HRM) on the converted nucleic acid to determine the methylation of said nucleic acid.

Embodiment 298

The method of embodiment 297, wherein said providing a DNA sample comprises preparing a sample according to any one of embodiments 228-234 or according to any one of embodiments 243-252.

Embodiment 299

A kit for detection of methylation state of a DNA, said kit comprising:
 a container containing a conversion reagent comprising DABSO; and
 a container containing a desulphonation reagent.

Embodiment 300

The kit of embodiment 299, wherein said kit comprises a column comprising an affinity matrix.

Embodiment 301

The kit according to any one of embodiments 299-300, wherein said kit comprises a container containing a binding buffer.

Embodiment 302

The kit according to any one of embodiments 299-301, wherein said kit comprises a container containing an elution buffer.

Embodiment 303

The kit according to any one of embodiments 299-302, wherein said kit comprises a container containing a wash buffer.

Embodiment 304

The kit according to any one of embodiments 299-303, wherein said kit comprises a container containing a lysis solution according to any one of embodiments 169-171, and/or a container containing a lysis solution according to any one of embodiments 172-174.

Embodiment 305

The kit according to any one of embodiments 299-304, wherein said kit comprises a cartridge according to any one of embodiments 143-155 and/or a cartridge according to any one of embodiments 155-166.

Embodiment 306

The kit according to any one of embodiments 299-305, said kit comprising instructional materials teaching the use of said kit to convert a nuclei acid for determination of the methylation state of said nucleic acid.

Embodiment 307

A set of primers and probes for the determination of methylation of MGMT using a nested PCR reaction, said set comprising the following primers and probes:
 an external forward primer comprising the nucleotide sequence GTTTT(T*)AGAAYG(T*)TTTGYGTTT (SEQ ID NO:263);
 an external reverse primer comprising the nucleotide sequence AAAAAAC(T*)CCRCACTCTTCC (SEQ ID NO:265);
 an internal forward primer comprising the nucleotide sequence TTTCGACGTTCGTAGGTTTTCGC (SEQ ID NO:266);
 an internal reverse primer comprising the nucleotide sequence GCACTCTTCCGAAAACGAAACG (SEQ ID NO:267); and
 a probe comprising the nucleotide sequence fluor-CCAAACAC(T*)CACCAAATC(N*)CAAAC-blocker (SEQ ID NO: 268).

Embodiment 308

A set of primers and probes for the determination of methylation of ACTB (e.g., as a control) using a nested PCR reaction, said set comprising the following primers and probes:
 an external forward primer (102) comprising the nucleotide sequence GTGATGGAGGAGGTTTAGTAAGTT (SEQ ID NO:103);
 an external reverse primer (103) comprising the nucleotide sequence CCAATAAAACCTACTCCTCCCTTAA (SEQ ID NO:104);
 an internal forward primer (148) comprising the nucleotide sequence GGTTTAGTAAGTTTTTTGGATTGTG (SEQ ID NO:149);
 an internal reverse primer (149) comprising the nucleotide sequence CCTTAAAAATTACAAAAACCACAAC (SEQ ID NO:150); and
 a probe (178) comprising the nucleotide sequence fluor-CCACCACCCAACACA(N*)CAA(T*)AACAAACAC-blocker (SEQ ID NO:179).

Embodiment 309

A set of primers and probes for the determination of methylation of MGMT using a nested PCR reaction with determination of the methylation of ACTB as a control, comprising the primers and probes of embodiment 307 and the primers and probes of embodiment 308.

Embodiment 310

A method of determining the methylation of MGMT using methylation specific PCR said method comprising:
providing a converted (e.g., bisulfite converted) DNA containing a promoter region of the MGMT gene;
performing methylation specific PCR for MGMT methylation using a nested PCR reaction comprising the following primers and probes:
an external forward primer comprising the nucleotide sequence GTT TT(T*)AGAAYG(T*)TTTGYGTTT (SEQ ID NO:263);
an external reverse primer comprising the nucleotide sequence AAAAAAC(T*)CCRCACTCTTCC (SEQ ID NO:265);
an internal forward primer comprising the nucleotide sequence TTTCGACGTTCGTAGGTTTTCGC (SEQ ID NO:266);
an internal reverse primer comprising the nucleotide sequence GCACTCTTCCGAAAACGAAACG (SEQ ID NO:267); and
a probe comprising the nucleotide sequence fluor-CCAAACAC(T*)CACCAAATC(N*)CAAAC-blocker (SEQ ID NO: 268); and
detecting and/or quantifying the PCR amplification product to provide determine methylation of said MGMT gene.

Embodiment 311

The method of embodiment 310, wherein said method further comprises:
providing a converted (e.g., bisulfite converted) DNA containing a promoter region of the ACTB gene (e.g., as a control);
performing methylation specific PCR for ACTB methylation using a nested PCR reaction comprising the following primers and probes:
an external forward primer comprising the nucleotide sequence GTGATGGAGGAGGTTTAGTAAGTT (SEQ ID NO:103);
an external reverse primer comprising the nucleotide sequence CCAATAAAACCTACTCCTCCCTTAA (SEQ ID NO:104);
an internal forward primer comprising the nucleotide sequence GGTTTAGTAAGTTTTTTGGATTGTG (SEQ ID NO:149);
an internal reverse primer comprising the nucleotide sequence CCTTAAAAATTACAAAAACCACAAC (SEQ ID NO:150); and
a probe comprising the nucleotide sequence fluor-CCACCACCCAACACA(N*)CAA(T*) AACAAACAC-blocker (SEQ ID NO:179); and
detecting and/or quantifying the PCR amplification product to provide determine methylation of said ACTB gene.

Embodiment 312

The method according to any one of embodiments 310-311, wherein said methylation specific PCR for MGMT methylation and said methylation specific PCR for ACTB methylation are performed in a single multiplex PCR reaction.

Embodiment 313

The method according to any one of embodiments 310-312, wherein said methylation specific PCR is performed using a cartridge according to any one of embodiments 92-132.

Embodiment 314

The method of embodiment 313, wherein: said providing a converted DNA containing a promoter region of the MGMT gene comprises introducing an unconverted DNA containing a promoter region of the MGMT gene into said cartridge and operating said cartridge to convert said DNA in said cartridge using a conversion reagent; and/or said providing a converted DNA containing a promoter region of the ACTB gene comprises introducing an unconverted DNA containing a promoter region of the ACTB gene into said cartridge and operating said cartridge to convert said DNA in said cartridge using a conversion reagent.

Embodiment 315

The method of embodiment 314, wherein said conversion reagent comprises a compound selected from the group consisting of ammonium bisulfite, sodium metabisulfite, potassium bisulfite, cesium bisulfite, and DABSO.

Embodiment 316

The method according to any one of embodiments 313-315, wherein said operating said cartridge comprises heating said DNA and said conversion reagent in a thermocycling channel or chamber that is later used to perform said nested PCR reaction.

In certain embodiments the methods and/or cartridges expressly exclude magnetic materials including magnetic glass, magnetic hydroxyapatite, and magnetic matrix materials. In certain embodiments the methods and/or cartridges expressly exclude magnetic materials for DNA isolation.

BRIEF DESCRIPTION OF THE DRAWINGS

FIGS. 2A-2C illustrate one embodiment of a GENEXPERT® cartridge suitable for the determination of DNA methylation as described herein. FIG. 2A shows a cartridge; FIG. 2B shows an inverted, exploded view of the cartridge; and FIG. 2C shows a detail of central syringe barrel 206 which is in fluid communication with a valve body 210.

FIG. 3A illustrates a module for operation of a GENEXPERT® cartridge. FIG. 3B illustrates some components of one embodiment of a module for operation of a cartridge for the analysis of DNA methylation. FIG. 3C illustrates a system (e.g., processing unit) incorporating a plurality of modules.

FIGS. 4A-4D illustrate various strategies for the use of MethyLight protocols to detect/quantify DNA phosphorylation. FIG. 4A, modified from Eads et al. 92000) *Nucleic*

*Acids. Res.*, 28(8): e32) schematically illustrates MethyLight technology. DNA is modified by sodium bisulfite which generates methylation-dependent sequence differences, e.g., at CpG dinucleotides by converting unmethylated cytosine residues (locations indicated by white circles) to uracil, while methylated cytosine residues (locations indicated by black circles) are retained as cytosine. Fluorescence-based PCR is then performed with primers that either overlap methylation sites or that do not overlap any methylation sites. Sequence discrimination can occur either at the level of the PCR amplification process (panel D) or at the level of the probe hybridization process (panel B), or both (panel D). Sequence discrimination at the PCR amplification level utilizes primers and probes (panel D), or just primers (panel C), to overlap potential methylation sites (e.g., CpG dinucleotides). Only two (fully methylated (M) and fully unmethylated (U)) of the many theoretical methylation permutations are shown. The MethyLight assay can also be designed such that sequence discrimination does not occur at the PCR amplification level. If neither the primers nor the probe overlap sites of methylation (e.g., CpG dinucleotides) (panel A), then no methylation-dependent sequence discrimination occurs at the PCR amplification or probe hybridization level. This reaction represents amplification of the converted genomic DNA without bias to methylation status, which can serve as a control for the amount of input DNA. When just the probe overlaps methylation sites (panel B), then sequence discrimination can occur through probe hybridization. FIG. 4B illustrates a MethyLight approach using a single, e.g., methylation-specific, probe (PR3) along with methylation specific forward (FW) and reverse (RV) primers. FIG. 4C illustrates a MethyLight approach using multiple probes (PR1 . . . PR5) that each target different regions. FIG. 4D illustrates a MethyLight approach using multiple probes (PR1 . . . PR5) that each target the same region, but provide signals for different methylation patterns.

FIGS. 6A and 6B illustrate the results of a titration for bisulfite-converted ACTB using human genomic DNA (hgDNA) in a 15 cycle nested qPCR (FIG. 6A) and a 20 cycle nested qPCR (FIG. 6B).

FIGS. 7A-7C shows the result of 20 cycles of nested qPCR (in the cartridge) for six methylated targets (AKR1B1, HOXB4, TM6SF1, RAASGRF2, and RASSF1A). FIG. 7A shows the results for 25 ng of HSDNA or 5000 cells without bisulfite conversion. FIG. 7B shows the results of 20 cycles of nested qPCR for the bisulfite converted methylated targets using DNA from MBA-453 cells. FIG. 7C shows the results of 20 cycles of nested qPCR for the bisulfite converted methylated targets using DNA from MBA-453 cells in a carrier (1 µg of SS and 10 ng of HS DNA). Fallouts occur at around 25-50 copies or around 100 cells.

FIG. 18 illustrates controls for cfDNA extraction.

FIG. 27A illustrates the detection of both methylated DNA and mutations in the same cartridge. Top panel illustrates detection of methylated DNA and a Kras G12D mutation in one cartridge, while bottom panel illustrates detection of methylated DNA and wildtype Kras in one cartridge.

FIG. 28 illustrates temperature optimization for multiplex methylation analysis of ADAMTS1, and BNC1 of a forward strand (top) and a reverse strand (bottom) of bisulfate-converted DNA.

DEFINITIONS

Figure 1A:
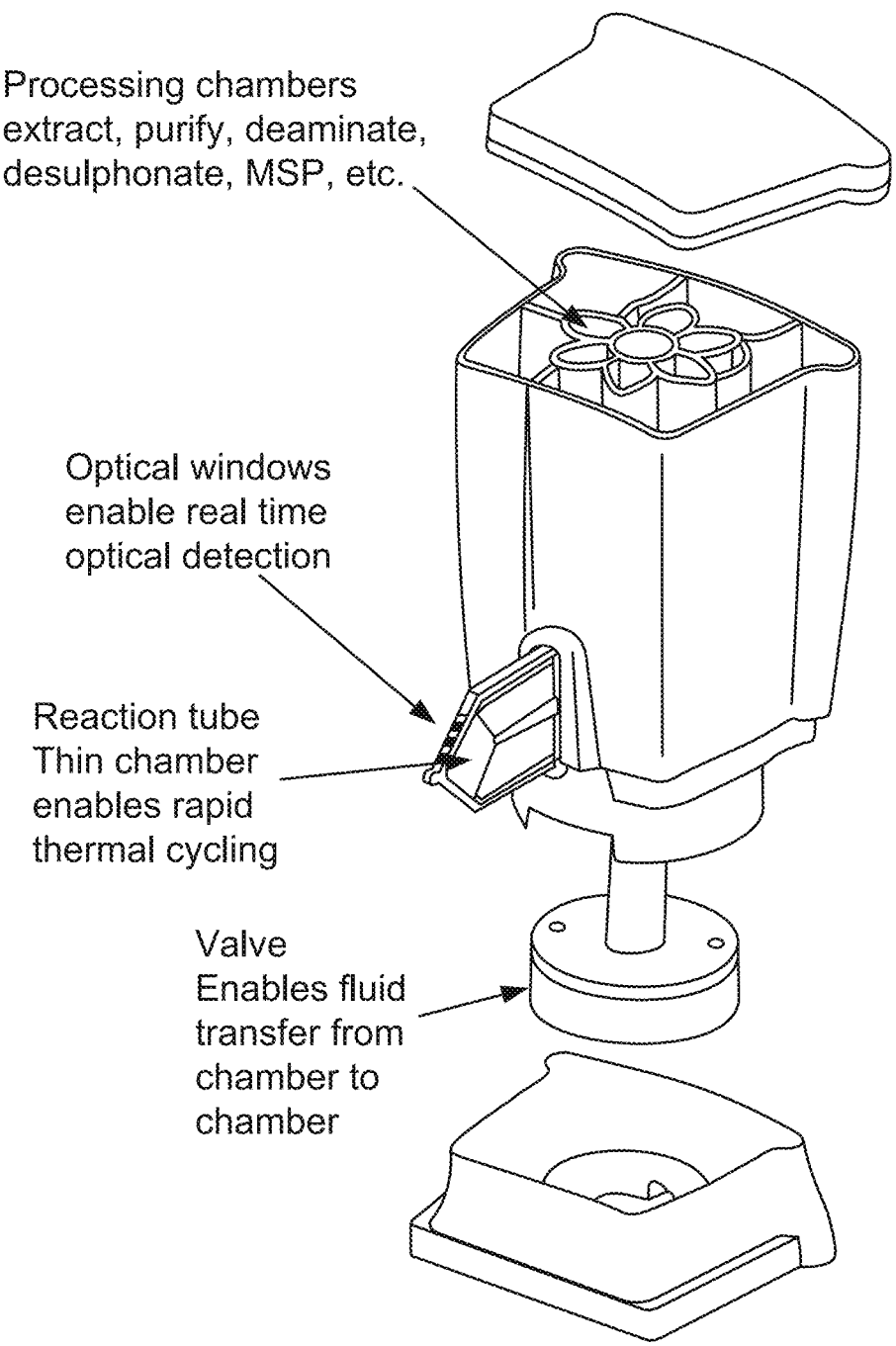
FIG. 1A illustrates major components of a cartridge (e.g., a GENEXPERT® cartridge) suitable for use with the methods described herein.

To facilitate an understanding of the present invention, a number of terms and phrases are defined below:

As used herein, the terms "detect", "detecting" or "detection" may describe either the general act of discovering or discerning or the specific observation of a detectably labeled composition.

As used herein, the term "detectably different" or "spectrally distinguishable" refers to a set of labels (such as dyes/fluorophores) that can be detected and distinguished simultaneously.

DNA methylation DNA methylation refers to the addition of a methyl group ($CH_3$) covalently to the base cytosine (C) typically in the dinucleotide 5'-CpG-3'. The term CpG refers to the base cytosine (C) linked by a phosphate bond to the base guanine (G) in the DNA nucleotide sequence.

The term "conversion reagent" refers to a reagent that deaminates cytosine to uracil in single stranded DNA, while leaving 5-MeC essentially unaffected. Illustrative conversion reagents include bisulfites (e.g., sodium metabisulfite, potassium bisulfite, cesium bisulfite, ammonium bisulfite, etc.) and/or compounds that can produce a bisulfite under appropriate reaction conditions (e.g., DABSO).

The phrase "detecting methylation of a gene" generally refers to the detection of methylation of cytosine, typically in CPG islands, in the promoter region of the gene.

As used herein, the terms "patient" and "subject" are typically used interchangeably to refer to a human. In some embodiments, the methods described herein may be used on samples from non-human animals, e.g., a non-human primate, canine, equine, feline, porcine, bovine, lagomorph, and the like.

As used herein, the terms "oligonucleotide," "polynucleotide," "nucleic acid molecule," and the like, refer to nucleic acid-containing molecules, including but not limited to, DNA. The terms encompass sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "oligonucleotide," refers to a single-stranded polynucleotide typically having fewer than 500 nucleotides. In some embodiments, an oligonucleotide is 8 to 200, 8 to 100, 12 to 200, 12 to 100, 12 to 75, or 12 to 50 nucleotides long. Oligonucleotides may be referred to by their length, for example, a 24 residue oligonucleotide may be referred to as a "24-mer."

As used herein, the term "complementary" to a target gene (or target region thereof), and the percentage of "complementarity" of the probe sequence to the target gene sequence is the percentage "identity" to the sequence of target gene or to the complement of the sequence of the target gene. In determining the degree of "complementarity" between probes used in the compositions described herein (or regions thereof) and a target gene, such as those disclosed herein, the degree of "complementarity" is expressed as the percentage identity between the sequence of the probe (or region thereof) and sequence of the target gene or the complement of the sequence of the target gene that best aligns therewith. The percentage is calculated by counting the number of aligned bases that are identical as between the 2 sequences, dividing by the total number of contiguous nucleotides in the probe, and multiplying by 100. When the term "complementary" is used, the subject oligonucleotide is at least 90% complementary to the target molecule, unless indicated otherwise. In some embodiments, the subject oligonucleotide is at least 91%, at least 92%, at least 93%, at least 94%, at least 95%, at least 96%, at least 97%, at least 98%, at least 99%, or 100% complementary to the target molecule.

A "primer" or "probe" as used herein, refers to an oligonucleotide that comprises a region that is complementary to a sequence of at least 8 contiguous nucleotides of a target nucleic acid molecule, such as a target gene. In some embodiments, a primer or probe comprises a region that is complementary to a sequence of at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 29, at least 30, at least 319, at least 32, at least 33, at least 34, at least 35, at least 36, at least 37, at least 38, at least 39, or at least 40 contiguous nucleotides of a target molecule. When a primer or probe comprises a region that is "complementary to at least x contiguous nucleotides of a target molecule," the primer or probe is at least 95% complementary to at least x contiguous nucleotides of the target molecule. In some embodiments, the primer or probe is at least 96%, at least 97%, at least 98%, at least 99%, or 100% complementary to the target molecule.

The term "nucleic acid amplification," encompasses any means by which at least a part of at least one target nucleic acid is reproduced, typically in a template-dependent manner, including without limitation, a broad range of techniques for amplifying nucleic acid sequences, either linearly or exponentially. Exemplary means for performing an amplifying step include polymerase chain reaction (PCR), ligase chain reaction (LCR), ligase detection reaction (LDR), multiplex ligation-dependent probe amplification (MLPA), ligation followed by Q-replicase amplification, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), and the like, including multiplex versions and combinations thereof, for example but not limited to, OLA/PCR, PCR/OLA, LDR/PCR, PCR/PCR/LDR, PCR/LDR, LCR/PCR, PCR/LCR (also known as combined chain reaction—CCR), digital amplification, and the like. Descriptions of such techniques can be found in, among other sources, Ausbel et al.; PCR Primer: A Laboratory Manual, Diffenbach, Ed., Cold Spring Harbor Press (1995); The Electronic Protocol Book, Chang Bioscience (2002); Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1):41-7, U.S. Pat. Nos. 6,027,998; 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18-(2002); Lage et al., Genome Res. 2003 February; 13(2):294-307, and Landegren et al., Science 241:1077-80 (1988), Demidov, V., Expert Rev Mol Diagn. 2002 November; 2(6):542-8, Cook et al., J Microbiol Methods. 2003 May; 53(2):165-74, Schweitzer et al., Curr Opin Biotechnol. 2001 February; 12(1):21-7, U.S. Pat. Nos. 5,830,711, 6,027,889, 5,686,243, PCT Publication No. W00056927A3, and PCT Publication No. W09803673A1.

In some embodiments, amplification comprises at least one cycle of the sequential procedures of: annealing at least one primer with complementary or substantially complementary sequences in at least one target nucleic acid; synthesizing at least one strand of nucleotides in a template-dependent manner using a polymerase; and denaturing the newly-formed nucleic acid duplex to separate the strands. The cycle may or may not be repeated. Amplification can comprise thermocycling or, in certain embodiments, can be performed isothermally.

The term "hybridize" is typically used herein refer to "specific hybridization" which is the binding, duplexing, or hybridizing of a nucleic acid molecule preferentially to a particular nucleotide sequence, in some embodiments, under stringent conditions. The term "stringent conditions" refers to conditions under which a probe will hybridize preferentially to its target sequence, and to a lesser extent to, or not at all to, other sequences. A "stringent hybridization" and "stringent hybridization wash conditions" in the context of nucleic acid hybridization are sequence-dependent and are different under different environmental parameters. An extensive guide to the hybridization of nucleic acids is found in, e.g., Tijssen (1993) Laboratory Techniques in Biochemistry and Molecular Biology—Hybridization with Nucleic Acid Probes part I, Ch. 2, "Overview of principles of hybridization and the strategy of nucleic acid probe assays," Elsevier, N.Y. ("Tijssen"). Generally, highly stringent hybridization and wash conditions for filter hybridizations are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. In certain embodiments very stringent conditions are selected to be equal to the $T_m$ for a particular probe. Dependency of hybridization stringency on buffer composition, temperature, and probe length are well known to those of skill in the art (see, e.g., Sambrook and Russell (2001) *Molecular Cloning: A Laboratory Manual* (3rd ed.) Vol. 1-3, Cold Spring Harbor Laboratory, Cold Spring Harbor Press, NY).

A "sample," as used herein, generally refers to a biological sample including biological fluids (e.g., blood or blood fractions, serum, plasma, pancreatic juice, cerebrospinal fluid, oral fluid, lymph, intraocular fluid, and the like) and/or tissue samples including, but not limited to biopsy samples, frozen tissue samples, formalin fixed paraffin embedded (FFPE) samples from various tissues including but not limited to breast tissue, endocervical tissue, vaginal tissue, colon/rectal tissue, throat tissue, and other types of human samples, such as blood, stool, and biopsy samples. The term sample also includes diluted and/or buffered forms of the above samples, for example, a buffer into which a swab sample has been placed, a urine sample to which a buffer has been added, and the like.

As used herein, the phrase "is indicative of the presence of a cancer or a predisposition to a cancer" means that a particular result tends to indicate that a cancer is present, and/or a precancerous condition is present or likely present. This phrase does not imply a definitive determination that the condition is present. A definitive determination can be made based on further examination or testing that a medical practitioner deems appropriate. Furthermore, this phrase does not require that a determination be made as to which condition may be present based only on the particular result. Rather, it is contemplated that a positive result will be considered in light of other examination or text results to arrive at a differential diagnosis.

The term "tubefill procedure" refers to a procedure that is run using standard laboratory instrumentation rather than on a cassette (e.g., rather than with a GENEXPERT®, or modified GENEXPERT® cartridge described herein).

DETAILED DESCRIPTION

In various embodiments devices and methods are provided that facilitate the rapid detection and/or characterization of methylation in DNA samples. In certain embodiments automated reaction cartridges are provided as are methods that that utilize the automated reaction cartridge(s) to facilitate analysis of the methylation of a DNA sample and, optionally, to measure mRNA levels along with the determination of DNA methylation. In various embodiments the DNA methylation is determined by bisulfite conversion and analysis of the bisulfite converted DNA (e.g., via methylation specific PCR, nucleic acid sequencing, melting point analysis, and the like). In certain embodiments the cartridge performs all or a part of the bisulfite conversion of DNA and all or a part of the analysis of the bisulfite converted DNA. In certain embodiments the cartridge performs all of the steps involved in bisulfite conversion and all or a part of the analysis of the bisulfite-converted DNA. In certain embodiments the cartridge performs all of the steps involved in bisulfite conversion and all of the analysis of the bisulfite-converted DNA. In certain embodiments the cartridge additionally performs an isolation and purification of the DNA to be analyzed.

There are several advantages to automating the methylation analysis including for example, reduction in overall processing time, improvements in efficiency, decreased user error and variability, minimization of loss between steps, and an improved ability to use smaller amounts of sample. Use of a cartridge-based process, as described herein, allows for rapid and easy testing of not only multiple sample types but also for evaluating methylation changes observed in several different types of cancers including, but not limited to breast cancer, colorectal cancer, prostate cancer, and lung cancer.

The cartridge-based methods described herein additionally permit measurement of mRNA derived from the same sample. Measurement of corresponding upstream and/or downstream mRNA involved in DNA methylation can be important to understand the mechanism and activity of the epigenetic modification. For example, the measurement of DNA methyltransferases (DNMT) mRNA has been studied along with DNA methylation for several cancers (see Table 1).

TABLE 1

Illustrative DNA methyltransferases and their importance in particular cancers (from Subramaniam et al. (2014) *Front Oncol.*, 4: Article 80, doi: 10.3389/fonc.2014.00080).

| Methyltransferase | Cancers |
| --- | --- |
| DNMT1 | Leukemia: upregulated - 5.3-fold expression |
| | Gastric cancer - 64.8% localized in the cytoplasm and nuclei |
| | Breast cancer - 16.6% |
| | Hepatocellular carcinoma - 100% |
| | Pancreatic cancer - highly expressed - Gli target gene |
| | Colon cancer - highly expressed |
| | Glioblastoma - overexpressed |

TABLE 1-continued

Illustrative DNA methyltransferases and their importance in particular cancers (from Subramaniam et al. (2014) *Front Oncol.*, 4: Article 80, doi: 10.3389/fonc.2014.00080).

| Methyltransferase | Cancers |
| --- | --- |
| DNMT2 or TRDMT1 | Hepatocellular carcinoma - reduced expression |
| | Colorectal and stomach cancers - lower mRNA expression |
| DNMT3A | Acute myeloid leukemia - 22.1% mutations and affect translation |
| | Gastric cancer - 70.4% localized in the cytoplasm |
| | Breast cancer - 14% |
| | Hepatocellular carcinoma - 60% |
| | Pancreatic cancer - highly expressed - regulated by Gli 1 |
| | Colon cancer - highly expressed |
| DNMT3B | Leukemia: upregulated- 11.7-fold expression |
| | Gastric cancer - 51.9% localized in the cytoplasm |
| | Breast cancer - 81.8% poor prognosis |
| | Breast cancer cell lines-hypermethylation defect resulted in aberrant - overexpression DNMT activity |
| | Hepatocellular carcinoma (60%) and mRNA levels high |
| | Colon cancer - highly expressed |
| | Prostate cancer - overexpressed |
| | Glioblastoma - overexpressed |
| DNMT3L | Cervical cancer - promising biomarker |
| | Embryonal carcinoma - novel biomarker |

Often separate independent extractions for DNA or RNA are used for studying and measuring genes and transcripts. Co-detection from the same sample preparation would be ideal to minimize sample preparation, assay to assay, sample-to-sample and cell-to-cell variability.

Cartridge-Based Bisulfite Conversion of DNA

In certain embodiments the extraction of DNA, bisulfite conversion, and methylation specific PCR are all performed in the cartridge. In one illustrative embodiment, the user will add the sample to a lysis/binding reagent, then mix/vortex the reagent briefly, and then add the sample to a sample port or chamber in the cartridge. Illustrative, but non-limiting lysis reagents (including reagents particularly well suited for FFPE sections) are described in PCT Patent Publication No: WO/2014/052551 (PCT/US2013/061863), which is incorporated herein by reference for the reagents described therein.

Additional illustrative lysis reagents for serum or plasma and for formalin-fixed paraffin embedded (FFPE) samples are shown in Example (Tables 11, and 12, respectively).

Figure 11:
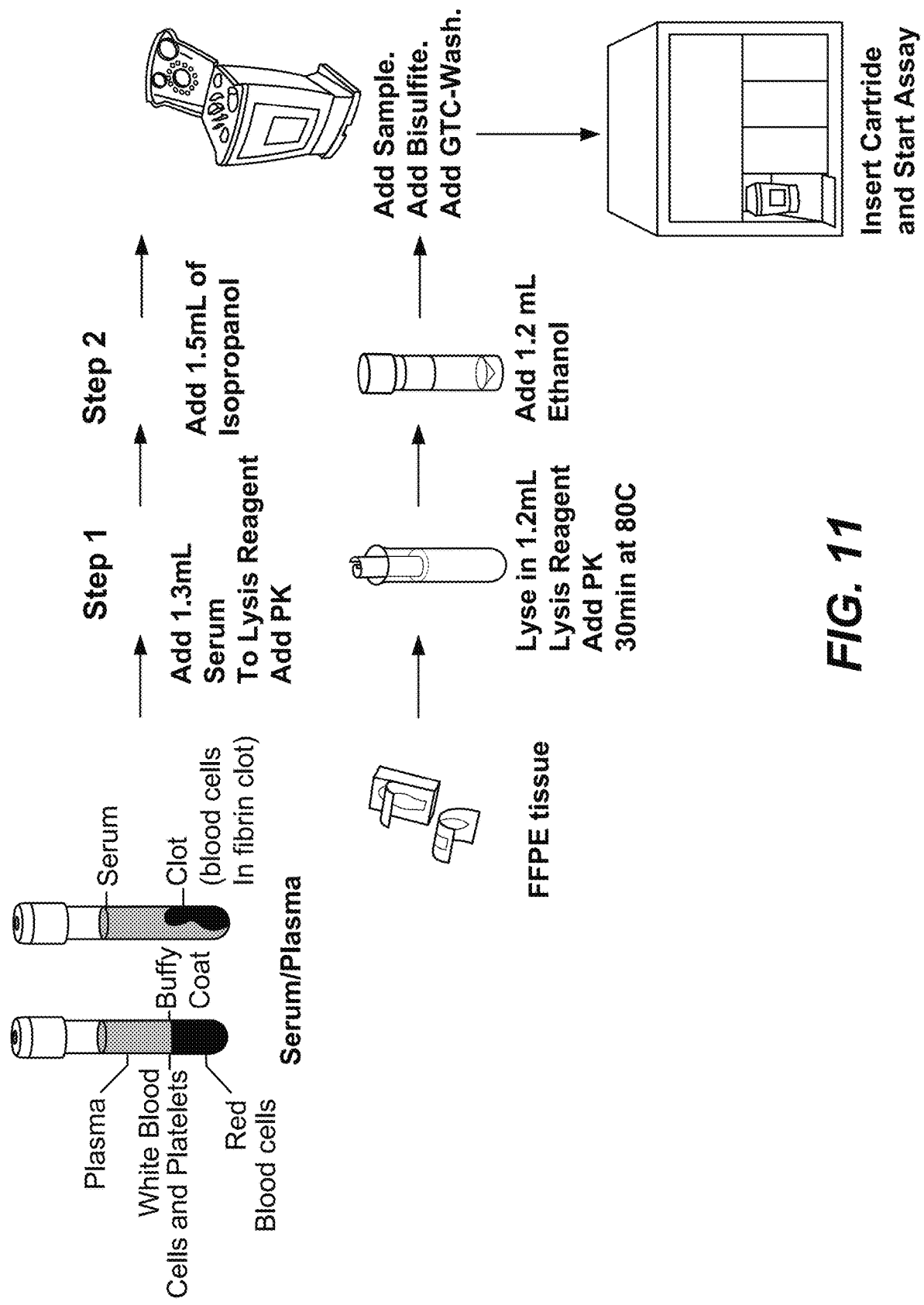
FIG. 11 shows illustrative but non-limiting workflows for analysis of methylation using a cartridge (e.g., a GENEXPERT® cartridge). Top illustrates one work flow for analysis of DNA methylation in a serum or plasma sample. Bottom illustrates one work flow for analysis of DNA methylation in a tissue section (e.g., frozen or formalin-fixed paraffin embedded (FFPE) section).

In certain embodiments the cartridge is placed into a processing module and the assay is initiated by clicking through a set of selections within software controlling the processing module (see, e.g., FIGS. 11A and 11B). The cartridge then performs the bisulfite conversion process and analysis of the bisulfite-converted DNA. In certain embodiments mRNA is also determined. While in certain embodiments, all of the operations are performed in the cartridge, in other embodiments, subsets of the various operations are performed in the cartridge as described below.

The sample can comprise any biological sample that contains DNA whose methylation state is to be evaluated. Illustrative samples include, but are not limited to isolated DNA and/or isolated total nucleic acids, a cell, a tissue, a biological fluid containing a nucleic acid, and the like. In certain embodiments the biological sample comprises a biological fluid selected from the group consisting of plasma, serum, amniotic fluid saliva, mucus, urine, pancreatic juice, and cerebrospinal fluid. In certain embodiments the sample comprises a tissue sample from a healthy tissue, or a tissue sample from a diseased sample. In certain embodiments the tissue sample is from a fetus, a neonate, a child, an adolescent, or an adult. In certain embodiments the tissue sample comprises tumor cell and/or is derived from a biopsy of a tumor (e.g., a breast cancer, a prostate cancer, a brain cancer, a cervical cancer, an ovarian cancer, a pancreatic cancer, a colon cancer, a gastric cancer, a hepatocellular cancer and the like. In certain embodiments the sample comprises a fixed tissue, e.g., a formalin fixed tissue sample. In certain embodiments the sample comprises an embedded tissue sample (e.g., a formalin-fixed paraffin embedded (FFPE) tissue sample).

Bisulfite conversion of DNA typically involves four steps:
1) DNA purification;
2) DNA denaturation;
3) DNA conversion (e.g., bisulfite deamination); and
4) Alkali desulphonation.

Typically DNA conversion (e.g., using a conversion reagent such as a bisulfite) involves: 1) Sulphonation: The addition of bisulphite to the 5-6 double bond of cytosine; and 2) Hydraulic Deamination: hydrolytic deamination of the resulting cytosine-bisulphite derivative to give a uracil-bisulphite derivative. This is followed by Alkali Desulphonation: Removal of the sulphonate group by an alkali treatment, to give uracil as indicated above.

As noted above, in certain embodiments, the DNA purification can be performed prior to placing a sample in the cartridge, or alternatively, can be performed by the cartridge itself. Accordingly, in certain embodiments the sample is added directly to the reaction cartridge, while in other embodiments, the sample is mixed with one or more reagents. In certain embodiments DNA preparation typically involves preparing substantially isolated DNA. This may involve lysing cells to release DNA, removing particulates and cellular debris, and/or removing protein components to provide a sample comprising substantially pure nucleic acids (e.g., substantially pure DNA and/or a substantially pure combination of DNA and RNA). In one illustrative, but non-limiting, embodiment, the sample (e.g., a tissue sample) is added to a lysis reagent, agitated and then inserted into the cartridge for further processing.

In certain embodiments, all of the reagents necessary to perform bisulfite conversion of the DNA are provided in the cartridge. In certain embodiments, to avoid degradation of reagents over time in the cartridge, certain reagents may be added to the cartridge immediately before use. Thus, for example in certain embodiments, it is contemplated that the cartridge may be loaded with a conversion reagent (e.g., a bisulfite reagent) and/or a guanidium thiocyanate reagent (e.g., GTC-EtOH-Tween) at or about the time the sample is loaded into the cartridge. In certain embodiments, the guanidinium thiocyanate reagent (e.g., GTC-EtOH-Tween) is combined with the sample and added to the cartridge in the sample receiving chamber (e.g., chamber 2 in the GENEXPERT® cartridge).

In certain embodiments when performing the bisulfite conversion of DNA using a reaction cartridge (e.g., GENEXPERT® cartridge), the method comprises
  i) contacting a biological sample comprising a nucleic acid to a first matrix material comprising a first column or filter where said matrix material binds and/or filters nucleic acids in said sample and thereby purifies the DNA;
  ii) eluting the bound DNA from the first matrix material (e.g., using an alkaline solution) and denaturing the DNA to produce eluted denatured DNA;
  iii) heating the eluted DNA in the presence of a conversion reagent (e.g., a reagent that provides bisulfite ions) to produce a converted (e.g., a deaminated) nucleic acid;
  iv) contacting the converted nucleic acid to a second matrix material comprising a second column to bind said deaminated nucleic acid to said second matrix material (note in certain embodiments the second column can be a column different than the first column, or in other embodiments, the same column used a second time);
  v) desulfonating the bound deaminated nucleic acid and/or simultaneously eluting and desulfonating the nucleic acid by contacting the deaminated nucleic acid with an alkaline solution to produce a converted (e.g., bisulfite converted) nucleic acid; and
  vi) eluting the converted nucleic acid from said second matrix material, wherein at least steps iv) through vi) are performed in a one reaction cartridge.

In certain embodiments the method further includes the analysis of the converted DNA. Accordingly, in certain embodiments, the method further comprises:
  vii) performing methylation specific PCR and/or nucleic acid sequencing, and/or high resolution melting analysis (HRM) on the converted nucleic acid to determine the methylation of the nucleic acid, wherein at least steps iv) through vi) are performed in a single reaction cartridge.

In certain embodiments at least steps iii) through vi) are performed in one reaction cartridge.

In certain embodiments at least steps ii) through vi) are performed in one reaction cartridge.

In certain embodiments at least steps i) through vi) are performed in one reaction cartridge.

In certain embodiments at least steps i) through vii) are performed in one reaction cartridge.

It is noted that the first column and, where present, the second column can refer to discrete columns. However, particularly when integrated into a reaction cartridge, the "column" can simply be a matrix material disposed in a chamber or channel in the cartridge. In various embodiments the "columns" act as filters and/or as affinity columns that bind nucleic acids. Accordingly, in certain embodiments the column contains a matrix material that binds a nucleic acid (e.g., DNA and/or RNA). Illustrative matrix materials include, but are not limited to, glass (silica), an ion exchange resin, hydroxyapatite, and the like. It will be recognized that the matrix materials can take a number of forms. Thus, in certain embodiments, the matrix material comprises a fibrous material a particulate material (e.g., microbeads, nanobeads, etc.), a structured material (e.g., porous "baffle" system", a serpentine channel, and the like). In certain embodiments the first column and second column are different columns (chambers or channels). In other embodiments the first column and the second column are the same column (chamber or channel) that is used twice (e.g., a first time and a second time).

In certain embodiments, the use of one or more additional filters, e.g., to clean up the initial sample prior to contacting with the first matrix material, is contemplated. Thus, for example, in certain embodiments, a filter matrix (e.g., polycarbonate filter, nylon filter, polypropylene filter, polyester filter, nylon filter, ceramic filter, polytetrafluoroethylene filter, and the like) is disposed in the sample receiving chamber or "downstream" from the sample receiving chamber and before the first "column". It is also recognized, that in certain embodiments, the sample, can be lysed and/or filtered prior to deposition into a sample receiving chamber.

In certain illustrative, but non-limiting embodiments, the methods described herein can be performed using a GENEXPERT® cartridge (Cepheid, Inc., Sunnyvale, Calif.) or a variant thereof. In various embodiments sample extraction, and/or amplification, and/or DNA conversion, and/or detection can all be carried out within this self-contained "laboratory in a cartridge" (see, e.g., U.S. Pat. Nos. 5,958,349, 6,403,037, 6,440,725, 6,783,736, and 6,818,185, each of which is herein incorporated by reference in its entirety). In various embodiments components of the cartridge can include, but are not limited to, processing chambers containing reagents, filters, and capture technologies useful to extract, purify, and amplify target nucleic acids. A valve enables fluid transfer from chamber to chamber and contains nucleic acids lysis and filtration components. An optical window enables real-time optical detection (e.g., of PCR amplification products). A reaction tube can be provided that permits very rapid heating and/or thermal cycling.

In certain embodiments an illustrative GENEXPERT® cartridge comprises a plurality of chambers disposed around a central valve assembly and selectively in fluid communication with the central valve assembly where the central valve assembly is configured to accommodate a plunger that is capable of drawing fluid into or out of a chamber in fluid communication with the central valve. Rotation of the valve assembly determines which chamber are in fluid communication with the central valve. One illustrative GENEXPERT® cartridge is illustrated in FIG. 1A which show the cartridge, processing/reagent chambers, a reaction tube (e.g., heating and/or thermocycling tube), optional optical windows, and a valve that facilitates fluid transfer from chamber to chamber.

Figure 1B:
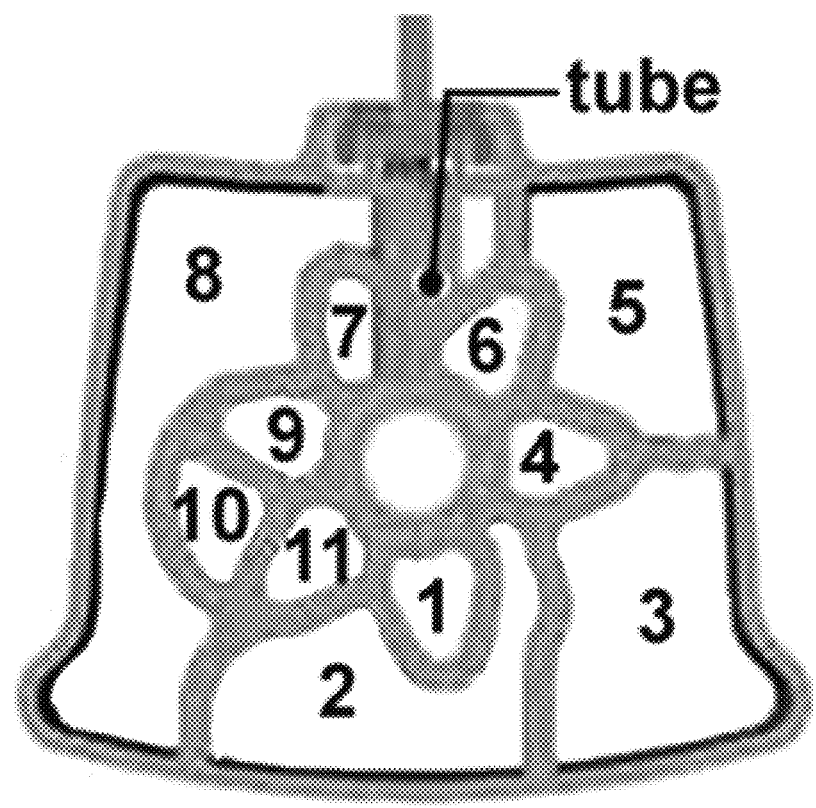
FIG. 1B shows a top view of the cartridge illustrating chambers disposed around a central valve.

An illustrative layout of the cartridge is shown in FIG. 1B which provides a top view of the cartridge identifying various chambers by number. In one illustrative, but non-limiting embodiment, the components of the chambers comprising the cartridge are as listed in Table 2. It will be recognized that this disposition of reagents and chamber is illustrative and non-limiting. Using the teachings provided herein other reagent dispositions and/or other chamber configurations will be available to one of skill in the art.

TABLE 2

One illustrative embodiment showing chamber contents for use of a GENEXPERT® cartridge for measurement of DNA methylation.

| Chamber # | Chamber Contents | Initial Volume (µL) |
|---|---|---|
| 1 | | — |
| 2* | Sample chamber (sample mixed with e.g., GTC-EtOH-Tween precipitation reagent) | |
| 3** | GTC-EtOH | |
| 4*** | Bisulfite reagent (e.g., 8M ammonium bisulfite) | |
| 5 | Buffer e.g., 50 mM Tris pH 8.5 | |
| 6 | | — |
| 7 | | — |
| 8 | Rinse (e.g., PEG 200) | |
| 9 | Beads (e.g., polymerase, primer, probe) | |

TABLE 2-continued

One illustrative embodiment showing chamber contents for use of a GENEXPERT® cartridge for measurement of DNA methylation.

| Chamber # | Chamber Contents | Initial Volume (µL) |
|---|---|---|
| 10 | Elution/Desulphonation reagent (e.g., 15 mM KOH) | |
| 11 | Beads (e.g., polymerase, primer, probe) | |

*Sample is added to chamber 2 by user
**In certain embodiments, GTC-EtOH is added at time of use (e.g., when sample is added). In certain embodiments GTC-EtOH is provided as reagent already disposed in cartridge.
***In certain embodiments, bisulfite reagent is added at time of use (e.g., when sample is added). In certain embodiments bisulfite reagent is already disposed in cartridge.

Figure 1C:
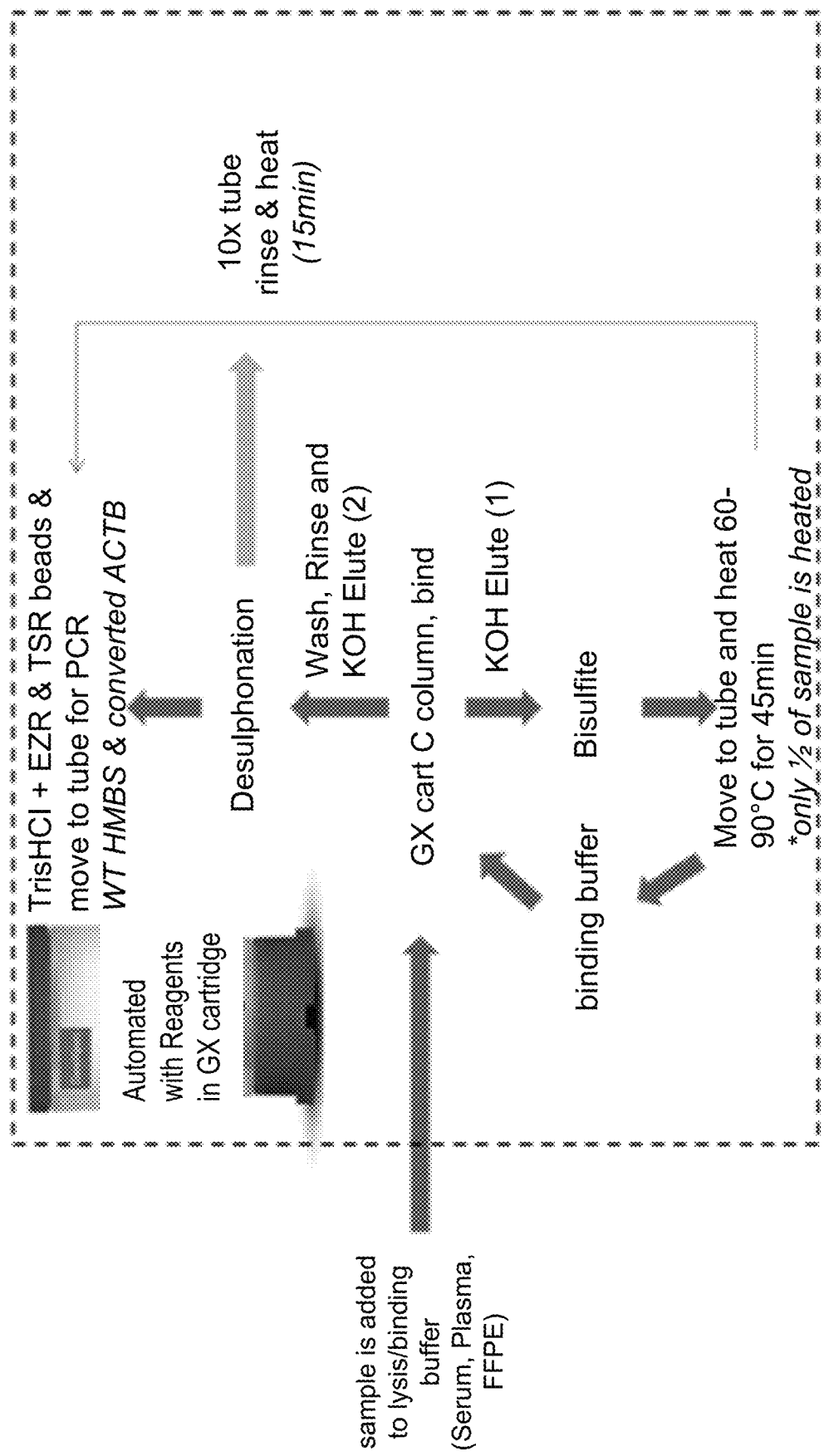
FIG. 1C shows an illustrative workflow for the determination of DNA methylation utilizing the reaction cartridge.

One embodiment of a step-by-step workflow for the determination of DNA methylation utilizing such a cartridge is shown in FIG. 1C. In this cartridge configuration, there are five chambers that, in use (e.g., when the cartridge is operating to determine DNA methylation), will hold reagents and buffers (e.g., chambers 3, 4, 5, 8, and 10), one chamber that will hold the sample added by the user (e.g., chamber 2), and one or two (or more) chambers holding analysis reagents (e.g., MSP reagents such as enzyme reaction, template specific reaction, and/or or 200 mM Tris pH 7.0, e.g., as beads) (e.g., chambers 9, and 11). In certain embodiments, the reagents (e.g., polymerase, reverse transcriptase, primer, probe) are provided in solution. In certain embodiments the reagents are provided as lyophilized powders. In certain embodiments the reagents are provided as lyophilized beads. The beads can further comprise agents to that improve reagent stability and/or activity (see, e.g., U.S. Patent Publication No: 2006/0068399 which is incorporated herein by reference for the beads, bead fabrication, and bead formulations described therein.

In certain embodiments the cartridge, as provided contains all of the reagents necessary to run the cartridge and only the sample (e.g., sample in buffer/lysis/precipitation solution) is added to the cartridge. In certain embodiments the cartridge is provided without the GTC-EtOH and/or the bisulfite reagents and one or both are added at the time of use. Thus, in certain embodiments, the GTC-EtOH reagent is added to the cartridge at the time of use, in certain embodiments the bisulfite reagent (in addition to the sample) is added to the chamber at the time of use, and in certain embodiments, both the GTC-EtOH and the bisulfite reagent (in addition to the sample) are added to the cartridge at the time of use. In certain embodiments these reagents are added directly to the desired chambers (see, e.g., Table 2). In certain embodiments ports are provided for loading the reagents and the ports are configured to deliver the reagent(s) to the desired chambers.

At the start of the assay, the cartridge dispenses the sample, e.g. from chamber 2 over a glass fiber column (e.g. the first column) in the cartridge. DNA is eluted off the column and simultaneously denatured by an alkali solution, e.g., a low concentration of potassium hydroxide from chamber 10 into a concentrated bisulfite reagent (e.g., concentrated ammonium bisulfite) in Chamber 4. In certain embodiments the DNA is eluted with an alkaline solution of KOH with a pH greater than about 10.5, or a pH greater than about pH 12. In certain embodiments the DNA is eluted with 10-15 mM KOH.

Figure 16:
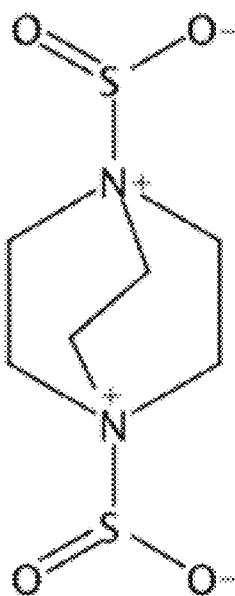
FIG. 16 illustrates the structure of DABSO (1,4-diazonibicyclo[2.2.2]octane-1,4-disulfinate).

As indicated above, the DNA is eluted (optionally with a burst of sonication) into the bisulfite reagent. In various embodiments the conversion reagent (e.g., bisulfite reagent)

is present at a concentration ranging from about 4 M to about 10 M, or from about 5 M to about 8 M, or from about 6 M or about 7 M. In certain embodiments the bisulfite solution comprises sodium metabisulfite, or potassium bisulfite, or ammonium bisulfite, or cesium bisulfite, or DABSO (1,4-diazoniabicyclo[2.2.2]octane-1,4-disulphinate, see, e.g., FIG. 16). In certain embodiments the conversion reagent (e.g., bisulfite reagent) contains radical scavengers, including, but not limited to one or more chemicals to prevent sulfite oxidation to sulfate (TROLOX and hydroquinone), and/or catalysts (polyamines).

The DNA-bisulfite (DNA/conversion reagent) mix is then introduced into a temperature controlled chamber or channel and incubated at a temperature ranging from about 40° C. to about 95° C. In certain embodiments the mix is incubated at a constant temperature, while in other embodiments, e.g., where the temperature controlled chamber or channel is a thermocycling chamber or channel (e.g., a smartcycler tube in the back of the cartridge), the mix is thermally cycled (e.g., between 60° C. and 95° C.). The mix is incubated until the DNA is converted (e.g., deaminated). In certain embodiments the incubation is for a period of time that ranges from about 5 minutes up to about 4 hours, or preferably from about 15 minutes up to about 45 minutes.

Following incubation the DNA/conversion reagent) (e.g., DNA-bisulfite) solution is mixed with fresh guanidinium thiocyanate-EtOH, e.g., from chamber 3 and dispensed over a matrix material. In certain embodiments the first column is reused, hence there is only one column and the second column and the first column are the same. In certain embodiments the second column is a separate column different than the first column.

The DNA bound to the second column matrix material is washed with fresh GTC-EtOH (e.g., from chamber 3) and rinsed (e.g., with a PEG 200 rinse, e.g., from chamber 8). The DNA is then desulfonated on the column, or is simultaneously eluted and desulfonated by contacting the deaminated nucleic acid with an alkaline solution (e.g., KOH from chamber 10 to produce a bisulfite converted nucleic acid. In certain embodiments the incubation is for a period of time ranging from about 1 minute to about 1 hour, or from about 5 minutes to about 30 minutes, or from about 10 minutes to about 20 minutes, or for about 15 minutes.

Where the initial incubation was in a thermocycling chamber that is to be further used, the thermocycling chamber or channel is washed with a buffer to remove residual bisulfite and neutralize pH. It was a surprising discovery that incubation with a conversion reagent (e.g., a bisulfite reagent), and/or desulphonation can be performed in a channel or chamber that is later used for PCR without bisulfite contamination substantially interfering with the later PCR reaction(s).

The eluted desulphonated bisulfite-converted DNA can be mixed with an appropriate buffer and analyzed for methylation. In certain embodiments the converted DNA is mixed with concentrated Tris, enzyme reaction, and template specific beads (e.g., beads comprising primers and/or probes for the PCR or nested PCR reaction(s)) in chambers 9 and 11, and the final mixture is aspirated into the thermocycling tube or chamber for the methylation specific quantitative PCR reaction.

Bisulfite contamination during the qPCR step can be the primary failure mode of the methylation cartridge. Residual bisulfite can result from either direct contamination of the PCR reaction tube (e.g., during the bisulfite conversion step) or from indirect contamination (e.g. cross contamination during bisulfite fluidic movements between chambers).

Figure 14:
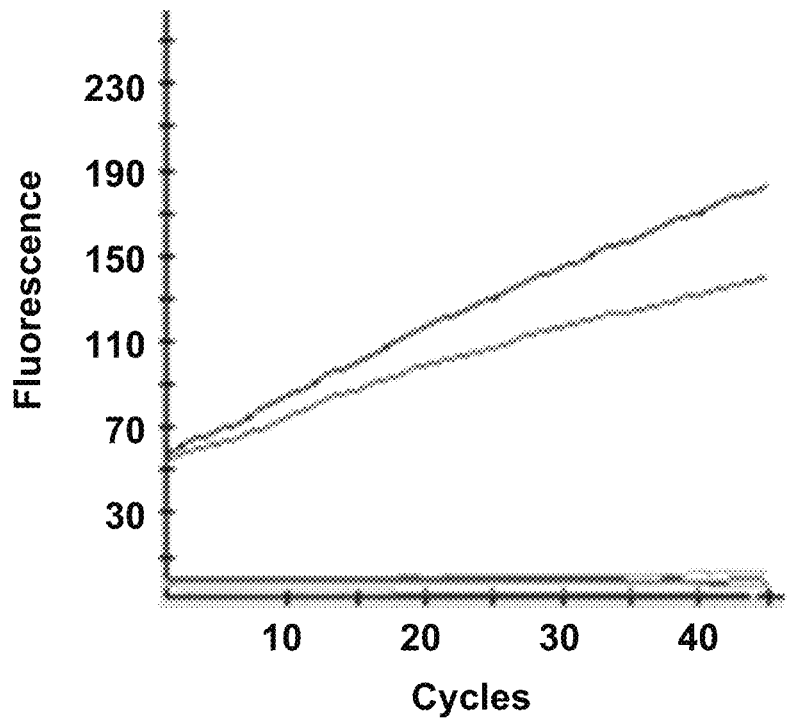
FIG. 14 illustrates a run in which some samples contain bisulfite contamination.

Residual bisulfite contamination, if present, can be measured by bisulfite-mediated probe cleavage during the qPCR step, which results in an increase in fluorescence during the earlier qPCR cycles (cycles 1-10) typically used for background subtraction. Accordingly, in certain embodiments, the cartridge comprises beads that provide one or more probes that are cleavable during PCR if bisulfite is present. Results of a run containing bisulfite contamination are shown in FIG. 14.

While the methods above (and in Example 4, see, e.g., FIG. 13A) are described with respect to specific chambers in the GENEXPERT® cartridge, it will be recognized that the particular reagent/chamber assignments can be varied depending on the particularities of the methylation analysis protocol applied.

Figure 13A:
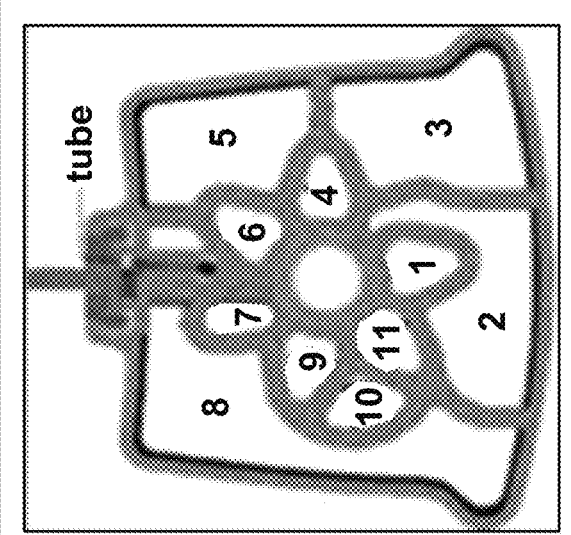
FIG. 13A and 13B illustrate[s] a cartridge layout and FIG. 13C illustrates a flow chart of the protocol used in Example 4.
Figure 13B:
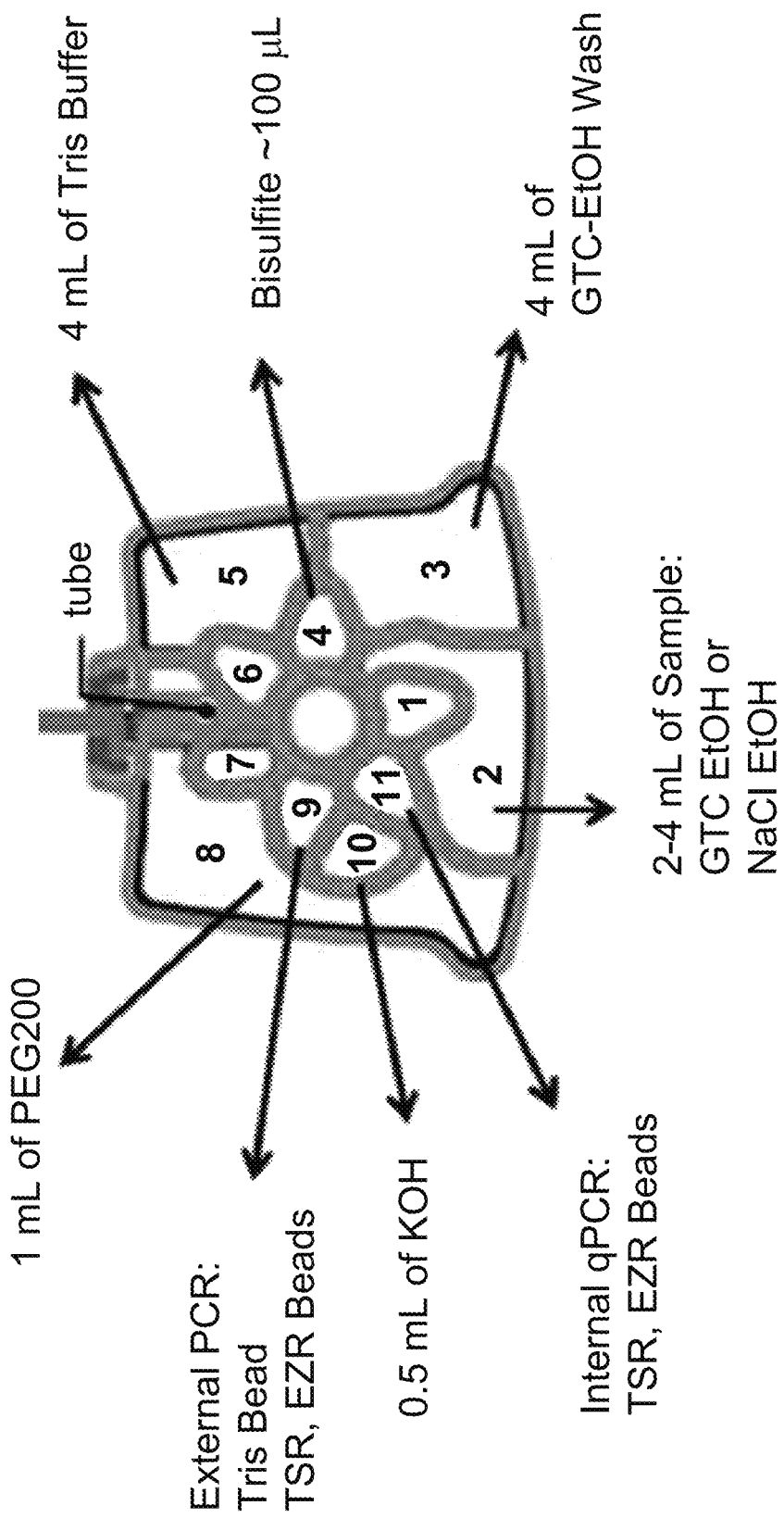
Figure 13C:
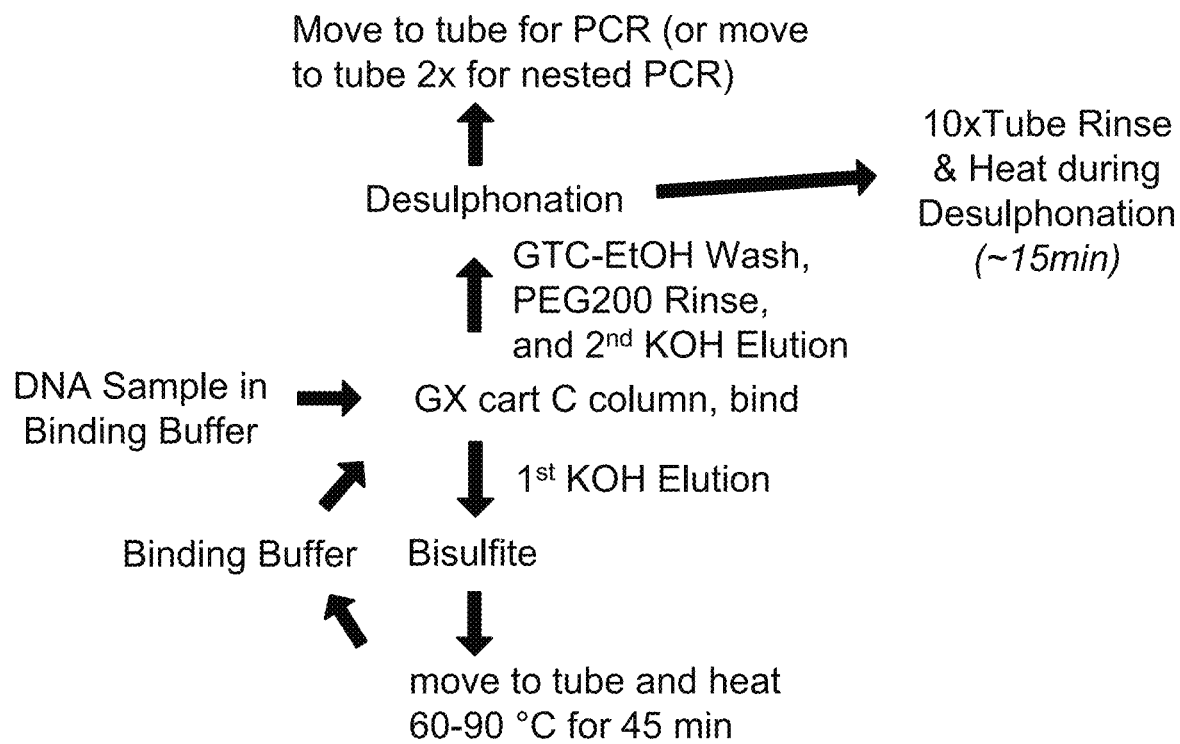

Thus, for example, operation of a methylation analysis cartridge (e.g., a GENEXPERT® cartridge can be generally described by a flow chart (see, e.g., FIGS. 1C and 13B). In the illustrative, but non-limiting embodiment shown in FIG. 13B, the DNA sample is provided in a binding buffer (e.g., a buffer comprising GTC-EtOH, in certain embodiments after the sample is processed with proteinase K and/or a lysis solution). In certain embodiments the sample is obtained from a sample preparation cartridge as described herein (see, e.g., FIG. 20).

The sample in binding buffer is introduced into a sample receiving chamber of the cartridge. In operation the cartridge is operated to deliver the sample solution to a matrix ("column") that binds the DNA. The bound DNA is then eluted from the column using an alkaline reagent (e.g., KOH solution) combined with a bisulfite reagent and moved to a heating tube (typically the PCR reaction tube) in the cartridge where the bisulfite reaction proceeds (e.g., at about 50° C. or about 60° C. to about 90° C. for about 45 minutes (or up to about 90 minutes), in this illustrative protocol). The reacted DNA is combined with a binding buffer (e.g., 2.25 M Guanidinium thiocyanate, 22.5 mM Tris pH 7.0, 0.5% Tween20, 50% Ethanol, and 0.005% SE-15 antifoam (a 10% emulsion of an active silicon antifoam and non-ionic emulsifiers)) and moved back to the same column, or to a different column, where it again binds to the column matrix. The reacted DNA is washed with GTC-EtOH, rinsed with PEG (e.g., PEG200) and eluted again from the column using an alkaline reagent (e.g., KOH) which also desulphonates the DNA. While the DNA is desulphonating the reaction tube (e.g., PCR reaction tube) can be heated and rinsed (e.g., 10× rinse) to remove any bisulfite reagent. The eluted DNA (or a portion thereof) can be moved to a reaction tube for PCR and/or nested PCR.

It will be appreciated that these operations can be performed on the entire sample or on a portion of the DNA sample. In the latter case a portion of the sample can be stored in one or more chambers and used as a control, or subjected to a different analysis/protocol.

Co-Purification and Detection of Both RNA Expression and DNA Methylation.

In certain embodiments methods for co-purification and detection of both altered RNA expression of genes along with DNA methylation (MSP) in a cartridge-based assay (e.g., utilizing a GENEXPERT® cartridge) are provided. In certain embodiments these assays would identify altered expression of e.g. DNMT correlated with tumor-specific methylation from the same sample preparation. In certain embodiments these assays can be used to verify expression and methylation status.

We have shown that we can elute nucleic acids off the column using a Tris buffered elution that retains a portion of nucleic acids on the column. In one illustrative embodiment, an RNA fraction is eluted and retained, e.g., in a chamber in the cartridge using a Tris solution.

After saving the RNA fraction, NaOH or KOH elution which will strip the column and elute and denature the DNA which would go into bisulfite for conversion as described above. Then, ether using the RNA elution fraction to elute the bisulfite converted DNA from the column or using the KOH elution mix the two fractions (RNA and converted DNA products) are mixed for RNA plus bisulfite converted qRT-PCR. This involves incorporating a reverse transcriptase (RT) step for the RNA plus MSP (or other analytic method) in the same tube from the same sample. Alternative methods include, but are not limited to performing the RT step independently prior to mixing with DNA (combine cDNA and DNA) for qPCR, or PCR for DNA or RT RNA could be done independently/serially using one thermocycling tube/chamber or simultaneously using multiple thermocycling tubes/chambers in the cartridge.

Analysis of Converted DNA

Numerous analytic methods can be performed in the cartridge to evaluate DNA methylation. Alternatively, in certain embodiments, the cartridge can be coupled to another device and/or system for further analysis of the converted (e.g., bisulfite or DABSO converted) DNA. Illustrative methods include, but are not limited to methylation specific PCR (MSP), direct sequencing, high resolution melting analysis (HRM), pyrosequencing (sequencing by addition), base-specific cleavage analysis (e.g. base-specific MALDI-TOF), and the like.

Methylation-Specific PCR (MSP).

In various embodiments methylation-specific PCR can be used to evaluate methylation status of the target DNA. MSP utilized primer and/or probe sets designed to be "methylated-specific" by including sequences complementing only unconverted 5-methylcytosines, or, on the converse, "unmethylated-specific", complementing thymines converted from unmethylated cytosines. Methylation is then determined by the ability of the specific primer to achieve amplification. This method is particularly effective for interrogating CpG islands in regions of high methylation density, because increased numbers of unconverted methylcytosines within the target to be amplified increase the specificity of the PCR. In certain embodiments placing the CpG pair at the 3'-end of the primer also improves the specificity.

In certain embodiments methylation is evaluated using a MethyLight method. The MethyLight method is based on MSP, but provides a quantitative analysis using quantitative PCR (see, e.g., Eades et al. (2000) *Nucleic Acids Res.*, 28(8): E32. doi:10.1093/nar/28.8.e32). Methylated-specific primers are used, and a methylated-specific fluorescence reporter probe is also used that anneals to the amplified region. In alternative fashion, the primers or probe can be designed without methylation specificity if discrimination is needed between the CpG pairs within the involved sequences. Quantitation can be made in reference to a methylated reference DNA. One modification to this protocol to increase the specificity of the PCR for successfully bisulphite-converted DNA (ConLight-MSP) uses an additional probe to bisulphite-unconverted DNA to quantify this non-specific amplification (see, e.g., Rand et al. (2002) *Methods* 27(2): 114-120).

In various embodiments the MethyLight methods utilize TAQMAN® technology, which is based on the cleavage of a dual-labeled fluorogenic hybridization probe by the 5' nuclease activity of Taq-polymerase during PCR amplification (Eads et al. (1999) *Cancer Res.*, 59: 2302-2306; Livak et al. (1995) *PCR Meth. Appl.*, 4: 357-362; Lee et al. (1993) *Nucleic Acids Res.*, 21: 3761-3766; Fink et al. (1998) *Nat. Med.*, 4: 1329-1333). The use of three different oligonucleotides in the TAQMAN® technology (forward and reverse PCR primers and the fluorogenic hybridization probe) offers the opportunity for several sequence detection strategies.

Figure 4A:
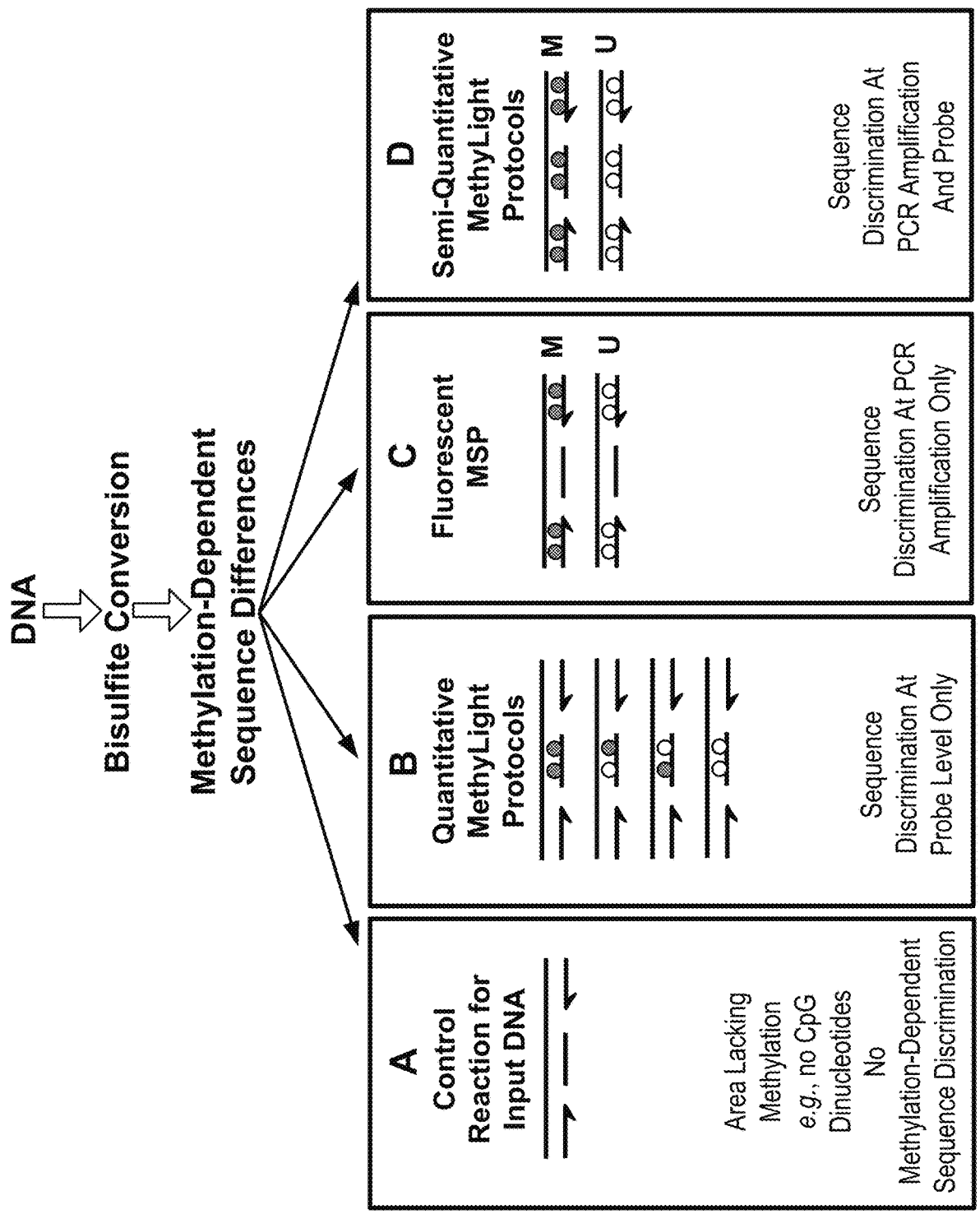

For example, the sequence discrimination can occur at the level of the PCR amplification process (see, e.g., FIG. 4A, panel C) and/or at the level of the fluorogenic probe hybridization (see, e.g., FIG. 4A, panel B). In both steps, the discrimination is based on the differential annealing of the perfectly matched, versus mismatched oligonucleotides. In the MethyLight technology, sequence discrimination at the PCR amplification level occurs by designing the primers and probe, or just primers, or just probes, to overlap potential sites of DNA methylation (e.g., CpG dinucleotides). One approach is simply a fluorescence-based version of the MSP technique (Herman et al. (1996) *Proc. Natl. Acad. Sci. USA*, 93: 9821-9826). Each oligonucleotide (primers and probe) can cover anywhere from zero to multiple CpG dinucleotides. Each CpG dinucleotide can result in two different sequence variations following bisulfite conversion, depending on whether that particular site was methylated (mCpG) or unmethylated (UpG). For example, if an oligonucleotide overlaps two CpG dinucleotides, then the number of possible sequence variants in the genomic DNA within the region covered by that oligonucleotide is 2×2=4. If both of the primers and the probe each overlap two CpGs, then the total number of variants contained within the sequence covered by the oligonucleotides is 4×4×4=64. In theory, one could design separate PCR reactions to analyze the relative amounts of each of these potential 64 sequence variants. However, significant methylation information can be derived from the analysis of a much smaller number of variants by designing reactions for the fully methylated and fully unmethylated molecules, which represent the two most extreme sequence variants this hypothetical example. The ratio between these two reactions or the ratio between the methylated reaction and a control reaction provides a measure of the prevalence of methylated molecules at this locus.

The MethyLight technology can also be modified to avoid sequence discrimination at the PCR amplification level. If the neither the primers nor the probe overlie any CpG dinucleotides, then the reaction represents unbiased amplification and can serve as a control for the amount of input DNA. One illustrative useful control reaction is one in which the entire amplicon is devoid of any CpG dinucleotides in the unconverted genomic sequence. When just the probe is designed to cover CpG dinucleotides, then sequence discrimination occurs solely at the level of probe hybridization. In this version, all sequence variants resulting from the sodium bisulfite conversion step are amplified with equal efficiency, as long as there is no amplification bias (see, e.g., Warnecke et al. (1997) *Nucleic Acids Res.*, 25: 4422-1426). In this case, the design of separate probes for each of the different sequence variants associated with a particular methylation pattern (2×2=4 probes in the case of two CpGs) allows a quantitative determination of the relative prevalence of each sequence permutation in the mixed pool of PCR products.

In certain embodiments the analysis methods also provide PCR specific for unconverted DNA. This PCR may interrogate SNPs, mutations, and/or translocations, etc. In this regard, it is noted that the detection of mutations and methylation in a single cartridge is illustrated in Example 12 (see, e.g., FIGS. 27A and 27B). Detection of SNPs, mutations, translocations and the like can readily be accomplished by the inclusion of primers and probe sets specific for the detection of these targets.

Nested PCR and Multiplex PCR Assays.

In certain embodiments methylated DNA can be detected using an PCR methods well known to those of skill in the art. In certain embodiments a nested PCR reaction is used to detect methylation targets. In one illustrative, but non-limiting, embodiment (see, e.g., Example 4), a nested PCR protocol can be used where the first 15-20 cycle PCR reaction is not specific for methylation but only the converted DNA sequences (i.e., they do not cross CpGs or in instances when they do a R=purine or Y=pyrimidine is used to catch both methylated and unmethylated template sequences). The second qPCR reaction (e.g., a 45 cycle qPCR reaction) can contain both primers and probes that are specific for typically 2-3 methylated CpGs.

It will be noted that in certain embodiments, a MethyLight analysis is performed using a single probe (see, e.g., FIG. 4B). In this approach, using a single, e.g., methylation-specific, probe (PR3) along with methylation specific forward (FW) and reverse (RV) primers, methylation specific PCR for the probe (PR3) provides a signal that is dependent on methylation and bisulfite conversion for the FW, RV and PR3 sequences.

Figure 4D:
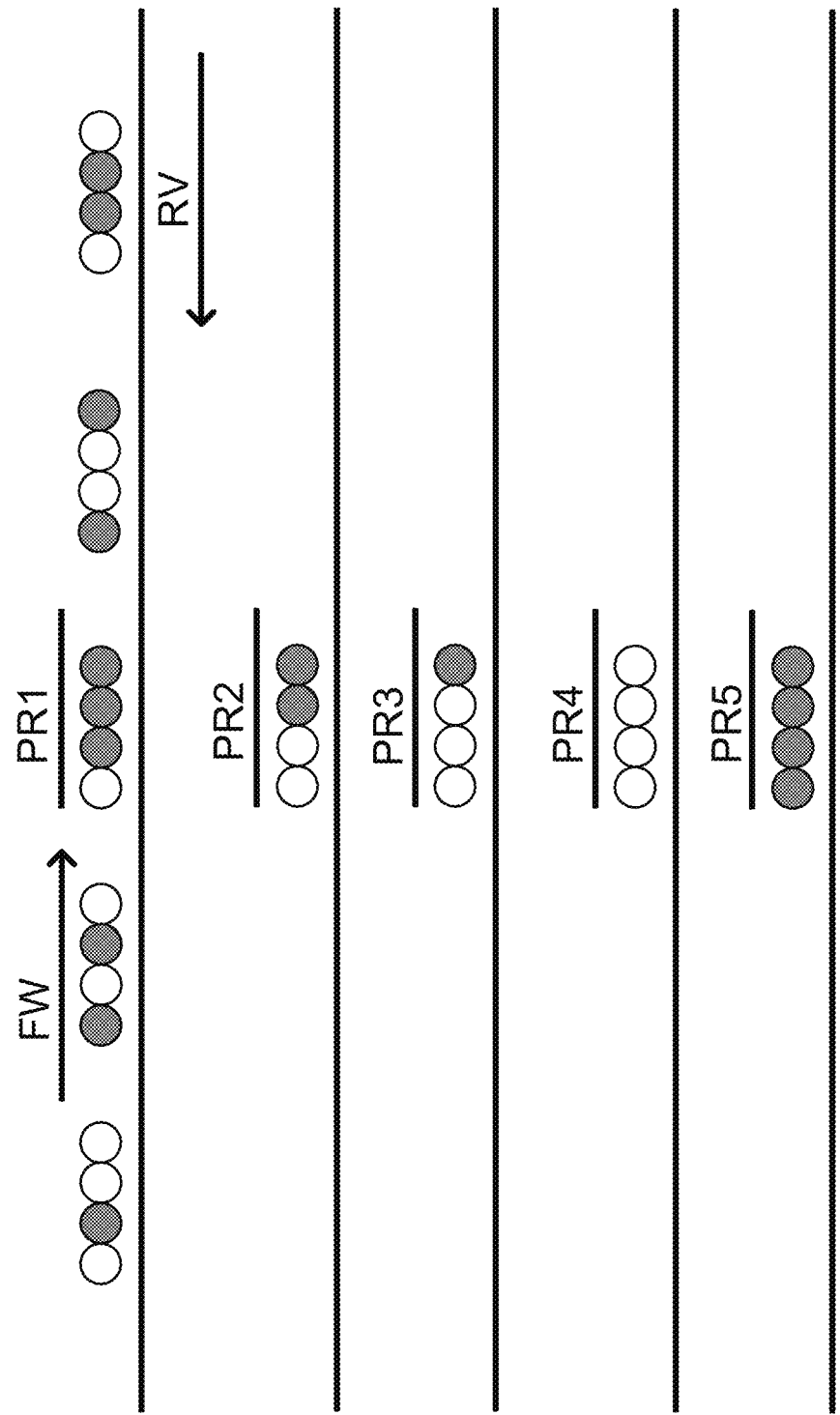

In various embodiments, multiplexed PCR assays are contemplated. By way of illustration, FIG. 4C illustrates a MethyLight approach using multiple probes (PR1, PR2, . . . PR5) that each target different regions. The combined signal from all the probes (PR1, PR2, PR3, PR4, and PR5) yields a measure of the amount/degree of methylation. In certain embodiments each probe has its own specific dye/fluor so that it is detectable independently of the other probes. Thus, even where one target is not methylated, a signal may still be detected, e.g., if PR3 is not methylated there will be no/less signal from the remaining probes. FIG. 4D illustrates a MethyLight approach using multiple probes (PR1 . . . PR5) that each target the same region, but provide signals for different methylation patterns. While the approach illustrated in FIG. 4C can provide detection from a larger region, this multi-probe approach on a single smaller region could be accomplished with sequence specific primers or probes interrogating the extent of methylation across a specific sequence after bisulfite conversion.

Figure 26:
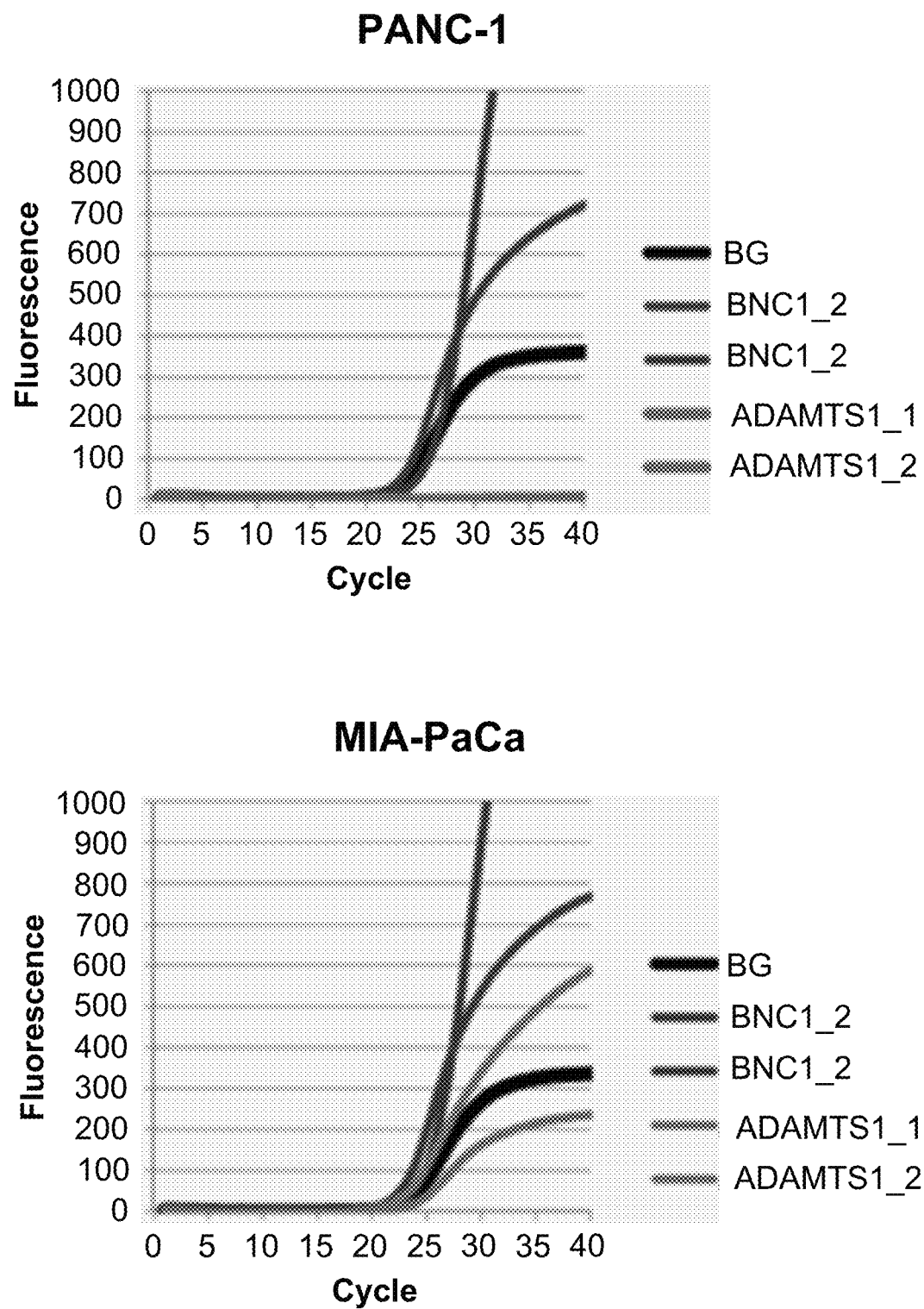
FIG. 26 illustrates the results for a reverse complement multiplex assay for both strands.

In certain embodiments a reverse complement multiplex assay for both strands can be used (see, e.g., FIG. 26). Following bisulfite conversion, both strands lose their complementarity. Thus, primer and probe sets can be designed for one strand or the other, and result in unique amplicons. In addition to providing "more opportunities" for detection, this approach can potentially help with sensitivity (at LOD, if only one strand or the other ends up in the tube, this approach would ensure the signal gets picked up). This approach permits the multiplex assay to be expanded to detect different CpGs at the same promoter site. The reverse complement multiplex provides more opportunities to detect target methylation and to pick up heterogenous methylation.

The foregoing methods are illustrative and non-limiting. Using the teachings provided herein numerous variations of MSP and/or MethyLight analysis will be available to one of skill in the art and implementable on a reaction cartridge, e.g. as described herein.

Direct Sequencing

In certain embodiments methylation status of the DNA can be determined using direct sequencing methods. In certain embodiments, the method can utilize PCR and standard dideoxynucleotide DNA sequencing to directly determine the nucleotides resistant to bisulphite conversion (see, e.g., Frommer et al. (1992) *Proc. Natl. Acad. Sci. USA,* 89 (5): 1827-1831). In various embodiments primers are designed to be strand-specific as well as bisulphite-specific (e.g., primers containing non-CpG cytosines such that they are not complementary to non-bisulphite-treated DNA), flanking (but not involving) the methylation site of interest. Therefore, it will amplify both methylated and unmethylated sequences, in contrast to methylation-specific PCR. All sites of unmethylated cytosines are displayed as thymines in the resulting amplified sequence of the sense strand, and as adenines in the amplified antisense strand. In certain embodiments nested PCR methods can be used to enhance the product for sequencing.

In certain embodiments the sequencing can be performed in the cartridge. In other embodiments, the cartridge can be coupled (e.g., fluidic coupled) to a sequencing machine to provide the sequencing analysis. Alternatively, in certain embodiments, the amplified product can be manually transferred from the cartridge to the sequencing system.

High Resolution Melting Analysis (HRM)

In certain embodiments high-resolution melting analysis (HRM) can be used to differentiate converted from unconverted bisulphite-treated DNA. HRM is a quantitative PCR technique in which the PCR amplicons are analyzed directly by temperature ramping and resulting liberation of an intercalating fluorescent dye during melting (see, e.g., Wojdacz and Dobrovic (2007) *Nucleic Acids Res.* 35(6): e41). The degree of methylation, as represented by the C-to-T content in the amplicon, determines the rapidity of melting and consequent release of the dye. This method allows direct quantitation, but assesses methylation in the amplified region as a whole rather than at specific CpG sites.

Pyrosequencing

In certain embodiments pyrosequencing (sequencing by synthesis) can be used to analyze bisulphite-treated DNA without using methylation-specific PCR (see, e.g., Colella et al. (2003). *BioTechniques* 35(1): 146-150; Tost et al. (2003) *BioTechniques* 35(1): 152-156; and the like). Sequencing by synthesis differs from Sanger sequencing in that it utilizes the detection of phosphate release on nucleotide incorporation, rather than chain termination with dideoxynucleotides. The DNA sequence is able to be determined by light emitted upon incorporation of the next complementary nucleotide by the fact that typically only one out of four of the possible A/T/C/G nucleotides are added and available at a time so that only one letter can be incorporated on the single stranded template (which is the sequence to be determined).

Following PCR amplification of the region of interest, pyrosequencing can be used to determine the bisulphite-converted sequence of specific regions (e.g., CpG sites). In certain embodiments the ratio of C-to-T at individual sites can be determined quantitatively based on the amount of C and T incorporation during the sequence extension.

A modification of this technique can utilize allele-specific primers that incorporate single-nucleotide polymorphisms (SNPs) into the sequence of the sequencing primer(s), thus allowing for separate analysis of maternal and paternal alleles (see, e.g., Wong et al. (2006) *BioTechniques* 41(6): 734-739). This modification is particularly of use for genomic imprinting analysis.

Base-Specific Cleavage Analysis.

In certain embodiments, base-specific cleavage/MALDI-TOF takes advantage of bisulphite-conversions by adding a base-specific cleavage step to enhance the information gained from the nucleotide changes (Ehrich et al. (2005) *Proc. Natl. Acad. Sci. USA,* 102 (44): 15785-15790). By first using in vitro transcription of the region of interest into RNA (by adding an RNA polymerase promoter site to the PCR primer in the initial amplification), RNase A can be used to cleave the RNA transcript at base-specific sites. RNase A cleaves RNA specifically at cytosine and uracil ribonucleotides and base-specificity is achieved by adding incorporating cleavage-resistant dTTP when cytosine-specific (C-specific) cleavage is desired, and incorporating dCTP when uracil-specific (U-specific) cleavage is desired. The cleaved fragments can then be analyzed by MALDI-TOF or other methods. Bisulphite treatment results in either introduction/removal of cleavage sites by C-to-U conversions or shift in fragment mass by G-to-A conversions in the amplified reverse strand. C-specific cleavage will cut specifically at all methylated CpG sites. By analyzing the sizes of the resulting fragments (e.g., using MALDI-TOF, capillary electrophoresis, microchip electrophoresis, and the like), it is possible to determine the specific pattern of DNA methylation of CpG sites within the region, rather than determining the extent of methylation of the region as a whole.

Methylation-Sensitive Single-Strand Conformation Analysis (MS-SSCA).

Methylation-sensitive single strand conformation analysis (MS-SSCA) is based on the single-strand conformation polymorphism analysis (SSCA) method developed for single-nucleotide polymorphism (SNP) analysis (Bianco et al. (1999) *Hum. Mutat.* 14(4): 289-293). SSCA differentiates between single-stranded DNA fragments of identical size but distinct sequence based on differential migration in non-denaturating electrophoresis. In MS-SSCA, this is used to distinguish between bisulphite-treated, PCR-amplified regions containing the CpG sites of interest. Although SSCA lacks sensitivity when only a single nucleotide difference is present, bisulphite treatment frequently makes a number of C-to-T conversions in most regions of interest, and the resulting sensitivity can be high. In certain embodiments MS-SSCA can also provide semi-quantitative analysis of the degree of DNA methylation based on the ratio of band intensities. Typically, however, MS-SSCA assesses all CpG sites as a whole in the region of interest rather than individual methylation sites.

Methylation Targets.

As noted above, DNA methylation is of interest in a wide number of contexts. In certain embodiments, the amount of DNA methylation is of clinical interest particularly in oncology. Aberrant DNA methylation patterns (hypermethylation and hypomethylation compared to normal tissue) have been associated with a large number of human malignancies. Hypermethylation typically occurs at CpG islands in the promoter region and is associated with gene inactivation. A lower level of leukocyte DNA methylation is associated with many types of cancer (Zhang et al. (2011) Epigenetics, 6(3): 293-299). Global hypomethylation has also been implicated in the development and progression of cancer through different mechanisms. Typically, there is hypermethylation of tumor suppressor genes and hypomethylation of oncogenes (see, e.g., Lund et al. (2004) *J. Biol. Chem.* 279(28): 29147-29154).

In this regard, it is noted that DNA methylation provides a prognostic indicator for Stage I Non-Small-Cell Lung Cancer (NSCLC). In particular, it was discovered that hypermethylation of five genes was significantly associated with shorter relapse-free survival (RFS) in stage I NSCLC: HIST1H4F, PCDHGB6, NPBWR1, ALX1, and HOXA9. A signature based on the number of hypermethylated events distinguished patients with high- and low-risk stage I NSCLC (see, e.g., Sandoval et al. (2013) *J. Clin. Oncol.,* 4140-4147).

Similarly it has been observed that malignant gliomas may have the MGMT gene inactivated due to methylation of its promoter region. The prediction, born out by current research, is that by methylating the MGMT gene, a better response to chemotherapy can occur (as the tumor has no means to repair the DNA damage induced by the alkylating agent). In gliomas, MGMT promoter methylation is a favorable prognostic marker in the setting of either radiation or chemotherapy (see, e.g., //neurosurgery.ucsd.edu/brain-tumor-research-mgmt/).

By way of further illustration, Table 3 illustrates various genes that are hypermethylated in certain cancers.

Table 3 shows illustrative, but non-limiting examples of genes hypermethylated in sporadic cancers (see, e.g., Baylin (2005) *Nature Clinical Practice Oncology,* 2: S4-S11).

| Gene or gene product | Tumor type |
|---|---|
| Rb | Retinoblastoma |
| APC | Colorectal and other cancers |
| p14/ARF | Colorectal cancer |
| p15/CDKN2B | Leukemias |
| p16/CDKN2A | Various cancers |
| BRCA1 | Breast, ovarian cancer |
| VHL | Renal cell cancers |
| hMLH1 | Colorectal, gastric, endometrial cancers |
| ER-α | Breast, colorectal, other cancers |

In various illustrative, but non-limiting, embodiments measurement of methylation of any one of more of the promoters of the following genes is contemplated: APC, ARF, CDKN2B, CDKN2A, BRCA1, VLH, hMLH1, MGMT. RASSF1A, ADAMTS1, BNC1, HIST1H3C, HOXB4, RASGRF2, TM6SF1, AKR1B1, HIST1H4F, PCDHGB6, NPBWR1, ALX1, and HOXA9.

Pancreatic Cancer.

In certain embodiments methylation status is determined for one or more promoters where methylation status is a marker for the presence and/or prognosis of pancreatic cancer. It was determined that the frequency of methylation of one or more of ADAMTS1, or BNC1, can be used to detect and/or stage pancreatic cancer. Thus, illustrative, but non-limiting methylation markers for pancreatic cancer include, but are not limited to ADAMTS1 and/or BNC1. Illustrative primers and probes for the detection of methylation at the promoters of these genes are shown in Table 4, below (referencing Table 5 for particular sequences), and in Table 10 in Example 4). In certain embodiments primers and probes are provided for the detection of methylation in the forward strand of the converted DNA and/or for the detection of methylation in the reverse strand of the converted DNA.

Breast Cancer.

In certain embodiments methylation status is determined for one or more promoters where methylation status is a marker for the presence and/or prognosis of breast cancer. Illustrative methylation markers for breast cancer include, but are not limited to RASSF1A, and/or AKR1B1, and/or HOXB4, and/or HIST1H3C, and/or RASGRF2, and/or TM6SF1. Illustrative primers and probes for the detection of methylation at the promoters of these genes are shown in Table 4, below (referencing Table 5 for particular sequences), and in Table 9 in Example 4.

In certain embodiments methylation status is determined for one or more promoters where methylation status is a marker for the presence or likelihood of lung cancer. Illustrative methylation markers for lung cancer include, but are not limited to CDO1, SOX17, TAC1, and/or HOXA7.

The methods described herein are not limited to determining methylation of the promoters of these genes. Using the methods described herein methylation of essentially any target of interest is possible.

It will be noted, however that measurement of DNA methylation need not be limited to measurement of methylation at CPG islands in promoters. For example, it has been demonstrated that gene body methylation can also alter gene expression and can provide a therapeutic target in cancer (see, e.g., Yang et al. (2014) Cancer Cell, 26(4): 577-590).

Additionally, measurement of DNA methylation has prognostic/therapeutic applications for pathologies other than cancer. For example, aberrant methylation on regions on chromosomes 13, 18, 21, X, and Y can be used to diagnose Down syndrome (see, e.g., Patsalis et al. (2012) Exp. Opin. Biol. Ther. 12(Suppl. 1): S155-S161). Because fetal DNA and maternal DNA are differentially methylated, cell-free DNA in maternal plasma can provide a source of fetal DNA, which can be obtained non-invasively and utilized to assess the methylation state of the aforementioned chromosomes (or other chromosomes or genes).

As noted above, in certain embodiments, the cartridges and methods described herein are also used to determine mRNA levels, e.g., to determine expression of various methyltransferases. In certain embodiments, expression level of RNA is determined for a methyltransferase selected from the group consisting of DNMT1, DNMT2, DNMT3A, DNMT3B, and TNMT3L.

Primers/Probes and Multiplex Analysis

In various embodiments the methods described herein can involve nested PCR reactions and the cartridges described herein can contain reagents (e.g., primers and probes) for such nested PCR reactions. For example, in certain embodiments, methylation is detected for one, two, three, four, five, or six genes (gene promoters). Since bisulfite conversion of a DNA changes cytosine resides to uracil, but leave 5-methyl cytosine residues unaffected, the forward and reverse strands of converted (bisulfite-converted) DNA are no longer complementary. Accordingly, it is possible to interrogate the forward and reverse strands independently (e.g., in a multiplex PCR reaction) to provide additional specificity and sensitivity to methylation detection. In such instances, assaying of a single target can involve a two-plex multiplex assay, while assaying of two, three, four, five, or six target genes can involve four-plex, six-plex, 8-plex, 10-plex, or 12-plex multiplex assays. In certain embodiments the assays can be divided into two multiplex reactions, e.g., to independently assay forward and reverse strands. However, it will be recognized that when split into multiple multiplex assays, the grouping of assays need not be by forward or reverse, but can simply include primer/probe sets that are most compatible for particular PCR reaction conditions.

As indicated above, numerous cancers can be identified, and/or staged and/or a prognosis therefor determined by the detection/characterization of the methylation state on the forward and/or reverse strand of gene promoters whose methylation (or lack thereof) is associated with a cancer. Illustrative gene (promoter) targets associated with various cancers are described above and shown below in Table 4. It will be recognized that methylation (forward strand and/or reverse strand) of one or more of the genes shown in Table 4 for each cancer can be determined to identify, and/or stage, and/or provide a prognosis for the indicated cancer. In certain embodiments methylation status of all of the genes shown for a particular cancer (forward and/or reverse strand) can be determined in a single multiplex PCR reaction.

TABLE 4

Illustrative primers and probes for the detection of methylation at the promoters of genes associated with various cancers using the devices and methods described herein. Primer and probe numbers refer to primer/probe numbers (primer/probe num) shown in Table 5, below.

| Indication/Gene | External Primers | Internal Primers | Probe |
|---|---|---|---|
| Breast Cancer | | | |
| AKR1B1: | 58/183 | 19/20 | 193 |
| HIST1H3C: | 42/43, | 59/54 | 194 |
| HOXB4: | 186/187, | 25/26 | 76 |
| RASGRF2: | 188/199, | 192/14 | 67 |
| RASSF1A: | 189/1, | 1/2 | 63 |
| TM6SF1: | 202/51, | 31/57 | 77 |
| BG: | 175/158, | 176/156 | 164 |
| Pancreatic Cancer Set 1: | | | |
| BNC1 | 213/214, | 221/222 | 229 |
| ADAMTS1: | 219/220, | 227/228 | 265 |
| ACTB: | 102/103, | 320/321 | 150 |
| Pancreatic Cancer Set 2: | | | |
| BNC1: | 217/218, | 225/226 | 264 |
| ADAMTS1: | 215/216, | 223/224 | 230 |
| ACTB: | 102/103, | 320/321 | 150 |
| Lung CPHD Set 2: | | | |
| CDO1: | 283/284, | 287/288 | 291 |
| TAC1: | 293/294, | 386/388 | 301 |
| SOX17: | 303/304, | 382/385 | 312 |
| ACTB: | 102/103, | 320/321 | 150 |
| Prostate: | | | |
| GSTP1: | 233/234, | 239/240 | 245 |
| APC: | 235/236, | 241/242 | 246 |
| PTGS2: | 237/238, | 243/244 | 247 |
| ACTB: | 102/103, | 320/321 | 150 |
| BRCA1: | | | |
| BRCA1: | 328/329, | 330/331 | 327 |
| ACTB: | 102/103, | 320/321 | 150 |
| MGMT: | | | |
| MGMT: | 248b/249b, | 250/251 | 252 |
| ACTB: | 102/103, | 320/321 | 150 |

Illustrative primers and probes for the detection of methylation at the promoters of various genes are shown below in Table 5, below, and in Tables 9 and 10 in Example 4. In certain embodiments these primers and/or probes are particularly suitable for use in a multiplex amplification.

TABLE 5

Illustrative primers and probes for the detection of methylation of various gene promoters.

| Primer/Probe Num | Target | Type | Sequence | SEQ ID NO |
|---|---|---|---|---|
| 1 | RASSF1A | I | GCGTTGAAGTCGGGGTTC | 2 |
| 2 | RASSF1A | I | CCCGTACTTCGCTAACTTTAAACG | 3 |
| 3 | RASSF1A | P | ACAAACGCGAACCGAACGAAACCA-quencher/blocker | 4 |
| 4 | RASSF1A STD | I | fluor-TTAGGGTAGATTGTGGATATTAG | 5 |
| 5 | RASSF1A STD | I | ATACTAACAACTATCCAATACAAC | 6 |
| 6 | RASSF1A STD | P | fluor-(C*)AGGTTGAAATTAG(T-quencher)ATGTGTTATTTTGGTATGG | 7 |
| 7 | HIST1H3C | I | AATAGTTCGTAAGTTTATCGGCG | 8 |
| 8 | HIST1H3C | I | CTTCACGCCACCGATAACCGA | 9 |
| 9 | HIST1H3C | P | fluor-TACTTACGCGAAACTTTACCGCCGA-quencher/blocker | 10 |
| 10 | HIST1H3C STD | I | GATTTAGAGTTGGATGTGTGGAT | 11 |
| 11 | HIST1H3C STD | I | ACCACCATACTAATAATCAAATCTA | 12 |
| 12 | HIST1H3C STD | P | fluor-AAATATCACTCATCACCAAATAAATCCAA-quencher/blocker | 13 |
| 13 | RASGRF2 | I | GTAAGAAGACGGTCGAGGCG | 14 |
| 14 | RASGRF2 | I | ACAACTCTACTCGCCCTCGAA | 15 |
| 15 | RASGRF2 | P | fluor-AACGAACCACTTCTCGTACCAACGA-quencher/blocker | 16 |
| 16 | RASGRF2 STD | I | TGTATGAGTTTGTGGTGAATAATG | 17 |
| 17 | RASGRF2 STD | I | AACTCACCATCAAACACTTTCCC | 18 |
| 18 | RASGRF2 STD | P | fluor-TACAAACCCAACATCCTCTATCTATTC-quencher/blocker | 19 |
| 19 | AKR1B1 | I | GCGCGTTAATCGTAGGCGTTT | 20 |
| 20 | AKR1B1 | I | CCCAATACGATACGACCTTAAC | 21 |
| 21 | AKR1B1 | P | fluor-CGTACCTTTAAATAACCCGTAAAATCGA-quencher/blocker | 22 |
| 22 | AKR1B1 STD | I | TTTGTTGATGTTTTGTGGAAGTAAG | 23 |
| 23 | AKR1B1 STD | I | ATTCATCAATACTTTCAAATAACACA | 24 |
| 24 | AKR1B1 STD | P | fluor-(C*)AAATACATTATCC(T-quencher)ACCACTAACAATACA | 25 |
| 25 | HOXB4 | I | CGGGATTTTGGGTTTTCGTCG | 26 |
| 26 | HOXB4 | I | CGACGAATAACGACGCAAAAAC | 27 |
| 27 | HOXB4 | P | fluor-AACCGAACGATAACGAAAACGACGAA-quencher/blocker | 28 |
| 28 | HOXB4 STD | I | GTTAGTTTTGTAGTGTATTGAGTAT | 29 |
| 29 | HOXB4 STD | I | CATCTTCCACAATAAACTTCCAATT | 30 |

TABLE 5-continued

Illustrative primers and probes for the detection of methylation of various gene promoters.

| Primer/Probe Num | Target | Type | Sequence | SEQ ID NO |
|---|---|---|---|---|
| 30 | HOXB4 STD | P | fluor-TAACTCCACCTATTCTACCTACCATTT-quencher/blocker | 31 |
| 31 | TM6SF1 | I | CGTTTAGCGGGATGCGGTGA | 32 |
| 32 | TM6SF1 | I | ACACGAAAACCCCGATAACCG | 33 |
| 33 | TM6SF1 | P | fluor-AAACACTCATCGCAACCGCCGCG-quencher/blocker | 34 |
| 34 | TM6SF1 STD | I | TTAGATGTTGATTGGTTGTGTTTG | 35 |
| 35 | TM6SF1 STD | I | ATCATCATAAAACTCAACAATCAATT | 36 |
| 36 | TM6SF1 STD | P | fluor-CCAAACATCAAATCTTTAACTTTTACCAA-quencher/blocker | 37 |
| 37 | RASSF1A STD | P | fluor-AGGTTGAAATTAGTATG(T-quencher)GTTATTTTGGTATGG-quencher/blocker | 38 |
| 38 | RASSF1A STD | P | fluor-AGGTTGAAATTAGTATGTGT(T-quencher)ATTTTGGTATGG-quencher/blocker | 39 |
| 39 | RASSF1A STD | P | fluor-AGGTTGAAATTAGTATGTGTTA(T-quencher)TTTGGTATGG-quencher/blocker | 40 |
| 40 | RASSF1A | E | GTTTTATAGTTTTTGTATTTAGG | 41 |
| 41 | RASSF1A | E | AACTCAATAAACTCAAACTCCC | 42 |
| 42 | HIST1H3C | E | GTGTGTGTTTTTATTGTAAATGG | 43 |
| 43 | HIST1H3C | E | ATAAAATTTCTTCACRCCACC | 44 |
| 44 | RASGRF2 | E | GAGGGAGTTAGTTGGGTTAT | 45 |
| 45 | RASGRF2 | E | CCTCCAAAAAATACATACCC | 46 |
| 46 | AKR1B1 | E | GTGTAATTAATTAGAAGGTTTTTT | 47 |
| 47 | AKR1B1 | E | AACACCTACCTTCCAAATAC | 48 |
| 48 | HOXB4 | E | TTAGAGGYGAGAGAGTAGTT | 49 |
| 49 | HOXB4 | E | AAACTACTACTAACCRCCTC | 50 |
| 50 | TM6SF1 | E | AGGAGATATYGTTGAGGGGA | 51 |
| 51 | TM6SF1 | E | TCACTCATACTAAACCRCCAA | 52 |
| 52 | RASSF1A STD | I | TTAGGGTAGATTGTGGATATTAGATAGG | 53 |
| 53 | RASSF1A STD | I | TAATACTAACAACTATCCAATACAACAC | 54 |
| 54 | HIST1H3C | I | CCGATAACCGAAACGCTCTTAC | 55 |
| 55 | AKR1B1 | I | GCGTTAATCGTAGGCGTTT | 56 |
| 56 | TM6SF1 | I | GTTTAGCGGGATGCGGTG | 57 |
| 57 | TM6SF1 | I | ACACGAAAACCCCGATAAC | 58 |
| 58 | AKR1B1 | E | GYGTAATTAAT(T*)AGAAGGTTTTTT | 59 |
| 59 | HIST1H3C | I | TCGTACGAAGTAAATAGTTCGTAAG | 60 |
| 60 | HIST1H3C | E | GGATTTTTGAAATATTATAGGATTAATTAG | 61 |
| 61 | RASSF1A | E | GTTTTATAGTT(T*)TTGTATTTAGG | 62 |

TABLE 5-continued

Illustrative primers and probes for the detection of methylation of various gene promoters.

| Primer/ Probe Num | Target | Type | Sequence | SEQ ID NO |
|---|---|---|---|---|
| 62 | RASSF1A | P | fluor-ACAAACGCGA(N*)ACCGAA(C**)GAAACCA-quencher/blocker | 63 |
| 63 | RASSF1A | P | fluor-(C*)TGGTTTCGT(T-quencher)CGGT(T*)CGCG-quencher/blocker | 64 |
| 64 | RASSF1A STD | P | fluor-(C*)AGGTTGAAATTAGTA(T-quencher)GTGTTAT(T*)TTGG(T*)ATGG-quencher/blocker | 65 |
| 65 | HIST1H3C | P | fluor-CAAACTACTTACGCGAAACTT(T*)ACCGCC-quencher/blocker | 66 |
| 66 | HIST1H3C STD | P | fluor-AAATATCACTCA(T*)CACCAAA(N*)TAAA(T*)CCAA-quencher/blocker | 67 |
| 67 | RASGRF2 | P | fluor-AAACGAACCACTTCTCG(T*)ACCAACGAC-quencher/blocker | 68 |
| 68 | RASGRF2 STD | P | fluor-CAAACCCAACATCCTC(T*)ATC(T*)ATTC-quencher/blocker | 69 |
| 69 | AKR1B1 | P | fluor-A(C*)GCGTACCTTT(N*)AAA(T*)AACCCG(T*)AAAATCG-quencher/blocker | 70 |
| 70 | AKR1B1 | P | fluor-A(C*)GCGTACCTT(T-quencher)AAA(T*)AACCCG(T*)AAAATCG-quencher/blocker | 71 |
| 71 | AKR1B1 STD | P | fluor-(C*)AAATACATTATCC(T-quencher)ACCAC(T*)AACAA(T*)ACA-quencher/blocker | 72 |
| 72 | HOXB4 | P | fluor-AACCGAACGATAACGAAAA(C**)GACGA-quencher/blocker | 73 |
| 73 | HOXB4 STD | P | fluor-TAACTCCACCTATTC(T*)ACCT(N*)ACCA(T*)TT-quencher/blocker | 74 |
| 74 | TM6SF1 STD | P | fluor-CAAACATCAAATCT(T*)TAAC(T*)TT(T*)AC-quencher/blocker | 75 |
| 75 | AKR1B1 | P | fluor-(C*)A(C*)GCGTACCT(T-quencher)TAAA(T*)AACCCG(T*)AAAATCG-quencher/blocker | 76 |
| 76 | HOXB4 | P | fluor-AACCGAACGA(T*)AACGAAA(N*)ACGACGAA-quencher/blocker | 77 |
| 77 | TM6SF1 | P | fluor-AAACACTCATCGCAACCGCCGCG-quencher/blocker | 78 |
| 78 | ACTB | P | fluor-TAACCACCACCCAACACA(C**)AATAAC-quencher/blocker | 79 |
| 79 | ALU Long Set 1 | P | fluor-CCCAACTACT(T*)AAAAAC(T*)AAAAC-quencher/blocker | 80 |
| 80 | ALU Short Set 1 | P | fluor-CACCTAAAA(T*)CAAAAATT(T*)AAAAC-quencher/blocker | 81 |

TABLE 5-continued

Illustrative primers and probes for the detection of methylation of various gene promoters.

| Primer/Probe Num | Target | Type | Sequence | SEQ ID NO |
|---|---|---|---|---|
| 81 | ALU Long Set 2 | P | fluor-CAAATAATTCTCC(T*)ACCTCAACC(T*)C-quencher/blocker | 82 |
| 82 | ALU Short Set 2 | P | fluor-CTTAACTCAC(T*)ACAACCTC(T*)ACC-quencher/blocker | 83 |
| 83 | INSL6 | P | fluor-CAAACCGAACGACGCGCACAAACAC-quencher/blocker | 84 |
| 84 | ACTB | E | GTATATAGGTTGGGGAAGTTTG | 85 |
| 85 | ACTB | E | AACTATACTCAACCAATAAAACC | 86 |
| 86 | ALU Long Set 1 | E | TGTTATTTAGGTTGGAGTGTAG | 87 |
| 87 | ALU Long Set 1 | E | TAATAACTCATACCTATAATCCC | 88 |
| 88 | ALU Long Set 1 | I | GGTTGGAGTGTAGTGGTATAATTTTAG | 89 |
| 89 | ALU Long Set 1 | I | TAATAACTCATACCTATAATCCCAACAC | 90 |
| 90 | ALU Short Set 1 | E | GTAGAGATAGGGTTTTATTATGTTG | 91 |
| 91 | ALU Short Set 1 | I | GGTTTTATTATGTTGGTTAGGTTGG | 92 |
| 92 | ALU Long Set 2 | E | GTATTTTGGGAGGTTAAGGTAG | 93 |
| 93 | ALU Long Set 2 | E | ATCTTACTCTTATTACCCAAAC | 94 |
| 94 | ALU Long Set 2 | I | GGTTAAGGTAGGTAGATTATTTGAGG | 95 |
| 95 | ALU Long Set 2 | I | ATCTTACTCTTATTACCCAAACTAAAATAC | 96 |
| 96 | ALU Short Set 2 | E | GTTATTTAGGAGGTTGAGGTAG | 97 |
| 97 | ALU Short Set 2 | E | GAGGTAGGAGAATTATTTGAATTTAGG | 98 |
| 98 | INSL6 | E | ATTTGAGATTTTTGAGTTGG | 99 |
| 99 | INSL6 | E | AACCCTACTCCCTATCTACG | 100 |
| 100 | INSL6 | I | GCGCGCGTTTTTTTTGAAG | 101 |
| 101 | INSL6 | I | GGCGTAGATAGGGAGTAGGGTT | 102 |
| 102 | ACTB | I | GTGATGGAGGAGGTTTAGTAAGTT | 103 |
| 103 | ACTB | I | CCAATAAAACCTACTCCTCCCTTAA | 104 |
| 104 | RASSF1A STD | P | fluor-(C*)(C*)ATACCAAAA(T-quencher)AACACA(T*)CTAAT(T*)TCAACCT-quencher/blocker | 105 |
| 105 | AKR1B1 STD | P | fluor-(C*)AAATACAT(T*)ATCC(T-quencher)ACCAC(T*)AACAA(T*)ACA-quencher/blocker | 106 |
| 106 | AKR1B1 | P | fluor-(C*)ACGCGTACCTT(T-quencher)AAA(T*)AACCCG(T*)AAAATCG-quencher/blocker | 107 |
| 107 | AKR1B1 | P | fluor-(C*)ACGCGTACCTT(T*)AAA(T-quencher)AACCCG(T*)AAAATCG-quencher/blocker | 108 |
| 108 | RASSF1A UM | P | fluor-CTAACAAACA(C-quencher)AAA(C**)CAAA(C**)AAAACCA-quencher/blocker | 109 |

TABLE 5-continued

Illustrative primers and probes for the detection of methylation of various gene promoters.

| Primer/Probe Num | Target | Type | Sequence | SEQ ID NO |
|---|---|---|---|---|
| 109 | RASSF1A UM | P | fluor-CTAACAAACA(C**)AAA(C-quencher)CAAA(C**)AAAACCA-quencher/blocker | 110 |
| 110 | HIST1H3C UM | P | fluor-AACTACTTACA(C**)AAAACTT(N*)TAC(C**)ACCAA-quencher/blocker | 111 |
| 111 | HIST1H3C UM | P | fluor-AACTACTTA(C**)ACAAAA(C**)TTTACCAC-quencher/blocker | 112 |
| 112 | RASGRF2 UM | P | fluor-AAACAAACCAC(T*)TCTCA(T*)ACCAACAAC-quencher/blocker | 113 |
| 113 | AKR1B1 UM | P | fluor-(C*)ACATACCTTTAAA(T-quencher)AACCCA(T*)AAAA(T*)CAAC-quencher/blocker | 114 |
| 114 | AKR1B1 UM | P | fluor-(C*)ACATACCTT(T-quencher)AAA(T*)AACCCA(T*)AAAATCAAC-quencher/blocker | 115 |
| 115 | HOXB4 UM | P | fluor-CAACAAAAACCCAAAA(T*)CCCAAC(N*)AAACCACA-quencher/blocker | 116 |
| 116 | HOXB4 UM | P | fluor-CAAAATCCCAA(C**)AAACCA(C**)ATAACA-quencher/blocker | 117 |
| 117 | TM6SF1 UM | P | fluor-AAACACTCATCACAACCA(C**)CACACC-quencher/blocker | 118 |
| 118 | AKR1B1 UM | I | TGGTGTGTTAATTGTAGGTGTTTT | 119 |
| 119 | AKR1B1 UM | I | CCCAATACAATACAACCTTAACC | 120 |
| 120 | HOXB4 UM | I | GTGGTGTGTATTGTGTAGTGTTA | 121 |
| 121 | HOXB4 UM | I | CAAACCAAACAATAACAAAAACAAC | 122 |
| 122 | TM6SF1 UM | I | TGTTTAGTGGGATGTGGTGAAG | 123 |
| 123 | TM6SF1 UM | I | ACACAAAAACCCCAATAACCACA | 124 |
| 124 | RASSF1A UM | I | GTTTAAAGTTAGTGAAGTATGGGTTT | 125 |
| 125 | HIST1H3C UM | I | TGTATGAAGTAAATAGTTTGTAAGTTTATTGG | 126 |
| 126 | AKR1B1 STD | I | TTTGTTGATGTTTTGTGGAAG(T*)AAG | 127 |
| 127 | AKR1B1 STD | I | ATTCATCAATACTTTCAAA(T*)AACACA | 128 |
| 128 | RASGRF2 | P | fluor-AAACGAACCACTTCTCG(T*)ACCAACGAC-quencher/blocker | 129 |
| 129 | RASGRF2 STD | P | fluor-CAAACCCAACATCCTC(T*)ATC(T*)ATTC-quencher/blocker | 130 |
| 130 | TM6SF1 | P | fluor-AAACACTCATCGCAACCGCCGCG-quencher/blocker | 131 |
| 131 | TM6SF1 STD | P | fluor-CCAAACATCAAATCT(T*)TAACTT(T*)TACCAA-quencher/blocker | 132 |
| 132 | TM6SF1 | P | fluor-AAACACTCATCGCAACCGCCGCG-quencher/blocker | 133 |

TABLE 5-continued

Illustrative primers and probes for the detection of methylation of various gene promoters.

| Primer/ Probe Num | Target | Type | Sequence | SEQ ID NO |
|---|---|---|---|---|
| 133 | RASSF1A UM | I | GGTGTTGAAGTTGGGGTTTG | 134 |
| 134 | RASSF1A UM | I | CCCATACTTCACTAACTTTAAAC | 135 |
| 135 | HIST1H3C UM | I | GTAAATAGTTTGTAAGTTTATTGGTG | 136 |
| 136 | HIST1H3C UM | I | TTTCTTCACACCACCAATAACCAA | 137 |
| 137 | RASGRF2 UM | I | GAGTAAGAAGATGGTTGAGGTG | 138 |
| 138 | RASGRF2 UM | I | CAACAACTCTACTCACCCTCAA | 139 |
| 139 |  | P | fluor-TCCCAACTACT(T*)AAAAAC(T*)AAAC-quencher/blocker | 140 |
| 140 | ALU Long Set 1 | P | fluor-TCCCAACTACT(T*)AAAAAC(T*)AAAC-quencher/blocker | 141 |
| 141 | ALU Long Set 1 | P | fluor-TCCCAACTACT(T*)AAAAAC(T*)AAAC-quencher/blocker | 142 |
| 142 | ALU Long Set 1 | P | fluor-TCCCAACTACT(T*)AAAAAC(T*)AAAC-quencher/blocker | 143 |
| 143 | ALU Long Set 1 | P | fluor-TCCCAACTACT(T*)AAAAAC(T*)AAAC-quencher/blocker | 144 |
| 144 | HMBS | I | GGATAAGATTTTTGATATTGTATTTTTAAGG | 145 |
| 145 | HMBS | I | CATATTCAAACTCCTTAATAAACAAACTTTTCTC | 146 |
| 146 | HMBS | P | fluor-CCGAACAAAAAAAA(C-quencher)CTAAA(T*)AAATCCC(T*)TC-quencher/blocker | 147 |
| 147 | ACTB | P | fluor-CCACCACCCAACACACAA(T*)AACAAACAC-quencher/blocker | 148 |
| 148 | ACTB | I | GGTTTAGTAAGTTTTTTGGATTGTG | 149 |
| 149 | ACTB |  | CCTTAAAAATTACAAAAACCACAAC | 150 |
| 150 | ACTB | P | fluor-CCACCACCCAACA(C-quencher)ACAA(T*)AACAAACAC-quencher/blocker | 151 |
| 151 | ACTB | P | fluor-CCACCACCCAAC(N*)ACA(C**)AATAA(C**)AAACAC-quencher/blocker | 152 |
| 152 | ACTB | P | fluor-CCACCACCCAACACA(N*)CAA(T*)AACAAACAC-quencher/blocker | 153 |
| 153 | BG | I | TTCAGTGCCGGTTGGTAATGTAA-quencher/blocker | 154 |
| 154 | BG | I | CAACAACTTTAATACCTGTTTCAAGGA | 155 |
| 155 | BG conv | I | GGTATTTTTGTATTTGTTGGTGTTG | 156 |
| 156 | BG conv | I | CATACATACACCAAACAATTCATTC | 157 |
| 157 | BG conv | E | GTATGGTGGTATTTTTGTATTTGTTG | 158 |

TABLE 5-continued

Illustrative primers and probes for the detection of methylation of various gene promoters.

| Primer/Probe Num | Target | Type | Sequence | SEQ ID NO |
|---|---|---|---|---|
| 158 | BG conv | E | CACACATACATACACCAAACAATTC | 159 |
| 159 | BG | P | fluor-AAGATCCGATTCACAGA(N*)CAAGCTCCGTCA-quencher/blocker | 160 |
| 160 | BG | I | fluor-AAGATCCGATTCACAGA(N*)CAAGCTCCGTCA-quencher/blocker | 161 |
| 161 | BG conv | P | fluor-(C*)AAATCATTT(C-quencher)CTT(C**)ACAAATA(C**)ACTC-quencher/blocker | 162 |
| 162 | BG conv | P | fluor-CCAAATACCA(T-quencher)AACCA(T*)TTTATTAA(T*)AACAC-quencher/blocker | 163 |
| 163 | BG conv | P | fluor-AAAATCATTTCCTT(C**)ACA(N*)AATA(C**)ACTC-quencher/blocker | 164 |
| 164 | BG conv | P | fluor-CCAAATACCA(T*)AACCAT(N*)TTTATTAA(T*)AACAC-quencher/blocker | 165 |
| 165 | short HMBS | I | CCCTAGTATGCTAGGTCTCTTGCTGGGA | 166 |
| 166 | short HMBS | I | CAGCCTCTCTGAGGGTTTAAGCCCA | 167 |
| 167 | short HMBS | P | fluor-TCAGCC(T*)ATC(T*)GACACCCCGGG-quencher/blocker | 168 |
| 168 | short β-Globin | I | GACTCCTGAGGAGAAGTCTGCCGTTA | 169 |
| 169 | short β-Globin | I | CCTTGATACCAACCTGCCCAGGG | 170 |
| 170 | short β-Globin | P | fluor-AGGTGAACG(T*)GGATGAAGT(T*)GGTGGTG-quencher/blocker | 171 |
| 171 | short BG | I | CAACATCGCGCAAGAGCACGG | 172 |
| 172 | short BG | I | CGTTTCCTTCACGAGTACGCTCTCCGA | 173 |
| 173 | short BG | P | fluor-ACCGGCGAA(T*)ACAGAGA(T*)ACCG-quencher/blocker | 174 |
| 174 | ACTB | P | fluor-CC(A*)CC(A*)CCCAAC(N*)ACA(C**)AATAA(C**)AAACAC-quencher/blocker | 175 |
| 175 | BG conv | I | GTTGGTGTTGGAGAGTGTATTTG | 176 |
| 176 | BG conv | I | GGAGAGTGTATTTGTGAAGGAAATG | 177 |
| 177 | BG conv | I | GGAAATGATTTTTTTTATGAGATGAGTG | 178 |
| 178 | ACTB | P | fluor-CCACCACCCAACACA(N*)CAA(T*)AACAAACAC-quencher/blocker | 179 |
| 179 | ACTB | P | fluor-CCACCACCCAACACA(N*)CAA(T*)AACAAACAC-quencher/blocker | 180 |
| 180 | ACTB | P | fluor-CCACCACCCAACACACAA(T*)AACAAACAC-quencher/blocker | 181 |
| 181 | ACTB | I | GATGGAGGAGGTTTAGTAAGTTTTT | 182 |

TABLE 5-continued

Illustrative primers and probes for the detection of methylation of various gene promoters.

| Primer/Probe Num | Target | Type | Sequence | SEQ ID NO |
|---|---|---|---|---|
| 182 | ACTB | I | AATAAAACCTACTCCTCCCTTAAAAA | 183 |
| 183a | AKR1B1 | E | CTTACCATAACTACTAC(dK)CTCC | 184 |
| 183b | AKR1B1 | E | CTTACCATAACTACTACRCTCC | 185 |
| 184 | HIST1H3C | E | GTGTGTGTTTTTATTGTAAATGGT | 186 |
| 185a | HIST1H3C | E | AAC(dK)ATAAC(dK)ATAAAATTTCTTCAC | 187 |
| 185b | HIST1H3C | E | AACRATAACRATAAAATTTCTTCAC | 188 |
| 186a | HOXB4 | E | GTTTGT(dP)GGGATTTTGGGT | 189 |
| 186b | HOXB4 | E | GTTTGTYGGGATTTTGGGT | 190 |
| 187a | HOXB4 | E | CC(dK)AACTCC(dK)AAAAAAAACC | 191 |
| 187b | HOXB4 | E | CCRAACTCCRAAAAAAAACC | 192 |
| 188a | RASGRF2 | E | GGTATTAAG(dP)G(dP)GGTTTTTG | 193 |
| 188b | RASGRF2 | E | GGTATTAAGYGYGGTTTTTG | 194 |
| 189a | RASSF1A | E | GT(dP)GTTTAGTTTGGATTTTGG | 195 |
| 189b | RASSF1A | E | GTYGTTTAGTTTGGATTTTGG | 196 |
| 190 | TM6SF1 | E | TTTCGAAGGGTAAGCGTTAAG | 197 |
| 191a | TM6SF1 | E | AACATAAATAACC(dK)AAA(T*)AACC | 198 |
| 191b | TM6SF1 | E | AACATAAATAACCRAAA(T*)AACC | 199 |
| 192 | RASGRF2 | I | CGGTTTTTTGAGTAAGAAGACGGTC | 200 |
| 193a | AKR1B1 | P | fluor-TACCTTTAAA(T-quencher)AACCC(dK)(T*)AAAA(T*)CGACAA-quencher/blocker | 201 |
| 193b | AKR1B1 | P | fluor-TACCTTTAAA(T-quencher)AACCCR(T*)AAAA(T*)CGACAA-quencher/blocker | 202 |
| 194a | HIST1H3C | P | fluor-ATAACAAACTACT(T*)AC(dK)CGAAAC(T*)TTAC-quencher/blocker | 203 |
| 194b | HIST1H3C | P | fluor-ATAACAAACTACT(T*)ACRCGAAAC(T*)TTAC-quencher/blocker | 204 |
| 195a | HOXB4 | P | fluor-AACAAACC(dK)AA(C**)GA(T*)AAC(N*)AAAAC-quencher/blocker | 205 |
| 195b | HOXB4 | P | fluor-AACAAACCRAA(C**)GA(T*)AAC(N*)AAAAC-quencher/blocker | 206 |
| 196 | RASGRF2 | P | fluor-CACATTCTAA(T*)AAAAAC(N* )AACCAC(T*)TC-quencher/blocker | 207 |
| 197a | RASSF1A | P | fluor-AACC(dK)AA(C**)GAAA(C-quencher)CA(C**)AAAAC-quencher/blocker | 208 |
| 197b | RASSF1A | P | fluor-AACCRAA(C**)GAAA(C-quencher)CA(C**)AAAAC-quencher/blocker | 209 |
| 198 | TM6SF1 | P | fluor-CAAAAACAC(T*)CATC(N*)CAACCGCC-quencher/blocker | 210 |

TABLE 5-continued

Illustrative primers and probes for the detection of methylation of various gene promoters.

| Primer/ Probe Num | Target | Type | Sequence | SEQ ID NO |
|---|---|---|---|---|
| 199 | RASGRF2 | E | ACAACCCTCCAAAAAATACATA | 211 |
| 200 | BG conv | P | fluor-CCAAATACCATAACCA(T*)TTTATTAA(T*)AACAC-quencher/blocker | 212 |
| 201 | BG conv | P | fluor-CCAAATACCATAACCA(T*)TTTATTAA(T*)AACAC-quencher/blocker | 213 |
| 202a | TM6SF1 | E | TTT(dP)GAAGGGTAAG(dP)GTTAAG | 214 |
| 202b | TM6SF1 | E | TTTYGAAGGGTAAGYGTTAAG | 215 |
| 203a | TM6SF1 | E | CAACAC(dK)AAAACCCC(dK)ATA | 216 |
| 203b | TM6SF1 | E | CAACACRAAAACCCCRATA | 217 |
| 204 | KRAS Multi | E | CCTGCTGAAAATGACTGAATATAACCGCTAAGAACCTCTCGGTCAGCTGAT | 218 |
| 205 | KRAS Multi | E | CCTGCTGAAAATGACTGAATATAAAGTCTCATTATAATCGTTCGAGCTGTT | 219 |
| 206 | KRAS Multi | E | CCTGCTGAAAATGACTGAATATAAGCAGACTTGGCGGTAGGTCCGAGCTTG | 220 |
| 207 | KRAS Multi | E | CCTGCTGAAAATGACTGAATATAAGTATCCTGAGCACGGTTGCGAGCTGCT | 221 |
| 208 | KRAS Multi | I | CTCTTGCCTACGCC(N*)CCGCTAAGAACCTCTCGGTC | 222 |
| 209 | KRAS Multi | I | CTCTTGCCTACGCC(N*)AGTCTCATTATAATCGTTCG | 223 |
| 210 | KRAS Multi | I | CTCTTGCCTACGCC(N*)GCAGACTTGGCGGTAGGTCC | 224 |
| 211 | KRAS Multi | I | CTCTTGCCTACGCC(N*)GTATCCTGAGCACGGTTGCG | 225 |
| 212 | ACTB | P | fluor-CCACCACCCAACACACAA(T*)AACAAACAC-quencher/blocker | 226 |
| 213 | BNC1 | E | CCCRCAAACCRCGAAAACCTC | 227 |
| 214 | BNC1 | E | GTTTTTTTTYGGGAGAGGTAAATA | 228 |
| 215 | ADAMTS1 | E | CRCCTCCRAAACTAAAACAAC | 229 |
| 216 | ADAMTS1 | E | GGGTTATTGTAAAGTTAGGGTG | 230 |
| 217 | BNC1 | E | GAGGT(dP)GTGGTTTT(dP)GTAGAT | 231 |
| 218 | BNC1 | E | AAAC(dK)CCAAAAAACTTCAAAAC | 232 |
| 219 | ADAMTS1 | E | TTTTGTTGGGATAAGAAG(dP)GTTT | 233 |
| 220 | ADAMTS1 | E | ACCAAAAACTATTACAAAACCAAA | 234 |
| 221 | BNC1 | I | CCGACGACCGACG | 235 |
| 222 | BNC1 | I | GGGAGAGGTAAATATCGATAC | 236 |
| 223 | ADAMTS1 | I | CGCGAAAATTAATACCTAACG | 237 |
| 224 | ADAMTS1 | I | TTAGGGTGCGTTATCGGAC | 238 |
| 225 | BNC1 | I | CGGAGGTGTTTGTTTTCGTC | 239 |
| 226 | BNC1 | I | CGAAAAAAACAAACACCGACACG | 240 |

TABLE 5-continued

Illustrative primers and probes for the detection of methylation of various gene promoters.

| Primer/Probe Num | Target | Type | Sequence | SEQ ID NO |
|---|---|---|---|---|
| 227 | ADAMTS1 | I | CGTTTTCGGGGTTGAGGTAAC | 241 |
| 228 | ADAMTS1 | I | CCAAAATACGCTACCGAACGA | 242 |
| 229 | BNC1 | P | fluor-AAAAT(A*)TCT(A*)(C**)CCC(C**)(dK)CC-quencher/blocker | 243 |
| 230 | ADAMTS1 | P | fluor-TATTACTCACTCTAC(T*)CAAAAC(T*)CTCC-quencher/blocker | 244 |
| 231 | BNC1 | P | fluor-ATATCTTTTACCAACAAA(T*)ACCT(T*)CAAA-quencher/blocker | 245 |
| 232 | ADAMTS1 | P | fluor-GTTTT(dP)GTTTTGGTTGCGA(T*)GTTGT-quencher/blocker | 246 |
| 233 | GSTP1 | E | GGGATTTTTTAGAAGAG(dP)GGT | 247 |
| 234 | GSTP1 | E | TACTCACTAATAAC(dK)AAAAC(T*)AC | 248 |
| 235 | APC | E | GGTTTTGTGTTTTATTG(dP)GGAG | 249 |
| 236 | APC | E | CCTAAC(dK)AACTACACCAATACAA | 250 |
| 237 | PTGS2 | E | GAGAGGGGATTTTTTG(dP)GTTT | 251 |
| 238 | PTGS2 | E | CC(dK)AAAACCAATTCTAAACTAATC | 252 |
| 239 | GSTP1 | I | TTTTTAGAAGAGCGGTCGGC | 253 |
| 240 | GSTP1 | I | CTAATAACGAAAACTACGACGACG | 254 |
| 241 | APC | I | TTGTGTTTTATTGCGGAGTGC | 255 |
| 242 | APC | I | AACCACATATCGATCACGTACG | 256 |
| 243 | PTGS2 | I | GCGTTTTCGGATTTTAGGGTC | 257 |
| 244 | PTGS2 | I | AACTAATCGCCTTAAATAAAATACCG | 258 |
| 245 | GSTP1 | P | fluor-CCTCC(dK)AACCTTA(T*)AA(N*)AAA(T*)AATCCC-quencher/blocker | 259 |
| 246 | APC | P | fluor-AAAAAC(dK)CCCTAATCC(N*)CA(T*)CCAAC-quencher/blocker | 260 |
| 247 | PTGS2 | P | fluor-CACTTAACTTCCTC(T*)CCAAAAATC(T*)AAAC-quencher/blocker | 261 |
| 248a | MGMT | E | GTTTT(T*)AGAA(dP)G(T*)TTTG(dP)GTTT | 262 |
| 248b | MGMT | E | GTTTT(T*)AGAAYG(T*)TTTGYGTTT | 263 |
| 249a | MGMT | E | AAAAAAC(T*)CC(dK)CACTCTTCC | 264 |
| 249b | MGMT | E | AAAAAAC(T*)CCRCACTCTTCC | 265 |
| 250 | MGMT | I | TTTCGACGTTCGTAGGTTTTCGC | 266 |
| 251 | MGMT | I | GCACTCTTCCGAAAACGAAACG | 267 |
| 252a | MGMT | P | fluor-CCAAACAC(T*)CACCAAATC(N*)CAAAC-quencher/blocker | 268 |

TABLE 5-continued

Illustrative primers and probes for the detection
of methylation of various gene promoters.

| Primer/<br>Probe Num | Target | Type | Sequence | SEQ<br>ID NO |
|---|---|---|---|---|
| 252b | MGMT | P | fluor-<br>CCAAACAC(T*)CACCAAATC(N*)CAAAC-<br>quencher/blocker | 269 |
| 264 | BNC1 | P | fluor-ATATCTTTTACCAA(C-<br>quencher)AAA(T*)ACCT(T*)CAAA-<br>quencher/blocker | 270 |
| 265 | ADAMTS1 | P | fluor-<br>GTTTT(dP)GTTTTGGTTGCGA(T*)GTTGT-<br>quencher/blocker | 271 |
| 283 | CDO1 | E | GGAGATAA(dP)GGGGTTTTTGG | 272 |
| 284 | CDO1 | E | CACTAAAAATATACCAAC(dK)ACC | 273 |
| 285 | CDO1 | E | GGAGAGTTATTTAAGAAAGGTGG | 274 |
| 286 | CDO1 | E | AAAATTAC(dK)C(dK)AAACCCAC | 275 |
| 287 | CDO1 | I | CGTGTTCGTAGGGTTTTTCGTTTTC | 276 |
| 288 | CDO1 | I | CCAACGACCCTCGAAAAAAAACG | 277 |
| 289 | CDO1 | I | GATTTTGCGGGTACGGTTTACGC | 278 |
| 290 | CDO1 | I | GATCCCTAAAACGCCGAAAACAACG | 279 |
| 291 | CDO1 | P | fluor-(C*)GTTATTTTT(T-<br>quencher)TTGGG(T*)GGTT(T*)TTCG-<br>quencher/blocker | 280 |
| 292 | CDO1 | P | fluor-C(dK)AAAAACCACC(C-<br>quencher)AAAAAAAA(T*)AAC-<br>quencher/blocker | 281 |
| 293 | TAC1 | E | GGATAAATAT(dP)GTAAGGTATTGAG | 282 |
| 294 | TAC1 | E | CGAAATACTAAATTTCTCTAATTCCTC | 283 |
| 295 | TAC1 | E | GAGTTTTTTGGTTTTT(dP)GAG | 284 |
| 296 | TAC1 | E | CTAAAATAAATACC(dK)CAAAACAC | 285 |
| 297 | TAC1 | I | CGCGTTCGGATTTTTTTTCGGC | 286 |
| 298 | TAC1 | I | AAATTTCTCTAATTCCTCCGAACGCACG | 287 |
| 299 | TAC1 | I | GCGTACGTTGGTCGTTTCGTATTTTC | 288 |
| 300 | TAC1 | I | GCAAAACACTAAACAAACGAAAAAACGCG | 289 |
| 301 | TAC1 | P | fluor-<br>GTAGTTAT(dP)GAGAG(T*)G(N*)GGAGCG<br>A(T*)TAG-quencher/blocker | 290 |
| 302 | TAC1 | P | fluor-<br>CTAATC(dK)CTCCGCAC(T*)CTC(N*)A(T*)<br>AACTAC-quencher/blocker | 291 |
| 303 | SOX17 | E | GTTTGGAG(dP)GTTATGAGTAG | 292 |
| 304 | SOX17 | E | CTTCATATCCCC(dK)ATAAAACTC | 293 |
| 305 | SOX17 | E | GGGTTTTTAGTCGGTTTAGTG | 294 |
| 306 | SOX17 | E | CTAAAAC(dK)TAAAACTC(dK)AACC | 295 |
| 307 | SOX17 | I | GATTTAGAGCGCGTTGTTCGC | 296 |
| 308 | SOX17 | I | CATATCCCCGATAAAACTCAACGACTCG | 297 |
| 309 | SOX17 | I | GTCGGTTTAGTGATATTGCGGGC | 298 |

TABLE 5-continued

Illustrative primers and probes for the detection of methylation of various gene promoters.

| Primer/Probe Num | Target | Type | Sequence | SEQ ID NO |
|---|---|---|---|---|
| 310 | SOX17 | I | CCACGACCTAAACGTAAACCTAACG | 299 |
| 311 | SOX17 | P | fluor-GATGGT(dP)GGGTTGGGTT(T*)TTGTTTTTGG-quencher/blocker | 300 |
| 312 | SOX17 | P | fluor-CCAAAAACAAAAACCCAA(C**)CCGACCATC-quencher/blocker | 301 |
| 313 | CDO1 | P | fluor-(C*)GTATATTTT(dP)GGTT(T*)TTT(N*)GGGT(T*)TCG-quencher/blocker | 302 |
| 314 | CDO1 | P | fluor-C(dK)AAACC(C**)GAAAAAA(C**)C(N*)AAAATATAC-quencher/blocker | 303 |
| 315 | TAC1 | P | fluor-GGTAGTTGT(dP)G(T*)CGGGAAGGAGGTTCG-quencher/blocker | 304 |
| 316 | TAC1 | P | fluor-C(dK)AACCTCCTTCCCGAC(N*)ACAAC(T*)ACC-quencher/blocker | 305 |
| 317 | SOX17 | P | fluor-GGTTTTTTTTGTA(T*)AGATGTGGT(T*)AATGG-quencher/blocker | 306 |
| 318 | SOX17 | P | fluor-CCATTAACCACA(T*)CTA(T*)ACAAAAAAAACC-quencher/blocker | 307 |
| 319 | SOX17 | E | GGTTTGGTTTATAG(dP)GTATTTAGG | 308 |
| 320 | ACTB | I | GAGGTTTAG(T*)AAGTTTTTTGGATTGTG | 309 |
| 321 | ACTB | I | CCCTTAAAAAT(T*)ACAAAAACCACAAC | 310 |
| 322 | BRCA1 | E | GTAGATTGGGTGGTTAATTTAGAG | 311 |
| 323 | BRCA1 | E | CTATAATTCCC(dK)C(dK)CTTTTC | 312 |
| 324 | BRCA1 | I | GGTGGTTAATTTAGAGTTTCGAGAGAC | 313 |
| 325 | BRCA1 | I | CGTTACCACGAAAACCAAAAAACTACCG | 314 |
| 326 | BRCA1 | P | fluor-GATTTCGTATTT(T*)GAGAGG(T*)TGTTGTTTAG-quencher/blocker | 315 |
| 327 | BRCA1 | P | fluor-CTAAACAACAACC(T*)CTCAAAA(T*)ACGAAATC-quencher/blocker | 316 |
| 328 | BRCA1 | E | GGTAGATTGGGTGGTTAATTTAGAG | 317 |
| 329 | BRCA1 | E | CCAAAAAATCTCAACRAACTC | 318 |
| 330 | BRCA1 | I | GGGTGGTTAATTTAGAGTTTCGAGAGAC | 319 |
| 331 | BRCA1 | I | ACCACGAAAACCAAAAAACTACCG | 320 |
| 336 | MGMT | E | GGGATTTTGTTTAAGTATGTTAAAGG | 321 |
| 337 | MGMT | E | CCTACCTTACCTCTAAATACCAACC | 322 |
| 338 | MGMT | I | GTATGTTAAAGGGTGTTGTAAGTTAAGG | 323 |
| 339 | MGMT | I | CCTCTAAATACCAACCCCAAACC | 324 |

TABLE 5-continued

Illustrative primers and probes for the detection of methylation of various gene promoters.

| Primer/Probe Num | Target | Type | Sequence | SEQ ID NO |
|---|---|---|---|---|
| 340 | MGMT | P | fluor-CCAACTACTC(C-quencher)AAAAAACTTCCAAAAACC-quencher/blocker | 325 |
| 341 | MGMT | P | fluor-CCAAC(T*)ACTC(C-quencher)AAAAAC(T*)TCCAAAAACC-quencher/blocker | 326 |
| 342 | MGMT | I | GTATGTTAAAGGGTTGT(T*)GTAAGTTAAGG | 327 |
| 343 | MGMT | I | CCTCTAAATACCAA(C**)CCCAAACC | 328 |
| 380 | ACTB | P | fluor-CCACCACCCAACACACAA(T*)AACAAACAC-quencher/blocker | 329 |
| 381 | ACTB | P | fluor-CCACCACCCAACACACAA(T*)AACAAACAC-quencher/blocker | 330 |
| 382 | SOX17 | I | ATTTAGAGCGCGTTGTTCGC | 331 |
| 383 | SOX17 | I | ATATCCCCGATAAAACTCAACGACTCG | 332 |
| 384 | SOX17 | I | TATCCCCGATAAAACTCAACGACTCG | 333 |
| 385 | SOX17 | I | ATCCCCGATAAAACTCAACGACTCG | 334 |
| 386 | TAC1 | I | GCGTTCGGATTTTTTTTCGGC | 335 |
| 387 | TAC1 | I | TTTCTCTAATTCCTCCGAACGCACG | 336 |
| 388 | TAC1 | I | CTCTAATTCCTCCGAACGCACG | 337 |
| 389 | SOX17 | I | GTGACGATTAGAGTTAGATTTAGAGCGC | 338 |
| 390 | TAC1 | P | fluor-GTAGTTATCGAGAG(T*)GCGGAGCGA(T*)TAG-quencher/blocker | 339 |
| 391 | SOX17 | P | fluor-CCAACCCGACCATCACCGCGAACAAC-quencher/blocker | 340 |
| 392 | BG converted | I | GGAGAGTGTATTTG(T*)GAAGGAAATG | 341 |
| 393 | BG converted | I | CATACATACACCAAACAA(T*)TCATTC | 342 |
| 394 | BG converted | P | fluor-CCAAATACCA(T*)AACCATTTTATTAA(T*)AACAC-quencher/blocker | 343 |
| 395 | BG converted | P | fluor-CCAAATACCA(T*)AACCATTTTATTAA(T*)AACAC-quencher/blocker | 344 |
| 396 | GSTP1 (Fwd) | E | GGTTTYGTTGGGGATTTG | 345 |
| 397 | GSTP1 (Fwd) | E | ACCRCTCTTCTAAAAAATCC | 346 |
| 398 | GSTP1 (Fwd) | I | AGGTTTTTTCGGTTAGTTGCGC | 347 |
| 399 | GSTP1 (Fwd) | I | AACGTCGACCGCAAAAAAACG | 348 |
| 400 | GSTP1 (Fwd) | P | fluor-(C*)GCGAT(T*)T(C-quencher)GGGGA(T*)T(T*)TAGG-quencher/blocker | 349 |
| 401 | GSTP1 (Fwd) | P | fluor-CC(T*)AAAA(T*)C(C-quencher)CCGAAA(T*)CGC-quencher/blocker | 350 |
| 402 | APC(Fwd) | E | GAAGTAGTTGTGTAATTYGTTGG | 351 |

TABLE 5-continued

Illustrative primers and probes for the detection of methylation of various gene promoters.

| Primer/Probe Num | Target | Type | Sequence | SEQ ID NO |
|---|---|---|---|---|
| 403 | APC(Fwd) | E | CACCCTAACRAACTACACC | 352 |
| 404 | APC(Fwd) | I | TGCGGATTAGGGCGTTTTTATTTTC | 353 |
| 405 | APC(Fwd) | I | TACAACCACATATCGATCACGTACG | 354 |
| 406 | APC(Fwd) | P | fluor-GGAGTTCGTCGA(T*)TGG(T*)TGGG-quencher/blocker | 355 |
| 407 | APC(Fwd) | P | fluor-CCCAACCAA(T*)CGACGAAC(T*)CC-quencher/blocker | 356 |
| 408 | EYA4(Fwd) | E | GAGTTTTTYGGAGGGTTATAG | 357 |
| 409 | EYA4(Fwd) | E | CAAACTACAAAAAACATTCAATCC | 358 |
| 410 | EYA4(Fwd) | I | GCGTTTGGGTTTTTCGGTGTC | 359 |
| 411 | EYA4(Fwd) | I | ATCGCCGCAATTAAAAAACCCG | 360 |
| 412 | EYA4(Fwd) | P | fluor-GGTTCGCGTTTTAAT(T*)TTTAGG(T*)ATTG-quencher/blocker | 361 |
| 413 | EYA4(Fwd) | P | fluor-CAATACC(T*)AAAAAT(T*)AAAACGCGAACC-quencher/blocker | 362 |
| 414 | OLIG2(Fwd) | E | GTTATGGATTYGGAYGTTAG | 363 |
| 415 | OLIG2(Fwd) | E | CTCCRACRAACAATCACTC | 364 |
| 416 | OLIG2(Fwd) | I | GTTTGGTGTTTAG(T*)CGTTCGTC | 365 |
| 417 | OLIG2(Fwd) | I | CACTCGAAATAAA(C**)GAAAACACG | 366 |
| 418 | OLIG2(Fwd) | P | fluor-GGTAGTAGCGG(T*)AGCGTT(T*)TTATTG-quencher/blocker | 367 |
| 419 | OLIG2(Fwd) | P | fluor-CAATAAAAACGC(T*)ACCGC(T*)ACTACC-quencher/blocker | 368 |
| 420 | ADAMTS12(Fwd) | E | GGYGTAGTTTATTTYGGTT | 369 |
| 421 | ADAMTS12(Fwd) | E | ATTTAACCRACTCRACCAAC | 370 |
| 422 | ADAMTS12(Fwd) | I | GTATGTTTCGCGGTTTCGTAGTTC | 371 |
| 423 | ADAMTS12(Fwd) | I | ACTAAACCTAACG(T*)TCGAAACG | 372 |
| 424 | ADAMTS12(Fwd) | P | fluor-(C*)GTTCGTTCGG(T-quencher)G(T*)ATTTTTT(T*)TTCGG-quencher/blocker | 373 |
| 425 | ADAMTS12(Fwd) | P | fluor-CCGAAAAAAAAA(T-quencher)A(C**)ACCGAA(C**)GAAC-quencher/blocker | 374 |
| 426 | POU4F1(Fwd) | E | GTTTGAGTTGTTTTGATTTTAGTG | 375 |
| 427 | POU4F1(Fwd) | E | CTCCAACCTCAACTCTAAAC | 376 |
| 428 | POU4F1(Fwd) | I | GATTTTAGTGTCGCGTATTTTGGTTC | 377 |
| 429 | POU4F1(Fwd) | I | CTAAACTAAATCCCGCGAACCTCG | 378 |
| 430 | POU4F1(Fwd) | P | fluor-GGTTTTAT(T*)GGGGGTT(N*)AT(T*)TCGGGTAG-quencher/blocker | 379 |

TABLE 5-continued

Illustrative primers and probes for the detection of methylation of various gene promoters.

| Primer/Probe Num | Target | Type | Sequence | SEQ ID NO |
|---|---|---|---|---|
| 431 | POU4F1(Fwd) | P | fluor-CTACCCGAAATAACCC(C**)CAA(N*)TAA AA(C**)C-quencher/blocker | 380 |
| 432 | ABCB1(Fwd) | E | GGTTTTTAGTATTTTTAYGAAGGT | 381 |
| 433 | ABCB1(Fwd) | E | CRATACRAAAACCTACTCTCTA | 382 |
| 434 | ABCB1(Fwd) | I | TTTGGATTTTGTTCGTCGTTAGTGC | 383 |
| 435 | ABCB1(Fwd) | I | CTACTCTCTAAACCCGCGAACG | 384 |
| 436 | ABCB1(Fwd) | P | fluor-GGTTTTAGTCG(T*)CGCGGACGATGT-quencher/blocker | 385 |
| 437 | ABCB1(Fwd) | P | fluor-ACATCGTCCGCGACGAC(T*)AAAACC-quencher/blocker | 386 |
| 438 | SOX17 | I | GAGTTAGATTTAGAGCGCGTTGTTC | 387 |
| 439 | TAC1 | I | GAGCGCGTTCGGATTTTTTTTC | 388 |

Note
Y is C/T;
R is A/G;
C* is an optionally functionalized (e.g., to alter probe $T_m$) C;
T* is an optionally functionalized (e.g., to alter probe $T_m$) T;
A* is an optionally functionalized (e.g., to alter probe $T_m$) A;
N* is a nucleotide optionally a quencher;
dP is a universal pyrimidine;
dK is a universal purine.

It is noted that these primers and probes identify the locations of various fluorophores and quenchers. However, it will be recognized that the particular fluorophores and quenchers are illustrative and not limiting and numerous amplification and/or detection strategies can be employed in the cartridges described herein. Accordingly, in various embodiments the methods and devices described herein can employ many different nucleic acid hybridization probes. Typically, for signal generation, the probes utilize a change in the fluorescence of a fluorophore due to a change in its interaction with another molecule or moiety brought about by changing the distance between the fluorophore and the interacting molecule or moiety. Alternatively, other methods of detecting a polynucleotide in a sample, including, but not limited to, the use of radioactively-labeled probes, are contemplated.

Fluorescence-based assays typically rely for signal generation on fluorescence resonance energy transfer, or "FRET", according to which a change in fluorescence is caused by a change in the distance separating a first fluorophore from an interacting resonance energy acceptor, either another fluorophore or a quencher. Combinations of a fluorophore and an interacting molecule or moiety, including quenching molecules or moieties, are known as "FRET pairs." The mechanism of FRET-pair interaction typically requires that the absorption spectrum of one member of the pair overlaps the emission spectrum of the other member, the first fluorophore. If the interacting molecule or moiety is a quencher, its absorption spectrum typically overlaps the emission spectrum of the fluorophore (see, e.g., Stryer (1978) Ann. Rev. Biochem. 47: 819-846; Selvin (1995) Meth. Enzymol. 246: 300-335; and the like). Efficient FRET interaction is typically achieved when the absorption and emission spectra of the pair have a large degree of overlap. The efficiency of FRET interaction is linearly proportional to that overlap. Typically, a large magnitude of signal (i.e., a high degree of overlap) is desired. FRET pairs, including fluorophore-quencher pairs, are therefore typically chosen on that basis.

A variety of labeled nucleic acid hybridization probes and detection assays that utilize FRET and FRET pairs are known. One such scheme is described by Cardullo et al. (1988) Proc. Natl. Acad. Sci. USA, 85: 8790-8794 and in Heller et al. EP 0070685. It uses a probe comprising a pair of oligodeoxynucleotides complementary to contiguous regions of a target DNA strand. One probe molecule contains a fluorescent label, a fluorophore, on its 5' end, and the other probe molecule contains a different fluorescent label, also a fluorophore, on its 3' end. When the probe is hybridized to the target sequence, the two labels are brought very close to each other. When the sample is stimulated by light of an appropriate frequency, fluorescence resonance energy transfer from one label to the other occurs. FRET produces a measurable change in spectral response from the labels, signaling the presence of targets. One label could be a "quencher," which can be, inter alia, an interactive moiety (or molecule) that releases the accepted energy as heat.

Another type of nucleic acid hybridization probe assay utilizing a FRET pair is the "TaqMan®" assay described in Gelfand et al. U.S. Pat. No. 5,210,015, and Livak et al. U.S. Pat. No. 5,538,848. The probe is typically a single-stranded oligonucleotide labeled with a FRET pair. In a TaqMan® assay, a DNA polymerase releases single or multiple nucleotides by cleavage of the oligonucleotide probe when it is hybridized to a target strand. That release provides a way to separate the quencher label and the fluorophore label of the FRET pair.

In certain embodiments non-FRET fluorescent probes, such as those described in, e.g., Tyagi et al., U.S. Pat. No. 6,150,097 can also be used. For example, the Tiyagi et al. patent describes how changes in the absorption spectra of the label pair can be used as a detectable signal as an alternative to change in fluorescence. When change in absorption is utilized, the label pair may include any two chromophores, that is, fluorophores, quenchers and other chromophores. The label pair may even be identical chromophores.

In some embodiments, dyes and other moieties, such as quenchers, are introduced into primers and/or probes used in the methods and cartridges described herein. In certain embodiments such dyes and quenchers include, but are not limited to dyes (fluors) suitable for use as FRET probes. In certain embodiments the dyes and/or quenchers comprise modified nucleotides. A "modified nucleotide" refers to a nucleotide that has been chemically modified, but still functions as a nucleotide. In some embodiments, the modified nucleotide has a chemical moiety, such as a dye or quencher, covalently attached, and can be introduced into a polynucleotide, for example, by way of solid phase synthesis of the polynucleotide. In some embodiments, the modified nucleotide includes one or more reactive groups that can react with a dye or quencher before, during, or after incorporation of the modified nucleotide into the nucleic acid. In some embodiments, the modified nucleotide is an amine-modified nucleotide, i.e., a nucleotide that has been modified to have a reactive amine group. In some embodiments, the modified nucleotide comprises a modified base moiety, such as uridine, adenosine, guanosine, and/or cytosine. In some embodiments, the amine-modified nucleotide is selected from 5-(3-aminoallyl)-UTP; 8-[(4-amino)butyl]-amino-ATP and 8-[(6-amino)butyl]-amino-ATP; N6-(4-amino)butyl-ATP, N6-(6-amino)butyl-ATP, N4-[2,2-oxy-bis-(ethylamine)]-CTP; N6-(6-Amino)hexyl-ATP; 8-[(6-Amino)hexyl]-amino-ATP; 5-propargylamino-CTP, 5-propargylamino-UTP. In some embodiments, nucleotides with different nucleobase moieties are similarly modified, for example, 5-(3-aminoallyl)-GTP instead of 5-(3-aminoallyl)-UTP. Many amine modified nucleotides are commercially available from, e.g., Applied Biosystems, Sigma, Jena Bioscience and TriLink. An illustrative, but non-limiting list of suitable fluors is shown in Table 6.

TABLE 6

Illustrative, but non-limiting fluorophores (fluorescent labels) for use in the primers and/or probes described herein.

| Dye | Absorbance Wavelength | Emission Wavelength |
|---|---|---|
| Alexa fluor | 345 | 442 |
| Alexa fluor 430 | 430 | 545 |
| Alexa fluor 488 | 494 | 517 |
| Alexa fluor 532 | 530 | 555 |
| Alexa fluor 546 | 556 | 573 |
| Alexa fluor 555 | 556 | 573 |
| Alexa fluor 568 | 578 | 603 |
| Alexa fluor 594 | 590 | 617 |
| Alexa fluor 633 | 621 | 639 |
| Alexa fluor 633 | 650 | 668 |
| Alexa fluor 660 | 663 | 690 |
| Alexa fluor 680 | 679 | 702 |
| Allophycocyanin | 650 | 660 |
| Aminocoumarin | 350 | 445 |

TABLE 6-continued

Illustrative, but non-limiting fluorophores (fluorescent labels) for use in the primers and/or probes described herein.

| Dye | Absorbance Wavelength | Emission Wavelength |
|---|---|---|
| Cy2 | 490 | 510 |
| Cy3 | 550 | 570 |
| Cy3.5 581 | 581 | 596 |
| Cy5 | 650 | 670 |
| Cy5.5 | 675 | 694 |
| Cy7 | 743 | 770 |
| FAM | 495 | 516 |
| Fluorescein FITC | 495 | 518 |
| HEX | 535 | 556 |
| Hydroxycoumarin | 325 | 386 |
| Methoxycoumarin | 360 | 410 |
| Red 613 | 480; 565 | 613 |
| Rhodamine Red-X | 560 | 580 |
| Rox | 575 | 602 |
| R-phycoerythrin (PE) | 480; 565 | 578 |
| Tamara | 565 | 580 |
| Texas Red | 615 | 615 |
| TRITC | 547 | 572 |
| TruRed | 490; 675 | 695 |

If the assay is designed to detect one target DNA sequence then only one fluorescent hybridization probe needs to be used and, in certain embodiments, FAM, TET, or HEX (or one of their alternatives listed in Table 7) will be a good fluorophore to label the probe. These fluorophores can readily be excited and detected in various spectrofluorometric thermal cyclers. In addition, because of the availability of phosphoramidites derivatives of these fluorophores and the availability of quencher-linked control-pore glass columns, fluorescent hybridization probes with these labels can be entirely synthesized in an automated DNA synthesis process, with the advantage of relatively less expensive and less labor intensive probe manufacture.

TABLE 7

Additional illustrative fluorophore labels for fluorescent hybridization probes.

| Fluorophore | Alternative Fluorophore | Excitation (nm) | Emission (nm) |
|---|---|---|---|
| Cy3[3] | NED[2], Quasar 570[1], Oyster 556[4] | 550 | 570 |
| Cy5[3] | LC red 670[5], Quasar 670[1], Oyster 645[4] | 650 | 670 |
| HEX | JOE, VIC[B], CAL Fluor Orange 560[1] | 535 | 555 |
| LC red 640[5] | CAL Fluor Red 635[4] | 625 | 640 |
| LC red 705[5] | Cy5.5[3] | 680 | 710 |
| ROX | LC red 610[5], CAL Fluor Red 610[1] | 575 | 605 |
| TET | CAL Fluor Gold 540[1] | 525 | 540 |
| Texas red | LC red 610[5], CAL Fluor Red 610[1] | 585 | 605 |
| TMR | CAL Fluor Red 590[1] | 555 | 575 |

[1]CAL and Quasar fluorophores are available from Biosearch Technologies;
[2]VIC and NED are available from Applied Biosystems;
[3]Cy dyes are available from Amersham Biosciences;
[4]Oyster fluorophores are available from Integrated DNA Technologies; and
[5]LC (Light Cycler) fluorophores are available from Roche Applied Science.

In certain embodiments, multiple target genes are detected in a single multiplex reaction. In some embodiments, each probe that is targeted to a different gene is spectrally distinguishable (detectably different) from the other probes utilized in the multiplex reaction. Probe combinations suitable for multiplex detection are known to those of skill in the art. For example, illustrative combinations of detectably different fluorophores in four target multiplex systems include, but are not limited to:

1) FAM, TMR, Texas red, and Cy5;
2) FAM, TET, TMR, and Texas Red;
3) FAM, HEX, Texas red, and Cy5; and
4) FAM, Cy3, Texas red, and Cy5.

An illustrative combination of detectably different fluorophores in a five target multiplex systems is FAM, TET, TMR, Texas Red, and Cy5. Illustrative combinations of detectable different fluorophores in a six target multiplex system include, but are not limited to:

1) FAM, TET, HEX, TMR, ROX, and Texas red; and
2) FAM, HEX, LC red 610, LC red 640, LC red 670, and LC red 705.

It will be recognized that these combinations of fluorophores are illustrative and non-limiting and numerous other fluorophores will be available to those of skill in the art.

As noted above, for the design of fluorescent hybridization probes that utilize fluorescence resonance energy transfer (FRET), fluorophore-quencher pairs that have sufficient spectral overlap should be chosen. Fluorophores with an emission maximum between 500 and 550 nm, such as FAM, TET and HEX, are best quenched by quenchers with absorption maxima between 450 and 550 nm, such as dabcyl, BHQ-1, and the like (see, e.g., Table 8 for illustrative quencher labels). Fluorophores with an emission maximum above 550 nm, such as rhodamines (including TMR, ROX and Texas red) and Cy dyes (including Cy3 and Cy5) are effectively quenched by quenchers with absorption maxima above 550 nm (including BHQ-2).

For the design of fluorescent hybridization probes that utilize contact quenching, any non-fluorescent quencher can serve as a good acceptor of energy from the fluorophore. For example, Cy3 and Cy5 are effectively quenched by the BHQ-1 and BHQ-2 quenchers.

TABLE 8

Illustrative quencher labels for fluorescent hybridization probes.

| Quencher | Absorption Maximum (nm) |
| --- | --- |
| BHQ-1[4] | 534 |
| BHQ-2[4] | 580 |
| BHQ-3[4] | 670 |
| Dabcyl | 475 |
| DDQ-I[1] | 430 |
| DDQ-II[1] | 630 |
| Eclipse[2] | 530 |
| Iowa Black FQ[3] | 532 |
| Iowa Black RQ[3] | 645 |
| QSY-21[5] | 660 |
| QSY-7[5] | 571 |

[1]DDQ or Deep Dark Quenchers are available from Eurogentec;
[2]Eclipse quenchers are available from Epoch Biosciences;
[3]Iowa quenchers are available from Integrated DNA Technologies;
[4]BHQ or Black Hole quenchers are available from Biosearch Technologies; and
[5]QSY quenchers are available from Molecular Probes.

In certain embodiments nucleotides can quench the fluorescence of fluorophores, with guanosine being the most efficient quencher, followed by adenosine, cytidine and thymidine. In general, fluorophores with an excitation wavelength between 500 and 550 nm are quenched more efficiently by nucleotides than fluorophores with longer excitation wavelengths. In designing fluorescent hybridization probes, it can be desirable to avoid placing a fluorophore label directly next to a guanosine, to ensure higher fluorescence signals from the fluorophore.

The stabilizing effect of some fluorophore-quencher pairs that interact by contact quenching can have important consequences for the design of hybridization probes (see, e.g., Marras et al. (2002) Nucleic Acids Res. 30: e122; Johansson et al. (2002) J. Am. Chem. Soc. 124: 6950-6956). For example, it has been observed that hybridization probes labeled with a fluorophore quenched by either BHQ-1 or BHQ-2 show an increase in hybrid melting temperature of about 4° C., compared to hybridization probes with the same probe sequence, but labeled with fluorophores quenched by dabcyl. It is also noted that strong affinity has been observed between the Cy dyes, Cy3 and Cy5, and the Black Hole quenchers, BHQ-1 and BHQ-2.

In view of the foregoing and the Examples and teachings provided herein, numerous primer/probe combinations will be available for use in the methods and cartridges described herein.

Cartridge, Modules, and Systems for DNA Methylation Analysis.

In certain embodiments cartridges are provided for performing the methods described herein (e.g., determination of DNA methylation and, optionally RNA expression). In certain embodiments the cartridge comprises a column comprising a first matrix material, a sample receiving chamber, a temperature controlled channel or chamber, a plurality of chambers containing reagents and/or buffers, and when in use at least one of said chambers contains a DNA conversion reagent (e.g., DABSO and/or a bisulfite reagent), and at least one of said chambers contains a desulphonation/elution buffer, and wherein said cartridge optionally comprises a second column comprising said second matrix material. In certain embodiments the cartridge is configured so that in use, the cartridge comprises a chamber containing a reagent comprising guanidinium thiocyanate ethanol (GTC-EtOH). In certain embodiments the second column is absent, while in other embodiments the second column is present. In certain embodiments the temperature controlled channel or chamber can simply be a heating channel or chamber, or it can be a thermocycling channel or chamber. In certain embodiments the cartridge further comprises a second heating channel or chamber (e.g., a second thermocycling channel or chamber). In certain embodiments the cartridge is configured so that a DNA conversion step (e.g., bisulfite incubation) and/or a desulphonation step occurs in the same reaction tube or chamber in which one or more PCR reactions are later performed.

In certain embodiments the bisulfite reagent is provided as a component of the cartridge. In certain other embodiments the cartridge is configured for the bisulfite reagent to be added to the cartridge at or near the time the sample is placed in the cartridge. In certain instances, the bisulfite reagent is added directly into a chamber in the cartridge, while in other embodiments, the bisulfite reagent is introduced into a loading port on the cartridge (e.g., an injection port) to introduce the bisulfite reagent into the cartridge. In certain embodiments the bisulfite reagent is introduced into the cartridge by the system operating the cartridge (e.g., a processing module) while the cartridge is operating to determine DNA methylation.

In certain embodiments the reagent comprising guanidinium thiocyanate (e.g., GTC-EtOH) is provided as a component of the cartridge. In certain other embodiments the cartridge is configured for the reagent comprising guanidinium thiocyanate to be added to the cartridge at or near the time the sample is placed in the cartridge. In certain instances, the reagent comprising guanidinium thiocyanate is added directly into a chamber in the cartridge, while in other embodiments, the reagent comprising guanidinium thiocyanate is introduced into a loading port on the cartridge (e.g., an injection port) to introduce the bisulfite reagent into the cartridge. In certain embodiments the reagent comprising guanidinium thiocyanate is introduced into the cartridge by the system operating the cartridge (e.g., a processing module) while the cartridge is operating to determine DNA methylation.

In various illustrative, but non-limiting embodiments, the conversion reagent (e.g., bisulfite reagent) comprises a compound selected from the group consisting of sodium metabisulfite, potassium bisulfite, cesium bisulfite, DABSO, and ammonium bisulfite. In certain embodiments the bisulfite is provided in a reagent mix comprising scavengers (e.g., Trolox, hydroquinone, etc.) to prevent sulfite oxidation and/or catalysts. In certain embodiments the bisulfite is provided in a reagent mix comprising polyamines as catalysts.

In various embodiments the first matrix material and/or said second matrix material, when present, comprises a material selected from the group consisting of glass or silica, an ion exchange resin, and hydroxyapatite.

In various embodiments the cartridge comprises one or more chambers (e.g., 1 chamber, 2 chambers, 3 chambers, 4 chambers, etc.) each containing one or more reagents selected from the group consisting of methylation specific PCR primers, methylation specific PCR probes, PCR enzyme(s) (e.g., polymerase), reverse transcriptase, and PCR reaction buffer.

In certain embodiments the cartridge contains one or more chambers containing primers specific for bisulfite-converted methylated and/or unmethylated sequences. In certain embodiments the cartridge comprises one or more chambers containing primers and probes for a MethyLight PCR protocol. In certain embodiments the cartridge comprises one or more chambers containing reagents for TaqMan PCR reactions. In certain embodiments the cartridge comprises one or more chambers containing one or more fluorescent probes that are markers for amplified methylated sequences and/or one or more fluorescent probes that are markers for amplified unmethylated sequences. In certain embodiments the probes comprise a fluorescent reporter dye and a quencher dye, where the probes provides a signal upon cleavage by the 5' to 3' nuclease activity of Taq DNA polymerase. In certain embodiments the cartridge comprises a plurality of probes each specific to a different methylated region in an amplified region of interest. In certain embodiments the cartridge comprises a single probe specific to a methylated region in an amplified region of interest. In certain embodiments the cartridge comprises a plurality of probes each specific to the same methylated region in an amplified region of interest.

Illustrative primers and probes include, but are not limited to primers and/or probes to determine methylation of a promoter region of a gene selected from the group consisting of APC, ARF, CDKN2B, CDKN2A, BRCA1, VLH, hMLH1, MGMT. RASSF1A, ADAMTS1, BNC1, HIST1H3C, HOXB4, RASGRF2, TM6SF1, AKR1B1, HIST1H4F, PCDHGB6, NPBWR1, ALX1, and HOXA9. In certain embodiments the primers and/or probes are selected to determine methylation of a promoter region of a gene selected from the group consisting of MGMT, RASSF1A, ADAMTS1, BNC1, HIST1H3C, HOXB4, RASGRF2, TM6SF1, and AKR1B1. In various embodiments the PCR primers, and/or probes, and/or enzymes are provided as beads, e.g., as described in U.S. Patent Publication No: 2006/0068399, which is incorporated herein by reference for the beads and bead formulations described therein.

In various embodiments the cartridge is configured so that the sample receiving chamber, said column(s), the plurality of chambers, and the temperature controlled channel or chamber, are selectively in fluid communication. In certain embodiments the selective fluid communication is provided by microfluidic channels and valves. In certain embodiments the selective fluid communication is provided by providing the sample receiving chamber, said column(s), said plurality of chambers, the heating channel or chamber or a port into the heating channel or chamber, disposed around a central valve and selectively in fluid communication with a channel in said central valve.

In certain embodiments the cartridge is configured so that, when in use, the cartridge comprises: a first chamber containing a sample; a second chamber containing a guanidinium thiosulfate-ethanol (GTC-EtOH) solution; a third chamber containing a bisulfite reagent; a fourth chamber containing a buffer; a fifth chamber containing a rinse solution; and a sixth chamber containing an elution/desulfonation reagent. In certain embodiments the cartridge comprises a seventh chamber containing PCR primers and/or probes and/or PCR enzymes. In certain embodiments the cartridge comprises an eighth chamber also containing PCR primers and/or probes and/or PCR enzymes.

FIGS. 1A, 1B and 2 illustrate one cartridge suitable for practice of the methods described herein. The illustrated cartridges are based on the GENEXPERT® cartridge (Cepheid, Inc., Sunnyvale, Calif.). As shown in FIG. 2, panel A the cartridge 200 comprises a cartridge body 202 containing a plurality of reagent and/or buffer chambers 208. The chambers are disposed around a central syringe barrel 206 that is in fluid communication with a valve body 210 (panel B and FIG. 1B) and that is sealed with a gasket 204. The valve body 210 can comprise a cap 212 and the entire cartridge body can be supported on a cartridge base 226. A "plunger" not shown can be operated to draw fluid into the syringe barrel 206 and rotation of the syringe barrel 206 and associated valve body 212 provides selective fluid communication between the chambers 208 a cavity 214 that can contain a matrix material as described herein and function as a column. In various embodiments the cartridge further comprises one or more temperature controlled channels or chambers 216 that can, in certain embodiments, function as thermocycling chambers. The temperature controlled channels or chambers are also selectively in fluid communication with the cavity 214 and/or the chambers 208. As shown in FIG. 1A, in certain embodiments, the cartridge provides optical windows to provide real-time detection of, e.g., amplification products, base identity in sequencing operations, and the like.

Figure 3A:
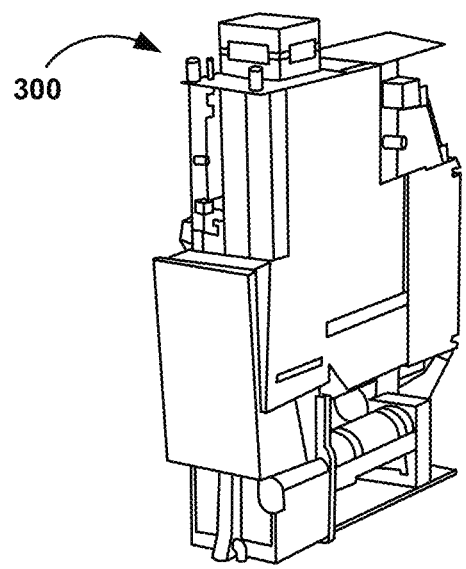
FIGS. 3A-3C show illustrative, but non-limiting embodiments of the modules, and systems (e.g., processing units) for the determination of DNA methylation.
Figure 3B:
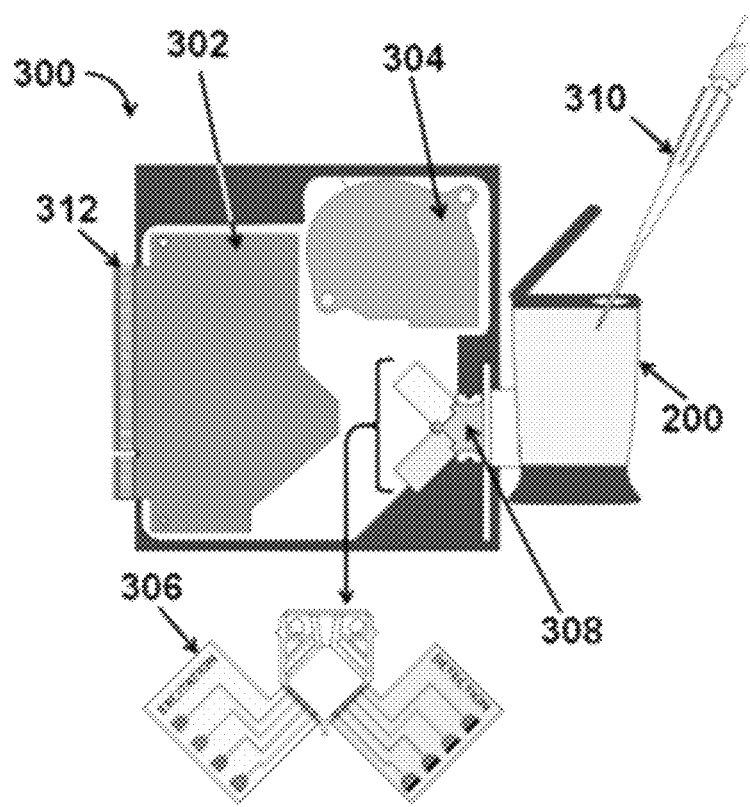

In certain embodiments the cartridge 200 is configured for insertion into a reaction module 300, e.g., as shown in FIG. 3A. As illustrated in FIG. 3B the module is configured to receive the cartridge 200. In certain embodiments the reaction module provides heating plates 308 to heat the temperature controlled chamber or channel. The module can optionally additionally include a fan 304 to provide cooling where the temperature controlled channel or chamber is a thermocycling channel or chamber. Electronic circuitry 302 can be provided to pass information (e.g., optical information) top a computer for analysis. In certain embodiments the module can contain optical blocks 306 to provide excitation and/or detection of one or more (e.g., 1, 2, 3, 4, or more) optical signals representing, e.g., various nucleic acid targets. In various embodiments an electrical connector 312 can be provided for interfacing the module with a system (e.g. system controller or with a discrete analysis/controller unit. As illustrated, in FIG. 3B the sample can be introduced into the cartridge using a pipette 310.

In certain embodiments, the module also contains a controller that operates a plunger in the syringe barrel and the rotation of the valve body.

Figure 3C:
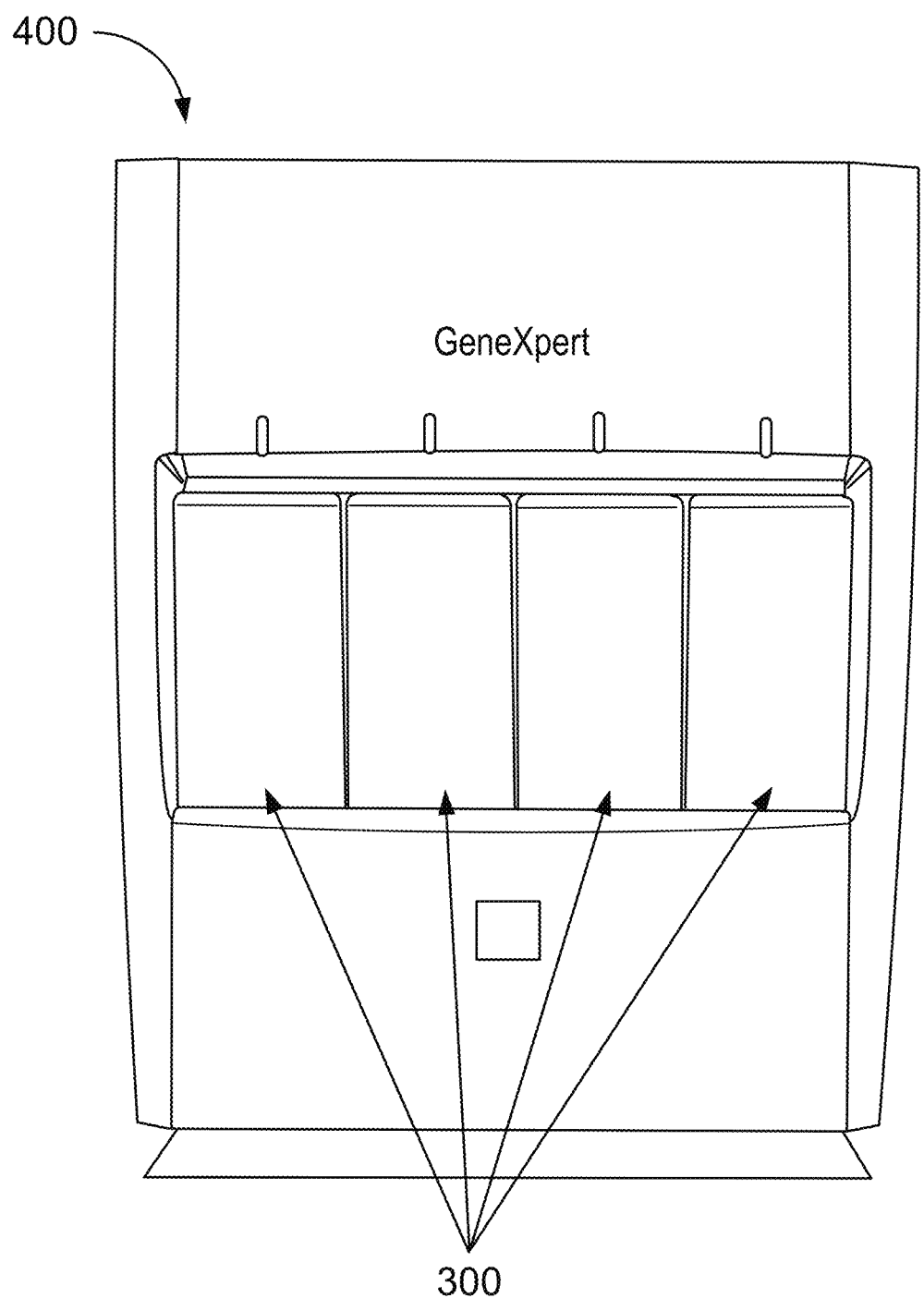

In certain embodiments a system (e.g., a processing unit) is provided. One illustrative, but non-limiting embodiment is shown in FIG. 3C. In certain embodiments, the processing unit comprises an enclosure configured to contain one or more sample processing modules where each processing module is configured to hold and operate a removable cartridge as described herein. In certain embodiments the system is configured to operate the sample processing modules to perform sample processing to determine methylation of one or more target nucleic acids and optionally to determine the level of one or more target RNA/DNA sequences within a corresponding removable sample cartridge, wherein the processing on a sample within the corresponding removable sample cartridge performs a method as described herein. In certain embodiments the system is configured to contain one sample processing module. In certain embodiments the system is configured to contain at least two sample processing modules, or at least 4 sample processing modules, or at least 8 sample processing modules, or at least 12 sample processing modules, or at least 16 sample processing modules, or at least 20 sample processing modules, or at least 24 sample processing modules, or at least 28 sample processing modules, or at least 32 sample processing modules, or at least 64 sample processing modules, or at least 128 sample processing modules. In certain embodiments the system provides a user interface that allows the user input operational instructions and/or to monitor operation of the cartridges to determine DNA methylation.

While the methods described herein are described primarily with reference to the GENEXPERT® cartridge by Cepheid Inc. (Sunnyvale, Calif.) (see, e.g., FIG. 1A), it will be recognized, that in view of the teachings provided herein the methods can be implemented on other cartridge/microfluidic systems. Such cartridge/microfluidic systems can include, for example microfluidic systems implemented using soft lithography, micro/nano-fabricated microfluidic systems implemented using hard lithography, and the like.

High Volume Sample Preparation (HVSP) Cartridge.

In various embodiments cartridges are provided for the preparation of large sample volumes. In certain embodiments the sample preparation cartridges comprises GENEXPERT® cartridges modified for high volume sample preparation (e.g., as shown in FIG. 20). In certain embodiments, e.g., when the cartridge is based on a GENEXPERT® cartridge comprises one or more channels or chambers comprising an affinity matrix that binds DNA, a plurality of chambers disposed around a central valve assembly and selectively in fluid communication with said central valve assembly where the central valve assembly is configured to accommodate a plunger that is capable of drawing fluid into or out of a chamber in fluid communication with the central valve wherein said plurality of chambers comprises at least two different chambers each configured to receive up to about 4 ml (or up to about 5 ml) of sample solution (in certain embodiments chamber 2 has a maximum volume of about 4 ml, while chamber 3 has a maximum volume of about 4.5 ml), a chamber containing PEG (e.g., PEG200), a chamber containing an alkaline solution (e.g., KOH solution), and a chamber containing a buffer (e.g., Tris). In certain embodiments the plurality of chambers comprises at least three different chambers each configured to receive up to about 4 ml (or up t about 5 ml) of sample solution. In certain embodiments the plurality of chambers comprises a chamber containing a wash solution (e.g., GTC-ethanol wash solution which is typically 1.25 M guanidinium thiocyanate, 25 mM Tris pH 7.0, 50% ethanol). In certain embodiments the cartridge comprises a chamber configured for removal of a processed sample. In certain embodiments the sample chambers, when in use, contain sample solution, GTC and alcohol (e.g., isopropanol). In certain embodiments the sample chambers, when in use contain sample solution, GTC and alcohol in substantially equal volumes. In certain embodiments the cartridge, when in use, comprises 4 ml of sample solution GTC and isopropanol disposed in each of said chambers configured to receive a sample. In certain embodiments the cartridge provides DNA or RNA recovery that is substantially linear with respect to the sample volume between 0.5 ml and about 4 ml of sample.

In certain embodiments the HVSP cartridge is configured to perform a DNA conversion (e.g., bisulfite conversion) to provide a methylation analysis. Accordingly in certain embodiments, the HVSP cartridge is configured to contain, or to receive immediately or shortly prior to use, a conversion reagent (e.g. a bisulfite reagent, DABSO, etc.). In certain embodiments, the HVSP cartridge can be configured to also contain reagents for and to provide a desulphonation of converted DNA. Alternatively, in certain embodiments, the conversion is performed in the HSVP cartridge while the desulphonation and methylation analysis (e.g., PCR) is performed in the second cartridge (e.g., as illustrated in the work flows shown in FIG. 20B).

cfDNA Sample Preparation Cartridge.

Figure 17:
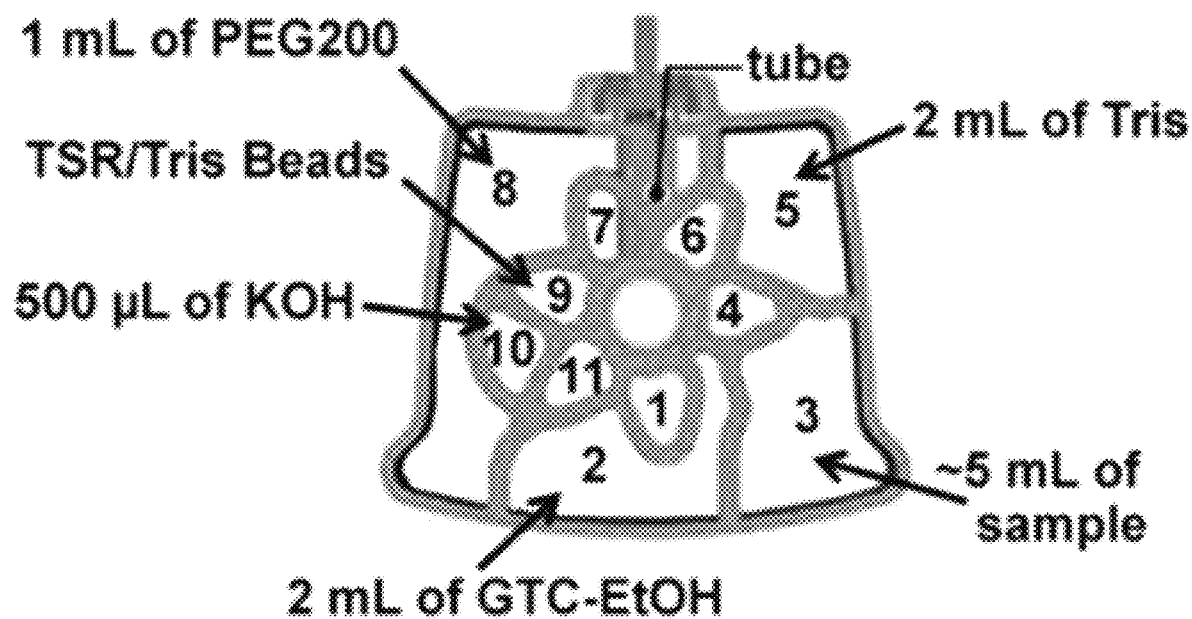
FIG. 17 illustrates one embodiment of a cfDNA sample preparation cartridge. The cartridge is effective for both DNA and RNA isolation. The cartridge provides three GTC-ethanol washes (GTC-ethanol washes are typically 1.25 M guanidinium thiocyanate, 25 mM Tris pH 7.0, 50% ethanol), a PEG200 rinse, and a 15 mM KOH elution.

In certain embodiments a sample preparation cartridge is provided that is particular well suited to the preparation (and optional analysis) of nucleic acids from plasma or serum is provide. One illustrative, but non-limiting embodiment is shown in FIG. 17. As illustrated therein in certain embodiments the cartridge comprises a channel or chamber comprising an affinity matrix that binds DNA, a plurality of chambers disposed around a central valve assembly and selectively in fluid communication with the central valve assembly where the central valve assembly is configured to accommodate a plunger that is capable of drawing fluid into or out of a chamber in fluid communication with the central valve where the plurality of chambers comprises: a chamber configured to receive up to about 5 ml or up to about 4 ml of sample solution; a chamber containing PEG (e.g., PEG200); a chamber containing GTC-EtOH; a chamber containing an alkaline solution (e.g., KOH); and a chamber containing a buffer (e.g., Tris). In certain embodiments the plurality of chambers further comprises a chamber containing a conversion reagent (e.g., a bisulfite reagent). In certain embodiments the plurality of chambers comprises a chamber containing a wash solution (e.g., GTC-ethanol wash (typically 1.25 M guanidinium thiocyanate, 25 mM Tris pH 7.0, 50% ethanol)). In certain embodiments the plurality of chambers comprises a chamber containing beads comprising one or more PCR primers and/or probes. In certain embodiments the chamber containing PEG contains about 1 ml of PEG. In certain embodiments the chamber containing an alkaline solution contains about 500 μL of solution. In certain embodiments the chamber containing GTC-EtOH contains about 2 ml GTC-EtOH. In certain embodiments the chamber containing a buffer contains about 2 mL of buffer.

It will be recognized that this configuration is illustrative, and using the teaching provided herein numerous other preparation cartridge configurations will be available to one of skill in the art.

Use of DABSO as an Alternative to Bisulfite

It was a surprising discovery that DABSO can be used to perform a conversion of DNA in a manner analogous to the use of bisulfites for the conversion of DNA and detection of methylation. Accordingly, in certain embodiments, methods of utilizing DABSO to converting cytosine residues in a DNA to uracil, while leaving 5-methylcytosine residues substantially unaffected are provided. In certain embodiments the methods involve contacting a sample comprising DNA with DABSO to convert the DNA, and desulfonating the converted DNA, to produce a DNA in which cytosine residues are converted to uracil, but 5-methylcytosine residues substantially unaffected. In certain embodiments the DABSO is provided at a concentration ranging from about 2 M up to about 5 M. In certain embodiments the DABSO is provided at a concentration of about 2.5 M. In certain embodiments the DABSO is dissolved in an alkaline aqueous solution (e.g., a KOH solution). In certain embodiments the reagent comprising DABSO comprises DABSO dissolved in a solution comprising KOH.

In certain embodiments the methods involve heating the DABSO/DNA solution to a temperature ranging from about 55° C. to about 90° C. In certain embodiments the DABSO is reacted with the DNA for a period of time ranging from about 15 minutes up to about 90 minutes. After the DNA is converted, it is desulphonated (e.g., by contacting the converted DNA with an alkaline reagent (e.g., KOH solution). In certain embodiments the conversion and/or desulphonation is performed on the DNA bound to a column, while in other embodiments the conversion and/or desulphonation is performed on the DNA in solution.

Also provided are methods of analyzing DNA methylation, where the methods involve providing a DNA sample, converting DNA in the sample using a DABSO reagent, e.g., as described above, and performing methylation specific PCR and/or nucleic acid sequencing, and/or high resolution melting analysis (HRM) on the converted nucleic acid to determine the methylation of said nucleic acid. In certain embodiments the providing of a DNA sample comprises preparing a sample as described herein (e.g., using lysis solutions and/or preparation cartridges as described herein.

Kits.

Kits for Methylation Detection.

In certain embodiments kits are provided for performing the methods described herein. In one illustrative embodiment, the kits comprise a container containing a reaction cartridge as described herein, a container containing a sample processing reagent as described herein, and a container containing a conversion reagent (e.g., a bisulfite reagent) as described herein. In certain embodiments the bisulfite reagent is provided in a chamber of the cartridge. In certain embodiments the bisulfite reagent is provided in a container separate from the cartridge. In certain embodiments, the sample processing reagent is provided in a chamber of the cartridge. In certain embodiments, particularly where the sample processing reagent comprises guanidinium thiocyanate the sample processing reagent is provided in a container separate from the cartridge.

In addition, the kits optionally include labeling and/or instructional materials providing directions (i.e., protocols) for the use of the cartridges described herein to determine DNA methylation and, optionally, RNA expression.

In certain embodiments a kit for the determination of DNA methylation is provided where the kit comprises a container containing a cartridge for determining the methylation state of a nucleic acid as described herein. In certain embodiments the kit further comprises a lysis solution as described herein (e.g., a lysis solution for serum or plasma, e.g., as described in Table 11, and/or a lysis solution for FFPE samples, e.g., as described in Table 12). In certain embodiments the kit comprises a container containing proteinase K. In certain embodiments the kit contains a conversion reagent (e.g., a bisulfite reagent) in the cartridge or in a container separate from the cartridge. In certain embodiments the separate container can contain a pre-measured volume of conversion reagent suitable for one "run" of the cartridge. In certain embodiments the conversion reagent comprises a compound selected from the group consisting of sodium metabisulfite, potassium bisulfite, cesium bisulfite, ammonium bisulfite, and DABSO. In certain embodiments the kit comprises a container containing a sample processing reagent. In certain embodiments the sample processing reagent comprises guanidium thiocyanate and/or ethanol.

In various embodiments the kit can additionally contain a cartridge for sample preparation as described herein (e.g., as illustrated in FIG. 20).

In certain embodiments the kit contains instructional materials teaching the use of a cartridge for the determination of DNA methylation. Where a sample preparation cartridge is included in the kit the kit can additionally contain instructional materials teaching the use and operation of the sample preparation cartridge.

Kits for DABSO DNA Conversion and Methylation Detection.

In certain embodiments kits are provided for the use of DABSO as a conversion reagent, e.g., in the detection of the methylation state of a DNA. In certain embodiments the kits comprise a container containing a conversion reagent comprising DABSO, and a container containing a desulphonation reagent. In certain embodiments the kit comprises a column comprising an affinity matrix (e.g., a silica matrix material). In certain embodiments the kits comprise a container containing a binding buffer and/or a container containing an elution buffer. In certain embodiments the kit comprises a container containing a wash buffer.

In certain embodiments the kit further comprises a lysis solution as described herein (e.g., a lysis solution for serum or plasma, e.g., as described in Table 11, and/or a lysis solution for FFPE samples, e.g., as described in Table 12). In certain embodiments the kit comprises a container containing proteinase K.

In various embodiments the kit can additionally contain a cartridge for sample preparation as described herein (e.g., as illustrated in FIG. 20).

In certain embodiments the kit contains instructional materials teaching the use of the kit to convert a nuclei acid for determination of the methylation state of the nucleic acid.

While the instructional materials in the kits described above typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

To validate the method human genomic DNA (HGDNA) was used as a starting sample to monitor sample preparation, bisulfite conversion, sample cleanup, and methylation specific qPCR in a Cepheid GENEXPERT® cartridge. In order to measure bisulfite conversion efficiency, half of the DNA-bisulfite mix was loaded and heated in the 50 µL cartridge tube during the bisulfite conversion step. Therefore, under optimal conversion conditions approximately half of the HGDNA is converted and the other half remains unconverted.

Primers and Taqman probes for the qPCR step were designed for one unconverted gene (HMBS (hydroxymethylbilane synthase housekeeping gene)) and one converted gene (ACTB (beta actin)), and the conversion efficiency was then quantitated by comparison of cycle threshold values (Cts). Both ACTB and HMBS are commonly used as single or low copy reference genes, and thus we expect similar copy numbers per ng of HGDNA.

Figure 5:
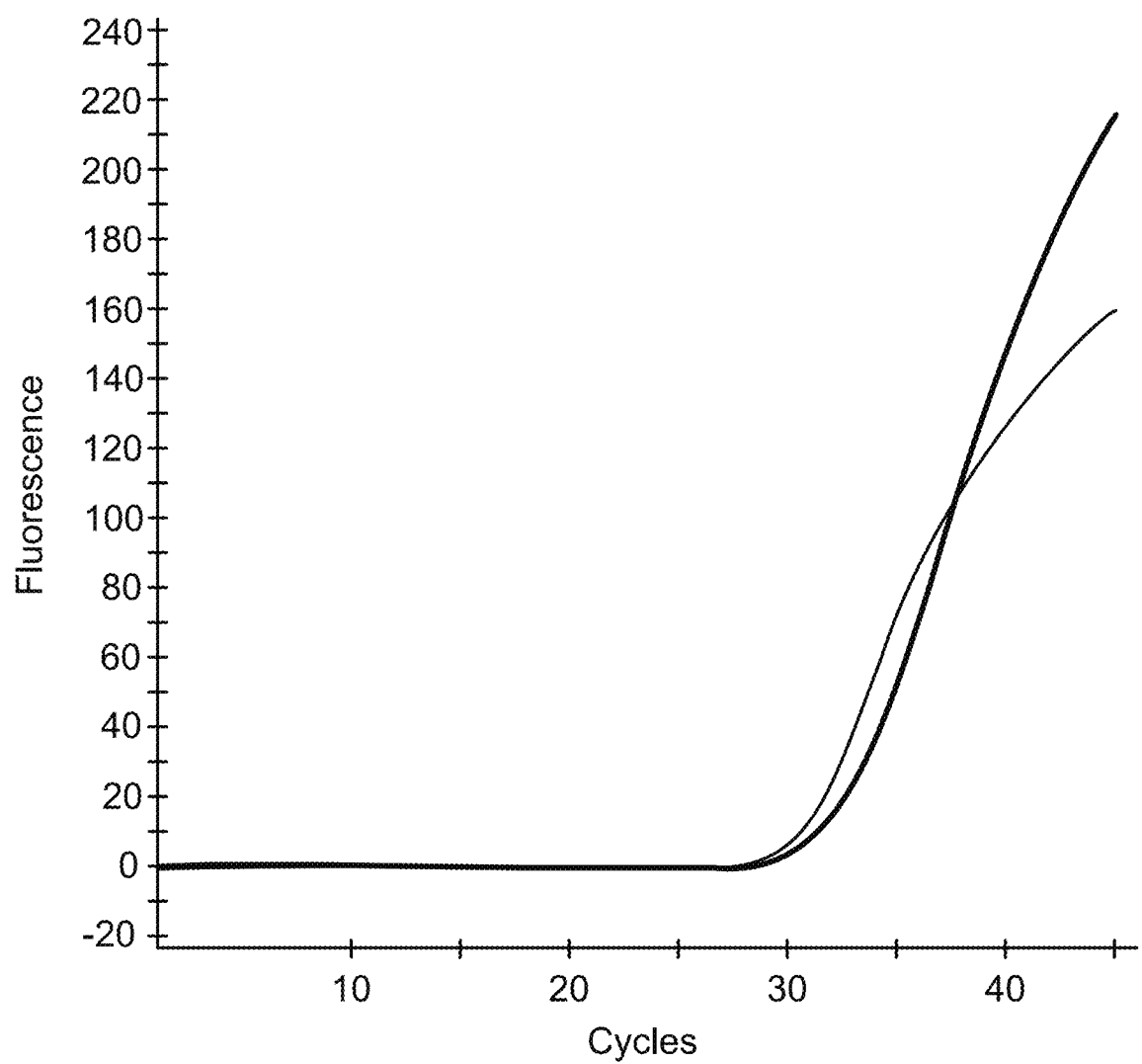
FIG. 5 illustrates results from a representative GeneXpert run from 300 ng of HGDNA showing an ACTB qPCR curve and an HMBS qPCR curve.

A representative GENEXPERT® run from 300 ng of HGDNA is shown below in FIG. 5, with the ACTB qPCR curve in green and the HMBS qPCR curve in blue. The qPCR reaction was run for 45 cycles with a 3 temperature cycle of 96° C. for 5 seconds, 60° C. for 15 seconds, and 72° C. for 15 seconds. At a manual threshold setting of 20 fluorescence units we observed a Ct of 31.7 for the converted ACTB gene and a Ct of 32.7 for the unconverted HMBS gene. Importantly, this result demonstrates that we are able to achieve near-optimal bisulfite conversion efficiency of HGDNA in our cartridge at physiological relevant concentrations of DNA found in FFPE tissue slices and plasma/serum samples. Further specificity for fully converted sequences can be achieved through a nested qPCR reaction or by heating the entire sample. However, neither option would be absolutely required for methylation specific qPCR in the GENEXPERT® because primer and probe sets are designed to amplify only the converted sequences. Thus remaining unconverted DNA sequences would act as carrier DNA, which notably is frequently added during bisulfite conversion, DNA isolation, and PCR methods.

Example 2

FIGS. 6A and 6B show the linearity of converted ACTB. In particular, FIG. 6A shows the results of a 15 cycle nested qPCR for ACTB using hgDNA. As can be seen from the panel on the right the signal (Ct value) is substantially linear between about 25,000 copies and about 100 copies. FIG. 6B shows the results of a 20 cycle nested qPCR for ACTB using hgDNA. These plots demonstrate the sensitivity of the cartridge for hgDNA. Dropouts start occurring around 20-50 copies with a sensitivity of about 25 copies of converted DNA.

Figure 7A:
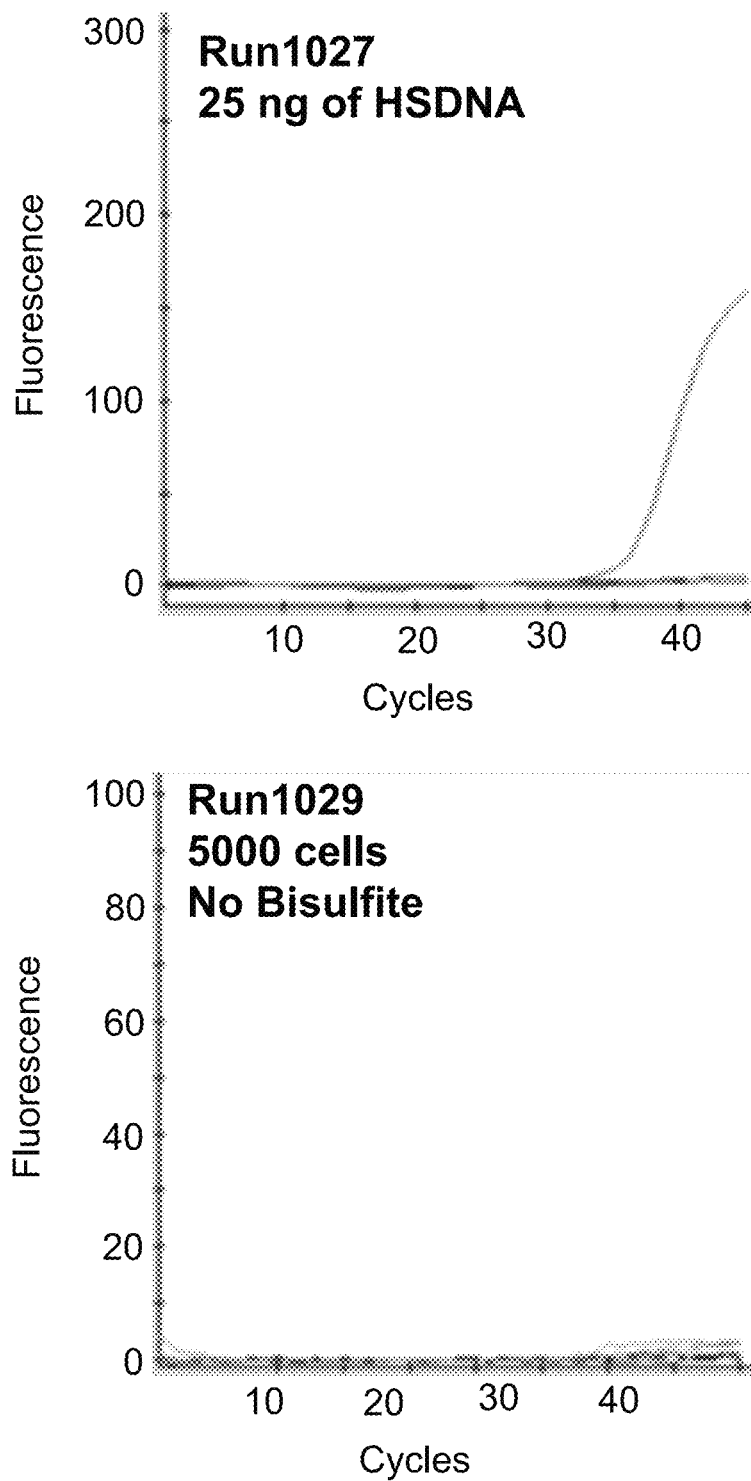

FIGS. 7A, 7B, and 7C show the results of qPCR for six methylated targets (AKR1B1, HOXB4, TM6SF1, RASGRF2, and RASSF1A). FIG. 7A show the results of 20 cycle nested qPCR for controls (25 ng of HSDNA, and 5000 MBA-453 cells whose DNA is not bisulfite-converted). FIG. 7B shows the results of 20 cycle nested qPCR for the six methylated targets using DNA from MBA-453 cells that has been bisulfite converted. A strong signal is shown for all targets. HIST1H3C was not reliably detected. FIG. 7C shows the results of 20 cycle nested qPCR for the six methylated targets using DNA from MBA-453 cells that has been bisulfite converted and is in a carrier comprising 1 µg of SS and 10 ng of HS DNA. Dropouts were observed at about 100 cells and below, however, with the carrier, there were significantly fewer dropouts.

Example 3

Figure 8:
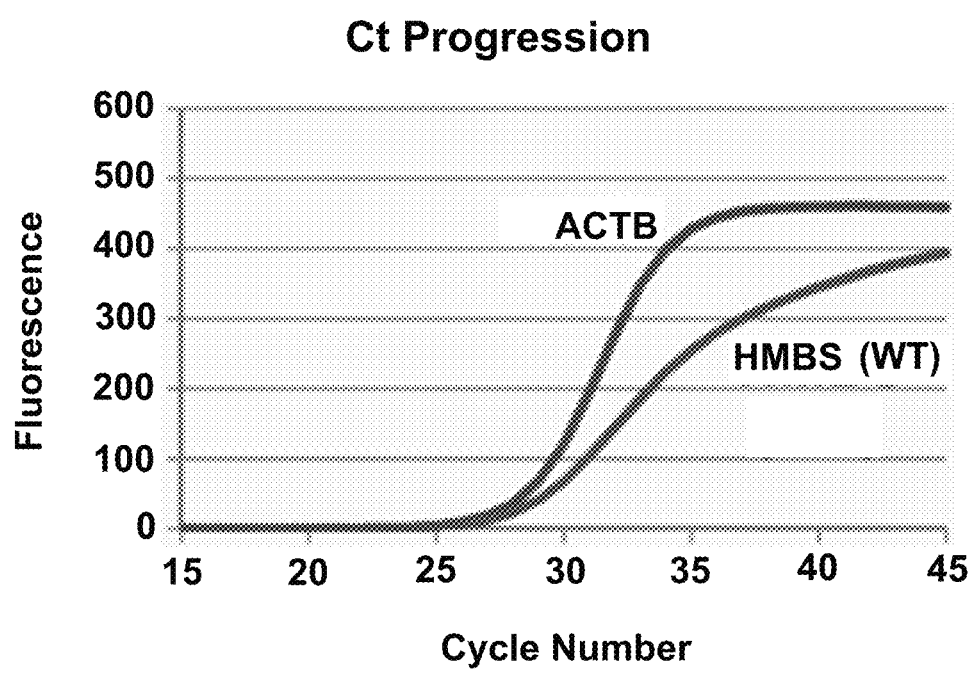
FIG. 8 illustrates the results of a determination of conversion efficiency. The conversion efficiency is about 66% (~1 Ct) the difference between unconverted HMBS and converted ACTB.

FIG. 8 illustrates the results of a determination of conversion efficiency. The conversion efficiency is about 66% (~1 Ct) the difference between unconverted HMBS and converted ACTB. Ideal Ct with 100% binding/elution, 100% conversion, and 100% binding elution is about 24-25. The experiments appear to show a 50% binding/elution, 50-66% conversion, and 50% binding/elution for a 10-fold reduction and a Ct of about 27.

Figure 9:
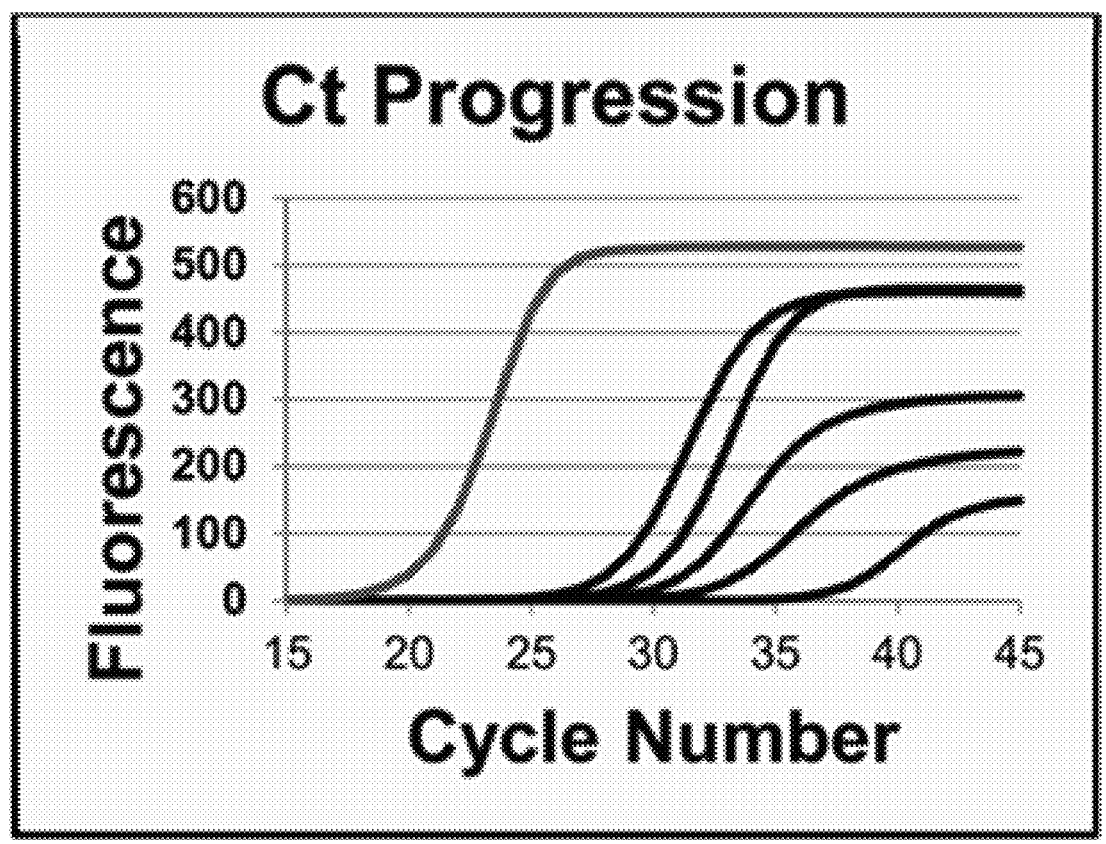
FIG. 9 illustrates the increase in specificity for converted DNA produced by nested qPCR.

FIG. 9 illustrates the increase in specificity for converted DNA produced by nested qPCR. Nested PCR appears to increase the specificity for converted DNA, to increase the specificity for methylated DNA and to reduce contamination issues.

Figure 10:
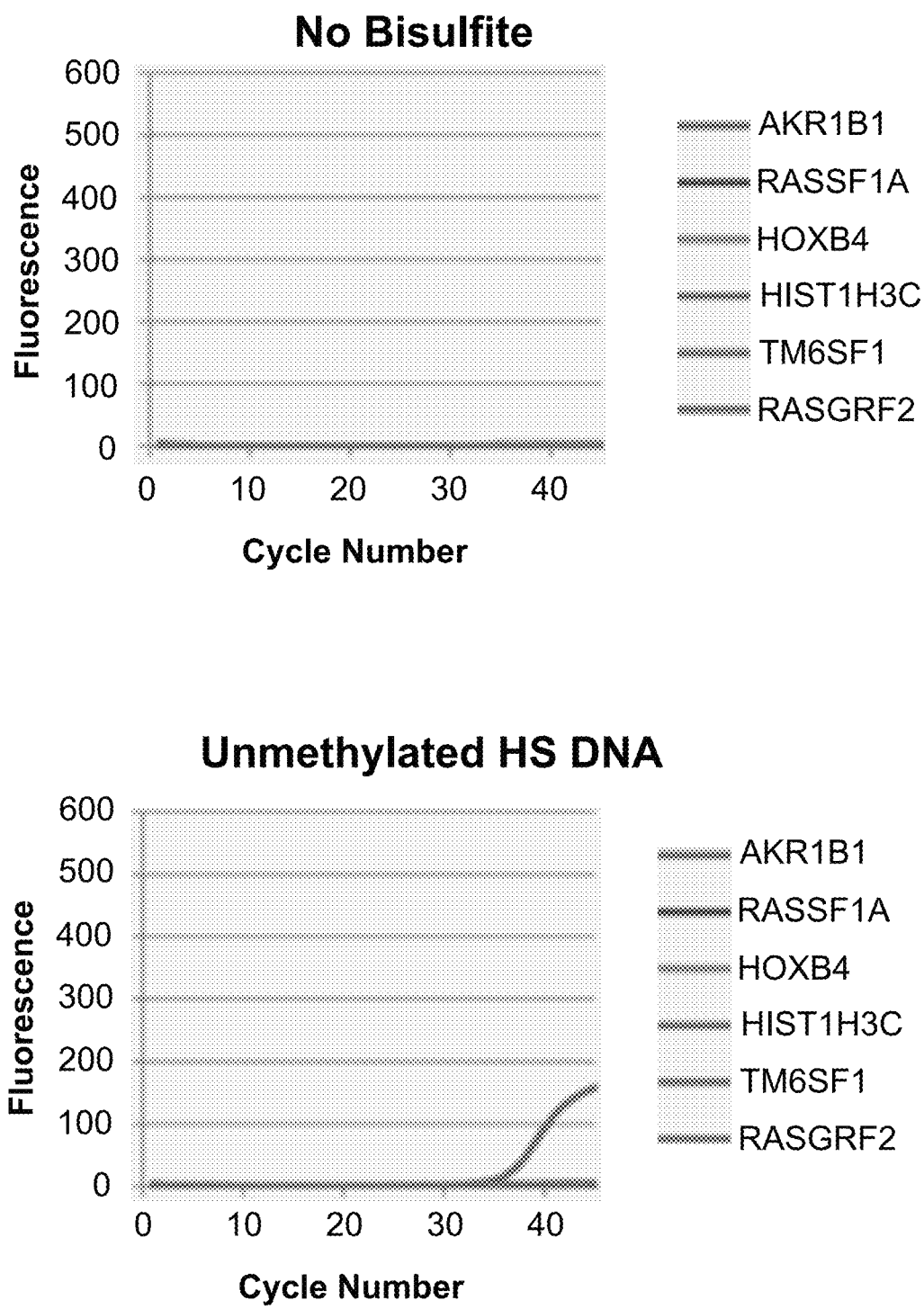
FIG. 10 illustrates the specificity of the methylation cartridge. There is no priming off of unconverted DNA (top panel) or unmethylated DNA (bottom panel) except for HIST1H3C.

FIG. 10 illustrates the specificity of the methylation cartridge. No specificity is shown for unconverted DNA (top panel) or unmethylated DNA (bottom panel) except for HIST1H3C.

FIGS. 11A and 11B show some illustrative but non-limiting workflows for analysis of methylation using a cartridge (e.g., a GENEXPERT® cartridge). FIG. 11A illustrates one work flow for analysis of DNA methylation in a serum sample. As illustrated in this workflow, serum is added to a lysis reagent vial and mixed/vortexed. The sample is then dispensed into a sample port in the cartridge. The cartridge is placed in the system for analysis.

FIG. 11A illustrates one work flow for analysis of DNA methylation in a tissue section (e.g., frozen or formalin-fixed paraffin embedded (FFPE) section). As shown therein, in one embodiment, a tissue section (e.g., a 4 µm FFPE section) is provided. FFPE lysis reagents are added (see, e.g., PCT/US2013/061863 (WO/2014/052551 for illustrative lysis reagents) and the mixture can be heated. Ethanol can be added and the mixture vortexed. The sample is then dispensed into a sample port in the cartridge. The cartridge is placed in the system for analysis.

Figure 12:
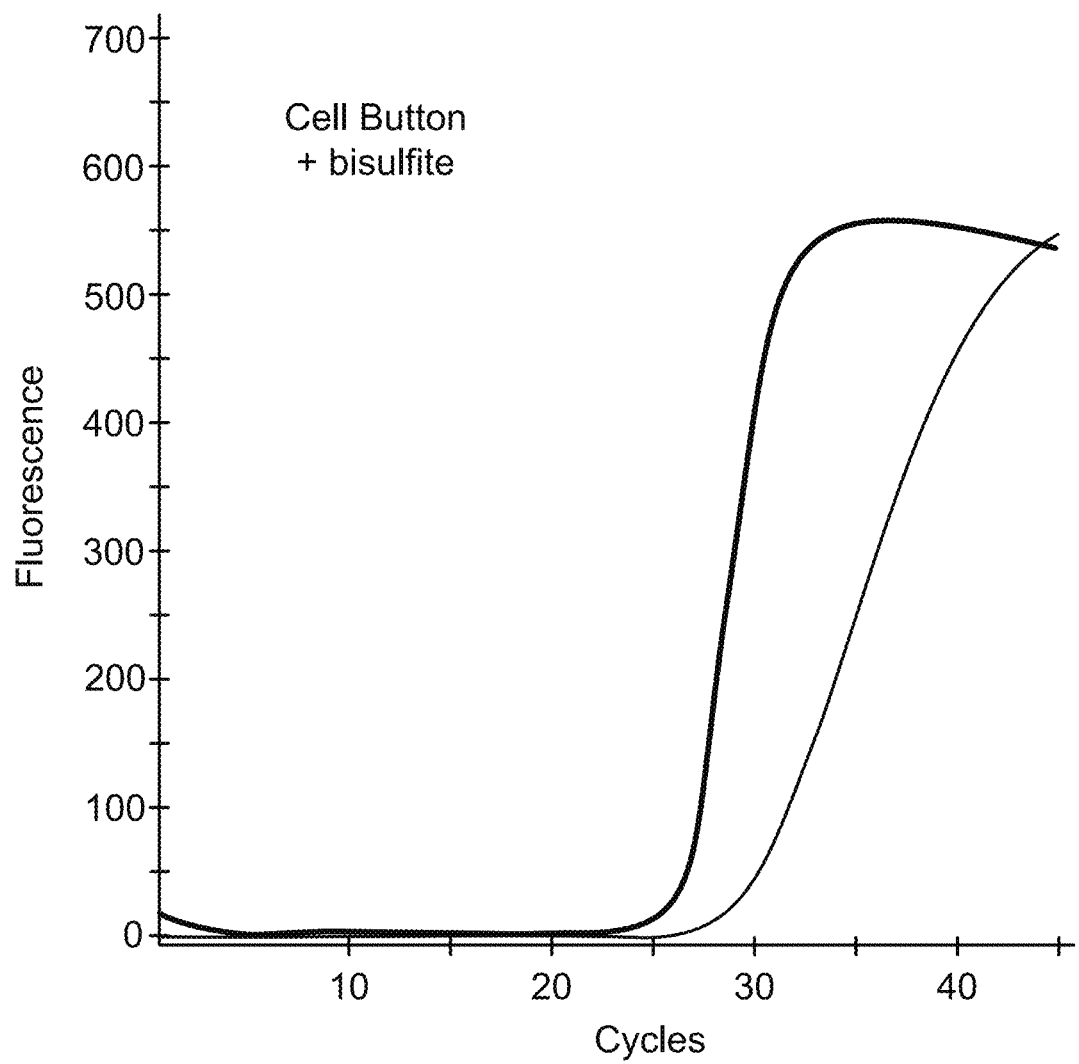
FIG. 12 illustrates the results for a FFPE cell button for converted ALU (Blue) and methylated RASSF1A (Gray).

FIG. 12 illustrates the results for a FFPE cell button for converted ALU and methylated RASSF1A.

Example 4

Detection of Markers for Breast Cancer Monitoring

Materials and Methods:

Either 1000 MBA-453 cells or 25 ng of human sperm (HS) DNA were added to 2.5 mL of binding buffer (2.25 M Guanidinium thiocyanate, 22.5 mM Tris pH 7.0, 0.5% Tween20, 50% Ethanol, and 0.005% SE-15 antifoam). The 2.5 mL solution of cells or DNA was added to chamber 2 of the Cepheid methylation cartridge (layout in FIG. 13A). The remaining chambers in the methylation cartridge were filled as follows: Chamber 3—3.2 mL of Wash buffer (1.25 M Guanidinium thiocyanate, 25 mM Tris pH 7.0, 50% Ethanol), Chamber 4—90 µL of 7 M Ammonium Bisulfite, Chamber 5—4 mL of 50 mM Tris pH 8.5, Chamber 8—1 mL of PEG200 Rinse, Chamber 9—quantitative PCR beads including EZR (Taq) and TSR (6 target breast cancer multiplex for RASSF1A, AKR1B1, HOXB4, HIST1H3C, RASGRF2, TM6SF1, see Table 9, below), Chamber 10—500 µL of 15 mM KOH, and Chamber 11—nested beads including EZR (Taq) and TSR (6 target breast cancer multiplex for RASSF1A, AKR1B1, HOXB4, HIST1H3C, RASGRF2, TM6SF1). The methylation cartridge was then loaded into a Cepheid GeneXpert and the entirety of the methylation assay was completed by the GeneXpert—the first DNA sample prep, the bisulfite conversion, the second post conversion DNA sample prep, the desulphonation, and the 20 cycle nested and quantitative PCR reactions.

A flow chart illustrating the methylation protocol is shown in FIG. 13B. It is noted that the PEG200 was filled in the waste chamber 8, and after the assay starts the PEG200 is dispensed into Chamber 1. The PEG200 is a viscous liquid that cannot easily be directly loaded in the smaller chamber 1. Additionally, chamber 1 acts as an air chamber when the cartridge is first loaded before becoming the PEG200 chamber. Thus, the assay begins with Chamber 1=air and Chamber 8=PEG200 and is quickly switched to Chamber 1=PEG200 and Chamber 8=Waste after cartridge loading.

The numbers shown in the "Initial Vol." column of FIG. 13A just refer to liquid volumes. In this case there are just 2× beads in chamber 11— 1×TSR bead (primer and probes for the 6 targets) and 1×EZR bead (Phoenix Taq). These beads are for the final qPCR reaction. Similarly, there are 3× beads in chamber 9-1×TSR bead (primers for the 6 targets), 1× Tris bead (to quench KOH) and 1×EZR bead (Phoenix Taq). These beads are for the first 15-20 cycle PCR reaction.

It is also noted that Chamber 6 is an air chamber throughout the entire assay and is never filled. Chamber 7 is used as sort of a gateway to the PCR tube in the back of the cartridge. It is not filled to start the assay but is filled during the assay on 3 occasions before loading into the tube: 1) the DNA-bisulfite mix that is heated in the tube for conversion; 2) the 15-20 cycle PCR reaction; and 3) the final qPCR reaction.

The primers shown in the Table 9 provided shows five sequences for each gene—two extension primers and 2 qPCR primers for each nested amplification and one probe. The first 15-20 cycle PCR reaction was not specific for methylation but only the converted DNA sequences (i.e., they do not cross CpGs and in a couple instances when they do we use an R=purine or Y=pyrimidine to catch both methylated and unmethylated). The second 45 cycle qPCR reaction contains both primers and probes that are specific for typically 2-3 methylated CpGs.

Figure 15A:
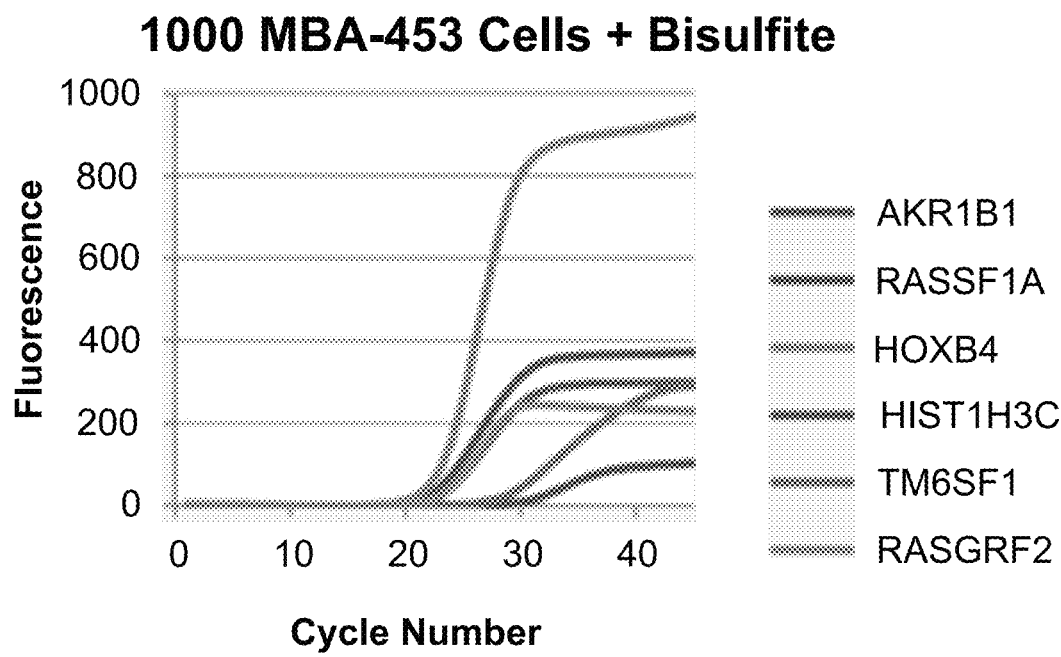
FIG. 15A illustrates the results of 1000 MBA-453 cells with bisulfite conversion.
Figure 15B:
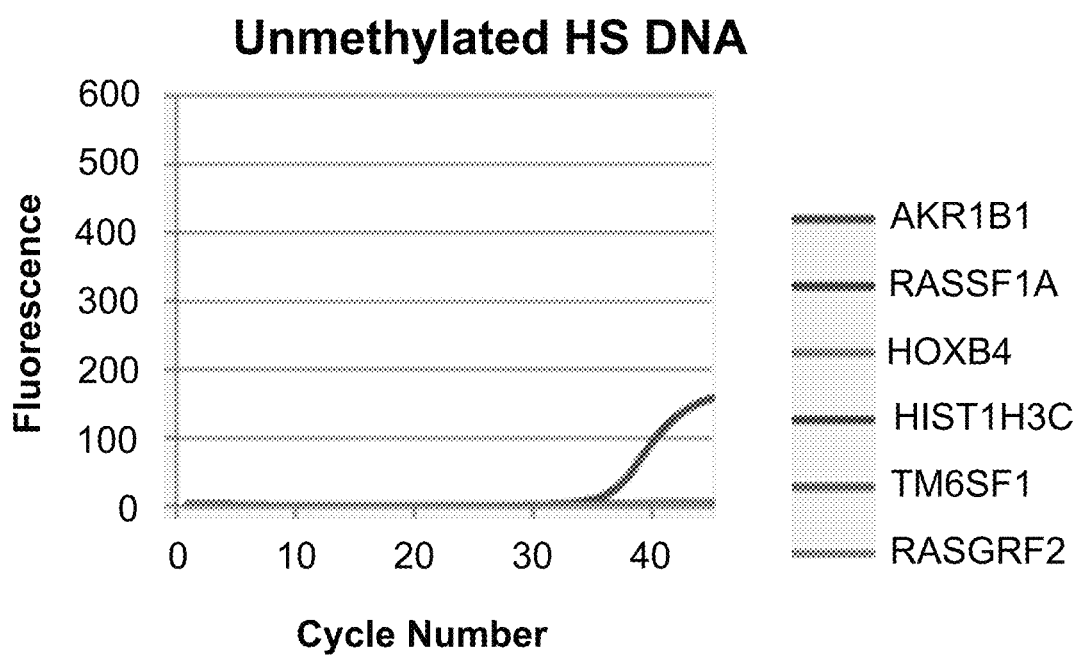
FIG. 15B illustrates results of 25 ng of HS DNA control.

Results:

The methylation cartridge was run using 1000 MBA-453 cells with and without bisulfite (FIGS. 15A-15B) and 25 ng of HS DNA with bisulfite (FIG. 15C) that was primarily unmethylated at each gene promoter with the exception of HIST1H3C. There was little or no amplification of any of the targets in either the no bisulfite or unmethylated HS DNA control reactions (FIG. 15A, 15C). With the addition of bisulfite, the methylation cartridge picked up high levels of methylation at multiple gene promoters from 1000 MBA-453 cells, specifically AKR1B1, RASSF1A, HOXB4, and RASGRF2.

TABLE 9

Nested primers for RASSF1A, AKR1B1, HOXB4, HIST1H3C, RASGRF2, and TM6SF1. C*, T* are optionally functionalized (e.g., to alter probe $T_m$) bases.

| Gene/Probe name | Type | SEQUENCE | SEQ ID NO |
|---|---|---|---|
| RASSF1A | | | |
| o1AK61 | ext primer | GTTTTATAGTT(T*)TTGTATTTAGG | 62 |
| o1AK41 | ext primer | AACTCAATAAACTCAAACTCCC | 42 |
| o1AK1 | qPCR primer | GCGTTGAAGTCGGGGTTC | 2 |
| o1AK2 | qPCR primer | CCCGTACTTCGCTAACTTTAAACG | 3 |

TABLE 9-continued

Nested primers for RASSF1A, AKR1B1, HOXB4, HIST1H3C, RASGRF2, and TM6SF1. C*, T* are optionally functionalized (e.g., to alter probe $T_m$) bases.

| Gene/Probe name | Type | SEQUENCE | SEQ ID NO |
|---|---|---|---|
| o1AK63 | qPCR probe | fluor-(C*)TGGTTTCGT(T-quencher)CGGT(T*)CGCG-quencher/blocker | 64 |
| HIST1H3C | | | |
| o1AK60 | ext primer | GGATTTTTGAAATATTATAGGATTAATTAG | 61 |
| o1AK43 | ext primer | ATAAAATTTCTTCACRCCACC | 44 |
| o1AK59 | qPCR primer | TCGTACGAAGTAAATAGTTCGTAAG | 60 |
| o1AK54 | qPCR primer | CCGATAACCGAAACGCTCTTAC | 56 |
| o1AK65 | qPCR probe | fluor-CAAACTACTTACGCGAAACTT(T*)ACCGCC-quencher/blocker | 66 |
| RASGRF2 | | | |
| o1AK44 | ext primer | GAGGGAGTTAGTTGGGTTAT | 45 |
| o1AK45 | ext primer | CCTCCAAAAAATACATACCC | 46 |
| o1AK13 | qPCR primer | GTAAGAAGACGGTCGAGGCG | 14 |
| o1AK14 | qPCR primer | ACAACTCTACTCGCCCTCGAA | 15 |
| o1AK67 | qPCR probe | fluor-AAACGAACCACTTCTCG(T*)ACCAACGAC-quencher/blocker | 129 |
| AKR1B1 | | | |
| o1AK58 | ext | GYGTAATTAAT(T*)AGAAGGTTTTT | 59 |
| o1AK47 | ext | AACACCTACCTTCCAATAC | 48 |
| o1AK19 | qPCR | GCGCGTTAATCGTAGGCGTTT | 20 |
| o1AK20 | qPCR | CCCAATACGATACGACCTTAAC | 12 |
| o1AK75 | qPCR | fluor-(C*)A(C*)GCGTACCT(T-quencher)TAAA(T*)AACCCG(T*)AAAATCG-quencher/blocker | 76 |
| HOXB4 | | | |
| o1AK48 | ext primer | TTAGAGGYGAGAGAGTAGTT | 49 |
| o1AK49 | ext primer | AAACTACTACTAACCRCCTC | 50 |

TABLE 9-continued

Nested primers for RASSF1A, AKR1B1, HOXB4, HIST1H3C, RASGRF2, and TM6SF1. C*, T* are optionally functionalized (e.g., to alter probe $T_m$) bases.

| Gene/Probe name | Type | SEQUENCE | SEQ ID NO |
|---|---|---|---|
| o1AK25 | qPCR primer | CGGGATTTTGGGTTT TCGTCG | 26 |
| o1AK26 | qPCR primer | CGACGAATAACGACG CAAAAAC | 27 |
| o1AK76 | qPCR probe | fluor-AACCGAACG A(T*)AACGAAA(N*) ACGACGAA-quencher/blocker | 77 |
| TM6SF1 | | | |
| o1AK50 | ext primer | AGGAGATATYGTTGA GGGGA | 51 |
| o1AK51 | ext primer | TCACTCATACTAAAC CRCCAA | 52 |
| o1AK56 | qPCR primer | GTTTAGCGGGATGCG GTG | 57 |
| o1AK57 | qPCR primer | ACACGAAAACCCCGA TAAC | 58 |
| o1AK77 | qPCR probe | fluor-AAACACTCA TCGCAACCGCCGCG-quencher/blocker | 34 |

The primers shown in Table 9 are illustrative and not limiting. Numerous other primers and nested primer sets will be available to those of skill in the art. By way of example, illustrative primers for the detection of methylation of ADAMTS1 and BNC1 genes associated with pancreatic cancer and for the detection of methylation of the MGMT gene associated with glioma are shown in Table 10.

TABLE 10

Illustrative primers for the detection of methylation of ADAMTS1 and BNC1 genes associated with pancreatic cancer and for the detection of methylation of the MGMT gene associated with glioma.

| Gene/Probe name | Type | Sequence | SEQ ID NO |
|---|---|---|---|
| BNC1 | external primer | CCCRCAAACCRCGAAAACC TC | 227 |
| | external primer | GTTTTTTTTYGGGAGAGGT AAATA | 228 |
| | qPCR internal primer | CCGACGACCGACG | 235 |
| | qPCR internal primer | GGGAGAGGTAAATATCGAT AC | 236 |
| | qPCR probe | fluor-TGGYGGGGG(T*) AGA(T*)ATTTT-quencher/blocker | 389 |
| ADAMTS1 | external primer | CRCCTCCRAAACTAAAACA AC | 229 |
| | external primer | GGGTTATTGTAAAGTTAGG GTG | 230 |

TABLE 10-continued

Illustrative primers for the detection of methylation of ADAMTS1 and BNC1 genes associated with pancreatic cancer and for the detection of methylation of the MGMT gene associated with glioma.

| Gene/Probe name | Type | Sequence | SEQ ID NO |
|---|---|---|---|
| | qPCR internal primer | CGCGAAAATTAATACCTAA CG | 237 |
| | qPCR internal primer | TTAGGGTGCGTTATCGGAC | 238 |
| | qPCR probe | fluor-TCTACTCAAAACT CTCCCCTCTCC-quencher/blocker | 390 |
| MGMT | external primer | GTTTT(T*)AGAAYG(T*) TTTGYGTTT | 263 |
| | external primer | AAAAAAC(T*)CCRCACTC TTCC | 265 |
| | qPCR internal primer | TTTCGACGTTCGTAGGTTT TCGC | 266 |
| | qPCR internal primer | GCACTCTTCCGAAAACGAA ACG | 267 |
| | qPCR probe | fluor-CCAAACAC(T*) CACCAAATC(N*)CAAAC-quencher/blocker | 268 |

Example 5

Sample Preparation for Plasma and FFPE Samples

FIG. 17 illustrates one configuration of a cartridge that can be used to prepare DNA samples for PCR and/or methylation detection. The sample, obtained from serum or plasma, or an FFPE sample can simply be introduced into a sample chamber of the cartridge (e.g., chamber 3) and operation of the cartridge as described herein provides a sample ready for PCR and/or methylation detection.

Sample Preparation

In one illustrative, but non limiting embodiment, a serum or plasma sample is prepared (e.g., for analysis of cfDNA) by treating the serum or plasma with proteinase K. Then the proteinase K treated serum/plasma is mixed with a lysis solution comprising guanidinium thiocyanate (GTC), buffer (e.g., Tris pH 7.0), a detergent (e.g., Tween 20), and an optional antifoam (e.g., antifoam SE15). An alcohol (e.g., isopropanol) is added to the solution which is then introduced into the cartridge for sample processing. In one embodiment the lysis solution is formulated as shown in Table 11. The proteinase K treated serum/plasma can be mixed with lysis solution and alcohol in a ratio corresponding to 1.3 mL proteinase K treated serum/plasma, 2.2 mL lysis solution, and 1.5 ml alcohol. In certain embodiments the serum/plasma sample is treated with proteinase K for about 15 minutes. The lysis solution is added cold and held/mixed for about 10 minutes. Then isopropanol is added to the mixture which is then loaded into the cartridge for processing.

As noted above, for serum/plasma the alcohol (e.g., isopropanol) precipitations are typically done at RT, and in particular typically not performed with "salty" solutions. In certain embodiments longer room temperature precipitation times can be used.

TABLE 11

Lysis solution for serum or plasma.

| Reagent | Amount |
| --- | --- |
| Guanidine thiocyanate (GTC) | 4.5M |
| Buffer (e.g., Tris) pH 7.0 | 45 mM |
| Detergent (e.g., Tween20) | 1% |
| Antifoam SE15 | 0.01% |

In another illustrative, but non-limiting embodiment, a formalin fixed paraffin-embedded (FFPE) sample is prepared by combining the FFPE sample with proteinase K and a lysis solution comprising a buffer (e.g., HEPES), a chelator (e.g., EDTA), NaCl, $MgCl_2$, and optionally sodium azide and/or an antifoaming agent. The solution is heated (e.g., at 70° C. to 90° C.) for a period of time ranging, for example from about 10 minutes up to about 4 hours. An alcohol is added to the solution and the solution is then introduced into the cartridge for sample processing. In one embodiment the lysis solution is formulated as shown in Table 12. In one illustrative, but non-limiting embodiment, 1.2 mL of the lysis solution shown in Table 12 is added to the FFPE section(s). Proteinase K is added and the mixture is heated, e.g. at 80° C. for about 15 minutes. In certain embodiments heating is performed at 56° C. for 2 hours followed by 90° C. for 30 minutes. Then 1.2 mL of ethanol is added to the mixture and the mixture is loaded into a sample chamber of the cartridge for processing.

TABLE 12

Lysis buffer for formalin fixed paraffin embedded (FFPE) sample.

| Tween20 | 1% |
| --- | --- |
| NaCl | 400 mM |
| EDTA | 25 mM |
| $MgCl_2$ | 10 mM |
| HEPES pH 7.2 | 50 mM |
| Sodium Azide | 0.01% |
| SE15 | 0.01% |

Cartridge Operation and Extraction Performance.

When cfDNA is being prepared, in certain embodiments, it is possible to include extraction controls to permit monitoring of the quality of the DNA preparation. As illustrated in FIG. 18, there are two different bead sets. One bead set contains an endogenous HMBS primer and probe set for a SAC (sample assay control) and exogenous BG primer and probe set for a SPC (sample prep control). The other contains an endogenous Beta-Globin PP set for SAC (as well as BG SPC).

It was discovered, inter alia, that the use of GTC in the cartridge may be less important for serum than plasma samples. Without being bound by a particular theory it is believed that this may be due to the fact that serum contains less protein. Accordingly, in certain embodiments, the cartridge may contain less GTC or may omit GTC.

Figure 19A:
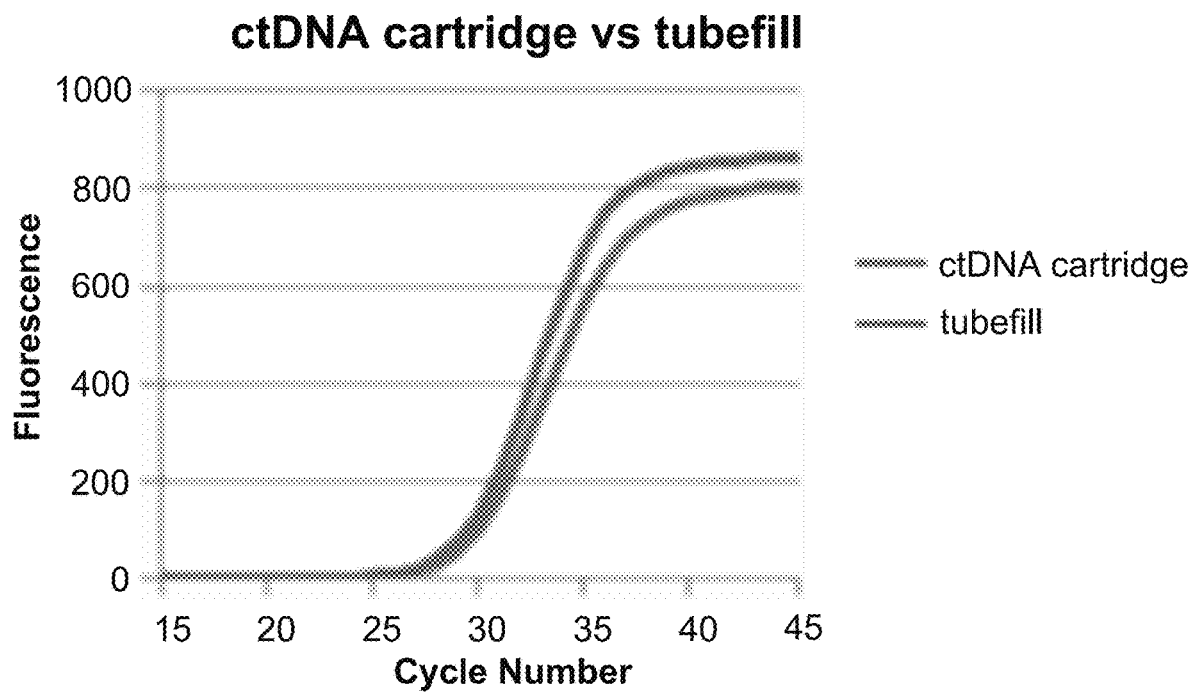
FIG. 19A shows a comparison of cfDNA preparation using a sample preparation cartridge as described herein compared to a standard tube-fill (i.e. tube-based kit) preparation. The cartridge preparation yield is very comparable to that obtained using a tube fill method.
Figure 19B:
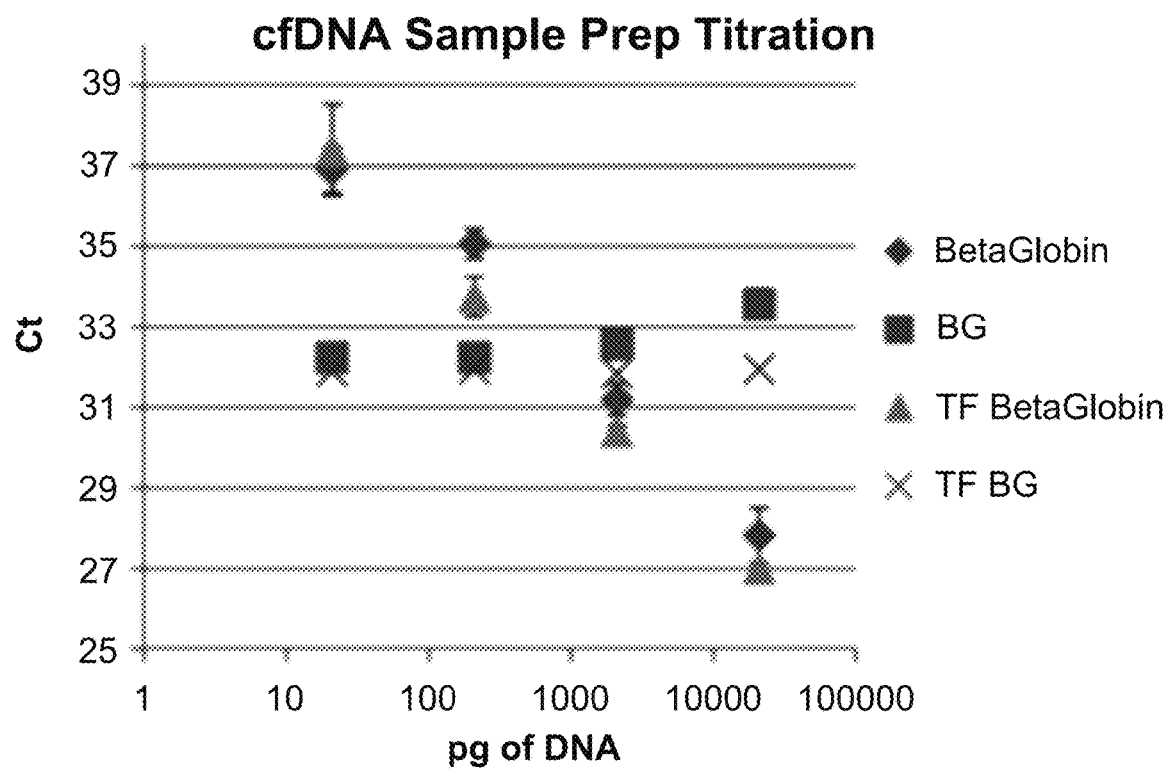
FIG. 19B shows a comparison of the amount of extracted DNA detected using a cartridge-based DNA cleanup as compared to a standard tube-fill as a function of DNA amount. The cartridge-based method is conservatively within 1 Ct of the tube-fill methods and is believed to be closer at higher DNA concentration.

FIGS. 19A and 19B show a comparison of the results of cfDNA preparation performed using a cartridge as described herein compared to the results obtained using a conventional "tubefill" procedure. As illustrated in the qPCR results shown in FIG. 19A, the binding and elution efficiencies obtained using the cartridge are extremely close (within one Ct) to those obtained using the tubefill protocol. As illustrated in FIG. 19B titrations of sample concentrations show that the cartridge preparation is conservatively within 1 Ct of the tubefill preparation down to a sample concentration as low as about 10 pg. It is believe the cartridge preparation is even closer to the tubefill protocol at higher sample concentrations.

Example 6

Testing a High-Volume Sample Preparation Cartridge

Figure 20A:
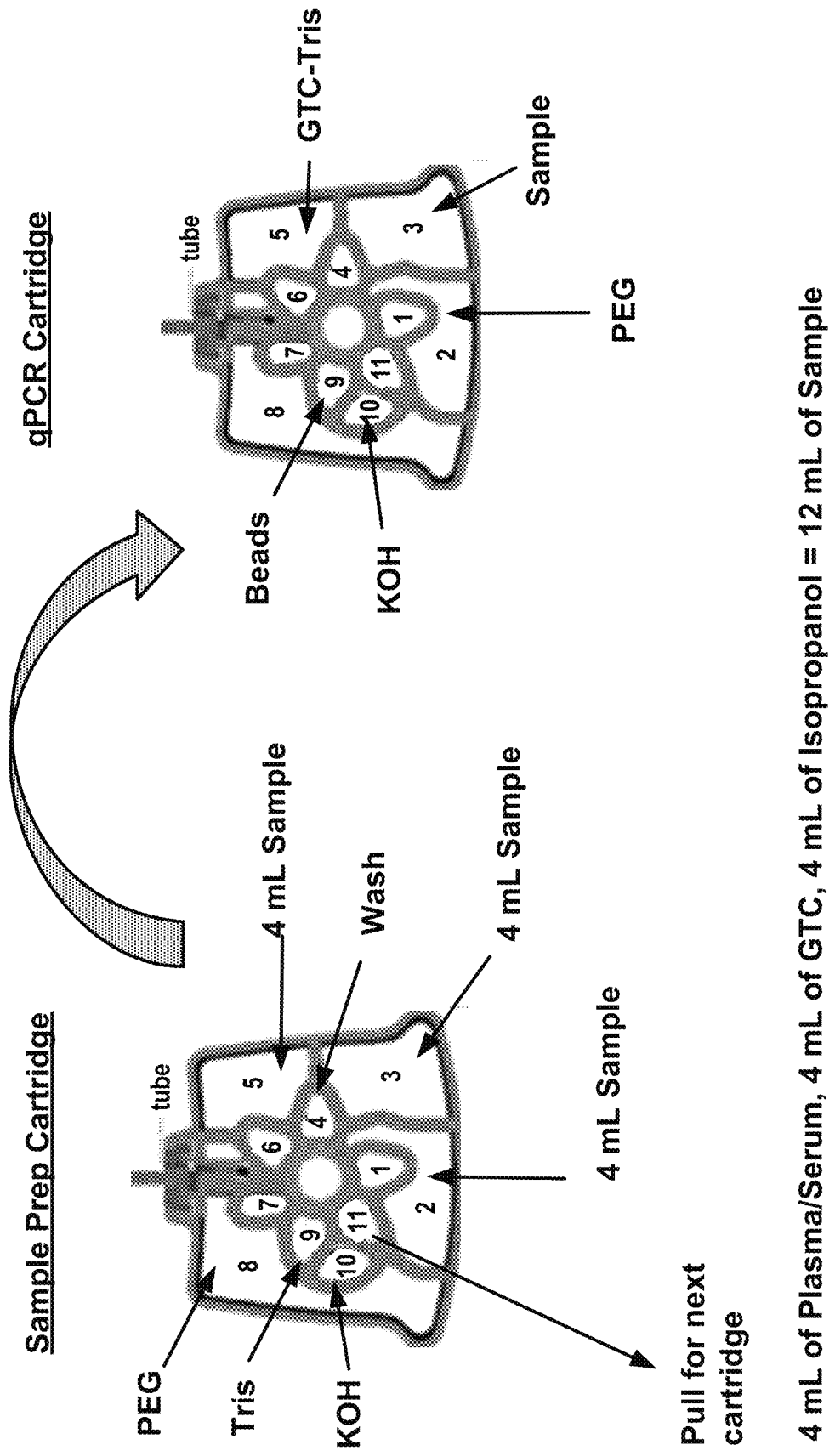
FIG. 20A illustrates one embodiment of a high-volume (e.g., up to 12 ml) sample preparation (HVSP) cartridge that can be used with a qPCR cartridge and/or with a methylation detection cartridge.

In certain embodiments high volume sample preparation (HSVP) cartridges are provided for the preparation of large volumes of sample (e.g., up to about 12 ml to 15 ml). This is particularly useful where the sample contains DNA at a low concentration (e.g., cfDNA in serum or plasma). One such cartridge is schematically illustrated in FIG. 20A. As shown therein the cartridge provides three chambers (chambers 2, 3, and 5) that can be used to receive a sample. In the illustrated embodiment, each of these chambers can receive about 4 mL of sample and, in certain embodiments, the sample comprises 4 mL of plasma/serum combined with 4 mL of GTC and 4 mL of alcohol (e.g., isopropanol).

Figure 20B:
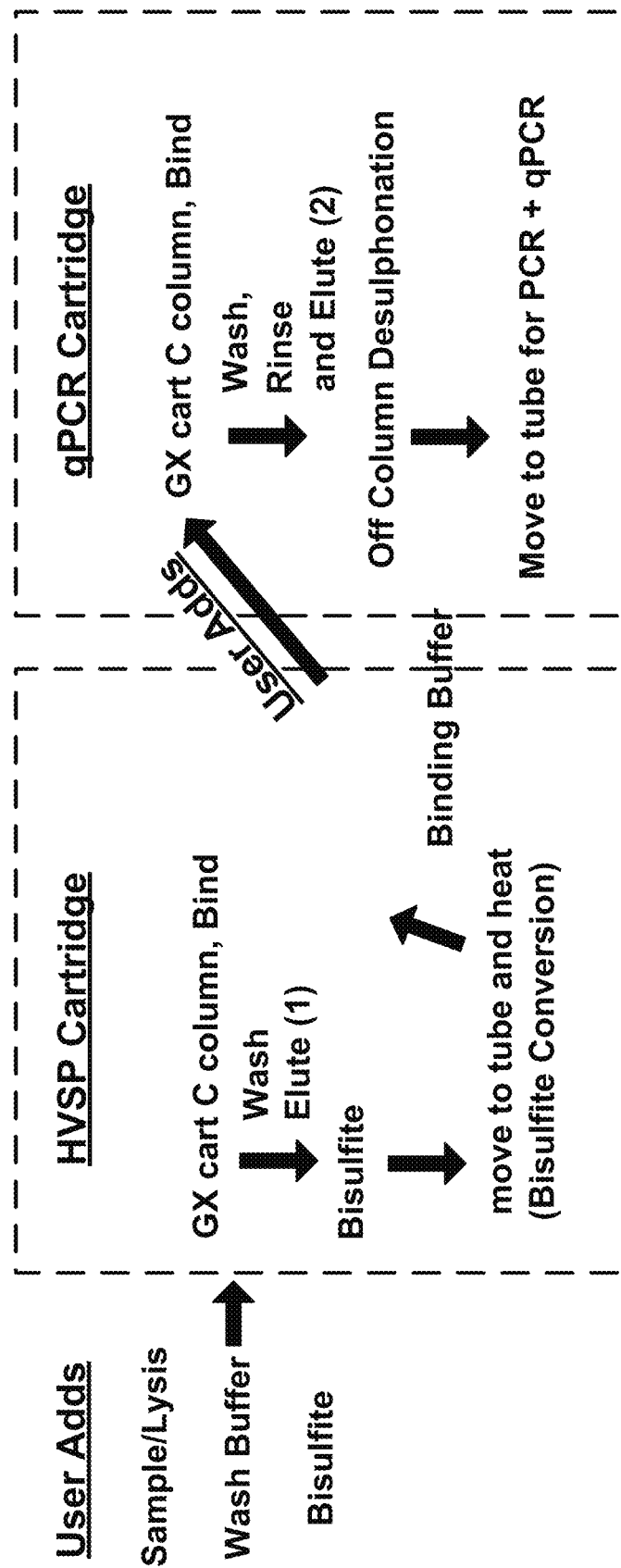
FIG. 20B schematically illustrates one variation of work flows in the HVSP cartridge when used in combination with a qPCR cartridge to perform a methylation analysis.

The sample is introduced into these chambers and the cartridge is operated as described herein to prepare the sample for PCR and/or methylation analysis. By way of illustration, in certain embodiments, operation of this cartridge can comprise binding DNA to an affinity column (e.g., for cleanup) and eluting the DNA. In certain embodiments where a methylation analysis is to be performed, the operation of the cartridge can further comprise combining the DNA with a conversion reagent (e.g., a bisulfite as described herein) and heating the mixture to convert the DNA. In certain embodiments, the HSVP cartridge can also be configured to desulphonates the converted DNA. In other embodiments, the DNA can be desulphonated in the second (e.g., qPCR) cartridge as schematically illustrated in FIG. 20B. The second cartridge can also perform the methylation analysis (e.g. a qPCR analysis).

Figure 21:
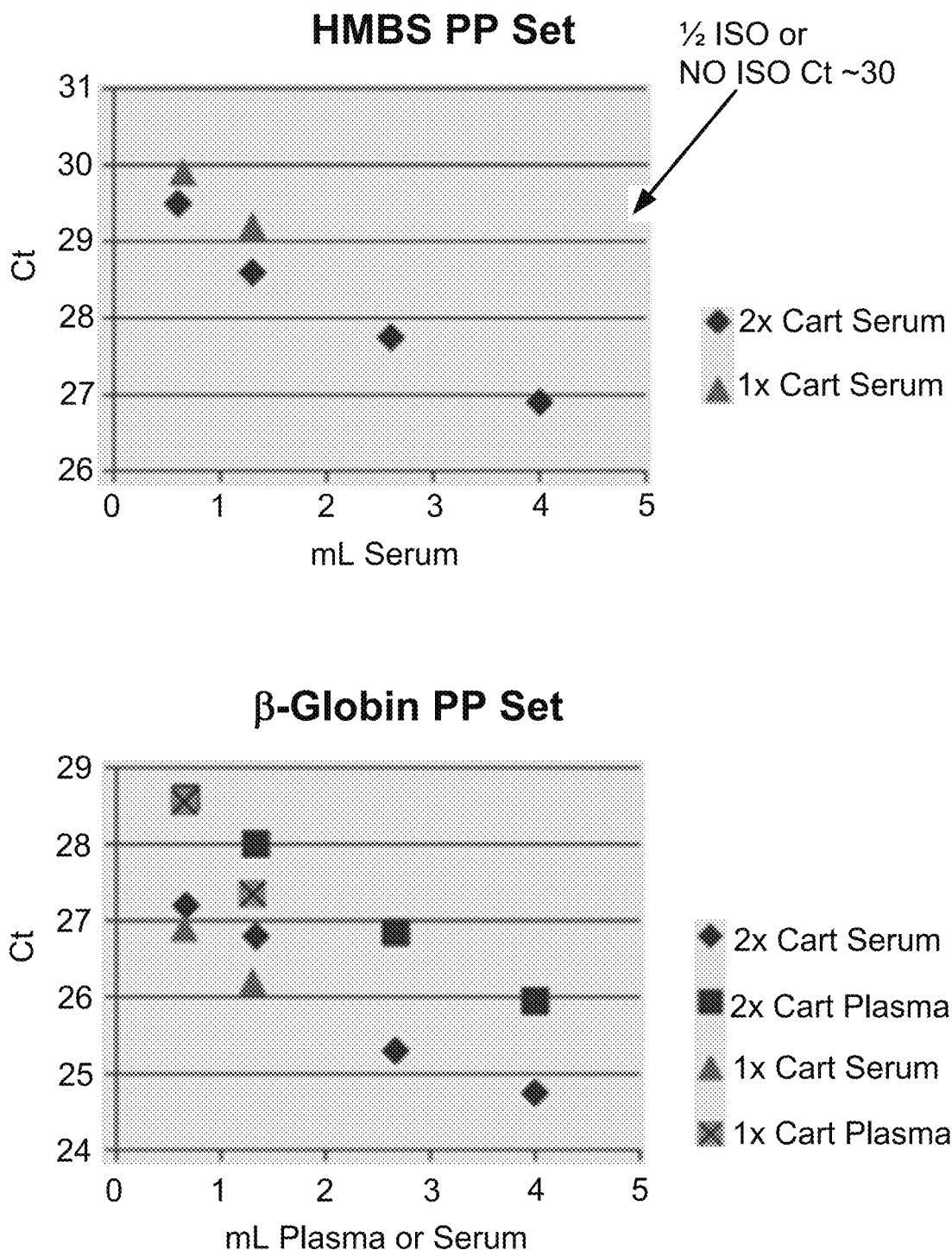
FIG. 21 illustrates the detection of HBMS or β-globin using a two cartridge cleanup using a high-volume sample preparation cartridge (see, e.g., FIG. 20) where the sample is transferred from the high volume cartridge to the PCR analysis cartridge compared to detection using a sample applied to a single PCR analysis cartridge resulting in less sample volume.

FIG. 21 shows a comparison of sample preparation results of DNA from plasma and serum between one cartridge and two cartridge protocols using the HMBS or β-globin primer and probe set. As shown therein, there was a linear increase in DNA recovery between 0.5 mL and 4 mL of serum or plasma. Moreover there was little to no loss when using one cartridge for the preparation and analysis or when using separate cartridges for preparation and analysis.

Example 7

Optimizing Bisulfite Conversion

In certain embodiments when using a cartridge for a methylation analysis as described herein one potential issue is the optimization of elution efficiently using the smallest volume possible. Small elution volumes are easier to deal with using spin columns. This problem can be addressed by using multiple heating steps to process larger sample volumes.

A second technical concern arises when heating a larger sample (e.g., minimum 100 μL) when using a smaller (e.g., 50 μL) heating tube or chamber. In certain instances, pressurizations between heating steps can make it difficult to reproducibly account for volume aspirates and dispenses. Secondly, the absence of pressurization can lead to volume changes and bubbles especially at higher temperatures. Thirdly, it is possible to pick up air between heated and unheated samples during port changes in between heat steps.

To investigate these optimization of bisulfite conversion in a 50 µL tube using single and double heating steps was investigated. This experiment was performed as follows:

Pull 75-80 µL of bisulfite-DNA; heat 95° C.-10 s, 65° C.-300 s×8;

Pull rest+5-10 µL; pressurize; heat 95° C.-480 s, 65° C.-1800 s×1.

Figure 22:
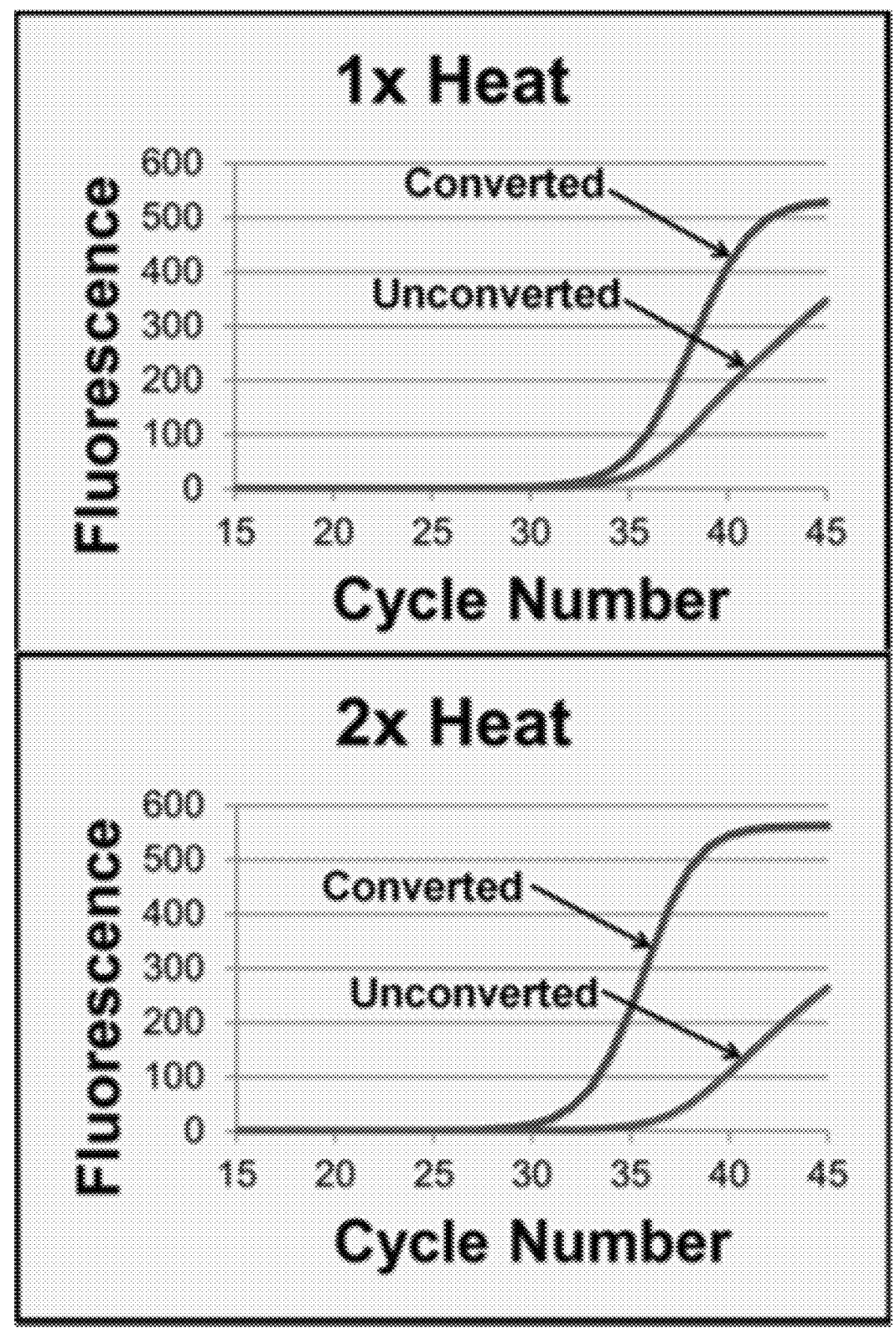
FIG. 22 illustrates the results of bisulfite conversion using multiple heating steps (bottom panel) compared to a single heating step (top panel).

The results for 0.5 mL of serum are shown in FIG. 22 where the top panel is 1× Heat (converted 33.0, unconverted 34.4) N=4, and the bottom panel is 2× Heat (converted 31.9, unconverted 36.1) N=4.

There is a gain of about 1 Ct in the converted ACTB signal when going from 1× heat to 2× heat. This suggests almost all of the DNA is converted. This is supported by the fact that there is also a loss of about 2 Ct's in the unconverted HMBS signal. A 1 Ct increase is logical since we went from heating 50/100 µL to 100/100 µL of DNA-bisulfite sample.

Example 8

Comparison of a DNA Methylation Cartridge with Tube-Based Commercial Kits

Figure 23A:
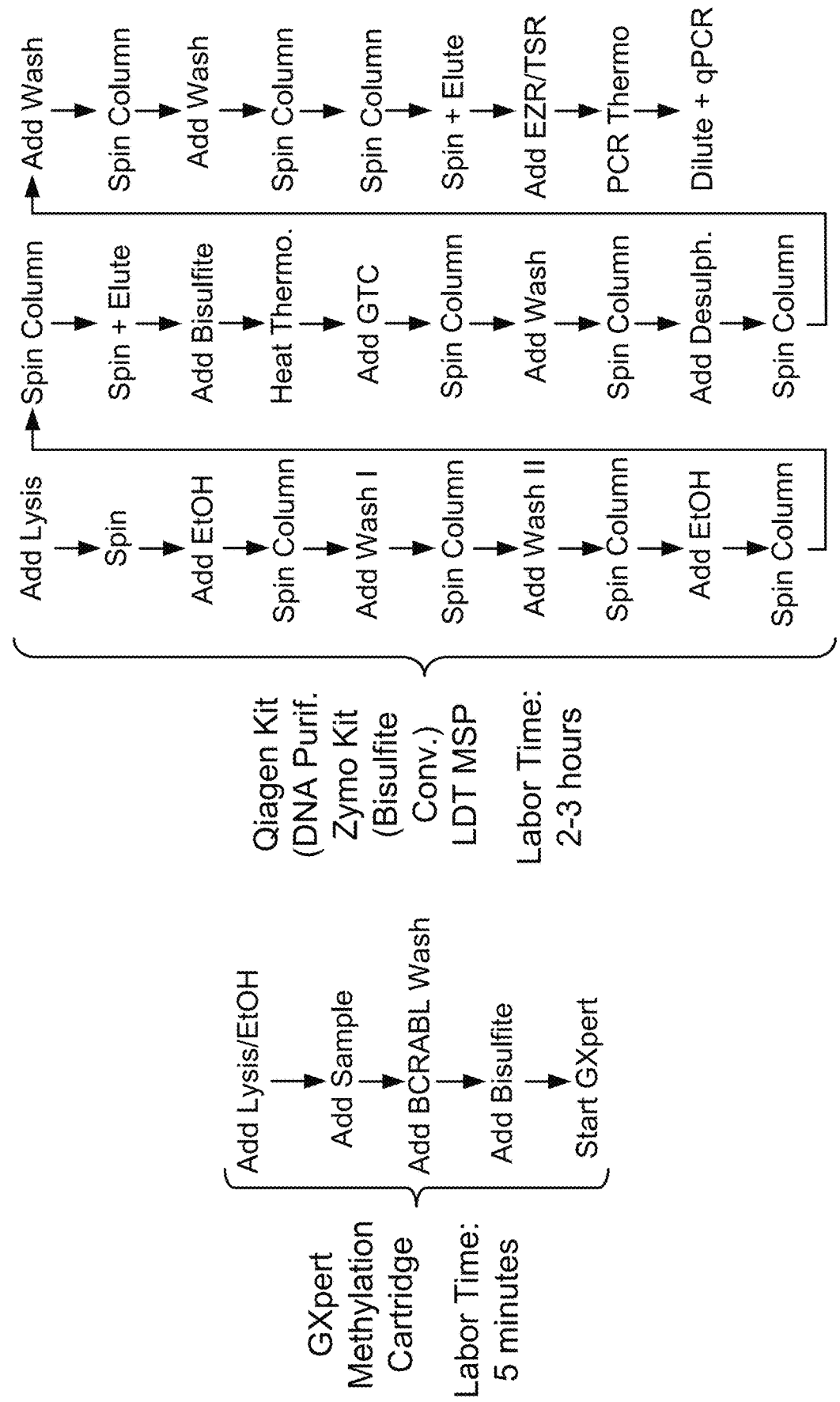
FIG. 23A illustrates the steps and labor time for a methylation analysis using a standard Qiagen DNA purification kit combined with a Zymo DNA methylation kit (right) compared to a methylation analysis using a Methylation analysis cartridge described herein.

FIG. 23A shows a comparison of the user steps required when performing a methylation analysis using cartridge as described herein (left) as compared to the steps required when using commercial kits (QIAamp MinElute Virus Spin Kit (Qiagen, Inc.), and EZ DNA Methylation-Lightning™ Kit (Zymo Research, Inc.)) to perform the same analysis. As can readily be seen the cartridge-based methylation analysis requires far few user steps with a labor time of about 5 minutes as compared to the 2-3 hour labor time required using the kits.

Figure 23B:
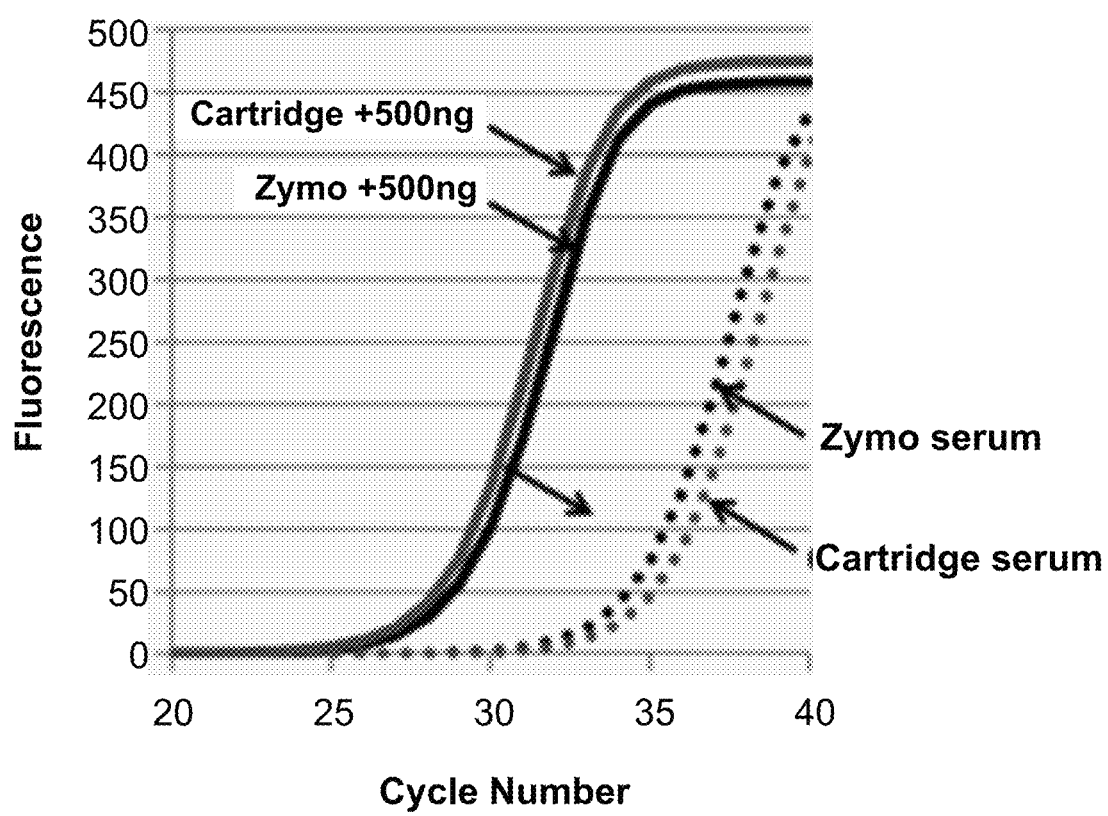
FIG. 23B shows a comparison of the results obtained using the two different protocols.

To compare the results produced by the different methods, 200 µL of serum was purified using the Qiagen kit. The DNA was converted using the Zymo kit, purified with a second spin column and eluted with 10 µL. Ran all 10 µL using converted unmethylated ACTB primers and probes (TSR). In comparison, 200 µL of serum were run in the methylation cartridge as described herein. Results are shown in FIG. 23B. As is readily evident, the cartridge method produced results extremely comparable to those obtained using the commercial kits. However, this was accomplished with far less labor and time.

Example 9

Use of DABSO for DNA Conversion

It was initially attempted to dissolve 5 g DABSO in 5 mL H2O. Ultimately a few mLs of 10 M KOH and a mL of water were added and heated to solubilize the DABSO and to raise the pH up to between about pH 5 and pH 5.5 at an estimated final DABSO concentration of ~2.5 M.

Figure 24:
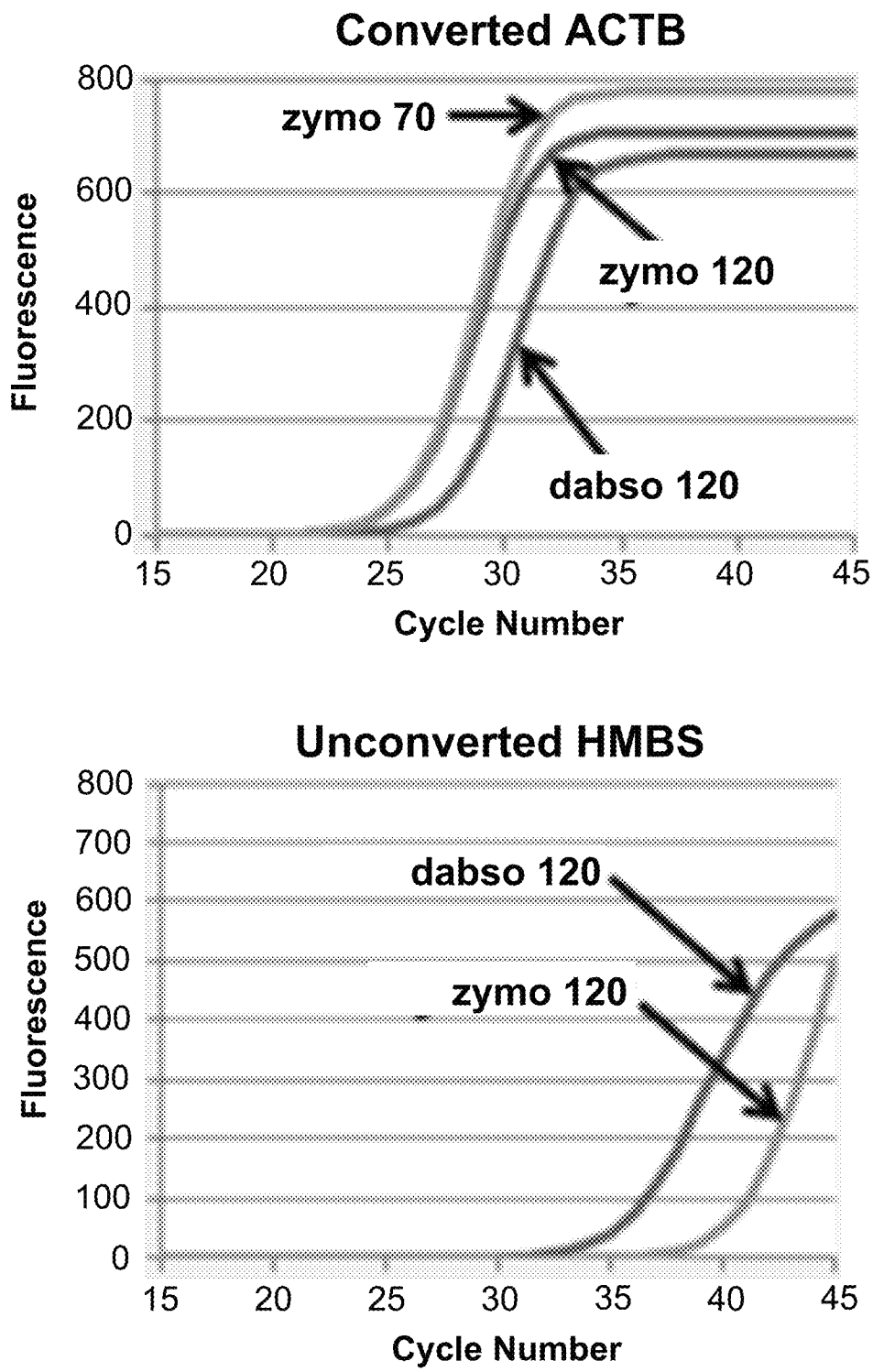
FIG. 24 shows a comparison of DNA conversion using DABSO as the conversion reagent compared to DNA conversion using the Zymo bisulfite conversion reagent.

FIG. 24 shows graphs of tubefills of 750 ng of DNA converted using DABSO or the Zymo conversion reagent. The materials were offboard heated (1 µg) in a thermocycler and purified with spin columns and run as tubefills. The 3 different experiments were:

1) 120 µL DABSO/30 µL DNA;
2) 120 µL Zymo/30 µL DNA; and
3) 70 µL Zymo/30 µL DNA (ratio currently in the cartridge).

As shown in FIG. 24, DABSO provided good conversions almost comparable to those obtained using the Zymo reagent.

Example 10

Sensitivity of Detection of Methylated DNA

To evaluate the sensitivity of detection of DNA methylation, converted ACTB gene promoter was detected as a function of copy number using a cartridge as described herein. The goal was to detect less than 25 copies of converted, unmethylated DNA. As previously shown, fallouts were observed at about 10-50 copies (1 fallout each). Similar sensitivity was observed for methylated DNA targets in a serum background.

Figure 25A:
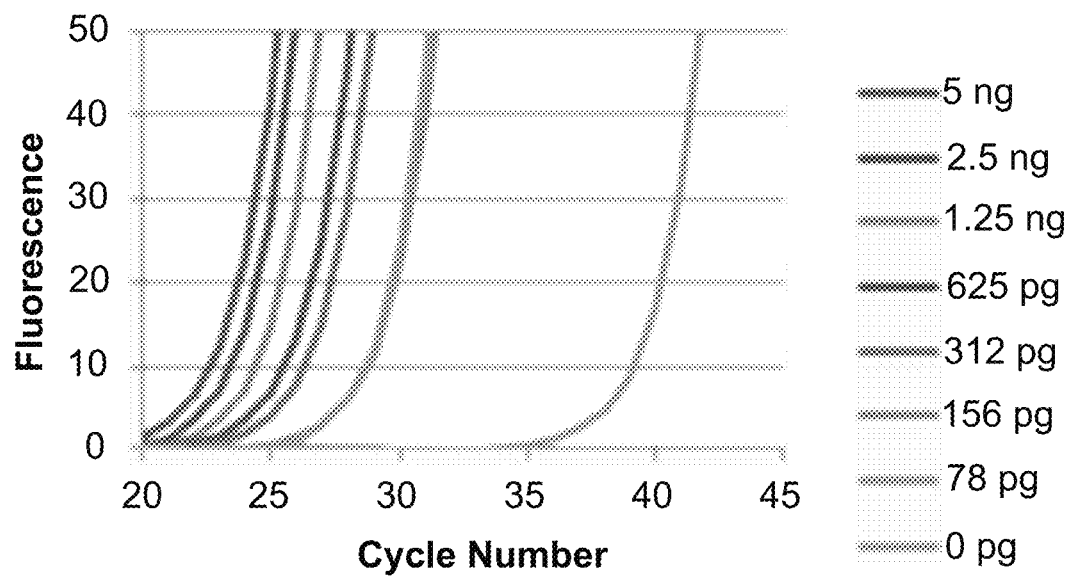
FIG. 25, panels A and B, illustrates sensitivity of detection of methylated DNA. Panel A shows a dilution series of methylated DNA (MGMT). Panel B illustrates the sensitivity of detection of methylated pancreatic cancer markers.
Figure 25B:
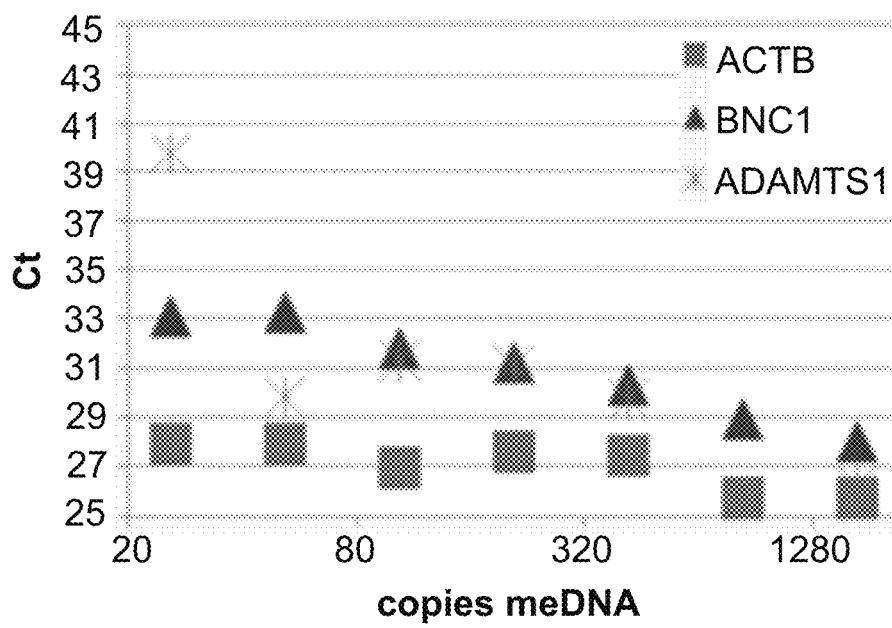

FIG. 25, panel A, illustrates the detection of methylated DNA in a dilution series (MGMT (O-6-Methylguanine-DNA Methyltransferase gene)). As shown therein MGMT was detected down to a level of 78 pg.

The detection of methylated breast cancer markers RASSF1A and AKR1B1 in MBA-453 cells is shown in FIG. 25, panel B. As shown therein, breast cancer markers were detected down to 100 cells.

The detection of methylated pancreatic cancer markers ACTB, BNC1, and ADAMTS1 in a dilution series is shown in FIG. 25, panel C. As shown therein, pancreatic markers were detected down to 25 copies.

Table 13 shows the hit rate of pancreatic cancer markers BNC1 and ADAMTS1 as a function of concentration. As shown therein these markers could be detected below 120 pg. Note a positive "hit rate" is an amplification in either gene for a replicate.

TABLE 13 illustrates the hit rate for pancreatic marker detection as a function of concentration

| Concentration | Hit rate (#/replicates) |
|---|---|
| 0 pg | 0/3 |
| 16 pg | 6/8 |
| 30 pg | 5/8 |
| 60 pg | 4/8 |
| 120 pg | 4/4 |

Example 11

Reverse Complement Multiplex Assay for Both Strands

FIG. 26 illustrates the results for a reverse complement multiplex assay for both DNA strands. Following bisulfite conversion, both strands lose their complementarity. Thus, primer and probe sets have to be designed for one strand or the other, and result in unique amplicons. In addition to providing "more opportunities", this approach might potentially help with sensitivity (at LOD, if only one strand or the other ends up in the tube, this approach would ensure the signal gets picked up).

The multiplex assay allows detection of different CpGs at the same promoter site. The reverse complement multiplex provides more queries on target and the possibility to pick up heterogamous methylation.

Example 12

Detection of DNA Methylation and Mutation in a Single Cartridge

In certain embodiments the multiplex PCR reactions can contain primers and probes that permit the detection of mutations in addition to methylation in the same cartridge. FIG. 27A illustrates the detection of methylated BNC1 and ADAMTS1 along with the KRAS G12D mutation along with control BG (Top Panel) and the detection of methylated BNC1 and ADAMTS1 along with the KRAS wildtype along with control BG (Bottom Panel).

Figure 27B:
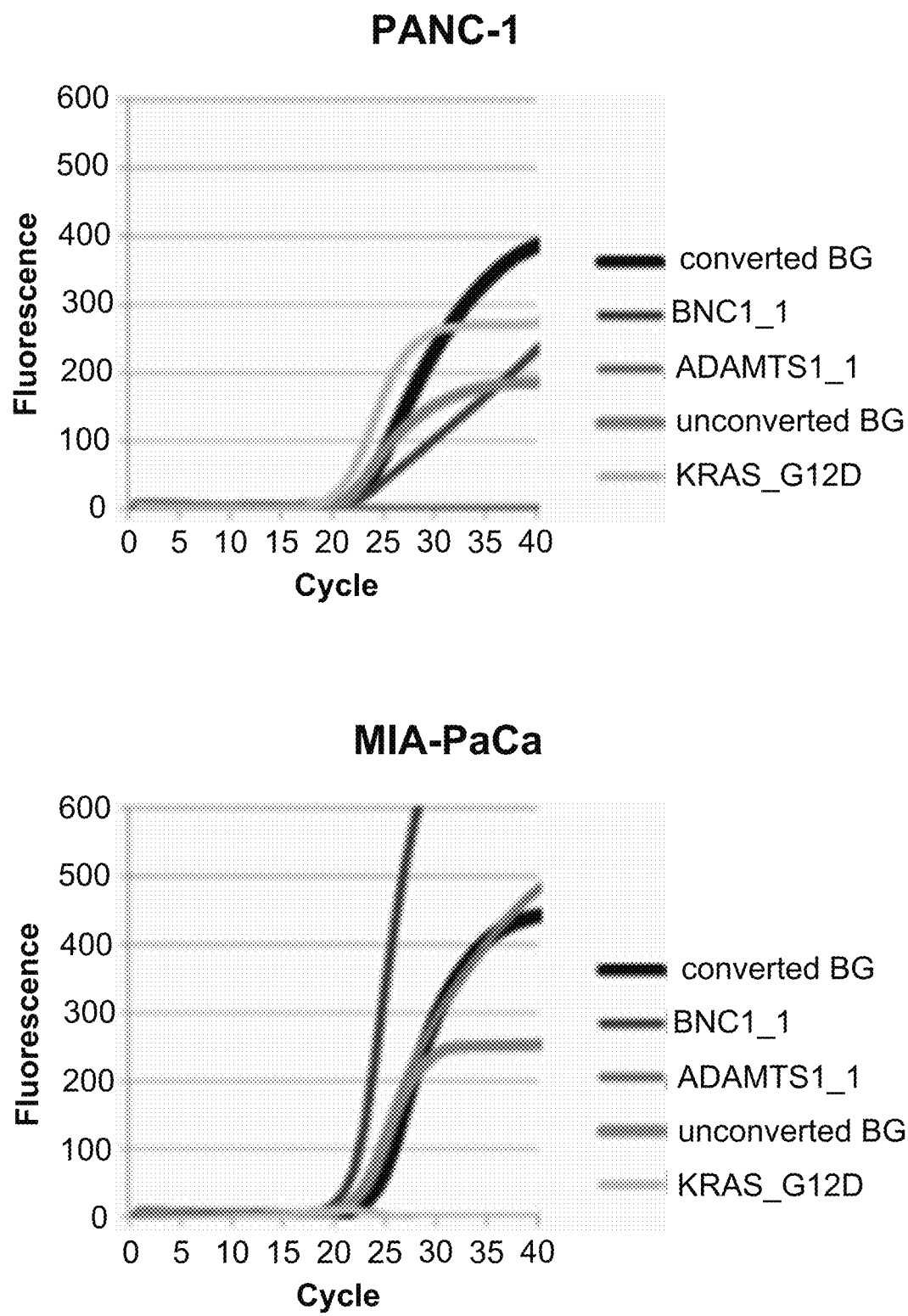
FIG. 27B illustrates detection of methylated DNA and mutations I the same cartridge in two pancreatic cancer cell lines: PANC-1 cells (top panel) and MIA-PaCa cells (bottom panel).

FIG. 27B illustrates the simultaneous detection of BNC1 and ADAMTS1 methylation in PANC-1 cells (top panel) and MIA-PaCa cells (bottom panel) along with the KRAS G12D mutation.

Example 13

Multiplex Optimization of Pancreatic Cancer

It was determined that methylation analysis of ADAMTS1, BNC1, (and certain other genes) permits detection and/or staging of pancreatic cancer. Accordingly, the initial multiplex assay for BNC1 and ADAMTS1 was optimized to facilitate incorporation of probes for other genes. To optimize this assay temperature gradients were run on external and internal PCRs for forward/reverse bisulfite converted strands. Single-plexes (fwd/rev for each gene) were run at external temperatures of 56° C., 58° C., and 60° C. and internal temperatures of 64° C., 66° C., and 68° C. (see, e.g., FIG. 28). In certain embodiments the assays were developed as two 4-plexes for BNC1 and ADAMTS1 and two other genes, one 4-plex for methylation analysis of a forward strand and one 4-plex for methylation analysis of a reverse strand.

Figure 29:
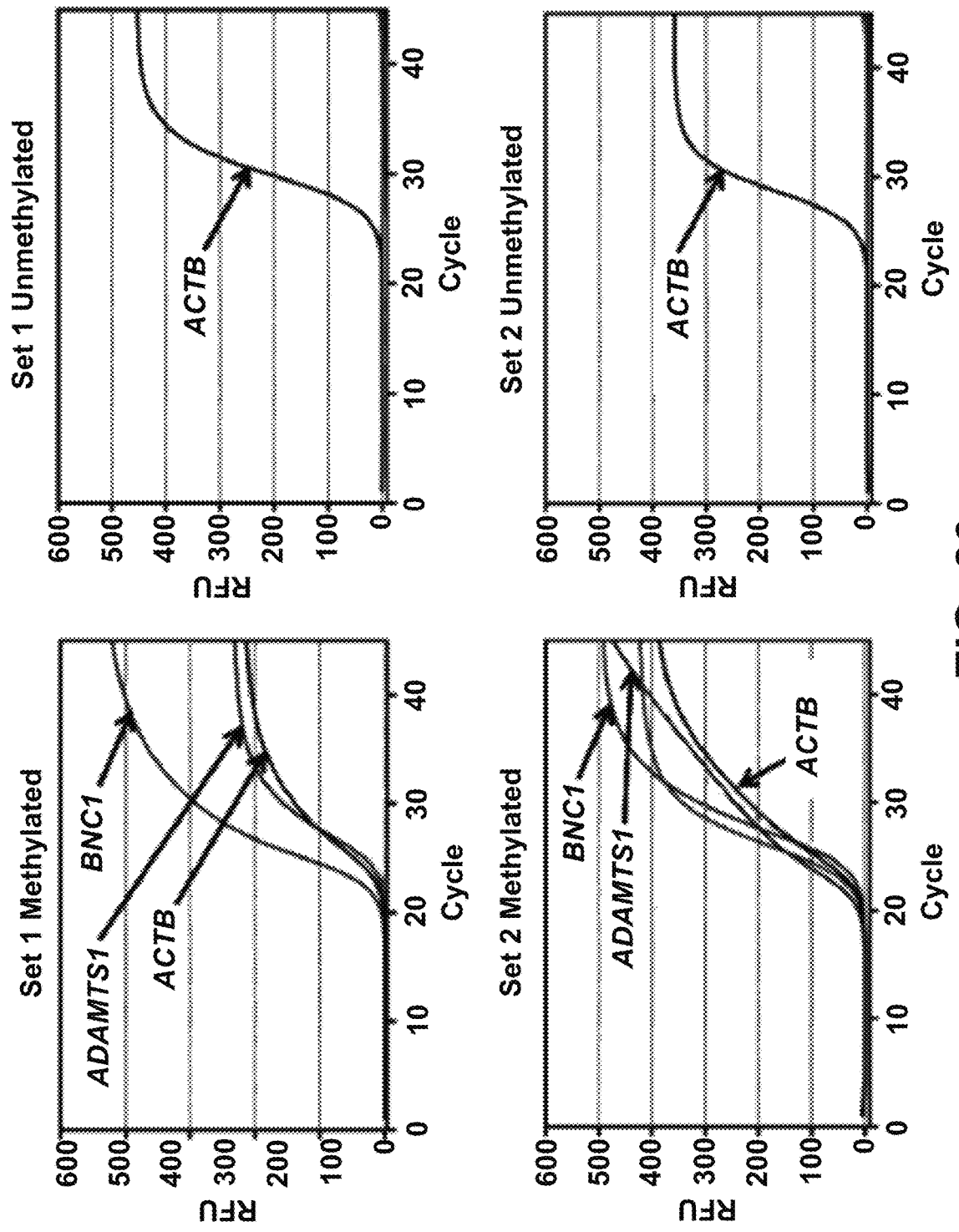
FIG. 29 illustrates the ability to multiplex the MSP primer and probe sets for BNC1, ADAMTS1, and a control gene ACTB. Probes were combined into two sets based on preferred conditions.

The probes were combined into two sets (see, FIG. 29) based on preferred reaction conditions (salt conditions 40 mM (LS), 60 mM (MS), 80 mM (HS) KCl, 15 mM NH$_4$SO$_4$) and optimized for specificity. The final optimized salt condition for multiplex 1 was 80 mM KCl, 5 mM MgCl$_2$, 20 mM Tris pH 8.5, and 10 mM NH$_4$ and for multiplex 2 was 62 mM KCl, 4 mM MgCl$_2$, 20 mM Tris pH 8.5, and 10 mM NH$_4$.

Example 14

Detection of MGMT Methylation

The O(6)-methylguanine-DNA methyltransferase (MGMT) gene encodes a DNA repair enzyme that can abrogate the effects of alkylating chemotherapy such as temozolamide. If the MGMT gene is active, the damage is rapidly repaired. It is believed that malignant gliomas may have the MGMT gene inactivated due to methylation of its promoter region. Methylated MGMT gene is a predictive indicator for better response to chemotherapy (as the tumor has no means to repair the DNA damage induced by the alkylating agent).

Figure 30:
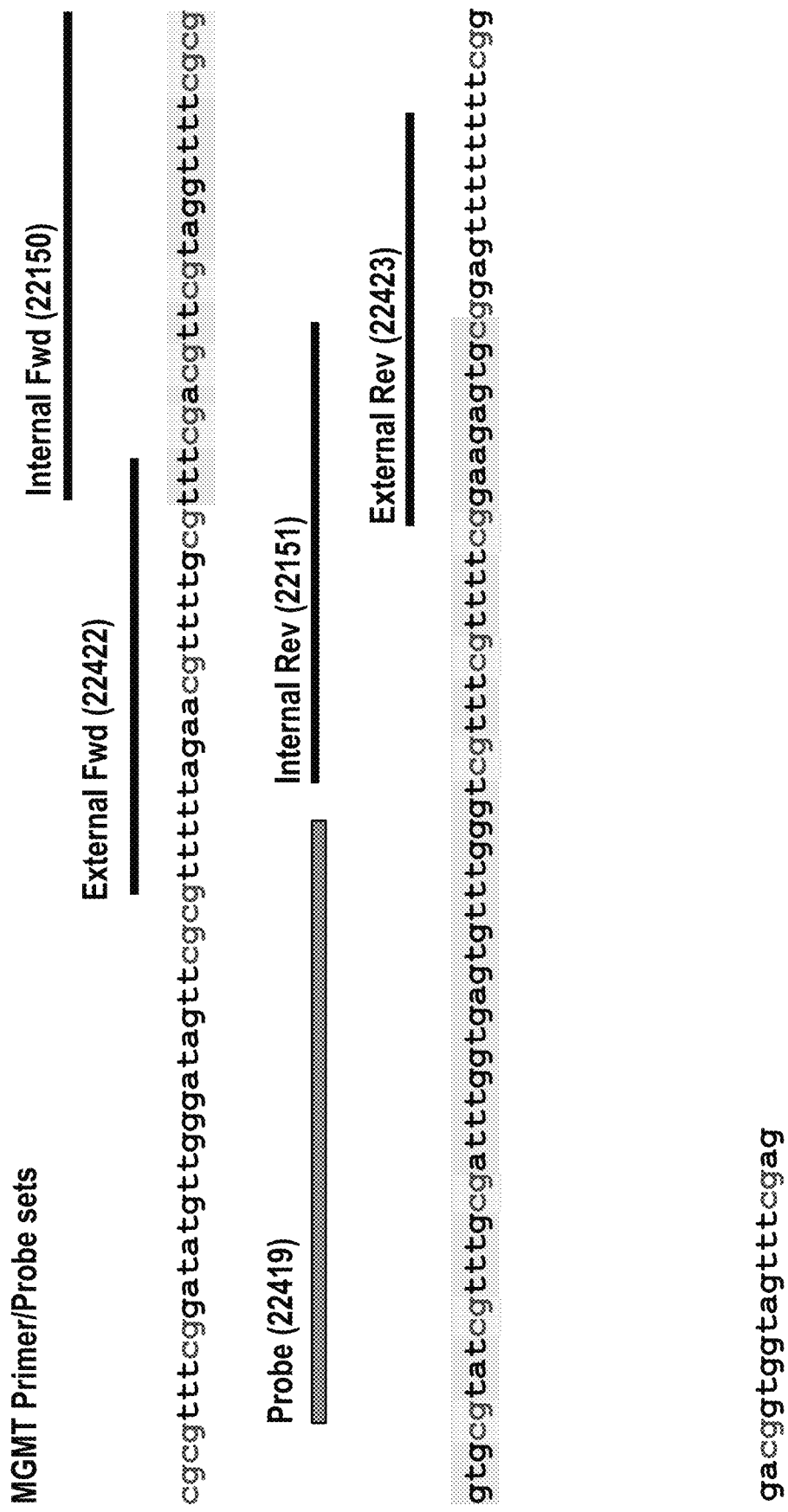
FIG. 30 illustrates one set of primers and probes used for detection of MGMT methylation. Internal fwd 22150 (SEQ ID NO: 266); External fwd 22422 (SEQ ID NO: 263); Probe 22419 (SEQ ID NO: 268), Internal rev 22151 (SEQ ID NO: 267); external rev 22423 (SEQ ID NO: 265); template (SEQ ID NO: 1).

Primers and probes were developed for the detection of MGMT methylation as illustrated in FIG. 30 and summarized below in Table 14. In particular, FIG. 30 illustrates the converted template with CPGs (as determined from pyrosequencing) shown in grey. As illustrated after bisulfite conversion the forward and reverse strand are no longer complementary permitting separate analysis of each strand.

TABLE 14

Illustrative primer/probe set for detection of MGMT methylation (see, e.g., FIG. 30).

| Probe | | Probe Type | Sequence | SEQ ID NO |
|---|---|---|---|---|
| External | 22422 | MGMT Fwd-4 | GTTTT(T*)AGAAY G(T*)TTTGYGTTT | 263 |
| | 22423 | MGMT Rev-4 | AAAAAAC(T*)CCR CACTCTTCC | 265 |
| Internal | 22150 | MGMT Fwd-2 | TTTCGACGTTCGTA GGTTTTCGC | 266 |
| | 22151 | MGMT Rev-2 | GCACTCTTCCGAAA ACGAAACG | 267 |
| | 22419 | MGMT Fluor-TaqMan-2 | Fluor-CCAAACAC (T*)CACCAAATC (N*)CAAAC | 268 |

To evaluate detection sensitivity a MGMT dilution series (5 ng to 78 pg MGMT DNA in a background of 20 ng of HS DNA)) was evaluated using ACTB as a control. In an illustrative experiment, 78 pg of methylated MGMT DNA was only about 10 cycles off the Ct of only unmethylated HS DNA.

Figure 31:
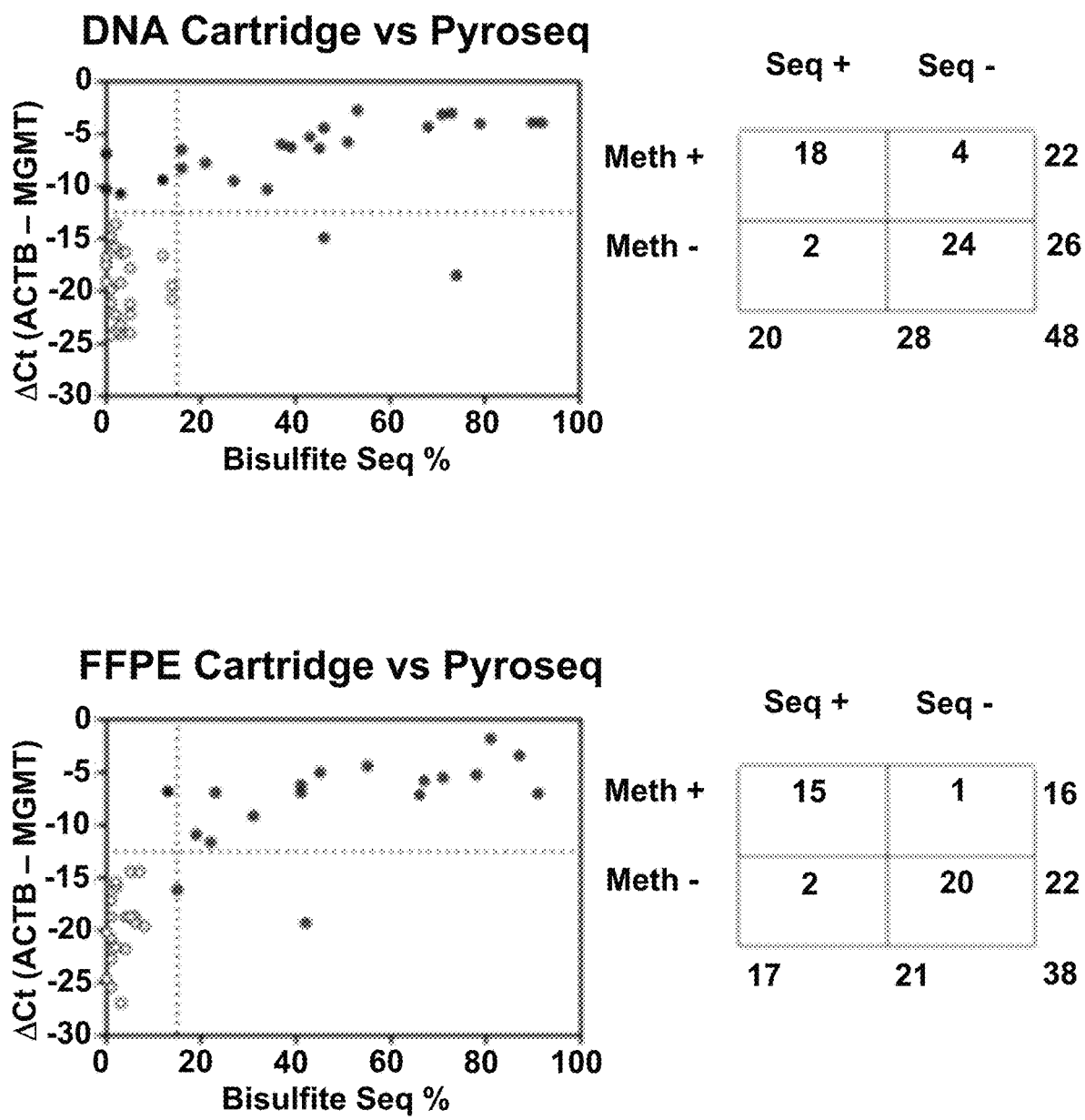
FIG. 31 shows the results of a comparison between bisulfite pyrosequencing and a MGMT methylation cartridge for extracted DNA (top) and for an FFPET sample (bottom).

As shown in FIG. 31 results produced using the methylation cartridge described herein for the detection of MGMT methylation was compared to the results produced by pyrosequencing for extracted DNA (FIG. 31, top) and for a FFPE sample (FIG. 31, bottom). Pyrosequencing typically uses a cutoff between 10-15% to determine patient stratification. We used an arbitrary cutoff of 12.5 (between ACTB and MGMT) to match pyrosequencing results as closely as possible. Accordingly, in this example a cutoff was set at delta Ct=12.5 and calculated concordance with >15% methylation. The cartridge analysis of the extracted DNA show a sensitivity of 90% and a specificity at 86% while the cartridge analysis of the FFPE sample showed a sensitivity of 88% and a specificity of 95%.

It is noted that specificity can be improved in two ways: 1) the annealing temperature can be increased as the 62° C. annealing temperature was rather low. Additionally methylation probes that cover 3 (or more) CpGs can be utilized.

Example 15

Detection of BRCA1 Methylation

BRCA1 is a caretaker gene responsible for repairing DNA. It is believe that BRCA1 is involved in homologous, recombination, non-homologous end joining, and nucleotide excision repair. Women with an abnormal BRCA1 gene have an 80% chance of developing breast cancer.

Without being bound to a particular theory, it is believed that BRCA1 methylation is a potential predictive marker of response to chemotherapy in triple negative BC patients. Study of NSCLC patient's treated with cisplatin showed those with low BRCA1 expression had improved survival rates. High levels reduced the effectiveness of chemotherapy by repairing the damage caused to cancer cells.

Figure 32:
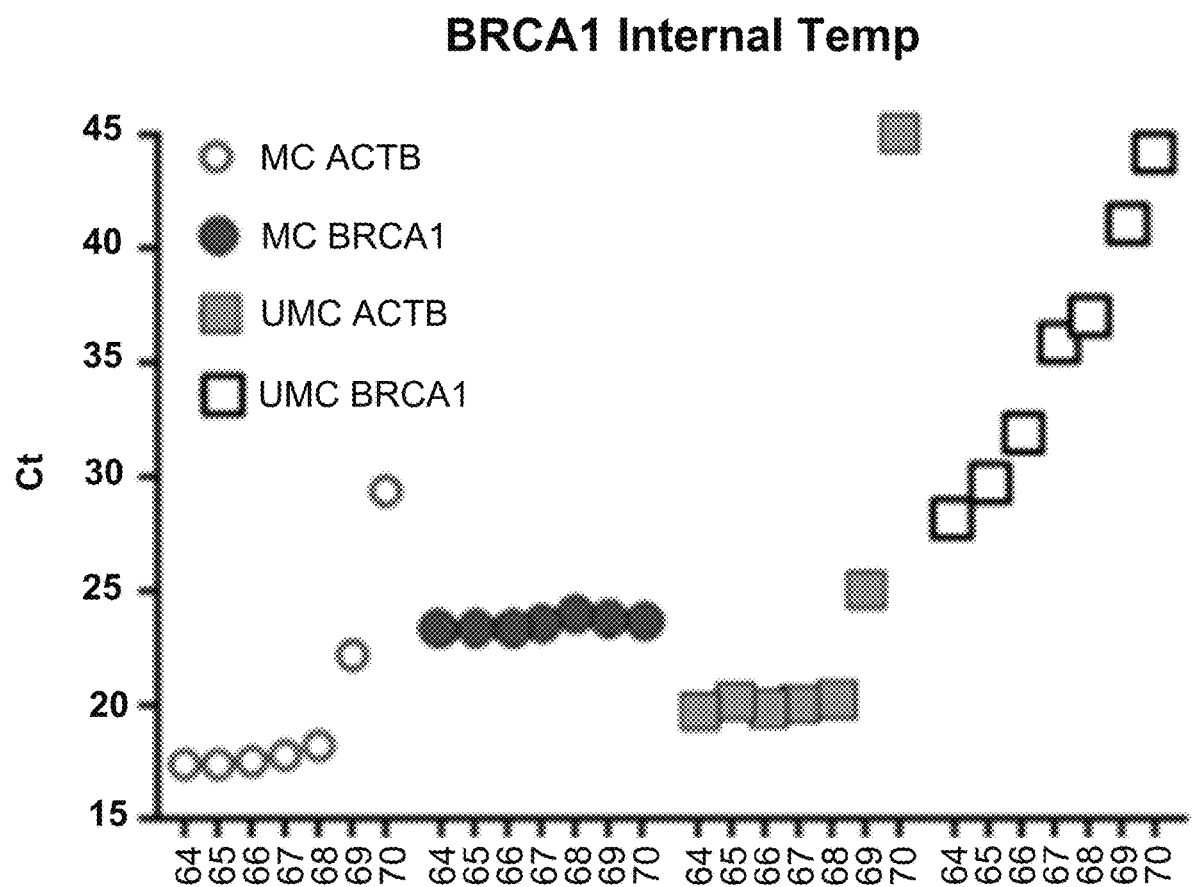
FIG. 32 illustrates BRCA1 primer and probe set optimization of ΔCt between methylated converted and unmethylated converted DNA.

In view of these, and other, observations cartridges and methods of use were developed for detection of BRCA1 methylation. In particular, the PCR condition were optimized as follows: 1) External temperature was evaluated between 56-62° C. and we settled on a 3 step 56° C. annealing PCR protocol; 2) Internal temperature was evaluated between 64° C.-70° C. and we settled on a two-step 68° C. annealing PCR protocol. Results are shown in FIG. 32.

Figure 33:
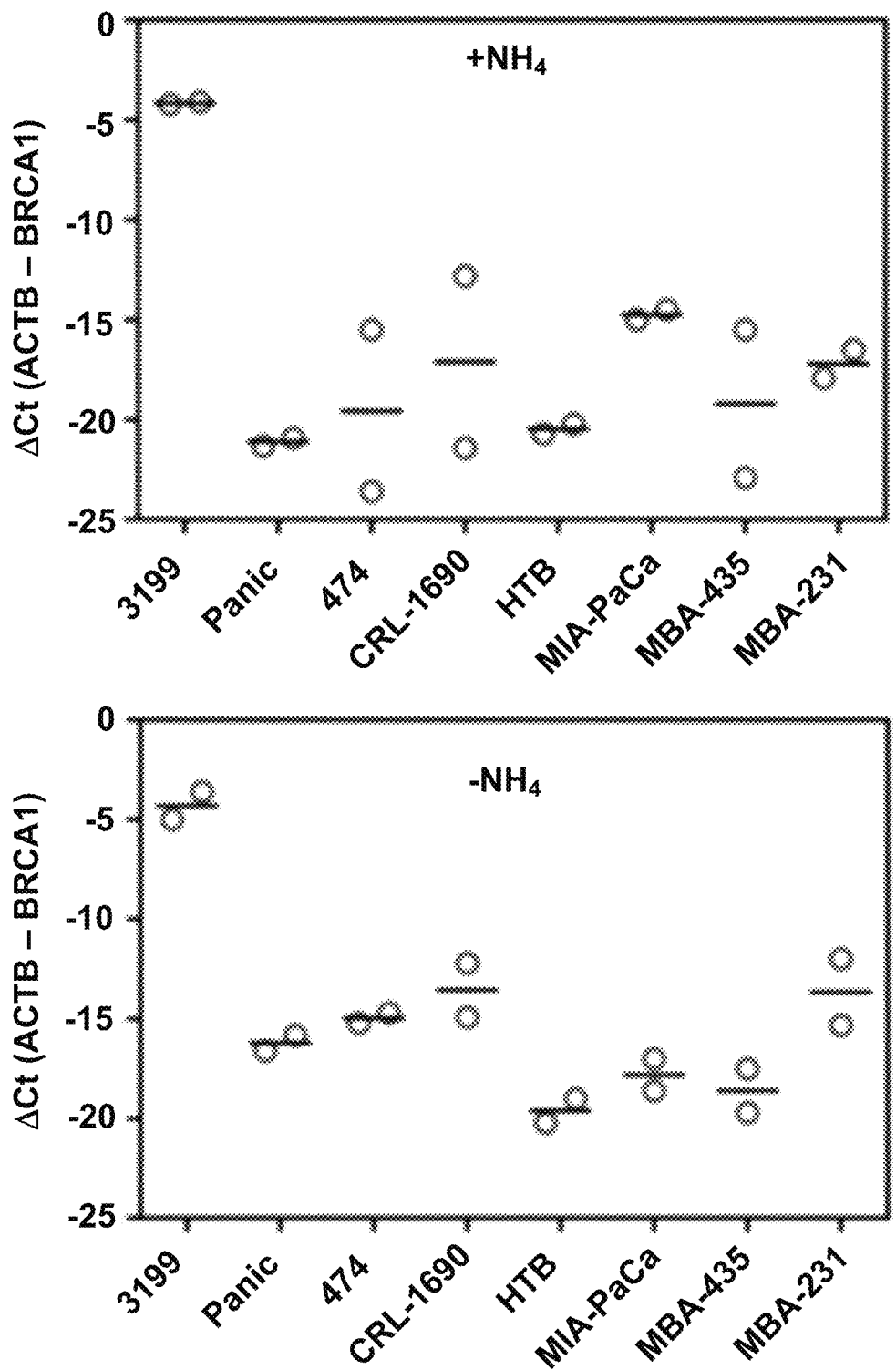
FIG. 33 illustrates a one target assay for BRCA1 methylation tested with the ACTB control gene. As shown, eight different cell lines were tested and the effect of adding $NH_4$ was compared.

For BRCA1, a one target assay was tested with the ACTB control gene. Eight different cell lines were tested and the effect of adding NH$_4$ was compared (see, FIG. 33). BRCA1 methylation was expected to be observed in the 3199 cell line.

Example 16

Detection of Gene Methylation Associated with Lung Cancer

Figure 34:
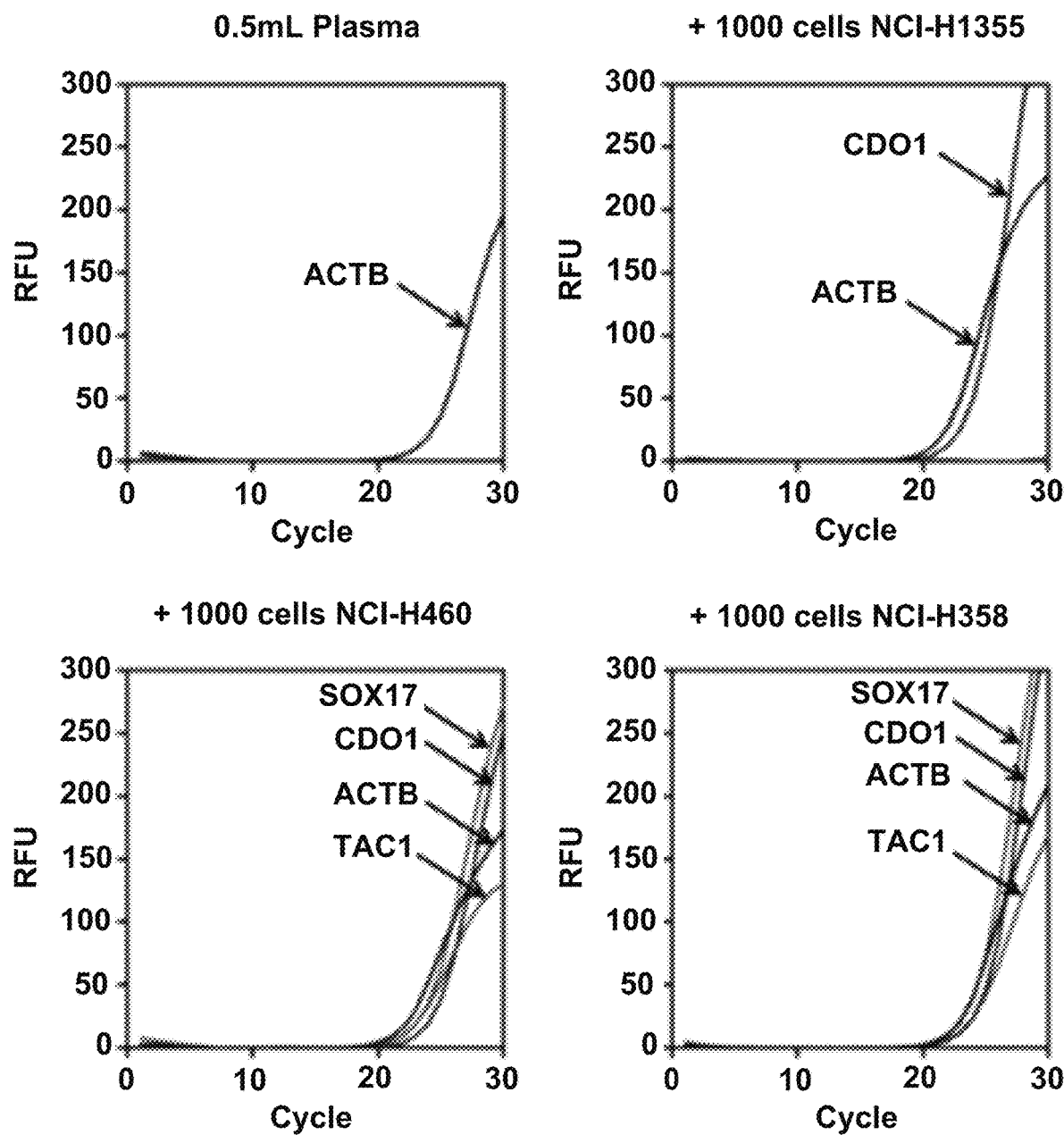
FIG. 34 illustrates the results of a three target methylation assay for genes whose methylation is associated with lung cancer (SOX17, CD01, TAC1) in a background of normal plasma and in three different lung cancer cell lines.

A three target methylation assay for genes whose methylation is associated with lung cancer (SOX17, CD01, TAC1) was tested along with the ACTB control gene. The data shown in FIG. 34 indicate that, as expected, the 3 targets do not come up in a background of normal plasma but are present to some degree in three different lung cancer cell lines.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of producing a converted nucleic acid, said method comprising:
   i) contacting a solution comprising nucleic acids from a biological sample to a first matrix material comprising a first column or filter where said matrix material binds and/or filters nucleic acids in said sample and thereby purifies DNA;
   ii) eluting any bound DNA, if present, from the first matrix material and denaturing the eluted or purified DNA to produce denatured DNA;
   iii) heating the denatured DNA in the presence of a bisulfite conversion reagent that deamidates cytosine to produce a deaminated nucleic acid;
   iv) contacting said deaminated nucleic acid with a second matrix material comprising a second column to bind said deaminated nucleic acid to said second matrix material;
   v) desulfonating the bound deaminated nucleic acid with a desulfonation reagent to produce a converted nucleic acid;
   vi) eluting said converted nucleic acid from said second matrix material, wherein steps iv) through vi) are performed in a single reaction cartridge; and
   vii) amplifying the converted nucleic acid by polymerase chain reaction (PCR), wherein the heating with the bisulfite conversion reagent is performed in a reaction channel or chamber that can be temperature controlled and subjected to thermocycling and that is later used for PCR.

2. The method of claim 1, wherein:
   at least steps iii) through vi) are performed in said cartridge; or
   at least steps ii) through vi) are performed in said cartridge; or
   at least steps i) through vi) are performed in said cartridge.

3. The method of claim 1, wherein the method comprises:
performing methylation specific PCR and/or nucleic acid sequencing, and/or high resolution melting analysis (HRM) on said converted nucleic acid to determine the methylation of said nucleic acid.

4. The method of claim 3, wherein said methylation specific PCR is performed in said reaction channel or chamber.

5. The method of claim 1, wherein said cartridge comprises said first matrix material comprising said first column, a sample receiving chamber, said reaction channel or chamber, a plurality of chambers containing reagents and/or buffers, wherein said sample receiving chamber, said column(s), said plurality of chambers, and said reaction channel or chamber are selectively in fluid communication, and, when in use, at least one of said chambers contains said desulfonation reagent.

6. The method of claim 5, wherein, when in use, at least one of said chambers contains a bisulfite salt selected from the group consisting of sodium metabisulfite, potassium bisulfite, cesium bisulfite, and ammonium bisulfite as the conversion reagent.

7. The method of claim 6, wherein said bisulfite salt is ammonium bisulfite.

8. The method of claim 5, wherein said cartridge comprises one or more chambers containing one or more primers and probes for detection of methylation of a forward and/or a reverse strand of a converted DNA, wherein at least one primer and/or probe is detectably labeled.

9. The method of claim 5, wherein said sample receiving chamber, said column(s), said plurality of chambers, and said reaction channel or chamber or a port into said reaction channel or chamber, are disposed around a central valve and selectively in fluid communication with a channel in said central valve, wherein said central valve is configured to accommodate a plunger that is capable of drawing fluid into or out of a chamber in fluid communication with said central valve.

10. The method of claim 5, wherein said cartridge, when in use, comprises:
said sample receiving chamber is a first chamber containing the sample; and said plurality of chambers containing buffers and/or reagents comprises:
a second chamber containing a guanidinium thiocyanate-ethanol (GTC-EtOH) solution;
a third chamber containing the bisulfite conversion reagent that deamidates cytosine;
a fourth chamber containing a buffer;
a fifth chamber containing a rinse solution; and
a sixth chamber containing said desulfonation reagent.

11. The method of claim 10, wherein the bisulfate conversion reagent is provided as a reagent in the cartridge.

12. The method of claim 5, wherein said cartridge comprises a seventh chamber containing PCR primers and/or probes, wherein at least one PCR primer and/or probe is detectably labeled, and/or PCR enzymes.

13. The method of claim 1, wherein said heating in clause iii) comprises transferring the DNA in a solution comprising the bisulfate conversion reagent into said reaction channel or chamber and heating the solution in said reaction channel or chamber.

14. The method of claim 1, wherein said desulfonating and eluting comprise simultaneously desulfonating and eluting the nucleic acid by contacting the deaminated nucleic acid with an alkaline solution.

\* \* \* \* \*